US012251436B2

(12) United States Patent
Kawaoka et al.

(10) Patent No.: US 12,251,436 B2
(45) Date of Patent: *Mar. 18, 2025

(54) RECOMBINANT INFLUENZA VIRUSES WITH STABILIZED HA FOR REPLICATION IN EGGS

(71) Applicants: Wisconsin Alumni Research Foundation (WARF), Madison, WI (US); The University of Tokyo, Tokyo (JP)

(72) Inventors: Yoshihiro Kawaoka, Middleton, WI (US); Shinya Yamada, Bunkyo-ku (JP); Shiho Chiba, Madison, WI (US)

(73) Assignees: Wisconsin Alumni Research Foundation (WARF), Madison, WI (US); The University of Tokyo, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/546,967

(22) Filed: Dec. 9, 2021

(65) Prior Publication Data

US 2022/0202927 A1 Jun. 30, 2022

Related U.S. Application Data

(63) Continuation of application No. 16/170,321, filed on Oct. 25, 2018, now Pat. No. 11,197,926.

(60) Provisional application No. 62/633,400, filed on Feb. 21, 2018, provisional application No. 62/577,049, filed on Oct. 25, 2017.

(51) Int. Cl.

| | |
|---|---|
| ***A61K 39/145*** | (2006.01) |
| ***A61K 9/00*** | (2006.01) |
| ***A61P 31/16*** | (2006.01) |
| ***C07K 14/005*** | (2006.01) |
| ***C12N 7/00*** | (2006.01) |
| ***C12N 9/24*** | (2006.01) |
| ***C12N 15/63*** | (2006.01) |

(52) U.S. Cl.

CPC .......... *A61K 39/145* (2013.01); *A61K 9/0019* (2013.01); *A61K 9/0043* (2013.01); *A61P 31/16* (2018.01); *C07K 14/005* (2013.01); *C12N 7/00* (2013.01); *C12N 9/2402* (2013.01); *C12N 15/63* (2013.01); *C12N 2760/16021* (2013.01); *C12N 2760/16022* (2013.01); *C12N 2760/16034* (2013.01); *C12N 2760/16051* (2013.01); *C12Y 302/01018* (2013.01)

(58) Field of Classification Search

None

See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,578,473 | A | 11/1996 | Palese et al. |
| 5,716,821 | A | 2/1998 | Wertz et al. |
| 5,750,394 | A | 5/1998 | Palese et al. |
| 5,786,199 | A | 7/1998 | Palese |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,001,634 | A | 12/1999 | Palese et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,270,958 | B1 | 8/2001 | Olivo et al. |
| 6,271,011 | B1 | 8/2001 | Lee et al. |
| 6,358,733 | B1 | 3/2002 | Motwani et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,843,996 | B1 | 1/2005 | Parkin et al. |
| 6,872,395 | B2 | 3/2005 | Kawaoka |
| 6,890,710 | B1 | 5/2005 | Palese et al. |
| 6,951,752 | B2 | 10/2005 | Reiter et al. |
| 6,951,754 | B2 | 10/2005 | Hoffmann |
| 6,974,695 | B2 | 12/2005 | Vogels et al. |
| 7,037,707 | B2 | 5/2006 | Webster et al. |
| 7,176,021 | B2 | 2/2007 | Kawaoka |
| 7,211,378 | B2 | 5/2007 | Kawaoka et al. |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

U.S. Appl. No. 16/785,449, filed Feb. 7, 2020, Humanized Cell Line.

(Continued)

*Primary Examiner* — Nicole Kinsey White

(74) *Attorney, Agent, or Firm* — Schwegman Lundberg & Woessner, P.A.

(57) ABSTRACT

Modified influenza virus neuraminidases are described herein that improve viral replication, thus improving the yield of vaccine viruses. Expression of such modified. neuraminidases by influenza virus may also stabilize co-expressed hemagglutinins so that the hemagglutinins do not undergo mutation.

20 Claims, 43 Drawing Sheets

Specification includes a Sequence Listing.

(56) References Cited

U.S. PATENT DOCUMENTS

| | | | |
|---|---|---|---|
| 7,226,774 | B2 | 6/2007 | Kawaoka |
| 7,312,064 | B2 | 12/2007 | Hoffmann |
| 7,335,356 | B2 | 2/2008 | Hart et al. |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,601,356 | B2 | 10/2009 | Jin et al. |
| 7,670,837 | B2 | 3/2010 | Schwartz |
| 7,682,618 | B2 | 3/2010 | Bavari et al. |
| 7,723,094 | B2 | 5/2010 | Kawaoka et al. |
| 7,833,788 | B2 | 11/2010 | Pau et al. |
| 7,883,844 | B2 | 2/2011 | Nouchi et al. |
| 7,955,833 | B2 | 6/2011 | Reiter et al. |
| 7,959,930 | B2 | 6/2011 | De Wit et al. |
| 7,968,101 | B2 | 6/2011 | Kawaoka et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,043,856 | B2 | 10/2011 | Kawaoka et al. |
| 8,048,430 | B2 | 11/2011 | Yang et al. |
| 8,057,806 | B2 | 11/2011 | Kawaoka et al. |
| 8,093,033 | B2 | 1/2012 | Kemble et al. |
| 8,114,415 | B2 | 2/2012 | Hoffmann et al. |
| 8,119,337 | B2 | 2/2012 | Gregersen |
| 8,119,388 | B2 | 2/2012 | Schwartz et al. |
| 8,298,805 | B2 | 10/2012 | Kawaoka |
| 8,309,099 | B2 | 11/2012 | Hoffmann |
| 8,354,114 | B2 | 1/2013 | Lu et al. |
| 8,357,376 | B2 | 1/2013 | Liu et al. |
| 8,409,843 | B2 | 4/2013 | Kemble et al. |
| 8,460,914 | B2 | 6/2013 | Gregersen |
| 8,465,960 | B2 | 6/2013 | Kawaoka et al. |
| 8,475,806 | B2 | 7/2013 | Kawaoka |
| 8,507,247 | B2 | 8/2013 | Kawaoka et al. |
| 8,524,497 | B2 | 9/2013 | Reiter et al. |
| 8,546,123 | B2 | 10/2013 | Lewis |
| 8,574,591 | B2 | 11/2013 | Hoffmann et al. |
| 8,574,593 | B2 | 11/2013 | Yang et al. |
| 8,580,277 | B2 | 11/2013 | Yang et al. |
| 8,591,914 | B2 | 11/2013 | Yang et al. |
| 8,597,661 | B2 | 12/2013 | Kawaoka et al. |
| 8,679,819 | B2 | 3/2014 | Kawaoka |
| 8,877,209 | B2 | 11/2014 | Kawaoka et al. |
| 8,900,595 | B2 | 12/2014 | Kawaoka et al. |
| 9,101,653 | B2 | 8/2015 | Kawaoka et al. |
| 9,109,013 | B2 | 8/2015 | Kawaoka et al. |
| 9,222,118 | B2 | 12/2015 | Kawaoka et al. |
| 9,254,318 | B2 | 2/2016 | Kawaoka et al. |
| 9,284,533 | B2 | 3/2016 | Bilsel et al. |
| 9,474,798 | B2 | 10/2016 | Watanabe et al. |
| 9,757,446 | B2 | 9/2017 | LeFebvre et al. |
| 9,890,363 | B2 | 2/2018 | Kawaoka |
| 9,926,535 | B2 | 3/2018 | Kawaoka et al. |
| 9,950,057 | B2 | 4/2018 | Kawaoka et al. |
| 10,053,671 | B2 | 8/2018 | Kawaoka et al. |
| 10,059,925 | B2 | 8/2018 | Kawaoka et al. |
| 10,119,124 | B2 | 11/2018 | Watanabe et al. |
| 10,130,697 | B2 | 11/2018 | Watanabe |
| 10,172,934 | B2 | 1/2019 | Kawaoka et al. |
| 10,246,686 | B2 | 4/2019 | Kawaoka et al. |
| 10,358,630 | B2 | 7/2019 | Kawaoka et al. |
| 10,494,613 | B2 | 12/2019 | Kawaoka et al. |
| 10,513,692 | B2 | 12/2019 | Kawaoka et al. |
| 10,633,422 | B2 | 4/2020 | Kawaoka et al. |
| 10,808,229 | B2 | 10/2020 | Kawaoka et al. |
| 11,007,262 | B2 | 5/2021 | Watanabe et al. |
| 11,046,934 | B2 | 6/2021 | Kawaoka et al. |
| 11,180,737 | B2 | 11/2021 | Kawaoka et al. |
| 11,197,925 | B2 | 12/2021 | Kawaoka et al. |
| 11,197,926 | B2 | 12/2021 | Kawaoka et al. |
| 11,241,492 | B2 | 2/2022 | Kawaoka et al. |
| 11,384,339 | B2 | 7/2022 | Kawaoka et al. |
| 11,389,523 | B2 | 7/2022 | Kawaoka et al. |
| 11,390,649 | B2 | 7/2022 | Kawaoka et al. |

| | | | |
|---|---|---|---|
| 11,739,303 | B2 | 8/2023 | Kawaoka et al. |
| 11,807,872 | B2 | 11/2023 | Kawaoka et al. |
| 11,851,648 | B2 | 12/2023 | Kawaoka et al. |
| 2002/0010143 | A1 | 1/2002 | Barbosa et al. |
| 2002/0164770 | A1 | 11/2002 | Hoffmann |
| 2002/0197705 | A1 | 12/2002 | Kawaoka |
| 2003/0035814 | A1 | 2/2003 | Kawaoka et al. |
| 2003/0044962 | A1 | 3/2003 | Makizumi et al. |
| 2003/0073223 | A1 | 4/2003 | Groner et al. |
| 2003/0119183 | A1 | 6/2003 | Groner |
| 2003/0194694 | A1 | 10/2003 | Kawaoka |
| 2003/0215794 | A1 | 11/2003 | Kawaoka et al. |
| 2004/0002061 | A1 | 1/2004 | Kawaoka |
| 2004/0029251 | A1 | 2/2004 | Hoffman et al. |
| 2004/0057967 | A1 | 3/2004 | Bavari et al. |
| 2004/0063141 | A1 | 4/2004 | Lok |
| 2004/0077086 | A1 | 4/2004 | Reiter et al. |
| 2004/0132164 | A1 | 7/2004 | Doyle et al. |
| 2004/0142322 | A1 | 7/2004 | Malcolm et al. |
| 2004/0219170 | A1 | 11/2004 | Kawaoka |
| 2004/0241139 | A1 | 12/2004 | Hobom et al. |
| 2004/0242518 | A1 | 12/2004 | Chen et al. |
| 2005/0003349 | A1 | 1/2005 | Kawaoka |
| 2005/0037487 | A1 | 2/2005 | Kawaoka et al. |
| 2005/0095583 | A1 | 5/2005 | Pekosz et al. |
| 2005/0118140 | A1 | 6/2005 | Vorlop et al. |
| 2005/0158342 | A1 | 7/2005 | Kemble et al. |
| 2005/0186563 | A1 | 8/2005 | Hoffmann |
| 2005/0202553 | A1 | 9/2005 | Groner et al. |
| 2005/0232950 | A1 | 10/2005 | Kawaoka |
| 2005/0266023 | A1 | 12/2005 | Bavari et al. |
| 2005/0266026 | A1 | 12/2005 | Hoffmann et al. |
| 2006/0057116 | A1 | 3/2006 | Kawaoka et al. |
| 2006/0088909 | A1 | 4/2006 | Compans |
| 2006/0099609 | A1 | 5/2006 | Bavari et al. |
| 2006/0134138 | A1 | 6/2006 | Kawaoka et al. |
| 2006/0166321 | A1 | 7/2006 | Kawaoka et al. |
| 2006/0188977 | A1 | 8/2006 | Schwartz et al. |
| 2006/0216702 | A1 | 9/2006 | Compans et al. |
| 2006/0240515 | A1 | 10/2006 | Dimitrov et al. |
| 2006/0246092 | A1 | 11/2006 | Neirynck et al. |
| 2007/0141699 | A1 | 6/2007 | Kawaoka |
| 2007/0231348 | A1 | 10/2007 | Kawaoka et al. |
| 2008/0009031 | A1 | 1/2008 | Kawaoka |
| 2008/0187557 | A1 | 8/2008 | Sambhara |
| 2008/0233560 | A1 | 9/2008 | Hoffmann |
| 2008/0254067 | A1 | 10/2008 | Trepanier et al. |
| 2008/0274141 | A1 | 11/2008 | Groner et al. |
| 2008/0292658 | A1 | 11/2008 | De Wit et al. |
| 2008/0293040 | A1 | 11/2008 | Kawaoka et al. |
| 2008/0311148 | A1 | 12/2008 | Hoffmann |
| 2008/0311149 | A1 | 12/2008 | Hoffmann |
| 2009/0017444 | A1 | 1/2009 | Kawaoka et al. |
| 2009/0047728 | A1 | 2/2009 | Kawaoka et al. |
| 2009/0074812 | A1 | 3/2009 | Watanabe et al. |
| 2009/0081252 | A1 | 3/2009 | Gregersen |
| 2009/0181446 | A1 | 7/2009 | Nouchi et al. |
| 2009/0311669 | A1 | 12/2009 | Kawaoka |
| 2009/0324640 | A1 | 12/2009 | Kawaoka et al. |
| 2010/0080825 | A1 | 4/2010 | Kawaoka et al. |
| 2010/0112000 | A1 | 5/2010 | Schwartz |
| 2010/0183671 | A1 | 7/2010 | Gregersen et al. |
| 2010/0247572 | A1 | 9/2010 | Kawaoka |
| 2010/0267116 | A1 | 10/2010 | Kawaoka et al. |
| 2011/0020374 | A1 | 1/2011 | Frazer |
| 2011/0027314 | A1 | 2/2011 | Broeker |
| 2011/0045022 | A1 | 2/2011 | Tsai |
| 2011/0081373 | A1 | 4/2011 | Kawaoka et al. |
| 2011/0110978 | A1 | 5/2011 | Kawaoka et al. |
| 2011/0159031 | A1 | 6/2011 | Falkner et al. |
| 2011/0236417 | A1 | 9/2011 | Watanabe et al. |
| 2011/0263554 | A1 | 10/2011 | Kawaoka et al. |
| 2011/0300604 | A1 | 12/2011 | Kawaoka et al. |
| 2012/0020997 | A1 | 1/2012 | Hoffman et al. |
| 2012/0034600 | A1 | 2/2012 | Gregersen |
| 2012/0058124 | A1 | 3/2012 | Kurosawa et al. |
| 2012/0115206 | A1 | 5/2012 | Schwartz et al. |
| 2012/0156241 | A1 | 6/2012 | De Wit et al. |
| 2012/0207785 | A1 | 8/2012 | Fabry et al. |

(56) References Cited

U.S. PATENT DOCUMENTS

| | | | |
|---|---|---|---|
| 2012/0251568 | A1 | 10/2012 | Garcia-Sastre et al. |
| 2013/0095135 | A1 | 4/2013 | Collignon et al. |
| 2013/0183741 | A1 | 7/2013 | Park et al. |
| 2013/0230552 | A1 | 9/2013 | Kawaoka et al. |
| 2013/0243744 | A1 | 9/2013 | Betenbaugh |
| 2013/0316434 | A1 | 11/2013 | Reiter et al. |
| 2014/0227310 | A1 | 8/2014 | Li et al. |
| 2015/0017205 | A1 | 1/2015 | Kawaoka et al. |
| 2015/0166967 | A1 | 6/2015 | Kawaoka et al. |
| 2015/0307851 | A1 | 10/2015 | Kawaoka et al. |
| 2015/0368621 | A1 | 12/2015 | Kawaoka et al. |
| 2016/0024193 | A1 | 1/2016 | Ayalon et al. |
| 2016/0024479 | A1 | 1/2016 | Kawaoka et al. |
| 2016/0115518 | A1 | 4/2016 | Kawaoka et al. |
| 2016/0208223 | A1 | 7/2016 | Kawaoka et al. |
| 2016/0215040 | A1 | 7/2016 | Kyratsous et al. |
| 2016/0355790 | A1 | 12/2016 | Kawaoka et al. |
| 2017/0058265 | A1 | 3/2017 | Kawaoka et al. |
| 2017/0067029 | A1 | 3/2017 | Kawaoka et al. |
| 2017/0096645 | A1 | 4/2017 | Watanabe et al. |
| 2017/0097334 | A1 | 4/2017 | Kawaoka et al. |
| 2017/0121391 | A1 | 5/2017 | Kawaoka et al. |
| 2017/0258888 | A1 | 9/2017 | Kawaoka |
| 2017/0298120 | A1 | 10/2017 | Sasisekharan |
| 2017/0354730 | A1 | 12/2017 | Kawaoka et al. |
| 2018/0245054 | A1 | 8/2018 | Kawaoka et al. |
| 2018/0273588 | A1 | 9/2018 | Kawaoka et al. |
| 2018/0340152 | A1 | 11/2018 | Kawaoka et al. |
| 2019/0032023 | A1 | 1/2019 | Kawaoka et al. |
| 2019/0048324 | A1 | 2/2019 | Kawaoka et al. |
| 2019/0117759 | A1 | 4/2019 | Wantanabe et al. |
| 2019/0167781 | A1 | 6/2019 | Kawaoka et al. |
| 2020/0188506 | A1 | 6/2020 | Kawaoka et al. |
| 2020/0237899 | A1 | 7/2020 | Kawaoka et al. |
| 2020/0263142 | A1 | 8/2020 | Kawaoka et al. |
| 2020/0263143 | A1 | 8/2020 | Kawaoka et al. |
| 2020/0291384 | A1 | 9/2020 | Kawaoka et al. |
| 2021/0061862 | A1 | 3/2021 | Kawaoka et al. |
| 2021/0102178 | A1 | 4/2021 | Kawaoka et al. |
| 2021/0121545 | A1 | 4/2021 | Knoll et al. |
| 2021/0228708 | A1 | 7/2021 | Smith et al. |
| 2021/0246432 | A1 | 8/2021 | Kawaoka et al. |
| 2021/0252130 | A1 | 8/2021 | Watanabe et al. |
| 2021/0290754 | A1 | 9/2021 | Kawaoka et al. |
| 2021/0299249 | A1 | 9/2021 | Kawaoka et al. |
| 2022/0025339 | A1 | 1/2022 | Kawaoka et al. |
| 2022/0202926 | A1 | 6/2022 | Kawaoka et al. |
| 2022/0241396 | A1 | 8/2022 | Kawaoka et al. |
| 2023/0321217 | A1 | 10/2023 | Kawaoka et al. |
| 2023/0346911 | A1 | 11/2023 | Kawaoka et al. |
| 2024/0010995 | A1 | 1/2024 | Kawaoka et al. |
| 2024/0076632 | A1 | 3/2024 | Kawaoka et al. |
| 2024/0238403 | A1 | 7/2024 | Kawaoka et al. |
| 2024/0318167 | A1 | 9/2024 | Kawaoka et al. |

FOREIGN PATENT DOCUMENTS

| | | | |
|---|---|---|---|
| AU | 2014290203 | B2 | 12/2020 |
| AU | 2017221444 | B2 | 11/2021 |
| BR | PI0410702 | B1 | 4/2022 |
| CA | 2379012 | A1 | 1/2001 |
| CA | 2816242 | C | 1/2019 |
| CN | 1826407 | A | 8/2006 |
| CN | 101472941 | A | 7/2009 |
| CN | 1826407 | B | 9/2013 |
| CN | 105296356 | A | 2/2016 |
| CN | 103540614 | B | 2/2018 |
| CN | 109477074 | A | 3/2019 |
| CN | 113874496 | A | 12/2021 |
| CN | 114929269 | A | 8/2022 |
| EP | 0687471 | A1 | 12/1995 |
| EP | 0700991 | A1 | 3/1996 |
| EP | 0702085 | A1 | 3/1996 |
| EP | 0704533 | A1 | 4/1996 |
| EP | 1201760 | A1 | 5/2002 |
| EP | 2010557 | B1 | 2/2014 |
| EP | 1572910 | B1 | 12/2015 |
| EP | 1631663 | B1 | 8/2016 |
| EP | 2747778 | B1 | 12/2017 |
| EP | 3009507 | B1 | 6/2020 |
| EP | 2493912 | B1 | 7/2020 |
| EP | 3022296 | B1 | 12/2022 |
| IL | 171831 | A | 5/2015 |
| JP | 07-203958 | | 8/1995 |
| JP | 2002536992 | A | 11/2002 |
| JP | 2003528570 | A | 9/2003 |
| JP | 2004500842 | A | 1/2004 |
| JP | 2004531232 | A | 10/2004 |
| JP | 2005523698 | A | 8/2005 |
| JP | 2005245302 | A | 9/2005 |
| JP | 2005535288 | A | 11/2005 |
| JP | 2006525815 | A | 11/2006 |
| JP | 2007518395 | A | 7/2007 |
| JP | 2007525175 | A | 9/2007 |
| JP | 2007529997 | A | 11/2007 |
| JP | 2008520248 | A | 6/2008 |
| JP | 2009511984 | A | 3/2009 |
| JP | 2009523252 | A | 6/2009 |
| JP | 2009532352 | A | 9/2009 |
| JP | 2010530248 | A | 9/2010 |
| JP | 2011530295 | A | 12/2011 |
| JP | 4927290 | | 5/2012 |
| JP | 4927290 | B2 | 5/2012 |
| JP | 2013507990 | A | 3/2013 |
| JP | 2013511289 | A | 4/2013 |
| JP | 2014039551 | A | 3/2014 |
| JP | 2014131516 | A | 7/2014 |
| JP | 2016500007 | A | 1/2016 |
| JP | 2016521553 | A | 7/2016 |
| JP | 2015144463 | A | 8/2016 |
| JP | 2016524915 | A | 8/2016 |
| JP | 2016169225 | A | 9/2016 |
| JP | 2017527557 | A | 9/2017 |
| JP | 2017197555 | A | 11/2017 |
| JP | 2018064493 | A | 4/2018 |
| JP | 6352974 | B2 | 6/2018 |
| JP | 6375329 | B2 | 7/2018 |
| JP | 2019510481 | A | 4/2019 |
| JP | 2020010711 | A | 1/2020 |
| JP | 2020114250 | A | 7/2020 |
| JP | 2021500891 | A | 1/2021 |
| JP | 2021036878 | A | 3/2021 |
| JP | 2021184761 | A | 12/2021 |
| JP | 2021533157 | A | 12/2021 |
| JP | 2021536228 | A | 12/2021 |
| JP | 2022066209 | A | 4/2022 |
| JP | 2022522112 | A | 4/2022 |
| JP | 2022527235 | A | 6/2022 |
| JP | 2022172369 | A | 11/2022 |
| JP | 2022551805 | A | 12/2022 |
| KR | 101113432 | B1 | 2/2012 |
| MX | 285206 | | 3/2011 |
| NO | 341506 | | 11/2017 |
| WO | WO-9610631 | A1 | 4/1996 |
| WO | WO-9610632 | A1 | 4/1996 |
| WO | WO-9640955 | A1 | 12/1996 |
| WO | WO-9737000 | A1 | 10/1997 |
| WO | WO-9802530 | A1 | 1/1998 |
| WO | WO-9848834 | A1 | 11/1998 |
| WO | WO-9853078 | A1 | 11/1998 |
| WO | WO-9928445 | A1 | 6/1999 |
| WO | WO-0053786 | A1 | 9/2000 |
| WO | WO-0060050 | A2 | 10/2000 |
| WO | WO-2000060050 | A2 | 10/2000 |
| WO | WO-0060050 | A3 | 1/2001 |
| WO | WO-2001004333 | A1 | 1/2001 |
| WO | WO-2001025462 | A1 | 4/2001 |
| WO | WO-0179273 | A2 | 10/2001 |
| WO | WO-2001079273 | A2 | 10/2001 |
| WO | WO-0183794 | A2 | 11/2001 |
| WO | WO-2001083794 | A2 | 11/2001 |
| WO | WO-0210143 | A1 | 1/2002 |
| WO | WO-02064757 | A2 | 8/2002 |
| WO | WO-02074795 | A2 | 9/2002 |

(56) References Cited

FOREIGN PATENT DOCUMENTS

| | | |
|---|---|---|
| WO | WO-03068923 A2 | 8/2003 |
| WO | WO-2003068923 A2 | 8/2003 |
| WO | WO-03076462 A1 | 9/2003 |
| WO | WO-2003080846 A1 | 10/2003 |
| WO | WO-03091401 A2 | 11/2003 |
| WO | WO-2003091401 A2 | 11/2003 |
| WO | WO-2004142322 A1 | 7/2004 |
| WO | WO-2004094466 A2 | 11/2004 |
| WO | WO-04112831 A2 | 12/2004 |
| WO | WO-2004112831 A2 | 12/2004 |
| WO | WO-2004112831 A3 | 12/2004 |
| WO | WO-05028658 A2 | 3/2005 |
| WO | WO-05028658 A3 | 3/2005 |
| WO | WO-2005028658 A2 | 3/2005 |
| WO | WO-2005062820 A2 | 7/2005 |
| WO | WO-2006051069 A2 | 5/2006 |
| WO | WO-2007004024 A2 | 4/2007 |
| WO | WO-2007044024 A3 | 4/2007 |
| WO | WO-2007126810 A2 | 11/2007 |
| WO | WO-2007126810 A3 | 11/2007 |
| WO | WO-2007146057 A2 | 12/2007 |
| WO | WO-2007146057 A3 | 12/2007 |
| WO | WO-08156681 A3 | 12/2008 |
| WO | WO-2008147496 A2 | 12/2008 |
| WO | WO-2008147496 A3 | 12/2008 |
| WO | WO-2008155681 A2 | 12/2008 |
| WO | WO-2008156778 A2 | 12/2008 |
| WO | WO-2008156778 A3 | 12/2008 |
| WO | WO-2008157583 A1 | 12/2008 |
| WO | WO 09008921 A3 | 1/2009 |
| WO | WO-09008921 A9 | 1/2009 |
| WO | WO-2009007244 A2 | 1/2009 |
| WO | WO-2009008921 A2 | 1/2009 |
| WO | WO-2009014919 A2 | 1/2009 |
| WO | WO-2008156778 A9 | 2/2009 |
| WO | WO-09128867 A2 | 10/2009 |
| WO | WO-2009152181 A1 | 12/2009 |
| WO | WO-2009128867 A3 | 3/2010 |
| WO | WO-2010053573 A2 | 4/2010 |
| WO | WO-2010053573 A3 | 7/2010 |
| WO | WO-2011014645 A1 | 2/2011 |
| WO | WO-2011056591 A1 | 5/2011 |
| WO | WO-2011087839 A1 | 7/2011 |
| WO | WO-2011126370 A1 | 10/2011 |
| WO | WO-2011130627 A2 | 10/2011 |
| WO | WO-2012045882 A2 | 4/2012 |
| WO | WO-2012177924 A2 | 12/2012 |
| WO | WO-2013032942 A1 | 3/2013 |
| WO | WO-2013032942 A9 | 3/2013 |
| WO | WO-2013034069 A1 | 3/2013 |
| WO | WO-2013087945 A2 | 6/2013 |
| WO | WO-2013148302 A1 | 10/2013 |
| WO | WO-2014195920 A2 | 12/2014 |
| WO | WO-2015009743 A1 | 1/2015 |
| WO | WO-2015134488 A1 | 9/2015 |
| WO | WO-2015142671 A2 | 9/2015 |
| WO | WO-2015196150 A2 | 12/2015 |
| WO | WO-2015196150 A3 | 12/2015 |
| WO | WO-2016144933 A1 | 9/2016 |
| WO | WO-2016207853 A2 | 12/2016 |
| WO | WO-2017007839 A1 | 1/2017 |
| WO | WO-2017040203 A1 | 3/2017 |
| WO | WO-2017136575 A1 | 8/2017 |
| WO | WO-2017143236 A1 | 8/2017 |
| WO | 2019084310 | 5/2019 |
| WO | WO-2019241579 A1 | 12/2019 |
| WO | WO-2020033527 A2 | 2/2020 |
| WO | WO-2020041311 A1 | 2/2020 |
| WO | 2020061443 | 3/2020 |
| WO | WO-2020/033527 A3 | 3/2020 |
| WO | WO-2020163804 A1 | 8/2020 |
| WO | WO-2020167432 A2 | 8/2020 |
| WO | WO-2020223699 A1 | 11/2020 |
| WO | WO-2020167432 A3 | 12/2020 |
| WO | WO-2020264141 A1 | 12/2020 |
| WO | WO-2021041624 A2 | 3/2021 |
| WO | WO-2021041624 A3 | 5/2021 |
| WO | WO-2021150874 A1 | 7/2021 |
| WO | WO-2021195410 A1 | 9/2021 |
| WO | WO-2021242597 A1 | 12/2021 |
| WO | 2022245888 | 11/2022 |
| WO | 2023125889 | 7/2023 |
| WO | 2023164556 | 8/2023 |
| WO | WO-2024015510 A1 | 1/2024 |
| WO | 2024197167 | 9/2024 |

OTHER PUBLICATIONS

U.S. Appl. No. 17/004,583, filed Aug. 27, 2020, Recombinant Influenza Viruses With Stabilized HA for Replication in Eggs.

U.S. Appl. No. 17/155,625, filed Jan. 22, 2021, Recombinant Influenza Viruses With Stabilized NA.

U.S. Appl. No. 17/212,836, filed Mar. 25, 2021, Recombinant Multivalent Influenza Viruses.

U.S. Appl. No. 18/173,535, filed Feb. 23, 2023, Broadly Protective Influenza B Virus Vaccines.

U.S. Appl. No. 17/936,194, filed Sep. 28, 2022, Compositions Comprising Complexes Displaying Antigens and Methods of Using the Compositions.

Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.

Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.

Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.

Result 17, NCBI Blast nucleotide search of SEQ ID No. 2, database "nr", (Jul. 18, 2006), 3 pgs.

Result 7, NCBI Blast nucleotide search of SEQ ID: 1, database "nr", (Jul. 18, 2006), 3 pgs.

FLUMISTTM Package Insert Template, [Online]. Retrieved from the Internet: http://www.fda.gov/downloads/BiologicsBioodVaccines!Vaccines/ApprovedProducts/UCM29 4307.pdf, (Mar. 1, 2012), 26 pgs.

"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 10/855,975 Response filed Aug. 28, 2007 to Final Office Action mailed Jun. 28, 2007", 16 pgs.

"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.

"Final O.A Jun. 28, 2007", 5 pgs.

"Application Serial No. 04809419.7, Office Action Mailed Sep. 9, 2009", 3 pgs.

"U.S. Appl. No. 09/834,095, Advisory Action mailed Jan. 8, 2004", 3 pgs.

"U.S. Appl. No. 09/834,095, Final Office Action mailed Aug. 26, 2003", 12 pgs.

"U.S. Appl. No. 09/834,095, Non-Final Office Action mailed Nov. 4, 2002", 12 pgs.

"U.S. Appl. No. 09/834,095, Notice of Allowance mailed Sep. 27, 2004", 13 pgs.

"U.S. Appl. No. 09/834,095, Office Action mailed Apr. 20, 2004", 11 pgs.

"U.S. Appl. No. 09/834,095, Response filed Feb. 4, 2003 to Office Action mailed Nov. 4, 2002", 14 pgs.

"U.S. Appl. No. 09/834,095, Response filed Jun. 12, 2003 to Restriction Requirement mailed Apr. 22, 2003", 2 pgs.

(56) References Cited

OTHER PUBLICATIONS

"U.S. Appl. No. 09/834,095, Response filed Jun. 18, 2004 to Office Action mailed Apr. 20, 2004", 11 pgs.
"U.S. Appl. No. 09/834,095, Response filed Aug. 1, 2002 to Restriction Requirement mailed Jul. 1, 2002", 3 pgs.
"U.S. Appl. No. 09/834,095, Response filed Nov. 26, 2003 to Final Office Action mailed Aug. 26, 2003", 10 pgs.
"U.S. Appl. No. 09/834,095, Restriction Requirement mailed Apr. 22, 2003", 5 pgs.
"U.S. Appl. No. 09/834,095, Restriction Requirement mailed Jul. 1, 2002", 9 pgs.
"U.S. Appl. No. 09/834,095, Supplemental Amendment filed Aug. 4, 2004", 7 pgs.
"U.S. Appl. No. 10/081,170, Advisory Action mailed Sep. 27, 2004", 3 pgs.
"U.S. Appl. No. 10/081,170, Final Office Action mailed Apr. 12, 2006", 7 pgs.
"U.S. Appl. No. 10/081,170, Final Office Action mailed Jul. 13, 2004", 8 pgs.
"U.S. Appl. No. 10/081,170, Non Final Office Action mailed Jan. 15, 2004", 9 pgs.
"U.S. Appl. No. 10/081,170, Non Final Office Action mailed Feb. 8, 2005", 9 pgs.
"U.S. Appl. No. 10/081,170, Non Final Office Action mailed Aug. 24, 2005", 9 pgs.
"U.S. Appl. No. 10/081,170, Notice of Allowance mailed Sep. 18, 2006", 8 pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action mailed Aug. 24, 2005", 11 pgs.
"U.S. Appl. No. 10/081,170, Response filed Apr. 12, 2004 to Non Final Office Action mailed Jan. 15, 2004", 12 pgs.
"U.S. Appl. No. 10/081,170, Response filed Jun. 8, 2005 to Non Final Office Action mailed Feb. 8, 2005", 11 pgs.
"U.S. Appl. No. 10/081,170, Response filed Aug. 17, 2006 to Final Office Action mailed Apr. 12, 2006", 9 pgs.
"U.S. Appl. No. 10/081,170, Response filed Sep. 13, 2004 to Final Office Action mailed Jul. 13, 2004", 10 pgs.
"U.S. Appl. No. 10/081,170, Response filed Oct. 10, 2003 to Restriction Requirement mailed Sep. 10, 2003", 3 pgs.
"U.S. Appl. No. 10/081,170, Restriction Requirement mailed Sep. 10, 2003", 4 pgs.
"U.S. Appl. No. 10/353,856, Final Office Action mailed Jun. 1, 2006", 10 pgs.
"U.S. Appl. No. 10/353,856, Non-Final Office Action mailed Sep. 30, 2005", 9 pgs.
"U.S. Appl. No. 10/353,856, Non-Final Office Action mailed Dec. 16, 2004", 11 pgs.
"U.S. Appl. No. 10/353,856, Notice of Allowance mailed Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment mailed Mar. 8, 2007", 2 pgs.
"U.S. Appl. No. 10/353,856, Response filed Feb. 28, 2006 to Non-Final Office Action mailed Sep. 30, 2005", 10 pgs.
"U.S. Appl. No. 10/353,856, Response filed Apr. 7, 2005 to Non-Final Office Action mailed Dec. 16, 2004", 10 pgs.
"U.S. Appl. No. 10/353,856, Response filed Aug. 17, 2006 to Final Office Action mailed Jun. 1, 2006", 11 pgs.
"U.S. Appl. No. 10/353,856, Response filed Oct. 8, 2004 to Restriction Requirement mailed Sep. 10, 2004", 2 pgs.
"U.S. Appl. No. 10/353,856, Restriction Requirement mailed Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/827,995, Final Office Action mailed Nov. 15, 2006", 10 pgs.
"U.S. Appl. No. 10/827,995, Non-Final Office Action mailed Jun. 2, 2006", 15 pgs.
"U.S. Appl. No. 10/827,995, Non-Final Office Action mailed Oct. 25, 2007", 7 pgs.
"U.S. Appl. No. 10/827,995, Notice of Allowance mailed Feb. 17, 2009", 9 pgs.
"U.S. Appl. No. 10/827,995, Notice of Allowance mailed Jul. 2, 2008", 9 pgs.
"U.S. Appl. No. 10/827,995, Notice of Allowance mailed Oct. 17, 2008", 7 pgs.
"U.S. Appl. No. 10/827,995, Notice of Non-Compliant Amendment Jul. 25, 2007", 4 pgs.
"U.S. Appl. No. 10/827,995, Proposed Examiner's Amendment mailed Jun. 5, 2008", 6 pgs.
"U.S. Appl. No. 10/827,995, Response filed Mar. 3, 2008 to Office Action mailed Oct. 25, 2007", 10 pgs.
"U.S. Appl. No. 10/827,995, Response filed May 14, 2007 Final Office Action mailed Nov. 15, 2006", 16 pgs.
"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action mailed Jun. 2, 2006", 15 pgs.
"U.S. Appl. No. 10/855,875 , Response filed May 17, 2012 to Non Final Office Action mailed Mar. 15, 2012", 15 pgs.
"U.S. Appl. No. 10/855,875, Final Office Action mailed Mar. 11, 2008", FOAR, 20 Pgs.
"U.S. Appl. No. 10/855,875, Final Office Action mailed Aug. 2, 2006", 34 pgs.
"U.S. Appl. No. 10/855,875, Final Office Action malled Dec. 10, 2010", 15 pgs.
"U.S. Appl. No. 10/855,875, Non Final Office Action mailed Mar. 15, 2012", 15 pgs.
"U.S. Appl. No. 10/855,875, Non-Final Office Action mailed Feb. 19, 2010", 7 pgs.
"U.S. Appl. No. 10/855,875, Non-Final Office Action mailed May 3, 2007", 13 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action mailed Aug. 2, 2007", 14 pgs.
"U.S. Appl. No. 10/855,875, Response filed Mar. 18, 2011 to Final Office Action mailed Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Dec. 7, 2009 to Non Final Office Action mailed Aug. 7, 2009", 15 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.
"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,975, Advisory Action mailed Sep. 6, 2006", 3 pgs.

(56) References Cited

OTHER PUBLICATIONS

"U.S. Appl. No. 10/855,975, Advisory Action mailed Sep. 13, 2007", 3 pgs.
"U.S. Appl. No. 10/855,975, Advisory Action mailed Dec. 24, 2008", 4 pgs.
"U.S. Appl. No. 10/855,975, Final Office Action mailed May 17, 2006", 7 pgs.
"U.S. Appl. No. 10/855,975, Final Office Action mailed Jun. 28, 2007", 7 pgs.
"U.S. Appl. No. 10/855,975, Final Office Action mailed Aug. 7, 2008", 5 pgs.
"U.S. Appl. No. 10/855,975, Non-Final Office Action mailed Jan. 4, 2008", 10 pgs.
"U.S. Appl. No. 10/855,975, Non-Final Office Action mailed Jan. 19, 2007", 7 pgs.
"U.S. Appl. No. 10/855,975, Non-Final Office Action mailed May 29, 2009", 5 pgs.
"U.S. Appl. No. 10/855,975, Non-Final Office Action mailed Nov. 30, 2005", 11 pgs.
"U.S. Appl. No. 10/855,975, Notice of Allowance mailed Dec. 16, 2009", 19 pgs.
"U.S. Appl. No. 10/855,975, Response filed Jan. 29, 2009 to Advisory Action mailed Dec. 24, 2008", 15 pgs.
"U.S. Appl. No. 10/855,975, Response filed Feb. 28, 2006 to Non-Final Office Action mailed Nov. 30, 2005", 15 pgs.
"U.S. Appl. No. 10/855,975, Response filed Apr. 3, 2008 to Non Final Office Action mailed Jan. 4, 2008", 16 pgs.
"U.S. Appl. No. 10/855,975, Response filed Apr. 19, 2007 to Non-Final Office Action mailed Jan. 19, 2007", 16 pgs.
"U.S. Appl. No. 10/855,975, Response filed Aug. 13, 2009 to Non Final Office Action mailed May 29, 2009", 19 pgs.
"U.S. Appl. No. 10/855,975, Response filed Aug. 17, 2006 to Final Office Action mailed May 17, 2006", 13 pgs.
"U.S. Appl. No. 10/855,975, Response filed Aug. 28, 2007 to Final Office Action mailed Jun. 28, 2007", 15 pgs.
"U.S. Appl. No. 10/855,975, Response filed Sep. 28, 2005 to Restriction Requirement mailed Jul. 12, 2005", 3 pgs.
"U.S. Appl. No. 10/855,975, Response filed Dec. 11, 2008 to Final Office Action mailed Aug. 7, 2008", 14 pgs.
"U.S. Appl. No. 10/855,975, Restriction Requirement mailed Jul. 12, 2005", 8 pgs.
"U.S. Appl. No. 10/855,875, Response filed Nov. 2, 2007 to Office Action mailed May 3, 2007", 16 pgs.
"U.S. Appl. No. 11/043,768 Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Jun. 23, 2009 to Non-Final Office Action mailed Feb. 23, 2009", 9 pgs.
"U.S. Appl. No. 11/043,768, Response filed Sep. 13, 2007 to Restriction Requirement mailed Mar. 13, 2007" 10 pgs.
"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,786, Final Office Action mailed Feb. 3, 2011", 10 pgs.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006". 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.
"U.S. Appl. No. 11/509,249, Final Office Action mailed Jun. 12, 2008", 5 pgs.
"U.S. Appl. No. 11/509,249, Non Final Office Action with Restriction Requirement mailed Aug. 24, 2007", 8 pgs.
"U.S. Appl. No. 11/509,249, Notice of Allowance mailed Apr. 9, 2009", 7 pgs.
"U.S. Appl. No. 11/509,249, Notice of Allowance mailed Nov. 17, 2008", 4 pgs.
"U.S. Appl. No. 11/509,249, Response filed Feb. 20, 2008 to Non Final Office Action mailed Aug. 24, 2007", 11 pgs.
"U.S. Appl. No. 11/509,249, Response filed Oct. 6, 2008 to Office Action mailed Jun. 12, 2008", 11 pgs.
"U.S. Appl. No. 11/644,179 , Response filed Oct. 21, 2013 to Final Office Action mailed May 21, 2013", 8 pgs.
"U.S. Appl. No. 11/644,179, Final Office Action mailed May 21, 2013", 11 pgs.
"U.S. Appl. No. 11/644,179, Final Office Action mailed Jul. 2, 2010", 8 pgs.
"U.S. Appl. No. 11/644,179, Non Final Office Action mailed Nov. 29, 2012", 19 pgs.
"U.S. Appl. No. 11/644,179, Non Final Office Action mailed Dec. 8, 2009", 7 pgs.
"U.S. Appl. No. 11/644,179, Notice of Allowance mailed Nov. 1, 2013", 11 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement mailed Oct. 30, 2007", 5 pgs.
"U.S. Appl. No. 11/644,179, Response filed Apr. 8, 2010 to Non Final Office Action mailed Dec. 8, 2009", 8 pgs,.
"U.S. Appl. No. 11/644,179, Response filed Aug. 17, 2010 to Final Office Action mailed Jul. 2, 2010", 8 pgs.
"U.S. Appl. No. 11/644,179, Restriction Requirement mailed Oct. 30, 2007", 7 pgs.
"U.S. Appl. No. 11/644,179, Supplemental Preliminary Amendment filed Feb. 6, 2008", 6 pgs.
"U.S. Appl. No. 11/644,179, Response filed Feb. 20, 2013 to Non Final Office Action mailed Nov. 29, 2012", 10 pgs.
"U.S. Appl. No. 11/654,863 Final Office Action mailed Jul. 17, 2017", 11 pgs.
"U.S. Appl. No. 11/654,863 Restriction Requirement mailed Sep. 3, 2010", 5 pgs.
"U.S. Appl. No. 11/654,863, Appeal Brief filed Apr. 30, 2014", 22 pgs.

(56) References Cited

OTHER PUBLICATIONS

"U.S. Appl. No. 11/654,863, Appeal Decision mailed Aug. 3, 2016", 11 pgs.
"U.S. Appl. No. 11/654,863, Decision on Pre-Appeal Brief Request mailed Dec. 5, 2013", 2 pgs.
"U.S. Appl. No. 11/654,863, Declaration of Dr. Heinz Feldmann dated Jan. 9, 2018". 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief mailed Jun. 18, 2014", 10 pgs.
"U.S. Appl. No. 11/654,863, Final Office Action mailed Jul. 11, 2013", 9 pgs.
"U.S. Appl. No. 11/654,863, Final Office Action mailed Sep. 12, 2018", 12 pgs.
"U.S. Appl. No. 11/654,863, Final Office Action mailed Oct. 25, 2011", 9 pgs.
"U.S. Appl. No. 11/654,863, Non Final Office Action mailed Feb. 11, 2013", 10 pgs.
"U.S. Appl. No. 11/654,863, Non Final Office Action mailed Mar. 29, 2018", 12 pgs.
"U.S. Appl. No. 11/654,863, Non Final Office Action mailed Jun. 27, 2011", 9 pgs.
"U.S. Appl. No. 11/654,863, Non Final Office Action mailed Dec. 2, 2010", 8 pgs.
"U.S. Appl. No. 11/654,863, Non Final Office Action mailed Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action mailed Jul. 17, 2017", 9 pgs.
"U.S. Appl. No. 11/654,863, Response filed Apr. 18, 2012 to Final Office Action mailed Oct. 25, 2011", 8 pgs.
"U.S. Appl. No. 11/654,863, Response filed Jun. 2, 2011 to Non Final Office Action mailed Dec. 2, 2010", 6 pgs.
"U.S. Appl. No. 11/654,863, Response filed Jun. 7, 2013 to Non Final Office Action mailed Feb. 11, 2013", 10 pgs.
"U.S. Appl. No. 11/654,863, Response filed Jun. 21, 2017 to Non Final Office Action mailed Dec. 21, 2016", 11 pgs.
"U.S. Appl. No. 11/654,863, Response filed Jul. 9, 2018 to Non Final Office Action mailed Mar. 29, 2018", 10 pgs.
"U.S. Appl. No. 11/654,863, Response filed Sep. 28, 2010 to Restriction Requirement mailed Sep. 3, 2010", 6 pgs.
"U.S. Appl. No. 11/654,863, Response filed Oct. 6, 2011 to Non Final Office Action mailed Jun. 27, 2011", 9 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non Final Office Action mailed Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.
"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Respons filed Jun. 22, 2010 to Non Final Office Action mailed Feb. 22, 2010", 33 pgs.
"U.S. Appl. No. 11/729,557, Response filed Apr. 27, 2011 to Final Office Action mailed Feb. 2, 2011". 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557, Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Response filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 11/810,956, Final Office Action mailed Mar. 22, 2010", 8 pgs.
"U.S. Appl. No. 11/810,956, Non-Final Office Action mailed Aug. 11, 2009", 9 pgs.
"U.S. Appl. No. 11/810,956, Response filed Jan. 11, 2010 to Non Final Office Action mailed Aug. 11, 2009", 8 pgs.
"U.S. Appl. No. 11/810,956, Response filed Apr. 23, 2009 to Restriction Requirement mailed Mar. 23, 2009", 6 pgs.
"U.S. Appl. No. 11/810,956, Restriction Requirement mailed Mar. 23, 2009", 6 pgs.
"U.S. Appl. No. 12/058,389, Advisory Action mailed Jan. 2, 2013", 2 pgs.
"U.S. Appl. No. 12/058,389, Final Office Action mailed Jan. 22, 2010", 8 pgs.
"U.S. Appl. No. 12/058,389, Final Office Action mailed Nov. 14, 2012", 7 pgs.
"U.S. Appl. No. 12/058,389, Non Final Office Action mailed Aug. 10, 2012", 5 pgs.
"U.S. Appl. No. 12/058,389, Non Final Office Action mailed Dec. 8, 2011", 8 pgs.
"U.S. Appl. No. 12/058,389, Non-Final Office Action malled Apr. 13, 2009", 12 pgs.
"U.S. Appl. No. 12/058,389, Notice of Allowability mailed Mar. 22, 2013", 8 pgs.
"U.S. Appl. No. 12/058,389, Notice of Allowance mailed Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action mailed Aug. 10, 2012", 7 pgs.
"U.S. Appl. No. 12/058,389, Response filed Feb. 6, 2009 to Restriction Requirement mailed Dec. 3, 2008", 7 pgs.
"U.S. Appl. No. 12/058,389, Response filed Apr. 10, 2012 to Non Final Office Action mailed Dec. 8, 2011", 7 pgs.
"U.S. Appl. No. 12/058,389, Response filed Jun. 16, 2010 to Final Office Action mailed Jan. 22, 2010". 6 pgs.
"U.S. Appl. No. 12/058,389, Response filed Oct. 13, 2009 to Non Final Office Action mailed Apr. 13, 2009", 9 pgs.
"U.S. Appl. No. 12/058,389, Response filed Dec. 18, 2012 to Non Final Office Action mailed Nov. 14, 2012", 7 pgs.
"U.S. Appl. No. 12/058,389, Restriction Requirement mailed Dec. 3, 2008", 7 pgs.
"U.S. Appl. No. 12/113,690, Final Office Action mailed Apr. 15, 2011", 10 pgs.
"U.S. Appl. No. 12/113,690, Non-Final Office Action mailed Nov. 10, 2010", 11 pgs.
"U.S. Appl. No. 12/113,690, Notice of Allowability mailed Aug. 19, 2013", 9 pgs.

(56) References Cited

OTHER PUBLICATIONS

"U.S. Appl. No. 12/113,690, Notice of Allowance mailed Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action mailed Apr. 15, 2011", 17 pgs.
"U.S. Appl. No. 12/113,690, Response filed Aug. 5, 2010 to Restriction Requirement mailed Apr. 6, 2010", 14 pgs.
"U.S. Appl. No. 12/113,690, Response filed Dec. 22, 2010 to Non Final Office Action mailed Nov. 10, 2010", 19 pgs.
"U.S. Appl. No. 12/113,690, Restriction Requirement mailed Apr. 6, 2010", 10 pgs.
"U.S. Appl. No. 12/139,183, Non Final Office Action mailed Jan. 6, 2011", 12 pgs.
"U.S. Appl. No. 12/139,183, Non-Final Office Action mailed Jan. 4, 2010", 6 pgs.
"U.S. Appl. No. 12/139,183, Non-Final Office Action mailed Jul. 13, 2010", 15 pgs.
"U.S. Appl. No. 12/139,183, Notice of Allowance mailed Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action mailed Jan. 6, 2011", 21 pgs.
"U.S. Appl. No. 12/139,183, Response filed Apr. 12, 2010 to Non Final Office Action mailed Jan. 4, 2010", 17 pgs.
"U.S. Appl. No. 12/139,183, Response filed Aug. 18, 2009 to Restriction Requirement mailed Jul. 24, 2009", 16 pgs.
"U.S. Appl. No. 12/139,183, Response filed Sep. 21, 2010 to Non Final Office Action mailed Jul. 13, 2010", 21 pgs.
"U.S. Appl. No. 12/139,183, Restriction Requirement mailed Jul. 24, 2009", 12 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.
"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action mailed Jun. 12, 2014", 28 pgs.
"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Oct. 14, 2014 to Non Final Office Action mailed Jun. 12, 2014", 16 pgs.
"U.S. Appl. No. 12/214,414, Response filed Dec. 21, 2011 to Advisory Action mailed Nov. 21, 2011", 10 pgs.
"U.S. Appl. No. 12/245,296, Final Office Action mailed Jul. 11, 2013", 15 pgs.
"U.S. Appl. No. 12/245,296, Final Office Action mailed Dec. 17, 2010", 16 pgs.
"U.S. Appl. No. 12/245,296, Non Final Office Action mailed Mar. 25, 2013", 14 pgs.
"U.S. Appl. No. 12/245,296, Non-Final Office Action mailed Jun. 1, 2010", 13 pgs.
"U.S. Appl. No. 12/245,296, Notice of Allowance mailed Aug. 1, 2014", 10 pgs.
"U.S. Appl. No. 12/245,296, Preliminary Amendment mailed Jan. 28, 2009", 14 pgs.
"U.S. Appl. No. 12/245,296, Response filed Jan. 8, 2013 to Final Office Action mailed Jul. 11, 2013", 10 pgs.
"U.S. Appl. No. 12/245,296, Response filed Apr. 8, 2010 to Restriction Requirement mailed Mar. 9, 2010", 6 pgs.
"U.S. Appl. No. 12/245,296, Response filed May 17, 2011 to Final Office Action mailed Dec. 17, 2010", 10 pgs.
"U.S. Appl. No. 12/245,296, Response filed Jun. 7, 2013 to Non Final Office Action mailed Mar. 25, 2013", 9 pgs.
"U.S. Appl. No. 12/245,296, Response filed Oct. 1, 2010 to Non Final Office Action mailed Jun. 1, 2010", 12 pgs.
"U.S. Appl. No. 12/245,296, Restriction Requirement mailed Mar. 9, 2010", 6 pgs.
"U.S. Appl. No. 12/467,492, Restriction Requirement mailed Nov. 22, 2010", 6 pgs.
"U.S. Appl. No. 12/470,287 , Response filed Jan. 23, 2012 to Non Final Office Action mailed Jul. 22, 2011", 13 pgs.
"U.S. Appl. No. 12/470,287 , Response filed May 31, 2012 to Final Office Action mailed Apr. 3, 2012", 14 pgs.
"U.S. Appl. No. 12/470,287, Corrected Notice of Allowability mailed Sep. 11, 2012", 2 pgs.
"U.S. Appl. No. 12/470,287, Final Office Action mailed Apr. 3, 2012", 7 pgs.
"U.S. Appl. No. 12/470,287, Non Final Office Action mailed Jul. 22, 2011", 9 pgs.
"U.S. Appl. No. 12/470,287, Notice of Allowance mailed Jun. 19, 2012", 5 pgs.
"U.S. Appl. No. 12/470,287, Response filed Apr. 28, 2011 to Restriction Requirement mailed Dec. 29, 2010", 8 pgs.
"U.S. Appl. No. 12/470,287, Restriction Requirement mailed Dec. 29, 2010", 6 pgs.
"U.S. Appl. No. 12/854,578 , Response filed Oct. 1, 2012 to Non Final Office Action mailed Jun. 29, 2012", 10 pgs.
"U.S. Appl. No. 12/854,578, Final Office Action mailed Nov. 29, 2012", 8 pgs.
"U.S. Appl. No. 12/854,578, Non Final Office Action mailed Jun. 29, 2012", 8 pgs.
"U.S. Appl. No. 12/854,578, Notice of Allowance mailed Apr. 10, 2013", 6 pgs.
"U.S. Appl. No. 12/854,578, PTO Response to 312 Amendment mailed Jul. 18, 2013", 2 pgs.
"U.S. Appl. No. 12/854,578, Response filed Feb. 28, 2013 to Final Office Action mailed Nov. 29, 2012", 8 pgs.
"U.S. Appl. No. 12/854,578, Restriction Requirement mailed Apr. 6, 2012", 6 pgs.
"U.S. Appl. No. 12/912,411, Advisory Action mailed Feb. 5, 2014", 3 pgs.
"U.S. Appl. No. 12/912,411, Examiner Interview Summary mailed Feb. 11, 2014", 2 pgs.
"U.S. Appl. No. 12/912,411, Final Office Action mailed Jan. 14, 2015", 10 pgs.
"U.S. Appl. No. 12/912,411, Final Office Action mailed Oct. 25, 2013", 11 pgs.
"U.S. Appl. No. 12/912,411, Non Final Office Action mailed Jun. 7, 2013", 8 pgs.
"U.S. Appl. No. 12/912,411, Non Final Office Action mailed Sep. 24, 2014", 11 pgs.

(56) References Cited

OTHER PUBLICATIONS

"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Jan. 27, 2014 to Final Office Action mailed Oct. 25, 2013", 11 pgs.
"U.S. Appl. No. 12/912,411, Response filed Feb. 18, 2013 to Restriction Requirement mailed Oct. 17, 2012", 9 pgs.
"U.S. Appl. No. 12/912,411, Response filed Feb. 25, 2014 to Final Office Action mailed Oct. 25, 2013", 11 pgs.
"U.S. Appl. No. 12/912,411, Response filed Mar. 16, 2015 to Final Office Action mailed Jan. 14, 2015", 9 pgs.
"U.S. Appl. No. 12/912,411, Response filed Oct. 7, 2013 to Non Final Office Action mailed Jun. 7, 2013", 10 pgs.
"U.S. Appl. No. 12/912,411, Response filed Dec. 31, 2014 to Non Final Office Action mailed Sep. 24, 2014", 12 pgs.
"U.S. Appl. No. 12/912,411, Restriction Requirement mailed Oct. 17, 2012", 9 pgs.
"U.S. Appl. No. 13/070,110 Response filed Feb. 14, 2017 to Final Office Action mailed Sep. 14, 2016", 8 pgs.
"U.S. Appl. No. 13/070,110, Advisory Action mailed Mar. 3, 2017", 5 pgs.
"U.S. Appl. No. 13/070,110, Examiner Interview Summary mailed Jan. 16, 2018", 3 pgs.
"U.S. Appl. No. 13/070,110, Final Office Action mailed Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Jul. 21, 2017", 14 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.
"U.S. Appl. No. 13/070,110, Non Final Office Action mailed Dec. 21, 2012", 7 pgs.
"U.S. Appl. No. 13/070,110, Notice of Allowance mailed Mar. 26, 2018", 6 pgs.
"U.S. Appl. No. 13/070,110, Notice of Allowance mailed Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication mailed Aug. 15, 2018", 2 pgs.
"U.S. Appl. No. 13/070,110, Response filed Jan. 22, 2018 to Non Final Office Action mailed Jul. 21, 2017", 10 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Jun. 20, 2017 to Advisory Action mailed Mar. 3, 2017", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action mailed Apr. 3, 2015", 11 pgs.
"U.S. Appl. No. 13/070,110, Response filed Nov. 12, 2013 to Final Office Action mailed Jun. 12, 2013". 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 13/113,244, Final Office Action mailed Feb. 27, 2014", 8 pgs.
"U.S. Appl. No. 13/113,244, Non Final Office Action mailed Jul. 5, 2013", 6 pgs.
"U.S. Appl. No. 13/113,244, Non Final Office Action mailed Oct. 1, 2012", 7 pgs.
"U.S. Appl. No. 13/113,244, Notice of Allowance mailed Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement mailed Oct. 31, 2011", 10 pgs.
"U.S. Appl. No. 13/113,244, Response filed Feb. 20, 2013 to Non Final Office Action mailed Oct. 1, 2012", 12 pgs.
"U.S. Appl. No. 13/113,244, Response filed Jun. 13, 2014 to Final Office Action mailed Feb. 27, 2014", 6 pgs.
"U.S. Appl. No. 13/113,244, Response filed Oct. 31, 2013 to Non Final Office Action mailed Jul. 5, 2013", 12 pgs.
"U.S. Appl. No. 13/113,244, Restriction Requirement mailed Oct. 31, 2011", 8 pgs.
"U.S. Appl. No. 13/127,951, Advisory Action mailed Jul. 16, 2014", 3 pgs.
"U.S. Appl. No. 13/127,951, Final Office Action mailed Apr. 9, 2014", 23 pgs.
"U.S. Appl. No. 13/127,951, Non Final Office Action mailed Sep. 26, 2013", 18 pgs.
"U.S. Appl. No. 13/127,951, Notice of Allowance mailed Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication mailed Oct. 23, 2015", 2 pgs.
"U.S. Appl. No. 13/127,951, Response filed Mar. 18, 2014 to Non Final Office Action nailed Sep. 26, 2013", 14 pgs.
"U.S. Appl. No. 13/127,951, Response filed Jul. 7, 2014 to Final Office Action mailed Apr. 9, 2014", 10 pgs.
"U.S. Appl. No. 13/127,951, Response filed Aug. 30, 2013 to Restriction Requirement mailed Apr. 30, 2013", Aug. 30, 2013.
"U.S. Appl. No. 13/127,951, Response filed Oct. 9, 2014 to Advisory Action mailed Jul. 16, 2014", 10 pgs.
"U.S. Appl. No. 13/127,951, Restriction Requirement mailed Apr. 30, 2013", 15 pgs.
"U.S. Appl. No. 13/594,611, Final Office Action mailed Aug. 15, 2014", 7 pgs.
"U.S. Appl. No. 13/594,611, Non Final Office Action mailed Apr. 24, 2014", 9 pgs.
"U.S. Appl. No. 13/594,611, Notice of Allowance mailed Jan. 13, 2015", 7 pgs.
"U.S. Appl. No. 13/594,611, PTO Response to Rule 312 Communication mailed Apr. 16, 2015", 2 pgs.
"U.S. Appl. No. 13/594,611, Response filed Feb. 25, 2014 to Restriction Requirement mailed Jan. 27, 2014", 8 pgs.
"U.S. Appl. No. 13/594,611, Response filed Jul. 7, 2014 to Non Final Office Action mailed Apr. 24, 2014", 9 pgs.
"U.S. Appl. No. 13/594,611, Response filed Dec. 15, 2014 to Final Office Action mailed Aug. 15, 2014", 10 pgs.
"U.S. Appl. No. 13/594,611, Restriction Requirement mailed Jan. 27, 2014", 8 pgs.
"U.S. Appl. No. 14/332,121, Non Final Office Action mailed May 16, 2016", 9 pgs.
"U.S. Appl. No. 14/332,121, Notice of Allowance mailed Feb. 15, 2017", 10 pgs.
"U.S. Appl. No. 14/332,121, Notice of Allowance mailed Jun. 15, 2017", 8 pgs.
"U.S. Appl. No. 14/332,121, Notice of Allowance mailed Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement mailed Jul. 30, 2015", 9 pgs.
"U.S. Appl. No. 14/332,121, Response filed Sep. 7, 2017 to Notice of Allowability mailed Jun. 15, 2017", 8 pgs.
"U.S. Appl. No. 14/332,121, Response filed Oct. 11, 2016 to Non Final Office Action mailed May 16, 2016", 9 pgs.
"U.S. Appl. No. 14/332,121, Restriction Requirement mailed Jul. 30, 2015", 9 pgs.

(56) References Cited

OTHER PUBLICATIONS

"U.S. Appl. No. 14/332,121, Supplemental Amendment filed Jan. 23, 2017", 10 pgs.
"U.S. Appl. No. 14/528,997, Advisory Action mailed Aug. 9, 2017", 3 pgs.
"U.S. Appl. No. 14/528,997, Final Office Action mailed Feb. 10, 2017", 9 pgs.
"U.S. Appl. No. 14/528,997, Non Final Office Action mailed Jun. 16, 2016", 12 pgs.
"U.S. Appl. No. 14/528,997, Non Final Office Action mailed Jun. 29, 2018", 7 pgs.
"U.S. Appl. No. 14/528,997, Notice of Allowance mailed Mar. 8, 2019", 7 pgs.
"U.S. Appl. No. 14/528,997, PTO Response to Rule 312 Communication mailed Jun. 19, 2019", 2 pgs.
"U.S. Appl. No. 14/528,997, Response filed Mar. 16, 2016 to Restriction Requirement mailed Sep. 16, 2015", 11 pgs.
"U.S. Appl. No. 14/528,997, Response filed Jul. 27, 2017 to Final Office Action mailed Feb. 10, 2017", 11 pgs.
"U.S. Appl. No. 14/528,997, Response filed Oct. 10, 2016 to Non Final Office Action mailed Jun. 16, 2016", 12 pgs.
"U.S. Appl. No. 14/528,997, Response filed Nov. 16, 2018 to Non Final Office Action mailed Jun. 29, 2018", 11 pgs.
"U.S. Appl. No. 14/528,997, Restriction Requirement mailed Sep. 16, 2015", 8 pgs.
"U.S. Appl. No. 14/699,213, Advisory Action mailed Mar. 7, 2018", 3 pgs.
"U.S. Appl. No. 14/699,213, Final Office Action mailed Dec. 1, 2017", 11 pgs.
"U.S. Appl. No. 14/699,213, Non Final Office Action mailed Jun. 2, 2017", 12 pgs.
"U.S. Appl. No. 14/699,213, Non-Final Office Action mailed Jan. 11, 2019", 10 pgs.
"U.S. Appl. No. 14/699,213, Notice of Allowance mailed Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication mailed Nov. 19, 2019", 2 pgs.
"U.S. Appl. No. 14/699,213, Response filed Feb. 15, 2017 to Restriction Requirement mailed Aug. 15, 2016", 9 pgs.
"U.S. Appl. No. 14/699,213, Response filed Feb. 27, 2018 to Final Office Action mailed Dec. 1, 2017", 34 pgs.
"U.S. Appl. No. 14/699,213, Response filed Aug. 22, 2017 to Non Final Office Action mailed Jun. 2, 2017", 12 pgs.
"U.S. Appl. No. 14/699,213, Response filed Apr. 11, 2019 to Non-Final Office Action mailed Jan. 11, 2019", 13 pgs.
"U.S. Appl. No. 14/699,213, Restriction Requirement mailed Aug. 15, 2016", 10 pgs.
"U.S. Appl. No. 14/745,236, Advisory Action mailed Nov. 15, 2017", 2 pgs.
"U.S. Appl. No. 14/745,236, Final Office Action mailed Aug. 25, 2017", 16 pgs.
"U.S. Appl. No. 14/745,236, Non Final Office Action mailed Feb. 2, 2017", 14 pgs.
"U.S. Appl. No. 14/745,236, Notice of Allowability mailed Jul. 5, 2018", 4 pgs.
"U.S. Appl. No. 14/745,236, Notice of Allowance mailed Feb. 5, 2018", 9 pgs.
"U.S. Appl. No. 14/745,236, PTO Response to Rule 312 Communication mailed Jul. 10, 2018", 2 pgs.
"U.S. Appl. No. 14/745,236, Response filed May 2, 2017 to Non Final Office Action mailed Feb. 2, 2017", 10 pgs.
"U.S. Appl. No. 14/745,236, Response filed Nov. 6, 2017 to Final Office Action mailed Aug. 25, 2017", 12 pgs.
"U.S. Appl. No. 14/745,236, Response filed Dec. 14, 2017 to Final Office Action mailed Aug. 25, 2017", 12 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 14/816,807, Non Final Office Action mailed Oct. 3, 2017", 7 pgs.
"U.S. Appl. No. 14/816,807, Notice of Allowance mailed Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication mailed Jul. 6, 2018", 2 pgs.
"U.S. Appl. No. 14/816,807, Response filed Jan. 3, 2018 to Non Final Office Action mailed Oct. 3, 2017", 8 pgs.
"U.S. Appl. No. 14/816,807, Response filed May 1, 2017 to Restriction Requirement mailed Nov. 1, 2016", 9 pgs.
"U.S. Appl. No. 14/816,807, Restriction Requirement mailed Nov. 1, 2016", 8 pgs.
"U.S. Appl. No. 14/919,431, Preliminary Amendment filed Jan. 4, 2016", 8 pgs.
"U.S. Appl. No. 15/000,851, Non Final Office Action mailed Jan. 26, 2017", 15 pgs.
"U.S. Appl. No. 15/000,851, Notice of Allowance mailed Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action mailed Jan. 26, 2017", 16 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"U.S. Appl. No. 15/170,556, Final Office Action mailed Jul. 30, 2019", 6 pgs.
"U.S. Appl. No. 15/170,556, Non Final Office Action mailed Feb. 8, 2019", 11 pgs.
"U.S. Appl. No. 15/170,556, Non Final Office Action mailed Jul. 27, 2018", 10 pgs.
"U.S. Appl. No. 15/170,556, Notice of Allowability mailed Jan. 29, 2020", 4 pgs.
"U.S. Appl. No. 15/170,556, Notice of Allowance mailed Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement mailed Feb. 16, 2018", 8 pgs.
"U.S. Appl. No. 15/170,556, Response filed Oct. 29, 2018 to Non Final Office Action mailed Jul. 27, 2018", 9 pgs.
"U.S. Appl. No. 15/170,556, Response filed Nov. 18, 2019 to Final Office Action mailed Jul. 30, 2019", 8 pgs.
"U.S. Appl. No. 15/170,556, Response filed Apr. 15, 2019 to Non Final Office Action mailed Feb. 8, 2019", 9 pgs.
"U.S. Appl. No. 15/170,556, Restriction Requirement mailed Feb. 16, 2018", 7 pgs.
"U.S. Appl. No. 15/170,556. PTO Response to Rule 312 Communication mailed Apr. 3, 2020", 2 pgs.
"U.S. Appl. No. 15/203,581, Examiners Interview Summary mailed Sep. 11, 2017", 1 pg.
"U.S. Appl. No. 15/203,581, Notice of Allowance mailed Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication mailed Dec. 27, 2017", 2 pgs.
"U.S. Appl. No. 15/203,581, Response filed Aug. 15, 2017 to Restriction Requirement mailed Jun. 16, 2017", 8 pgs.
"U.S. Appl. No. 15/203,581, Restriction Requirement mailed Jun. 16, 2017", 8 pgs.
"U.S. Appl. No. 15/204,381, Advisory Action mailed Feb. 7, 2019", 3 pgs.
"U.S. Appl. No. 15/204,381, Advisory Action mailed Aug. 25, 2020", 3 pgs.

(56) References Cited

OTHER PUBLICATIONS

"U.S. Appl. No. 15/204,381, Final Office Action mailed Feb. 27, 2020", 21 pgs.
"U.S. Appl. No. 15/204,381, Final Office Action mailed Jul. 9, 2021", 14 pgs.
"U.S. Appl. No. 15/204,381, Final Office Action mailed Sep. 21, 2018", 10 pgs.
"U.S. Appl. No. 15/204,381, Non Final Office Action mailed Feb. 23, 2018", 10 pgs.
"U.S. Appl. No. 15/204,381, Non Final Office Action mailed Jun. 13, 2019", 23 pgs.
"U.S. Appl. No. 15/204,381, Non Final Office Action mailed Oct. 6, 2020", 15 pgs.
"U.S. Appl. No. 15/204,381, Preliminary Amendment filed Oct. 25, 2016", 74 pgs.
"U.S. Appl. No. 15/204,381, Response filed Jan. 2, 2019 to Final Office Action mailed Sep. 21, 2018", 6 pgs.
"U.S. Appl. No. 15/204,381, Response filed Jan. 19, 2018 to Restriction Requirement mailed Oct. 13, 2017", 6 pgs.
"U.S. Appl. No. 15/204,381, Response filed Apr. 6, 2021 to Non Final Office Action mailed Oct. 6, 2020", 12 pgs.
"U.S. Appl. No. 15/204,381, Response filed May 30, 2018 to Non Final Office Action mailed Feb. 23, 2018", 9 pgs.
"U.S. Appl. No. 15/204,381, Response filed Jul. 27, 2020 to Final Office Action mailed Feb. 27, 2020". 11 pgs.
"U.S. Appl. No. 15/204,381, Response filed Aug. 27, 2020 to Advisory Action mailed Aug. 25, 2020", 2 pgs.
"U.S. Appl. No. 15/204,381, Response Filed Nov. 14, 2019 to Non Final Office Action mailed Jun. 13, 2019", 9 pgs.
"U.S. Appl. No. 15/204,381, Response Filed Mar. 21, 2019 to Advisory Action mailed Feb. 7, 2019", 7 pgs.
"U.S. Appl. No. 15/204,381, Restriction Requirement mailed Oct. 13, 2017", 10 pgs.
"U.S. Appl. No. 15/227,147, Preliminary Amendment filed Oct. 10, 2016", 7 pgs.
"U.S. Appl. No. 15/227,147, Restriction Requirement mailed Jan. 19, 2017", 14 pgs.
"U.S. Appl. No. 15/247,006 Response filed Jun. 4, 2019 to Final Office Action mailed Feb. 4, 2019", 7 pgs.
"U.S. Appl. No. 15/247,006, Examiner Interview Summary mailed Nov. 27, 2017", 4 pgs.
"U.S. Appl. No. 15/247,006, Final Office Action mailed Feb. 4, 2019", 8 pgs.
"U.S. Appl. No. 15/247,006, Non Final Office Action mailed Apr. 20, 2018", 7 pgs.
"U.S. Appl. No. 15/247,006, Non Final Office Action mailed Sep. 8, 2017", 8 pgs.
"U.S. Appl. No. 15/247,006, Notice of Allowance mailed Jun. 24, 2019", 7 pgs.
"U.S. Appl. No. 15/247,006, Notice of Allowance mailed Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement mailed Mar. 17, 2017", 12 pgs.
"U.S. Appl. No. 15/247,006, Response filed Oct. 22, 2018 to Non Final Office Action mailed Apr. 20, 2018", 14 pgs.
"U.S. Appl. No. 15/247,006, Response filed Dec. 7, 2017 to Non Final Office Action mailed Sep. 8, 2017", 13 pgs.
"U.S. Appl. No. 15/247,006, Restriction Requirement mailed Mar. 17, 2017", 9 pgs.
"U.S. Appl. No. 15/292,595, Non Final Office Action mailed Sep. 25, 2017", 13 pgs.
"U.S. Appl. No. 15/292,595, Notice of Allowance mailed Feb. 28, 2018", 9 pgs.
"U.S. Appl. No. 15/292,595, Notice of Allowance mailed Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action mailed Sep. 25, 2017", 9 pgs.
"U.S. Appl. No. 15/436,245, Corrected Notice of Allowability mailed Nov. 10, 2021", 2 pgs.
"U.S. Appl. No. 15/436,245, Final Office Action mailed Mar. 24, 2021", 9 pgs.
"U.S. Appl. No. 15/436,245, Final Office Action mailed Nov. 18, 2019", 9 pgs.
"U.S. Appl. No. 15/436,245, Non Final Office Action mailed Apr. 19, 2019", 9 pgs.
"U.S. Appl. No. 15/436,245, Non Final Office Action mailed Sep. 4, 2020", 9 pgs.
"U.S. Appl. No. 15/436,245, Notice of Allowance mailed Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication mailed Oct. 27, 2021", 2 pgs.
"U.S. Appl. No. 15/436,245, Response filed Apr. 27, 2020 to Final Office Action mailed Nov. 18, 2019", 10 pgs.
"U.S. Appl. No. 15/436,245, Response filed Jun. 24, 2021 to Final Office Action mailed Mar. 24, 2021", 11 pgs.
"U.S. Appl. No. 15/436,245, Response filed Dec. 4, 2020 to Non Final Office Action mailed Sep. 4, 2020", 12 pgs.
"U.S. Appl. No. 15/436,245, Response filed Jul. 29, 2019 to Non-Final Office Action mailed Apr. 19, 2019", 11 pgs.
"U.S. Appl. No. 15/436,245, Restriction Requirement mailed Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action mailed Feb. 6, 2018", 8 pgs.
"U.S. Appl. No. 15/593,039, Notice of Allowance mailed Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication mailed Oct. 9, 2018", 2 pgs.
"U.S. Appl. No. 15/593,039, Response filed Apr. 30, 2018 to Non Final Office Action mailed Feb. 4, 2018", 8 pgs.
"U.S. Appl. No. 15/593,039, Response filed Dec. 18, 2017 to Restriction Requirement mailed Oct. 18, 2017", 8 pgs.
"U.S. Appl. No. 15/593,039, Restriction Requirement mailed Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance mailed Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement mailed Jan. 3, 2019", 6 pgs.
"U.S. Appl. No. 15/915,486 Supplemental Preliminary Amendment Filed Mar. 12, 2019", 5 pgs.
"U.S. Appl. No. 15/915,486, Advisory Action mailed Jun. 28, 2021", 7 pgs.
"U.S. Appl. No. 15/915,486, Advisory Action mailed Jul. 13, 2020", 3 pgs.
"U.S. Appl. No. 15/915,486, Final Office Action mailed Jan. 11, 2022", 9 pgs.
"U.S. Appl. No. 15/915,486, Final Office Action mailed Jan. 27, 2020", 8 pgs.
"U.S. Appl. No. 15/915,486, Final Office Action mailed Feb. 1, 2021", 8 pgs.
"U.S. Appl. No. 15/915,486, Non Final Office Action mailed Sep. 2, 2021", 8 pgs.
"U.S. Appl. No. 15/915,486, Non Final Office Action mailed Sep. 15, 2020", 10 pgs.
"U.S. Appl. No. 15/915,486, Non Final Office Action mailed Oct. 24, 2019", 10 pgs.

(56) References Cited

OTHER PUBLICATIONS

"U.S. Appl. No. 15/915,486, Response filed Jan. 3, 2020 to Non Final Office Action mailed Oct. 24, 2019", 8 pgs.
"U.S. Appl. No. 15/915,486, Response filed Jun. 1, 2021 to Final Office Action mailed Feb. 1, 2021", 10 pgs.
"U.S. Appl. No. 15/915,486, Response filed Jun. 23, 2020 to Final Office Action mailed Jan. 27, 2020", 7 pgs.
"U.S. Appl. No. 15/915,486, Response filed Jul. 27, 2021 to Advisory Action mailed Jun. 28, 2021", 10 pgs.
"U.S. Appl. No. 15/915,486, Response filed Nov. 30, 2021 to Non Final Office Action mailed Sep. 2, 2021", 6 pgs.
"U.S. Appl. No. 15/915,486, Response filed Dec. 21, 2020 to Non Final Office Action mailed Sep. 15, 2020", 7 pgs.
"U.S. Appl. No. 15/915,486, Restriction Requirement mailed Aug. 5, 2019", 9 pgs.
"U.S. Appl. No. 15/966,092, Interview Summary mailed Mar. 2, 2021", 2 pgs.
"U.S. Appl. No. 15/966,092, Non Final Office Action mailed Jun. 26, 2020", 22 pgs.
"U.S. Appl. No. 15/966,092, Notice of Allowance mailed Feb. 11, 2021", 5 pgs.
"U.S. Appl. No. 15/966,092, Response filed Oct. 26, 2020 to Non Final Office Action mailed Jun. 26, 2020", 9 pgs.
"U.S. Appl. No. 16/046,250, Non Final Office Action mailed Mar. 6, 2020", 10 pgs.
"U.S. Appl. No. 16/046,250, Notice of Allowance mailed Jun. 15, 2020", 9 pgs.
"U.S. Appl. No. 16/046,250, Response filed Jun. 3, 2020 to Non Final Office Action mailed Mar. 6, 2020", 10 pgs.
"U.S. Appl. No. 16/046,250, Response filed Oct. 25, 2019 to Restriction Requirement mailed Jul. 25, 2019", 9 pgs.
"U.S. Appl. No. 16/046,250, Restriction Requirement mailed Jul. 25, 2019", 7 pgs.
"U.S. Appl. No. 16/173,605 Preliminary Amendment Filed Nov. 18, 2019", 5 pgs.
"U.S. Appl. No. 16/173,605, Final Office Action mailed Jul. 27, 2020", 7 pgs.
"U.S. Appl. No. 16/173,605, Non Final Office Action mailed Mar. 13, 2020", 10 pgs.
"U.S. Appl. No. 16/173,605, Notice of Allowance mailed Jan. 13, 2021", 6 pgs.
"U.S. Appl. No. 16/173,605, Response filed Jul. 13, 2020 to Non Final Office Action mailed Mar. 13, 2020", 13 pgs.
"U.S. Appl. No. 16/173,605, Response filed Dec. 21, 2020 to Final Office Action mailed Jul. 27, 2020", 7 pgs.
"U.S. Appl. No. 16/545,761, Final Office Action mailed Oct. 20, 2021", 10 pgs.
"U.S. Appl. No. 16/545,761, Non Final Office Action mailed Feb. 11, 2021", 12 pgs.
"U.S. Appl. No. 16/545,761, Notice of Allowance mailed Mar. 9, 2022", 6 pgs.
"U.S. Appl. No. 16/545,761, Preliminary Amendment filed Feb. 7, 2020", 9 pgs.
"U.S. Appl. No. 16/545,761, PTO Response to Rule 312 Communication mailed May 13, 2022", 2 pgs.
"U.S. Appl. No. 16/545,761, Response filed Feb. 16, 2022 to Final Office Action mailed Oct. 20, 2021", 10 pgs.
"U.S. Appl. No. 16/545,761, Response filed Jun. 30, 2021 to Non Final Office Action mailed Feb. 11, 2021", 13 pgs.
"U.S. Appl. No. 16/547,262, Non Final Office Action mailed Mar. 31, 2021", 13 pgs.
"U.S. Appl. No. 16/547,262, Notice of Allowance mailed Jul. 22, 2021", 7 pgs.
"U.S. Appl. No. 16/547,262, Response filed Jun. 30, 2021 to Non Final Office Action mailed Mar. 31, 2021", 12 pgs.
"U.S. Appl. No. 16/547,262, Response filed Dec. 17, 2020 to Restriction Requirement mailed Jul. 17, 2020", 12 pgs.
"U.S. Appl. No. 16/547,262, Restriction Requirement mailed Jul. 17, 2020", 6 pgs.
"U.S. Appl. No. 16/694,748, Non Final Office Action mailed Nov. 9, 2021", 6 pgs.
"U.S. Appl. No. 16/694,748, Notice of Allowance mailed Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 22 to Non Final Office Action mailed Nov. 9, 2021", 7 pgs.
"U.S. Appl. No. 16/694,748, Response filed Jul. 27, 2021 to Restriction Requirement mailed Jan. 27, 2021", 8 pgs.
"U.S. Appl. No. 16/694,748, Restriction Requirement mailed Jan. 27, 2021", 9 pgs.
"U.S. Appl. No. 16/749,910, Notice of Allowance mailed Sep. 22, 2021", 10 pgs.
"U.S. Appl. No. 16/749,910, Response filed Jun. 17, 2021 to Restriction Requirement mailed Apr. 19, 2021", 11 pgs.
"U.S. Appl. No. 16/749,910, Restriction Requirement mailed Apr. 19, 2021", 9 pgs.
"U.S. Appl. No. 16/785,449, Final Office Action mailed Mar. 18, 2022", 12 pgs.
"U.S. Appl. No. 16/785,449, Non Final Office Action mailed Jul. 21, 2021", 9 pgs.
"U.S. Appl. No. 16/785,449, Non Final Office Action mailed Sep. 22, 2022", 13 pgs.
"U.S. Appl. No. 16/785,449, Response filed Jan. 20, 2023 to Non Final Office Action mailed Sep. 22, 2022", 8 pgs.
"U.S. Appl. No. 16/785,449, Response filed Jun. 27, 2022 to Final Office Action mailed Mar. 18, 2022", 7 pgs.
"U.S. Appl. No. 16/785,449, Response filed Jul. 2, 2021 to Restriction Requirement mailed Jun. 21, 2021", 6 pgs.
"U.S. Appl. No. 16/785,449, Response filed Dec. 17, 2021 to Non Final Office Action mailed Jul. 21, 2021", 8 pgs.
"U.S. Appl. No. 16/785,449, Restriction Requirement mailed Jun. 21, 2021", 8 pgs.
"U.S. Appl. No. 16/785,449, Final Office Action mailed Mar. 22, 2023", 16 pgs.
"U.S. Appl. No. 16/865,194, Notice of Allowance mailed Mar. 3, 2022", 9 pgs.
"U.S. Appl. No. 16/865,194, Response filed Dec. 20, 2021 to Restriction Requirement mailed Oct. 20, 2021", 11 pgs.
"U.S. Appl. No. 16/865,194, Restriction Requirement mailed Oct. 20, 2021", 7 pgs.
"U.S. Appl. No. 17/004,583, 312 Amendment filed Mar. 16, 2023", 7 pgs.
"U.S. Appl. No. 17/004,583, Advisory Action mailed Aug. 30, 2022", 2 pgs.
"U.S. Appl. No. 17/004,583, Final Office Action mailed Jun. 9, 2022", 6 pgs.
"U.S. Appl. No. 17/004,583, Non Final Office Action mailed Feb. 24, 2022", 5 pgs.
"U.S. Appl. No. 17/004,583, Non Final Office Action mailed Sep. 29, 2022", 8 pgs.
"U.S. Appl. No. 17/004,583, Notice of Allowability mailed Feb. 10, 2023", 4 pgs.
"U.S. Appl. No. 17/004,583, Notice of Allowance mailed Feb. 1, 2023", 10 pgs.
"U.S. Appl. No. 17/004,583, Notice of Allowance mailed May 15, 2023", 7 pgs.
"U.S. Appl. No. 17/004,583, Preliminary Amendment filed Dec. 21, 2020", 6 pgs.
"U.S. Appl. No. 17/004,583, PTO Response to Rule 312 Communication mailed Feb. 23, 2023", 4 pgs.
"U.S. Appl. No. 17/004,583, PTO Response to Rule 312 Communication mailed Apr. 6, 2023", 3 pgs.
"U.S. Appl. No. 17/004,583, Response filed Jan. 31, 2022 to Restriction Requirement mailed Nov. 24, 2021", 7 pgs.
"U.S. Appl. No. 17/004,583, Response filed May 24, 2022 to Non Final Office Action mailed Feb. 24, 2022", 9 pgs.
"U.S. Appl. No. 17/004,583, Response filed Aug. 9, 2022 to Final Office Action mailed Jun. 9, 2022", 9 pgs.
"U.S. Appl. No. 17/004,583, Response filed Sep. 8, 2022 to Advisory Action mailed Aug. 30, 2022", 15 pgs.

(56) References Cited

OTHER PUBLICATIONS

"U.S. Appl. No. 17/004,583, Response filed Dec. 29, 2022 to Non Final Office Action mailed Sep. 29, 2022", 8 pgs.
"U.S. Appl. No. 17/004,583, Restriction Requirement mailed Nov. 24, 2021", 10 pgs.
"U.S. Appl. No. 17/004,583, Supplemental Amendment filed Mar. 28, 2023", 6 pgs.
"U.S. Appl. No. 17/155,625, Advisory Action mailed Jan. 20, 2023", 3 pgs.
"U.S. Appl. No. 17/155,625, Final Office Action mailed Sep. 28, 2022", 18 pgs.
"U.S. Appl. No. 17/155,625, Non Final Office Action mailed May 26, 2022", 10 pgs.
"U.S. Appl. No. 17/155,625, Notice of Allowance mailed Apr. 12, 2023", 11 pgs.
"U.S. Appl. No. 17/155,625, Response filed Feb. 28, 2023 to Advisory Action mailed Jan. 20, 2023", 8 pgs.
"U.S. Appl. No. 17/155,625, Response filed May 2, 2022 to Restriction Requirement mailed Mar. 3, 2022", 7 pgs.
"U.S. Appl. No. 17/155,625, Response filed Aug. 29, 2022 to Non Final Office Action mailed May 26, 2022", 8 pgs.
"U.S. Appl. No. 17/155,625, Response filed Dec. 28, 2022 to Final Office Action mailed Sep. 28, 2022", 8 pgs.
"U.S. Appl. No. 17/155,625, Restriction Requirement mailed Mar. 3, 2022", 9 pgs.
"U.S. Appl. No. 17/212,836, Non Final Office Action mailed Feb. 16, 2023", 12 pgs.
"U.S. Appl. No. 17/212,836, Response filed Oct. 19, 2022 to Restriction Requirement mailed Aug. 19, 2022", 6 pgs.
"U.S. Appl. No. 17/212,836, Restriction Requirement mailed Aug. 19, 2022", 7 pgs.
"U.S. Appl. No. 17/229,001, Preliminary Amendment filed Apr. 26, 2021", 7 pgs.
"U.S. Appl. No. 17/352,845, Non Final Office Action mailed Dec. 16, 2022", 15 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"U.S. Appl. No. 14/528,997, Preliminary Amendment filed Dec. 8, 2014", 3 pgs.
"U.S. Appl. No. 14/919,431, Restriction Requirement mailed Feb. 3, 2016", 18 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Australian Application Serial No. 2004249133, First Examiner's Report mailed May 5, 2008", 4 pgs.
"Australian Application Serial No. 2004249133, Response filed Mar. 30, 2009 to First Examiner's Report mailed May 5, 2008", 30 pgs.
"Australian Application Serial No. 2004274860, Office Action mailed May 21, 2008", 2 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2008203186, First Examiner Report mailed Jan. 28, 2011", 2 pgs.
"Australian Application Serial No. 2008203186, Office Action Received mailed Sep. 16, 2010", 1 page.
"Australian Application Serial No. 2008203186, Response filed Mar. 28, 2011 to First Examiner Report mailed Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Response filed Jul. 4, 2016 to Subsequent Examiners Report mailed Feb. 1, 2016", 3 pgs.
"Australian Application Serial No. 2014202470, Response filed Jul. 20, 2016 to Subsequent Examiners Report mailed Jul. 19, 2016", 15 pgs.
"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb. 1, 2016", 2 pgs.
"Australian Application Serial No. 2014202470, Subsequent Examiners Report mailed Jul. 19, 2016", 3 pgs.
"Australian Application Serial No. 2014290203, First Examination Report mailed Oct. 10, 2019", 4 pgs.
"Australian Application Serial No. 2014290203, Response filed Mar. 13, 2020 to First Examination Report mailed Oct. 10, 2019", 16 pgs.
"Australian Application Serial No. 2014290203, Response filed Jun. 24, 2020 to Subsequent Examiners Report mailed Mar. 23, 2020", 16 pgs.
"Australian Application Serial No. 2014290203, Response filed Sep. 29, 2020 to Subsequent Examiners Report mailed Jul. 21, 2020", 25 pgs.
"Australian Application Serial No. 2014290203, Response filed Dec. 9, 2020 to Subsequent Examiners Report mailed Oct. 6, 2020", 14 pgs.
"Australian Application Serial No. 2014290203, Subsequent Examiners Report mailed Mar. 23, 2020", 6 pgs.
"Australian Application Serial No. 2014290203, Subsequent Examiners Report mailed Jul. 21, 2020", 5 pgs.
"Australian Application Serial No. 2014290203, Subsequent Examiners Report mailed Oct. 6, 2020", 4 pgs.
"Australian Application Serial No. 2017221444, First Examination Report mailed Jul. 8, 2020", 6 pgs.
"Australian Application Serial No. 2017221444, Fourth Examiners Report mailed Jun. 29, 2021" 3 pgs.
"Australian Application Serial No. 2017221444, Response filed Jan. 25, 2021 to Subsequent Examiners Report mailed Nov. 27, 2020", 18 pgs.
"Australian Application Serial No. 2017221444, Response filed Jun. 2, 2021 to Subsequent Examiners Report mailed Feb. 24, 2021", 20 pgs.
"Australian Application Serial No. 2017221444, Response filed Jul. 6, 2021 to Fourth Examiners Report mailed Jun. 29, 2021", 7 pgs.
"Australian Application Serial No. 2017221444, Response filed Nov. 13, 2020 to First Examination Report mailed Jul. 8, 2020", 13 pgs.
"Australian Application Serial No. 2017221444, Subsequent Examiners Report mailed Feb. 24, 2021", 4 pgs.
"Australian Application Serial No. 2017221444, Subsequent Examiners Report mailed Nov. 27, 2020", 4 pgs.
"Australian Application Serial No. 2021201844, First Examination Report filed Sep. 29, 2022", 3 pgs.
"Australian Application Serial No. 2021201844, Voluntary Amendment filed Dec. 6, 2021", 17 pgs.
"Australian Application Serial No. 2008203186, Subsequent Examiner Report mailed Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.

(56) References Cited

OTHER PUBLICATIONS

"Brazil Application Serial No. PI 0410702-0, Office Action mailed Oct. 6, 2020", (w/ English Translation), 9 pgs.
"Brazil Application Serial No. PI 0410702-0, Response filed Dec. 14, 2020 to Office Action mailed Oct. 6, 2020", (w/ English Translation of Claims), 42 pgs.
"Brazil Application Serial No. PI0307679-2, Office Action mailed May 16, 2017", 2 pgs.
"Brazil Application Serial No. PI0307679-2, Response filed Jul. 13, 2017 to Office Action mailed May 16, 2017", 9 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI 0410702-0, Office Action mailed Nov. 1, 2019", (w/ English Translation), 6 pgs.
"Brazilian Application Serial No. PI 0410702-0, Response filed Feb. 6, 2020 to Office Action mailed Nov. 1, 2019", (w/ English Translation of Claims), 92 pgs.
"Brazilian Application Serial No. PI0307679-2, Final Office Action mailed Jul. 7, 2020", w/o English Translation, 6 pgs.
"Brazilian Application Serial No. PI0307679-2, Office Action mailed May 13, 2019", (w/ English Translation), 17 pgs.
"Brazilian Application Serial No. PI0307679-2, Office Action mailed Oct. 3, 2019", (w/ English Translation), 6 pgs.
"Brazilian Application Serial No. PI0307679-2, Office Action mailed Dec. 20, 2016", 2 pgs.
"Brazilian Application Serial No. PI0307679-2, Response filed Feb. 1, 2017 to Office Action mailed Dec. 20, 2016", 6 pgs.
"Brazilian Application Serial No. P10307679-2, Response filed Aug. 16, 2019 to Office Action mailed May 13, 2019", (w/ English Translation of Claims), 29 pgs.
"Brazilian Application Serial No. PI0307679-2, Response filed Dec. 11, 2019 to Office Action mailed Oct. 3, 2019", w/ English Claims, 59 pgs.
"Brazilian Application Serial No. PI0410702-0, Office Action mailed Feb. 23, 2012", w/ English Translation, 4 pgs.
"Brazilian Application Serial No. PI0410702-0, Office Action mailed Apr. 1, 2020", (w/ English Summary), 6 pgs.
"Brazilian Application Serial No. PI0410702-0, Response filed May 7, 2012 to Office Action mailed Feb. 23, 2012", w/ English Claims, 11 pgs.
"Brazilian Application Serial No. PI0410702-0, Response filed Aug. 28, 2020 to Office Action mailed Apr. 1, 2020", (w/ English Translation of Claims), 86 pgs.
"Canadian Application Serial No. 11/509,249, Response filed May 16, 2011 to Office Action mailed Nov. 18, 2010", 15 pgs.
"Canadian Application Serial No. 2,406,180, Office Action mailed Sep. 9, 2008", 5 pgs.
"Canadian Application Serial No. 2,406,180, Office Action mailed Nov. 10, 2011", 3 pgs.
"Canadian Application Serial No. 2,406,180, Office Action mailed Nov. 23, 2009", 3 pgs.
"Canadian Application Serial No. 2,406,180, Office Action mailed Dec. 10, 2010", 2 Pgs.
"Canadian Application Serial No. 2,406,180, Response filed Jan. 26, 2009 to Official Action mailed Sep. 9, 2008", 22 pgs.
"Canadian Application Serial No. 2,406,180, Response filed May 7, 2012 to Office Action mailed Nov. 10, 2011", 11 pgs.
"Canadian Application Serial No. 2,406,180, Response filed May 21, 2010 to Office action mailed Nov. 23, 2009", 13 pgs.
"Canadian Application Serial No. 2,406,180, Response filed Jun. 14, 2011 to Office Action mailed Dec. 10, 2010", 10 pgs.
"Canadian Application Serial No. 2,406,180, Response mailed Jun. 10, 2011 to Office Action mailed Dec. 10, 2010", 10 pgs.
"Canadian Application Serial No. 2,492,097, Office Action mailed Jan. 10, 2012", 4 pgs.
"Canadian Application Serial No. 2,492,097, Office Action mailed Apr. 24, 2008", 3 pgs.
"Canadian Application Serial No. 2,492,097, Office Action mailed Jul. 31, 2009", 3 pgs.
"Canadian Application Serial No. 2,492,097, Response filed Jan. 29, 2010 to Office Action mailed Jul. 31, 2009", 13 pgs.
"Canadian Application Serial No. 2,492,097, Response filed May 2, 2012 to Office Action mailed Jan. 10, 2012", 12 pgs.
"Canadian Application Serial No. 2,492,097, Response filed Oct. 23, 2008 to Office Action mailed Apr. 24, 2008", 14 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action mailed Jun. 6, 2011", 2 pgs.
"Canadian Application Serial No. 2,522,081, Office Action mailed Aug. 30, 2010", 2 pgs.
"Canadian Application Serial No. 2,522,081, Office Action mailed Oct. 8, 2009", 6 pgs.
"Canadian Application Serial No. 2,522,081, Response filed Feb. 28, 2011 to Office Action mailed Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action mailed Jun. 6, 2011", 11 pgs.
"Canadian Application Serial No. 2,525,953, Amendment and Response filed Feb. 1, 2017 to Office Action mailed Aug. 1, 2016", 28 pgs.
"Canadian Application Serial No. 2,525,953, Non Final Office Action mailed Mar. 30, 2022", 4 pgs.
"Canadian Application Serial No. 2,525,553, Officee Action maiied Jan. 21, 2016", 6 pgs
"Canadian Application Serial No. 2,525,953, Office Action mailed Jan. 29, 2020", 4 pgs.
"Canadian Application Serial No. 2,525,953, Office Action mailed Apr. 28, 2021", 7 pgs.
"Canadian Application Serial No. 2,525,953, Office Action mailed Jul. 31, 2012", 4 pgs.
"Canadian Application Serial No. 2,525,953, Office Action mailed Aug. 1, 2016", 6 pgs.
"Canadian Application Serial No. 2,525,953, Office Action mailed Aug. 16, 2013", 3 pgs.
"Canadian Application Serial No. 2,525,953, Office Action mailed Nov. 3, 2017", 4 pgs.
"Canadian Application Serial No. 2,525,953, Office Action mailed Nov. 2, 2018", 5 pgs.
"Canadian Application Serial No. 2,525,953, Office Action mailed Nov. 6, 2014", 3 pgs.
"Canadian Application Serial No. 2,525,953, Office Action mailed Jun. 22, 2011", 4 pgs.
"Canadian Application Serial No. 2,525,953, Office Action received Jun. 22, 2011", 4 pgs.
"Canadian Application Serial No. 2,525,953, Response filed Jan. 31, 2013 to Office Action mailed Jul. 31, 2012", 11 pgs.
"Canadian Application Serial No. 2,525,953, Response filed Feb. 1, 2017 to Office Action mailed Aug. 1, 2016", 28 pgs.
"Canadian Application Serial No. 2,525,953, Response filed Feb. 14, 2014 to Office Action mailed Aug. 16, 2013", 16 pgs.
"Canadian Application Serial No. 2,525,953, Response filed Apr. 3, 2018 to Office Action mailed Oct. 3, 2017", 46 pgs.
"Canadian Application Serial No. 2,525,953, Response filed May 1, 2015 to Office Action mailed Nov. 6, 2014", 23 pgs.
"Canadian Application Serial No. 2,525,953, Response filed May 2, 2019 to Office Action mailed Nov. 2, 2018", 31 pgs.
"Canadian Application Serial No. 2,525,953, Response filed May 25, 2020 to Office Action mailed Jan. 29, 2020", 35 pgs.
"Canadian Application Serial No. 2,525,953, Response filed Jul. 11, 2016 to Office Action mailed Jan. 21, 2016", 21 pgs.
"Canadian Application Serial No. 2,525,953, Response filed Aug. 26, 2021 to Office Action mailed Apr. 28, 2021", 16 pgs.
"Canadian Application Serial No. 2,525,953, Response filed Dec. 22, 2011 to Office Action mailed Jun. 22, 2011", 17 pgs.
"Canadian Application Serial No. 2,647,985 , Response filed Sep. 30, 2013 to Office Action mailed May 15, 2013", 20 pgs.

(56) References Cited

OTHER PUBLICATIONS

"Canadian Application Serial No. 2,647,985, Office Action mailed May 15, 2013", 3 pgs.
"Canadian Application Serial No. 2,816,242, Office Action mailed Jun. 16, 2014", 3 pgs.
"Canadian Application Serial No. 2,816,242, Office Action mailed Jul. 12, 2017", 4 pgs.
"Canadian Application Serial No. 2,816,242, Office Action mailed Sep. 16, 2016", 4 pgs.
"Canadian Application Serial No. 2,816,242, Office Action mailed Oct. 5, 2015", 6 pgs.
"Canadian Application Serial No. 2,816,242, Response filed Jan. 3, 2018 to Office Action mailed Jul. 12, 2017", 13 pgs.
"Canadian Application Serial No. 2,816,242, Response filed Mar. 10, 2017 to Office Action mailed Sep. 16, 2016", 18 pgs.
"Canadian Application Serial No. 2,816,242, Response filed Apr. 5, 2016 to Office Action mailed Oct. 5, 2015", 13 pgs.
"Canadian Application Serial No. 2,816,242, Response filed Dec. 16, 2014 to Office Action mailed Jun. 16, 2014", 9 pgs.
"Canadian Application Serial No. 2492097, Office Action mailed Nov. 18, 2010", 4 pgs.
"Canadian Application Serial No. 3,014,435, Office Action mailed Oct. 26, 2021", 4 pgs.
"Canadian Application Serial No. 3,014,435, Office Action mailed Nov. 6, 2020", 5 pgs.
"Canadian Application Serial No. 3,014,435, Office Action mailed Nov. 13, 2019", 4 pgs.
"Canadian Application Serial No. 3,014,435, Response filed Feb. 25, 2022 to Office Action mailed Oct. 26, 2021", 15 pgs.
"Canadian Application Serial No. 3,014,435, Response filed Mar. 5, 2021 to Office Action mailed Nov. 6, 2020", 20 pgs.
"Canadian Application Serial No. 3,014,435, Response filed Mar. 13, 2020 to Office Action mailed Nov. 13, 2019", 18 pgs.
"Chinese Application Serial No. 202080048487.4, Voluntary Amendment filed Dec. 5, 2022", w/ English Claims, 33 pgs.
"Chinese Application Serial No. 03808356.6, Office Action mailed Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Reexamination Notice mailed Nov. 26, 2012", (w/ English Translation), 9 pgs.
"Chinese Application Serial No. 03808356.6, Response filed Mar. 11, 2013 to Office Action mailed Nov. 26, 2012", (w/ English Translation of Amended Claims), 9 pgs.
"Chinese Application Serial No. 03808356.6, Response filed Mar. 16, 2009 to Office Action mailed Sep. 5, 2008", (w/ English Translation of Claims), 8 pgs.
"Chinese Application Serial No. 03808356.6, Response filed Oct. 14, 2011 to Office Action mailed Jul. 1, 2011", (w/ English Translation of Amended Claims), 25 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton mailed May 6, 2010", (w/ English Translation of Claims), 26 pgs.
"Chinese Application Serial No. 200480021259.9, First Office Action issued on Aug. 24, 2007", (w/ English Translation), 9 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Reexamination Decision mailed Mar. 25, 2013", (w/ English Translation), 17 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action issued on Aug. 24, 2007", (w/ English Translation of Claims), 13 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200480022014, First Office Action mailed Aug. 24, 2007", w/English Translation, 6 pgs.
"Chinese Application Serial No. 200580046922.5, Office Action mailed Jul. 24, 2009", 12 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.
"Chinese Application Serial No. 200780020095.1, Office Action mailed Apr. 26, 2016", (w/ English Summary), 4 pgs.
"Chinese Application Serial No. 200780020095.1, Office Action mailed May 3, 2012", (w/ English Translation), 10 pgs.
"Chinese Application Serial No. 200780020095.1, Office Action mailed Nov. 2, 2016", (w/ English Translation), 11 pgs.
"Chinese Application Serial No. 200780020095.1, Response filed Jan. 6, 2017 to Office Action mailed Nov. 2, 2016", (w/ English Translation of Claims), 15 pgs.
"Chinese Application Serial No. 200780020095.1, Response filed Jun. 9, 2013 to Office Action mailed Jan. 29, 2013", (w/ English Translation of Claims), 10 pgs.
"Chinese Application Serial No. 200780020095.1, Response filed Jun. 23, 2015 to Office Action mailed Mar. 5, 2015", (w/ English Translation of Claims), 16 pgs.
"Chinese Application Serial No. 200780020095.1, Response filed Jun. 30, 2016 to Office Action mailed Apr. 26, 2016", (w/ English Translation of Claims), 22 pgs.
"Chinese Application Serial No. 200780020095.1, Response filed Sep. 17, 2012 to Office Action mailed May 3, 2012", (w/ English Translation of Claims), 17 pgs.
"Chinese Application Serial No. 200780020095.1, Response filed Nov. 5, 2013 to to Decision on Rejection mailed Jul. 22, 2013", (w/ English Translation of Claims), 12 pgs.
"Chinese Application Serial No. 200780020095.1, Response filed Nov. 8, 2011 to Office Action mailed Jun. 24, 2011", (w/ English Translation of Amended Claims), 20 pgs.
"Chinese Application Serial No. 201310400039.8, Notice of Reexamination mailed Aug. 26, 2016", (w/ English Translation), 7 pgs.
"Chinese Application Serial No. 201310400039.8, Office Action mailed Feb. 12, 2015", (w/ English Translation), 10 pgs.
"Chinese Application Serial No. 201310400039.8, Office Action mailed Feb. 15, 2016", (w/ English Translation), 12 pgs.
"Chinese Application Serial No. 201310400039.8, Office Action mailed Apr. 1, 2017", (English Translation), 10 pgs.
"Chinese Application Serial No. 201310400039.8, Office Action mailed Aug. 7, 2015", (w/ English Translation), 10 pgs.
"Chinese Application Serial No. 201310400039.8, Office Action mailed Aug. 21, 2014", (w/ English Translation), 13 pgs.

(56) References Cited

OTHER PUBLICATIONS

"Chinese Application Serial No. 201310400039.8, Office Action Response mailed Jun. 16, 2017", W / English Claims, 8 pgs.
"Chinese Application Serial No. 201310400039.8, Response filed Jan. 4, 2015 to Office Action mailed Aug. 21, 2014", (w/ English Translation of Claims), 10 pgs.
"Chinese Application Serial No. 201310400039.8, Response filed Apr. 27, 2015 to Office Action mailed Feb. 12, 2015", (w/ English Translation of Claims), 16 pgs.
"Chinese Application Serial No. 201310400039.8, Response filed Jun. 1, 2016 to Office Action mailed Feb. 15, 2016", (w/ English Translation of Claims), 9 pgs.
"Chinese Application Serial No. 201310400039.8, Response filed Oct. 10, 2016 to Notice of Reexamination mailed Aug. 26, 2016", (w/ English Translation of Claims), 12 pgs.
"Chinese Application Serial No. 201310400039.8, Response filed Oct. 20, 2015 to Office Action mailed Aug. 7, 2015", (w/ English Translation of Claims), 11 pgs.
"Chinese Application Serial No. 201310400039.8, Response filed Aug. 14, 2017 to Office Action Response mailed Jun. 16, 2017", W/ English Claims, 11 pgs.
"Chinese Application Serial No. 201310400039.8, Response filed Aug. 7, 2017 to Office Action Response mailed Jun. 16, 2017", W/ English Claims, 10 pgs.
"Chinese Application Serial No. 201780024821.0, Office Action mailed Jun. 15, 2022", (w/ English Translation), 6 pgs.
"Chinese Application Serial No. 201780024821.0, Office Action mailed Nov. 30, 2021", (w/ English Translation), 21 pgs.
"Chinese Application Serial No. 201780024821.0, Response filed Apr. 12, 2022 to Office Action mailed Nov. 30, 2021", (w/ English Translation of Claims), 17 pgs.
"Chinese Application Serial No. 201780024821.0, Response filed Aug. 30, 2022 to Office Action mailed Jun. 15, 2022", w/ English Claims, 18 pgs.
"Chinese Application Serial No. 201780024821.0, Response to Examiner Telephone Interview filed Sep. 26, 2022", w/ English Claims, 10 pgs.
"Chinese Application Serial No. 202080048487.4, Notification to Make Rectification mailed Jan. 18, 2022", w/o English Translation, 1 pg.
"Chinese Application Serial No. 202080048487.4, Notification to Make Rectification mailed May 26, 2022", w/o English translation, 1 pg.
"Chinese Application Serial No. 200480021259.9, Office Action mailed May 8, 2009", (w/ English Translation), 6 pgs.
"Confirmed Cases of Avian Influenza A(H5N1)", World Health Organization, (Jan. 28, 2004), 1 pg.
"Declaration of Anne Koch Ballard dated Oct. 6, 2011", 1 pg.
"Eurasian Application No. 200501890, Notice of Allowance mailed Jun. 23, 2009", 1 pg.
"Eurasian Application Serial No. 200501890, Office Action mailed Mar. 23, 2007", (w English Translation), 2 pgs.
"Eurasian Application Serial No. 200501890, Office Action mailed Sep. 4, 2008", (English Translation), 1 pg.
"Eurasian Application Serial No. 200501890, Office Action mailed Dec. 17, 2007", (w/ English Translation), 6 pgs.
"Eurasian Application Serial No. 200501890, Response filed Mar. 26, 2008 to Office Action mailed Dec. 17, 2007", (w/ English Translation of Claims), 15 pgs.
"Eurasian Application Serial No. 200501890, Response filed Jun. 14, 2007 to Office Action mailed Mar. 23, 2007", (w/ English Translation of Claims), 11 pgs.
"Eurasian Application Serial No. 200501890, Response filed Dec. 17, 2008 to Office Action mailed Sep. 4, 2008", (w/ English Translation of Claims), 14 pgs.
"Eurasian Application Serial No. 200701097,Office Action mailed Sep. 4, 2008", OAR-MISC, 2 pgs.
"Eurasion Application Serial No. 200701097, Office Action mailed Jun. 16, 2009", 3 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial 17709236.8 , Response filed Apr. 26, 2019 to Communication Pursuant to Rules 161(1) and 162 EPC mailed Oct. 19, 2018", 9 pgs.
"European Application Serial No. 03716017.3, Office Action mailed Aug. 23, 2012", 4 pgs.
"European Application Serial No. 01928486.8 Office Action mailed Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action mailed Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication mailed Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action mailed Oct. 1, 2009", 11 pgs.
"European Application Serial No. 02724994.5, Office Action mailed Mar. 27, 2009", 2 pgs.
"European Application Serial No. 03716017.3, Communication and Supplementary European Search Report mailed Jan. 2, 2008", 8 pgs.
"European Application Serial No. 03716017.3, Communication mailed May 23, 2006", 3 pgs.
"European Application Serial No. 03716017.3, Communication mailed Jul. 26, 2006", 2 pgs.
"European Application Serial No. 03716017.3, Communication mailed Oct. 20, 2008", 7 pgs.
"European Application Serial No. 03716017.3, Further Written Submissions filed Mar. 19, 2015", 45 pgs.
"European Application Serial No. 03716017.3, Office Action mailed Jul. 27, 2010", 4 pgs.
"European Application Serial No. 03716017.3, Response filed Feb. 4, 2011 to Office Action mailed Jul. 27, 2010", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) mailed Aug. 23, 2012", 19 pgs.
"European Application Serial No. 03716017.3, Response filed Mar. 24, 2015 to Office Action mailed Nov. 3, 2014", 38 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"European Application Serial No. 03716017.3, Response filed Sep. 28, 2015", 13 pgs.
"European Application Serial No. 03716017.3, Result of Consultation mailed Mar. 17, 2015", 5 pgs.
"European Application Serial No. 03716017.3, Summons to Attend Oral proceedings mailed Nov. 3, 2014", 5 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04750333.9, Response filed Nov. 17, 2009 to Communication mailed Jan. 22, 2009", 17 pgs.
"European Application Serial No. 04750333.9, Summons To Attend Oral Proceedings mailed Aug. 3, 2011", 13 pgs.

(56) References Cited

OTHER PUBLICATIONS

"European Application Serial No. 04776133.3, Communication mailed Mar. 30, 2006", 3 pgs.
"European Application Serial No. 04776133.3, Examination Notification Art. 94(3) mailed Jul. 28, 2015", 4 pgs.
"European Application Serial No. 04776133.3, Examination Notification Art. 94(3) mailed Nov. 25, 2013", 5 pgs.
"European Application Serial No. 04776133.3, Office Action mailed Jan. 5, 2010", 4 pgs.
"European Application Serial No. 04776133.3, Response filed Jan. 25, 2007 to Communication mailed Mar. 30, 2006", 20 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Jul. 15, 2010 to Office Action mailed Jan. 5, 2010", 9 pgs.
"European Application Serial No. 04776133.3, Response filed Sep. 18, 2015 to Examination Notification Art. 94(3) mailed Jul. 28, 2015", 47 pgs.
"European Application Serial No. 04809419.7, Communication mailed Apr. 3, 2007", 3 pgs.
"European Application Serial No. 04809419.7, Response filed Oct. 19, 2007 to Communication mailed Apr. 3, 2007", 20 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC mailed Apr. 4, 2018", 7 pgs.
"European Application Serial No. 10777154.5, Communication Pursuant to Article 94(3) EPC mailed Jun. 11, 2019", 3 pgs.
"European Application Serial No. 10777154.5, Communication Pursuant to Article 94(3) EPC mailed Oct. 12, 2017", 7 pgs.
"European Application Serial No. 10777154.5, Examination Notification Art. 94(3) mailed Oct. 6, 2014", 7 pgs.
"European Application Serial No. 10777154.5, Office Action mailed May 2, 2016", 6 pgs.
"European Application Serial No. 10777154.5, Office Action mailed Jul. 4, 2012", 2 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Jan. 14, 2013 to Office Action mailed Jul. 4, 2012", 12 pgs.
"European Application Serial No. 10777154.5, Response filed Feb. 21, 2018 to Communication Pursuant to Article 94(3) EPC mailed Oct. 12, 2017", 12 pgs.
"European Application Serial No. 10777154.5, Response filed Jul. 29, 2019 to Communication Pursuant to Article 94(3) EPC mailed Jun. 11, 2019", 57 pgs.
"European Application Serial No. 10777154.5, Response filed Sep. 7, 2018 to Communication Pursuant to Article 94(3) EPC mailed Apr. 4, 2018", 18 pgs.
"European Application Serial No. 10777154.5, Response filed Sep. 8, 2016 to Office Action mailed May 2, 2016", 69 pgs.
"European Application Serial No. 10777154.5, Summons to Attend Oral Proceedings mailed Jan. 7, 2019", 5 pgs.
"European Application Serial No. 12761841.1, Communication pursuant to Article 94(3) EPC mailed Dec. 23, 2016", 6 pgs.
"European Application Serial No. 12761841.1, Response filed Feb. 23, 2017 to Communication pursuant to Article 94(3) EPC mailed Dec. 23, 2016", 9 pgs.
"European Application Serial No. 12761841.1, Voluntary Amendment filed Dec. 1, 2014", 5 pgs.
"European Application Serial No. 14745060.5, Communication Pursuant to Article 94(3) EPC mailed Feb. 6, 2018", 5 pgs.
"European Application Serial No. 14745060.5, Communication Pursuant to Article 94(3) EPC mailed Mar. 12, 2020", 4 pgs.
"European Application Serial No. 14745060.5, Communication Pursuant to Article 94(3) EPC mailed Jul. 18, 2019", 5 pgs.
"European Application Serial No. 14745060.5, Communication Pursuant to Article 94(3) EPC mailed Sep. 15, 2021", 4 pgs.
"European Application Serial No. 14745060.5, Communication Pursuant to Article 94(3) EPC mailed Sep. 18, 2018", 4 pgs.
"European Application Serial No. 14745060.5, Communication Pursuant to Article 94(3) EPC mailed Nov. 9, 2020", 4 pgs.
"European Application Serial No. 14745060.5, Office Action mailed Feb. 23, 2016", 2 pgs.
"European Application Serial No. 14745060.5, Response filed Jan. 5, 2022 to Communication Pursuant to Article 94(3) EPC mailed Sep. 15, 2021", 78 pgs.
"European Application Serial No. 14745060.5, Response filed Jan. 28, 2020 to Communication Pursuant to Article 94(3) EPC mailed Jul. 18, 2019", 9 pgs.
"European Application Serial No. 14745060.5, Response filed Mar. 27, 2019 to Communication Pursuant to Article 94(3) EPC mailed Sep. 18, 2018", 13 pgs.
"European Application Serial No. 14745060.5, Response filed May 12, 2021 to Communication Pursuant to Article 94(3) EPC mailed Nov. 9, 2020", 12 pgs.
"European Application Serial No. 14745060.5, Response filed Jun. 15, 2018 to Communication Pursuant to Article 94(3) EPC mailed Feb. 6, 2018", 14 pgs.
"European Application Serial No. 14745060.5, Response filed Jul. 17, 2020 to Communication Pursuant to Article 94(3) EPC mailed Mar. 12, 2020", 52 pgs.
"European Application Serial No. 14745060.5, Response filed Dec. 22, 2016 to Communication pursuant to Rules 161(1) and 162 EPC mailed Feb. 23, 2016", 6 pgs.
"European Application Serial No. 15197386.4, Communication Pursuant to Article 94(3) EPC mailed Feb. 21, 2018", 5 pgs.
"European Application Serial No. 15197386.4, Communication Pursuant to Article 94(3) EPC mailed Apr. 21, 2017", 5 pgs.
"European Application Serial No. 15197386.4, Communication Pursuant to Article 94(3) EPC mailed Jun. 19, 2019", 4 pgs.
"European Application Serial No. 15197386.4, extended European Search Report mailed Feb. 26, 2016". 11 pgs.
"European Application Serial No. 15197386.4, Response filed Jul. 3, 18 to Communication Pursuant to Article 94(3) EPC mailed Feb. 21, 2018", 7 pgs.
"European Application Serial No. 15197386.4, Response filed Aug. 27, 2019 to Communication Pursuant to Article 94(3) EPC mailed Jun. 19, 2019", 61 pgs.
"European Application Serial No. 15197386.4, Response filed Oct. 20, 2016 to Extended European Search Report mailed Feb. 26, 2016", 4 pgs.
"European Application Serial No. 15197386.4, Response filed Oct. 31, 2017 to Communication Pursuant to Article 94(3) EPC mailed Apr. 21, 2017", 5 pgs.
"European Application Serial No. 16778485.9, Communication Pursuant to Article 94(3) EPC mailed Feb. 18, 2022", 4 pgs.
"European Application Serial No. 16778485.9, Communication Pursuant to Article 94(3) EPC mailed May 25, 2020", 5 pgs.
"European Application Serial No. 16778485.9, Communication Pursuant to Article 94(3) EPC mailed Aug. 22, 2019", 5 pgs.
"European Application Serial No. 16778485.9, Office Action mailed Apr. 30, 2018", 3 pgs.
"European Application Serial No. 16778485.9, Response filed Aug. 9, 2022 to Communication Pursuant to Article 94(3) EPC mailed Feb. 18, 2022", 14 pgs.

(56) References Cited

OTHER PUBLICATIONS

"European Application Serial No. 16778485.9, Response filed Oct. 5, 2020 to Communication Pursuant to Article 94(3) EPC mailed May 25, 2020", 14 pgs.
"European Application Serial No. 16778485.9, Response filed Nov. 8, 2018 to Office Action mailed Apr. 30, 2018", 18 pgs.
"European Application Serial No. 16778485.9, Response filed Dec. 19, 2019 to Communication Pursuant to Article 94(3) EPC mailed Aug. 22, 2019", 20 pgs.
"European Application Serial No. 17709236.8, Communication Pursuant to Article 94(3) EPC mailed Jun. 8, 2022", 6 pgs.
"European Application Serial No. 17709236.8, Communication Pursuant to Article 94(3) EPC mailed Jul. 6, 2021", 10 pgs.
"European Application Serial No. 17709236.8, Response filed Jan. 17, 2022 to Communication Pursuant to Article 94(3) EPC mailed Jul. 6, 2021", 13 pgs.
"European Application Serial No. 17709236.8, Response filed Oct. 11, 2022 to Communication Pursuant to Article 94(3) EPC mailed Jun. 8, 2022", 65 pgs.
"European Application Serial No. 19778696.5, Response to Communication persuant to Rules 161 and 162 filed Oct. 15, 2021", 39 pgs.
"European Application Serial No. 20714015.3, Response to Communication persuant to Rules 161 and 162 filed Apr. 7, 2022", 10 pgs.
"European Application Serial No. 20731609.2, Response to Communication persuant to Rules 161 and 162 filed Mar. 16, 2022", 17 pgs.
"European Application Serial No. 20768781.5, Response to Communication pursuant to Rules 161 and 162 filed Oct. 17, 2022", 17 pgs.
"Evaluation of Medicines for human Use", EMEA/CPMP/BWP/2289/01, London The European Agency for the Evaluation of Medicinal Products, Committee for Proprietary Medicinal Products (CPMP), (Feb. 20, 2003), 14.
"Fluzone Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007 × Texas/1/1977)(H1N1))], (2012), 2 pgs.
"Gen Bank Accession JX414012", Influenza A virus (A/reassortant/IVR-148(Brisbane/59/2007 × Texas/1/1977)(H1 N1)) segment 7 matrix protein 2 (M2) and matrix protein 1 (M1) genes, complete cds, (2012), 2 pgs.
"Gen Bank Accessions QHU79173", surface glycoprotein [Severe acute respiratory syndrome coronavirus 2], (Mar. 17, 2020), 3 pgs.
"Genbank", CY002484.1, (2005), 2 pgs.
"Genbank Accession # AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam. [online]. [retrieved on Dec. 5, 2004]. Retrieved from the Internet: <URL: http://www.abcam.com/index.html?datasheet=6556>, (2004), 5 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"https://www.abcam.com/gfp-antibody-ab6556", [online]. [accessed on Dec. 5, 2004]. Retrieved from the Internet: http://www.abcam.com/index.html?datasheet=6556, (Dec. 5, 2004), 5 pgs.
"Indian Application Serial No. 02082/KOLNP/2005, Examination Report mailed Mar. 17, 2008", 1 pg.
"Indian Application Serial No. 02082/KOLNP/2005, Examination Report mailed Dec. 28, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 10, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 1026/KOLNP/2009, First Examiner Report mailed Mar. 13, 2014", 2 pgs.
"Indian Application Serial No. 2272/KOLNP/2005, First Examination Report mailed Mar. 17, 2008", 10 pgs.
"Indian Application Serial No. 2272/KOLNP/2005, Response filed Mar. 16, 2009 to Subsequent Examination Report mailed Mar. 6, 2009", 12 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009", 1 pg.
"Indian Application Serial No. 2388/KOLNP/2005, First Examination Report mailed Mar. 28, 2007", 10 pgs.
"Influenza B/Ann Arbor/1/66 (cold-adapted) nonstructural protein (seg 8) RNA, complete cds", GenBank Accession M20224, (Aug. 2, 1993), 2 pgs.
"Influenza B/lee/40, neuraminidase & nb (seg 6) rna", Database EM_VI E.B.I. Hinxton U.K., (Jun. 13, 1985), 10 pgs.
"Influenza virus A/CHR/ 157/83 genomic RNA for haemagglutinin", (2012), 2 pgs.
"International Application No. PCT/US2004/016680, International Search Report", (Feb. 2, 2005), 7 pgs.
"International Application Serial No. PCT/US2021/033365, International Search Report mailed Sep. 24, 2021", 6 pgs.
"International Application Serial No. PCT/US2021/033365, Written Opinion mailed Sep. 24, 2021", 6 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report mailed Oct. 15, 2002", 13 pgs.
"International Application Serial No. PCT/US01/11963, International Search Report mailed May 7, 2002", 5 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US02/05455, International Preliminary Examination Report dated Aug. 17, 2004", 4 pgs.
"International Application Serial No. PCT/US02/05455, International Search Report mailed Mar. 25, 2003", 3 pgs.
"International Application Serial No. PCT/US03/04233, International Search Report mailed Dec. 16, 2005", 7 pgs.
"International Application Serial No. PCT/US2004/012050, International Search Report mailed Feb. 2, 2005", 8 pgs.
"International Application Serial No. PCT/US2004/012050, International Search Report mailed Feb. 2, 2005", 8 pgs.
"International Application Serial No. PCT/US2004/012050, Written Opinion mailed Feb. 2, 2005", 12 pgs.
"International Application Serial No. PCT/US2004/016649, International Preliminary Report on Patentability mailed Dec. 15, 2005", 7 pgs.
"International Application Serial No. PCT/US2004/016649, International Search Report mailed Apr. 18, 2005", 6 pgs.
"International Application Serial No. PCT/US2004/016680, International Preliminary Report on Patentability mailed Dec. 15, 2005", 11 pgs.
"International Application Serial No. PCT/US2005/041991, International Search Report mailed Jun. 4, 2007", 5 pgs.
"International Application Serial No. PCT/US2005/041991, Written Opinion mailed Jun. 4, 2007", 6 pgs.

(56) References Cited

OTHER PUBLICATIONS

"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.
"International Application Serial No. PCT/US2007/013407, International Search Report mailed Oct. 24, 2008", 10 pgs.
"International Application Serial No. PCT/US2007/013407, Written Opinion mailed Oct. 24, 2008", 14 pgs.
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"International Application Serial No. PCT/US2008/005641, International Preliminary Report on Patentability dated Nov. 10, 2009", 9 pgs.
"International Application Serial No. PCT/US2008/005641, International Search Report mailed Feb. 4, 2009", 6 pgs.
"International Application Serial No. PCT/US2008/005641, Written Opinion mailed Feb. 4, 2009", 8 pgs.
"International Application Serial No. PCT/US2008/007417, International Search Report mailed Jan. 30, 2009", 20 pgs.
"International Application Serial No. PCT/US2008/007417, Written Opinion mailed Jan. 30, 2009", 10 pgs.
"International Application Serial No. PCT/US2008/007582, International Preliminary Report on Patentability mailed Jan. 7, 2010", 9 pgs.
"International Application Serial No. PCT/US2008/007582, International Search Report and Written Opinion mailed Feb. 18, 2009", 16 pgs.
"International Application Serial No. PCT/US2009/000056, International Search Report mailed Feb. 9, 2010", 3 pgs.
"International Application Serial No. PCT/US2009/000056, Written Opinion mailed Feb. 9, 2010". 5 pgs.
"International Application Serial No. PCT/US2009/006019, International Preliminary Report on Patentability mailed May 19, 2011", 8 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 7 Pgs.
"International Application Serial No. PCT/US2009/006019, Written Opinion mailed Jun. 10, 2010", 6 pgs.
"International Application Serial No. PCT/US2010/054128, Preliminary Report on Patentability mailed May 10, 2012", 10 pgs.
"International Application Serial No. PCT/US2010/054128, Search Report mailed Feb. 23, 2011", 6 pgs.
"International Application Serial No. PCT/US2010/054128, Written Opinion mailed Feb. 23, 2011", 8 pgs.
"International Application Serial No. PCT/US2012/052368, International Preliminary Report on Patentability mailed Mar. 13, 2014", 8 pgs.
"International Application Serial No. PCT/US2012/052368, International Search Report mailed Dec. 3, 2012", 4 pgs.
"International Application Serial No. PCT/US2012/052368, Written Opinion mailed Dec. 3, 2012", 6 pgs.
"International Application Serial No. PCT/US2014/046731, International Preliminary Report on Patentability mailed Jan. 28, 2016", 12 pgs.
"International Application Serial No. PCT/US2014/046731, International Search Report mailed Nov. 25, 2014", 9 pgs.
"International Application Serial No. PCT/US2014/046731, Written Opinion mailed Nov. 25, 2014", 10 pgs.
"International Application Serial No. PCT/US2015/036803, International Preliminary Report on Patentability mailed Dec. 29, 2016", 10 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Preliminary Report on Patentability mailed Jan. 18, 2018", 10 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"International Application Serial No. PCT/US2016/048691, International Preliminary Report on Patentability mailed Mar. 15, 2018", 7 pgs.
"International Application Serial No. PCT/US2016/048691, International Search Report mailed Nov. 22, 2016", 7 pgs.
"International Application Serial No. PCT/US2016/048691, Written Opinion mailed Nov. 22, 2016", 6 pgs.
"International Application Serial No. PCT/US2017/018443, International Preliminary Report on Patentability mailed Aug. 30, 2018", 11 pgs.
"International Application Serial No. PCT/US2017/018443, International Search Report mailed May 22, 2017", 9 pgs.
"International Application Serial No. PCT/US2017/018443, Written Opinion mailed May 22, 2017", 9 pgs.
"International Application Serial No. PCT/US2019/037084, International Preliminary Report on Patentability mailed Dec. 24, 2020", 12 pgs.
"International Application Serial No. PCT/US2019/037084, International Search Report mailed Nov. 14, 2019", 10 pgs.
"International Application Serial No. PCT/US2019/037084, Invitation to Pay Add'l Fees and Partial Search Report mailed Sep. 24, 2019", 10 pgs.
"International Application Serial No. PCT/US2019/037084, Written Opinion mailed Nov. 14, 2019", 10 pgs.
"International Application Serial No. PCT/US2019/045476, International Preliminary Report on Patentability mailed Feb. 18, 2021", 13 pgs.
"International Application Serial No. PCT/US2019/045476, International Search Report mailed Feb. 11, 2020", 8 pgs.
"International Application Serial No. PCT/US2019/045476, Invitation to Pay Additional Fees mailed Dec. 17, 2019", 14 pgs.
"International Application Serial No. PCT/US2019/045476, Written Opinion mailed Feb. 11, 2020", 13 pgs.
"International Application Serial No. PCT/US2019/047263, International Preliminary Report on Patentability mailed Mar. 4, 2021", 8 pgs.
"International Application Serial No. PCT/US2019/047263, International Search Report mailed Dec. 20, 2019", 5 pgs.
"International Application Serial No. PCT/US2019/047263, Written Opinion mailed Dec. 20, 2019", 6 pgs.
"International Application Serial No. PCT/US2020/014659, International Preliminary Report on Patentability mailed Aug. 5, 2021", 12 pgs.
"International Application Serial No. PCT/US2020/014659, International Search Report mailed Nov. 6, 2020", 7 pgs.
"International Application Serial No. PCT/US2020/014659, Invitation to Pay Additional Fees mailed Sep. 16, 2020", 11 pgs.
"International Application Serial No. PCT/US2020/014659, Written Opinion mailed Nov. 6, 2020", 10 pgs.
"International Application Serial No. PCT/US2020/017342, International Preliminary Report on Patentability mailed Aug. 19, 2021", 8 pgs.
"International Application Serial No. PCT/US2020/017342, International Search Report mailed Jun. 26, 2020", 6 pgs.
"International Application Serial No. PCT/US2020/017342, Written Opinion mailed Jun. 26, 2020", 6 pgs.
"International Application Serial No. PCT/US2020/031176, International Preliminary Report on Patentability mailed Nov. 11, 2021", 9 pgs.
"International Application Serial No. PCT/US2020/031176, International Search Report mailed Jul. 22, 2020", 6 pgs.

(56) References Cited

OTHER PUBLICATIONS

"International Application Serial No. PCT/US2020/031176, Written Opinion mailed Jul. 22, 2020", 7 pgs.
"International Application Serial No. PCT/US2020/048130, International Preliminary Report on Patentability mailed Mar. 10, 2022", 11 pgs.
"International Application Serial No. PCT/US2020/048130, International Search Report mailed Apr. 20, 2021", 9 pgs.
"International Application Serial No. PCT/US2020/048130, Invitation to Pay Additional Fees mailed Jan. 13, 2021", 7 pgs.
"International Application Serial No. PCT/US2020/048130, Written Opinion mailed Apr. 20, 2021", 9 pgs.
"International Application Serial No. PCT/US2021/014586, International Preliminary Report on Patentability mailed Aug. 4, 2022", 10 pgs.
"International Application Serial No. PCT/US2021/014586, International Search Report mailed May 20, 2021", 7 pgs.
"International Application Serial No. PCT/US2021/014586, Written Opinion mailed May 20, 2021", 8 pgs.
"International Application Serial No. PCT/US2021/024200, International Preliminary Report on Patentability mailed Oct. 6, 2022", 8 pgs.
"International Application Serial No. PCT/US2021/024200, International Search Report mailed Jul. 16, 2021", 6 pgs.
"International Application Serial No. PCT/US2021/024200, Written Opinion mailed Jul. 16, 2021", 6 pgs.
"International Application Serial No. PCT/US2021/033365, International Preliminary Report on Patentability mailed Dec. 8, 2022", 8 pgs.
"Israel Application Serial No. 163,546, Office Action mailed Nov. 12, 2009", w/English Translation, 1 pg.
"Israel Application Serial No. 163,546, Office Action mailed Dec. 26, 2007", w/English Translation, 1 pg.
"Israel Application Serial No. 163,546, Response filed May 9, 2008 to Office Action mailed Dec. 26, 2007", w/English Translation, 2 pgs.
"Israel Application Serial No. 163,546, Response filed Jun. 8, 2010 to Office Action mailed Nov. 12, 2009", w/English Claims, 3 pgs.
"Israel Application Serial No. 163,546, Response filed Aug. 16, 2009 to Substantive Examination Report mailed Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report mailed Jul. 28, 2008", w/English Claims, 13 pgs.
"Israel Application Serial No. 163546, Office Action mailed Jun. 8, 2010", w/English Translation, 2 pgs.
"Israel Application Serial No. 183026, Office Action mailed Feb. 9, 2009", w/English Translation, 2 pgs.
"Israel Application Serial No. 238584, Office Action mailed Jul. 24, 2017", w/English Translation, 2 pgs.
"Israel Application Serial No. 238584, Response filed Nov. 21, 2017 to Office Action mailed Jul. 24, 2017", W/English Translation, 2 pgs.
"Israeli Application Serial No. 171831, Notification of Defects mailed Nov. 10, 2008", w/English Translation, 10 pgs.
"Israeli Application Serial No. 163,546, First Examination Report mailed Jul. 28, 2008", (English Translation), 2 pgs.
"Israeli Application Serial No. 163,546, Substantive Examination Report mailed Feb. 23, 2009", w/English Translation, 3 pgs.
"Israeli Application Serial No. 171372, Office Action mailed Feb. 21, 2010", w/English Translation, 2 pgs.
"Israeli Application Serial No. 171372, Office Action mailed Nov. 6, 2008", (Translation), 12 pgs.
"Israeli Application Serial No. 171372, Response filed Nov. 18, 2010 to Office Action mailed Feb. 21, 2010", w/English Translation, 19 pgs.
"Israeli Application Serial No. 171831, Office Action mailed Feb. 21, 2010", w/English Translation, 2 pgs.
"Israeli Application Serial No. 171831, Office Action mailed Apr. 18, 2012", (English Translation), 2 pgs.
"Israeli Application Serial No. 171831, Response filed Jan. 20, 2011 to Office Action mailed Feb. 21, 2010", w/English Translation, 18 pgs.
"Israeli Application Serial No. 171831, Response filed Jun. 24, 2009 to Notification of Defects mailed Nov. 10, 2008", w/English Claims, 10 pgs.
"Israeli Application Serial No. 171831, Response filed Nov. 6, 2012 to Office Action mailed Apr. 18, 2012", w/English Claims, 54 pgs.
"Israeli Application Serial No. 211324, Office Action mailed Sep. 18, 2014", w/English Translation, 5 pgs.
"Israeli Application Serial No. 211324, Office Action mailed Oct. 18, 2015", w/English Translation, 4 pgs.
"Israeli Application Serial No. 211324, Response filed Feb. 16, 2016 to Office Action mailed Oct. 18, 2015", w/English Claims, 4 pgs.
"Israeli Application Serial No. 211324, Response filed Mar. 31, 2015 to Office Action mailed Sep. 8, 2014", w/English Translation, 21 pgs.
"Israeli Application Serial No. 238584, Notification of Defects in Patent Application mailed Jul. 21, 2019", (w/ English Translation), 5 pgs.
"Israeli Application Serial No. 238584, Office Action mailed Apr. 14, 2016", (English Translation), 3 pgs.
"Israeli Application Serial No. 238584, Office Action mailed Aug. 23, 2018", (w/ English Translation), 6 pgs.
"Israeli Application Serial No. 238584, Response filed Aug. 3, 2016 to Office Action mailed Apr. 14, 2016", (English Translation of Claims), 19 pgs.
"Israeli Application Serial No. 238584, Response filed Nov. 21, 2017 to Office Action mailed Jul. 24, 2017", (Translation), 2 pgs.
"Israeli Application Serial No. 238584, Response filed Nov. 21, 2019 to Notification of Defects in Patent Application mailed Jul. 21, 2019", (w/ English Translation of Claims), 6 pgs.
"Israeli Application Serial No. 238584, Response Filed Dec. 10, 2018 to Office Action mailed Aug. 23, 2018", (w/ English Translation of Claims), 10 pgs.
"Israeli Application Serial No. 171372,Office Action mailed Feb. 20, 2011", (Translation), 2 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2022-544779, Voluntary Amendment filed Sep. 9, 2022", w/ English Claims, 8 pgs.
"Japanese Application Serial No. 2001-576868, Office Action mailed Nov. 2, 2010", w/ English Translation), 10 pgs.
"Japanese Application Serial No. 2001-576868, Response filed Dec. 1, 2011 to Office Action mailed May 3, 2011", (w/ English Translation of Amended Claims), 37 pgs.
"Japanese Application Serial No. 2003-315106, Amended Claims filed Oct. 15, 2009 in Response to Office Action malled Jun. 24, 2009", (English Translation), 6 pgs.
"Japanese Application Serial No. 2003-315106, Notice of Allowance mailed Jan. 5, 2010", (w/ English Translation), 5 pgs.
"Japanese Application Serial No. 2003-315106, Office Action mailed Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance mailed Nov. 30, 2009", w/out English Translation, 3 pgs.
"Japanese Application Serial No. 2003-568038, Office Action mailed May 15, 2009", (w/ English Translation), 7 pgs.
"Japanese Application Serial No. 2003-568038, Office Action mailed Jul. 10, 2008", (w/ English Translation), 11 pgs.
"Japanese Application Serial No. 2003-568038, Office Action mailed Jul. 21, 2005", w/out English Translation, 3 pgs.
"Japanese Application Serial No. 2003-568038, Request for Examination filed Aug. 19, 2005 in Response to Official Action mailed Jul. 21, 2005", (w/ Partial English Translation of Specification), 8 pgs.

(56) References Cited

OTHER PUBLICATIONS

"Japanese Application Serial No. 2003-568038, Response filed Sep. 14, 2009 to Office Action mailed May 15, 2009", (w/ English Translation of Amended Claims), 10 pgs.
"Japanese Application Serial No. 2003-568038, Response filed Dec. 10, 2008 to Office Action mailed Jul. 10, 2008", (w/ English Translation of Amended Claims), 15 pgs.
"Japanese Application Serial No. 2006-513125, Office Action mailed Mar. 9, 2010", (English Translation), 11 pgs.
"Japanese Application Serial No. 2006-513125, Response filed Aug. 30, 2010 to Office Action mailed Mar. 9, 2010", (w/ English Translation of Amended Claims), 60 pgs.
"Japanese Application Serial No. 2006-533439, Decision of Final Rejection mailed Aug. 14, 2012", (w/ English Translation), 5 pgs.
"Japanese Application Serial No. 2006-533439, Office Action mailed Mar. 9, 2010", (w/ English Translations), 20 pgs.
"Japanese Application Serial No. 2006-533439, Office Action mailed Mar. 27, 2012", w/ English Translation, 8 pgs.
"Japanese Application Serial No. 2006-533439, Response filed May 21, 2012 to Office Action mailed Mar. 27, 2012", (w/ English Translation of Amended Claims), 19 pgs.
"Japanese Application Serial No. 2006-533439, Response filed Aug. 3, 2011 to Office Action mailed Feb. 15, 2011", (w/ English Translation of Amended Claims), 18 pgs.
"Japanese Application Serial No. 2006-533439,Office Action mailed Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2008-315106, Office Action mailed Jun. 24, 2009", (w/ English Translation), 10 pgs.
"Japanese Application Serial No. 2008-315106, Response filed Oct. 15, 2009 to Office Action mailed Jun. 24, 2009", w/English Translation, 103 pgs.
"Japanese Application Serial No. 2008-315106, Response filed Oct. 15, 2009 to Office Action mailed Jun. 24, 2009", (w/ English Translation of Amended Claims), 103 pgs.
"Japanese Application Serial No. 2008-315106, Response filed Dec. 3, 2009 to Office Action mailed Jun. 24, 2009", (w/ English Translation of Claims), 9 pgs.
"Japanese Application Serial No. 2009-238781, Office Action mailed Oct. 11, 2011", (w/ English Translation), 3 pgs.
"Japanese Application Serial No. 2009-502945, Examiners Decision of Final Refusal mailed Nov. 12, 2013", (w/ English Translation), 8 pgs.
"Japanese Application Serial No. 2009-502945, Office Action mailed Oct. 23, 2012", (w/ English Translation), 16 pgs.
"Japanese Application Serial No. 2009-502945, Response filed Apr. 10, 2013 to Office Action mailed Oct. 23, 2012", (w/ English Translation of Claims), 18 pgs.
"Japanese Application Serial No. 2011-111048, Office Action mailed Jun. 25, 2013", (w/ English Translation), 7 pgs.
"Japanese Application Serial No. 2011-111048, Office Action mailed Sep. 18, 2012", (w/ English Translation), 10 pga.
"Japanese Application Serial No. 2011-111048, Response filed Sep. 25, 2012 to Office Action mailed Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action mailed Jun. 10, 2014", (w/ English Translation), 7 pgs.
"Japanese Application Serial No. 2012-273898, Response filed Sep. 4, 2014 to Office Action mailed Jun. 10, 2014", W/ English Claims, 9 pgs.
"Japanese Application Serial No. 2012-536963, Amendment and Argument filed Jun. 26, 2015 to Office Action mailed Jan. 6, 2015", (w/ English Translation of Amended Claims), 12 pgs.
"Japanese Application Serial No. 2012-536963, Examiners Decision of Final Refusal mailed Nov. 17, 2015", (w/ English Translation), 8 pgs.
"Japanese Application Serial No. 2012-536963, Office Action mailed Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action mailed Jan. 6, 2015", (w/ English Translation), 9 pgs.
"Japanese Application Serial No. 2014-049025 Response filed Sep. 4, 2015 to Office Action mailed Jun. 16, 2015", (w/ Amended Claims), 12 pgs.
"Japanese Application Serial No. 2014-049025, Examiners Decision of Final Refusal mailed Feb. 2, 2016", W/ English Translation, 5 pgs.
"Japanese Application Serial No. 2014-049025, Office Action mailed Jun. 16, 2015", (w/ English Translation), 6 pgs.
"Japanese Application Serial No. 2014-527339, Examiners Decision of Final Refusal mailed Feb. 7, 2017", (w/ English Translation), 5 pgs.
"Japanese Application Serial No. 2014-527339, Office Action mailed May 31, 2016", (w/ English Translation), 10 pgs.
"Japanese Application Serial No. 2014-527339, Response filed Sep. 16, 2016 to Office Action mailed May 31, 2016", (w/ English Translation of Amended Claims), 33 pgs.
"Japanese Application Serial No. 2016-053990, Office Action mailed Jun. 6, 2017", (w/ English Translation), 4 pgs.
"Japanese Application Serial No. 2016-053990, Response filed Dec. 6, 2017 to Office Action mailed Jun. 6, 2017", (w/ English Translation of Amended Claims), 14 pgs.
"Japanese Application Serial No. 2016-110879, Office Action mailed May 30, 2017", (w/ English Translation), 7 pgs.
"Japanese Application Serial No. 2016-110879, Response filed Nov. 30, 2017 to Office Action mailed May 30, 2017", (w/ English Translation of Claims), 25 pgs.
"Japanese Application Serial No. 2016-527046, Examiners Decision of Final Refusal mailed May 21, 2019", (w/ English Translation), 20 pgs.
"Japanese Application Serial No. 2016-527046, Reasons For Rejection mailed Aug. 14, 2018", (w/ English Translation), 14 pgs.
"Japanese Application Serial No. 2016-527046, Response Filed Dec. 4, 2018 to Reasons For Rejection mailed Aug. 14, 2018", (w/ English Translation of Amended Claims), 18 pgs.
"Japanese Application Serial No. 2017-111526, Office Action malled May 14, 2019", (w/ English Translation), 6 pgs.
"Japanese Application Serial No. 2017-111526, Office Action mailed Jun. 26, 2018", (w/ English Translation), 5 pgs.
"Japanese Application Serial No. 2017-111526, Response Filed Dec. 21, 2018 to Office Action mailed Jun. 26, 2018", (w/ English Translation of Amended Claims), 7 pgs.
"Japanese Application Serial No. 2018-510751, Examiners Decision of Final Refusal mailed Dec. 17, 2019", w/ English Translation, 10 pgs.
"Japanese Application Serial No. 2018-510751, Notification of Reasons for Refusal mailed Mar. 13, 2019", (w/ English Translation), 14 pgs.
"Japanese Application Serial No. 2018-510751, Response filed Apr. 17, 2020 to Examiners Decision of Final Refusal mailed Dec. 17, 2019", w/ English Claims, 7 pgs.
"Japanese Application Serial No. 2018-510751, Response filed Aug. 9, 2019 to Notification of Reasons for Refusal mailed Mar. 13, 2019", (w/ English Translation of Claims), 24 pgs.
"Japanese Application Serial No. 2018-543688, Notification of Reasons for Rejection mailed Oct. 29, 2019", w/ English Translation, 14 pgs.
"Japanese Application Serial No. 2018-543688, Office Action mailed Jun. 30, 2020", w/ English translation, 11 pgs.
"Japanese Application Serial No. 2018-543688, Response filed Apr. 28, 2020 to Notification of Reasons for Rejection mailed Oct. 29, 2019", w/ English Claims, 12 pgs.
"Japanese Application Serial No. 2019-171818, Examiners Decision of Final Refusal mailed Oct. 5, 2021", (w/ English Translation), 15 pgs.

(56) References Cited

OTHER PUBLICATIONS

"Japanese Application Serial No. 2019-171818, Notification of Reasons for Rejection mailed Nov. 10, 2020", (w/ English Translation), 11 pgs.
"Japanese Application Serial No. 2019-171818, Preliminary Examination Report mailed May 10, 2022", (w/ English Translation), 2 pgs.
"Japanese Application Serial No. 2019-171818, Response filed Feb. 4, 2022 to Examiners Decision of Final Refusal mailed Oct. 5, 2021", (w/ English Translation of Claims), 21 pgs.
"Japanese Application Serial No. 2019-171818, Response filed May 10, 2021 to Notification of Reasons for Rejection mailed Nov. 10, 2020", (w/ English Translation of Claims), 12 pgs.
"Japanese Application Serial No. 2019-171818, Response filed Dec. 2, 2022 to Preliminary Examination Report mailed May 10, 2022", w/ English Claims, 44 pgs.
"Japanese Application Serial No. 2019-171818, Trial Brief filed Mar. 30, 2022", (w/ English Translation), 14 pgs.
"Japanese Application Serial No. 2020-073952, Examiners Decision of Final Refusal mailed Aug. 4, 2022", w/ English translation, 3 pgs.
"Japanese Application Serial No. 2020-073952, Final Notification of Reasons for Refusal mailed Jan. 25, 2022", w/ English Translation, 11 pgs.
"Japanese Application Serial No. 2020-073952, Notification of Reasons for Refusal mailed May 20, 2021", w/o English Translation, 2 pgs.
"Japanese Application Serial No. 2020-073952, Response filed Apr. 20, 2022 to Final Notification of Reasons for Refusal mailed Jan. 25, 2022", w/ English Claims, 40 pgs.
"Japanese Application Serial No. 2020-073952, Response filed Sep. 9, 2021 to Notification of Reasons for Refusal mailed May 20, 2021", w/ English Claims, 27 pgs.
"Japanese Application Serial No. 2020-073952, Response filed Dec. 2, 2022 to Examiners Decision of Final Refusal mailed Aug. 4, 2022", w/ English Claims, 36 pgs.
"Japanese Application Serial No. 2020-182549, Examiners Decision of Final Refusal mailed Jun. 7, 2022", (w/ English Translation), 11 pgs.
"Japanese Application Serial No. 2020-182549, Notification of Reasons for Refusal mailed Nov. 30, 2021", (w/ English Translation), 10 pgs.
"Japanese Application Serial No. 2020-182549, Response filed Feb. 28, 2022 to Notification of Reasons for Refusal mailed Nov. 30, 2021", (w/ English Translation of Claims), 52 pgs.
"Japanese Application Serial No. 2020-182549, Response filed Oct. 6, 2022 to Examiners Decision of Final Refusal mailed Jun. 7, 2022", w/ English Claims, 21 pgs.
"Japanese Application Serial No. 2021-146743, Notification of Reasons for Rejection mailed Aug. 17, 2022", w/ English Translation, 3 pgs.
"Japanese Application Serial No. 2021-506434, Notification of Reasons for Refusal mailed May 10, 2022", w/ English translation, 10 pgs.
"Japanese Application Serial No. 2021-506434, Response filed Feb. 18, 2022 to Office Action mailed Dec. 21, 2021", 135 pgs.
"Japanese Application Serial No. 2021-506434, Response filed Nov. 7, 2022 to Notification of Reasons for Refusal mailed May 10, 2022", w/ English Claims, 13 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal mailed (Dec. 13, 2022", w/ English Translation, 14 pgs.
"Japanese Application Serial No. 2006-513125,Final Office Action mailed Jan. 18, 2011", (English Translation), 4 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2004-7012647, Office Action mailed Feb. 26, 2010", (w/ English Translation), 7 pgs.
"Korean Application Serial No. 10-2004-7012647, Response filed Jun. 10, 2010 to Office Action mailed Feb. 26, 2010", (w/ English Translation of Claims), 17 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ English Translation), 9 pgs.
"Korean Application Serial No. 10-2005-7020077, Response filed Aug. 28, 2007 to Notice of Preliminary Rejection mailed Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action mailed Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.
"Korean Application Serial No. 10-2010-7011520, Office Action mailed Jul. 20, 2010", (w/ English Translation), 6 pgs.
"Korean Application Serial No. 10-2010-7011520, Response filed Oct. 20, 2010 to Office Action mailed Jul. 20, 2010", (w/ English Translation of Amended Claims), 30 pgs.
"Korean Application Serial No. 10-2010-7011520, Amended Claims filed May 24, 2011 in Response to Office Action mailed Feb. 24, 2011", (English Translation of Amended Claims), 22 pgs.
"Korean Application Serial No. 10-2010-7011520, Office Action mailed Feb. 24, 2011", (w/ English Translation), 5 pgs.
"Mexican Application No. PA/a/2005/012712 Office Action mailed Jul. 21, 2009", (w/ English Translation), 9 pgs.
"Mexican Application Serial No. MX/a/2009/006341, Office Action mailed Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action mailed May 19, 2015", (w/ English Translation of Claims), 21 pgs.
"Mexican Application Serial No. MX/a/2012/009249, Office Action mailed Feb. 5, 2016", W/ English Claims, 2 pgs.
"Mexican Application Serial No. MX/a/2012/009249, Office Action mailed May 19, 2015", (English Translation), 1 pg.
"Mexican Application Serial No. MX/a/2012/009249, Response filed Mar. 29, 2016 to Office Action mailed Feb. 5, 2016", (English Translation of Claims), 18 pgs.
"Mexican Application Serial No. PA/a/2004/007914, Office Action mailed Feb. 14, 2008", (w/ English Translation), 3 pgs.
"Mexican Application Serial No. PA/a/2004/007914, Office Action mailed Feb. 22, 2008", (English Translation), 3 pgs.
"Mexican Application Serial No. PA/a/2004/007914, Response filed Jun. 11, 2008 to Office Action mailed Feb. 22, 2008", (w/ English Translation of Claims), 68 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", (w/ English Translation of Claims), 14 pgs.
"Mexican Application Serial No. PA/a/2005/012712 , Office Action Mailed Aug. 11, 2009", (English Translation), 5 pgs.
"Mexican Application Serial No. PA/a/2005/012712 , Response filed Sep. 28, 2009 to Office Action Mailed Jul. 21, 2009", (w/ English Translation of Claims), 24 pgs.
"Mexican Application Serial No. PA/a/2005/012712, Office Action mailed May 12, 2010", (w/ English Translation), 19 pgs.

(56) References Cited

OTHER PUBLICATIONS

"Mexican Application Serial No. PA/a/2005/012712, Office Action mailed Jun. 9, 2010", (w/ English Translation), 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Official Action mailed Mar. 5, 2009", (English Translation), 2 pgs.
"Mexican Application Serial No. PA/a/2005/012712, Response filed Feb. 3, 2010 to Office Action mailed Nov. 30, 2009", (w/ English Translation of Amended Claims), 22 pgs.
"Mexican Application Serial No. PA/a/2005/012712, Response filed Sep. 27, 2010 to Office Action mailed May 12, 2010", (w/ English Translation of Claims), 19 pgs.
"Mexico Application Serial No. PA/a/2005/012712, Response filed Jun. 12, 2009 to Official Action mailed Mar. 5, 2009", (w/ English Translation of Claims), 11 pgs.
"Neuraminidase [Influenza A virus (A/Aichi/2/1968 (H3N2)]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 12, 2008", 1 pg.
"New Zealand Application Serial No. 543446, Response mailed Mar. 20, 2008 to Examination Report mailed Feb. 29, 2008", 2 pgs.
"New Zealand Application Serial No. 543587, Examination Report mailed Mar. 1, 2007", 1 pg.
"New Zealand Application Serial No. 543587, Examination Report mailed Jul. 7, 2006", 2 pgs.
"New Zealand Application Serial No. 543587, Response filed Aug. 7, 2007 to Examination Reports mailed Jul. 7, 2006 and Mar. 1, 2007", 24 pgs.
"New Zealand Application Serial No. 543587, Second Examination Report mailed Feb. 25, 2008", 2 pgs.
"New Zealand Application Serial No. 555245, First Examination Report mailed Aug. 26, 2008", 12 pgs.
"New Zealand Application Serial No. 555245, Subsequent Examiner Report malled Jul. 3, 2009", 1 pg.
"nonstructural protein 1 [influenza B virus (B/Hong Kong/330/2001)]", GenBank AAT69443.1, (2006), 1 pg.
"Norway Application Serial No. 20056074, Office Action mailed Jan. 17, 2017", (English Translation), 5 pgs.
"Norway Application Serial No. 20056074, Office Action mailed Apr. 25, 2017", (w English Translation), 3 pgs.
"Norway Application Serial No. 2005074, Office Action Response mailed Apr. 18, 2017", W/ English Claims, 27 Pgs.
"Norway Application Serial No. 20056074, Response filed Jul. 25, 2017 to Office Action mailed Apr. 25, 2017", (w/ English Translation of Amended Claims), 111 pgs.
"Norweigan Application Serial No. 20056074, Office Action mailed Apr. 25, 2017", (Translation), 3 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structure of Small Viral RNA Segment", Database UniProt EBI / Accession No. NC_002023, (Jul. 10, 2008), 15 pgs.
"PCT Application Serial No. PCT/US2005/041991, International Preliminary Report on Patentability / Written Opinion mailed Jul. 19, 2007", 8 pgs.
"Polymerase acidic [influenza A virus (A/swine/Shizuoka/120/97(H3N2))]", GenBank AAO15329.1, (2003), 1 pg.
"Polymerase PA [Influenza A virus (A/swine/Yangzhou/1/2008(H9N2))]", GenBank: ADK98493.1. [Online]. Retrieved from the Internet: <URL: https://www.ncbi.nlm.nih.gov/protein/ADK98493.1/>, 2 pgs.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AltName: Full=NS1 B", GenPept Accesion P08013, NS1 of Influenza B strain B/Yamagata/1/73, (Dec. 9, 2015), 2 pgs.
"RNA World", http://faculty.uca.edu/~benw/biol4415/lecture10a/tsld003.htm, (Observed Feb. 25, 2003), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion mailed Jun. 19, 2007", 5 pgs.
"Singaporean Application Serial No. 200506858-0, Examination Report mailed Feb. 9, 2007", 4 pgs.
"Singaporean Application Serial No. 200506858-0, Response filed Dec. 22, 2006 to Written Opinion mailed Jul. 26, 2006", 18 pgs.
"Singaporean Application Serial No. 200506858-0, Written Opinion mailed Jul. 26, 2006", 8 pgs.
"Singaporean Application Serial No. 200507468-7, Examination Report mailed Mar. 19, 2008", 5 pgs.
"Singaporean Application Serial No. 200507468-7, Invitation to Respond to Written Opinion mailed Jun. 12, 2007", 6 pgs.
"Singaporean Application Serial No. 200507468-7, Response filed Nov. 7, 2007 to Invitation to Respond to Written Opinion mailed Jun. 12, 2007", 9 pgs.
"ST3GAL6 Gene ID: 478535", ncbi, nlm, [Online]. Retrieved from the Internet: <URL: https://www.ncbi.nlm.nih.gov/gene/47853> Sep. 14, 2022, (Aug. 17, 2022), 14 pgs.
"The Influenza Virus: Structure and Replication", Rapid Reference to Influenza. Elsevier Ltd, [Online]. Retrieved from the Internet: http://www. rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action mailed Jun. 17, 2009", W/ English Claims, 14 pgs.
"Ukrainian Application Serial No. 200512619, Office Action mailed Feb. 27, 2009", (w/ English Translation), 21 pgs.
"Ukrainian Application Serial No. 200512619, Office Action mailed Jun. 17, 2009", (w/ English Translation), 4 pgs.

(56) References Cited

OTHER PUBLICATIONS

"Ukrainian Application Serial No. 200512619, Response filed Apr. 8, 2009 to Office Action mailed Feb. 27, 2009", (w/ English Translation of Claims), 9 pgs.
Abram, M. E, et al., "Nature, position, and frequency of mutations made in a single cycle of HIV-1 replication", J Virol., 84(19), (Oct. 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.
Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Bedford, M. T, et al., "FBP WW domains and the Abl SH3 domain bind to a specific class of proline-rich ligands", EMBO J., 16(9), (May 1, 1997), 2376-83.
Betakova, T., et al., "The NB protein is an integral component of the membrane of influenza B virus.", J Gen Virol., 77 ( Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4 1425-1427, (2010), 3 pgs.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(4948) 1306-1310, (1990), 5 pgs.
Boyer, J. C., et al., "Infectious transcripts and cDNA clones of RNA viruses", Virology, 198(2), (Feb. 1994), 415-426.
Bradfute, S. B., "The Early Clinical Development of Ebola Virus Treatments", Exp. Opin. Invest. Drugs 26(1):, (2017), 5 pgs.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: A Safe Madin Darby Canine Kidney (MDCK) Cell Culture-Based Influenza Vaccine", Dev. Biol. Stand., 98, (1999), 93-100.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al., "Immunodominance of Antigenic Site B in the Hemagglutinin of the Current H3N2 In?uenza Virus in Humans and Mice", Journal of Virology, 92(20): e01100-18, (Oct. 2018), 1-13.
Brooke, C B, "Biological activities of 'noninfectious' influenza A virus particles", Future Virol 9(1) 41-51, (Jan. 2014), 16 pgs.
Brown, E. G., et al., "Genetic analysis of mouse-adapted influenza A virus identifies roles for the NA, PB1, and PB2 genes in virulence", Virus Research, 61(1), (May 1999), 63-76.
Brown, TA, "Studying DNA", Genomes—NCBI Bookshelf, Brown TA. Genomes. 2nd edition. Oxford: Wiley-Liss; 2002, (2002), 26 pgs.
Bruhl, P., et al., "Humoral and Cell-Mediated Immunity to Vero Cell-Derived Influenza Vaccine", Vaccine, 19, (2001), 1149-1158.
Buchholz, U. J., et al., "Generation of Bovine Respiratory Syncytial Virus (BRSV) From cDNA: BRSV NS2 is Not Essential for Virus Replication in Tissue Culture, and the Human RSV Leader Region Acts as a Functional BRSV Genome Promoter", Journal of Virology, 73(1), (1999), 251-259.
Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.
Bukreyev, A., et al., "Recovery of infectious respiratory syncytial virus expressing an additional, foreign gene", Journal of Virology, 70(10), (Oct. 1996), 6634-6641.
Bullido, R., et al., "Influenza A Virus Nep (NS2 protein) Downregulates RNA Synthesis of Model Template RNAs", Journal of Virology, 75(10), (May 2001), 4912-4917.
Bullido, R., et al., "Influenza A virus NEP(NS2 protein) downregulates RNA synthesis of model template RNAs", Journal of Virology, vol. 75 4912-4917, (May 2001), 6 pgs.

(56) References Cited

OTHER PUBLICATIONS

Burmeister, W. P., et al., "The 2.2 A resolution crystal structure of influenza B neuraminidase and its complex with sialic acid", The EMBO Journal, 11(1), (1992), 49-56.
Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.
Cao, S., et al., "Characterization of the Nucleocytoplasmic Shuttle of the Matrix Protein of Influenza B Virus", Journal of Virology., 88(13), (Jul. 2014), 7464-7473.
Cardona, C. J., "Avian Influenza", http://www.vetmed.ucdavis.edu/vetex/INF-PO_AvianInfluenzaFS.html, ((Observed Feb. 22, 2003), 3 pgs.
Castrucci, M. R, et al., "Attenuation of Influenza A Virus by Insertion of a Foreign Epitope into the Neuraminidase", Journal of Virology, 66(8), (1992), 4647-4653.
Castrucci, M. R., et al., "Biologic Importance of Neuraminidase Stalk Length in Influenza A Virus", Journal of Virology, 67(2), (1993), 759-764.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Catchpole, A P, et al., "Alternative base pairs attenuate influenza A virus when introduced into the duplex region of the conserved viral RNA promoter of either the NS or the PA gene", Journal of General Virology, 84, (2003), 507-515.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chang, M. W., et al., "Analysis of HIV Wild-Type and Mutant Structures via in Silico Docking against Diverse Ligand Libraries", J. Chem. Inf. Model., 47(3), (2007), 1258-1262.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Chiba, Shiho, et al., "Multivalent nanoparticle-based vaccines protect hamsters against SARS-CoV-2 after a single immunization", Communications Biology, 4: 597, (2021), 1-9.
Cho, Alice, et al., "Implications of Broadly Neutralizing Antibodies in the Development of a Universal Influenza Vaccine", Current Opinion In Virology, vol. 17 110-115, (Apr. 1, 2016), 6 pgs.
Chothia, Cyrus, et al., "Canonical Structures for the Hypervariable Regions of Immunoglobulins.", J Mol Biol., 196(4), (1987), 901-917.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.
Chung, C, et al., "Glycoengineering of Chinese Hamster Ovary Cells for Improving Biotherapeutics Efficacies", A dissertation submitted to Johns Hopkins University in conformity with the requirements for the degree of Doctor of Philosophy, Retrieved from the Internet: <https://jscholarship.library.jhu.edu/handle/177>, (2016), 137 pgs.
Claas, E C. J., et al., "Human Influenza A H5N1 Virus Related to a Highly Pathogenic Avian Influenza Virus", The Lancet, 351, (1998), 472-477.
Clarke, D. K., et al., "Rescue of Mumps Virus From cDNA", Journal of Virology, 74(10), (2000), 4831-4838.
Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).
Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.
Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.
Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.
Cunningham, Brian C, et al., "High-Resolution Epitope Mapping of hGH-Receptor Interactions by Alanine-Scanning Mutagenesis", Science 244:4908, (1989), 6 pgs.
Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.
Daddario-Dicaprio, K. M, et al., "Cross-protection against Marburg virus strains by using a live, attenuated recombinant vaccine", J Virol., 80(19), (Oct. 2006), 9659-66.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.

(56) References Cited

OTHER PUBLICATIONS

De La Luna, S., et al., "Influenza Virus NS1 Protein Enhances the Rate of Translation Initiation of Viral mRNAs", Journal of Virology, 69(4), (1995), 2427-2435.
Del Guidice, G., et al., "What are the limits of adjuvanticity?", (Abstract), Vaccine, 20(Suppl 1), S38-S41, (2001), 1 pg.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., et al., "Membrane-Associated Respiratory Syncytial Virus F Protein Expressed From A Human Rhinovirus Type 14 Vector Is Immunogenic", Virology, 281(2), (Mar. 15, 2001), 216-230.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Du, Q., "Ribozyme Enzymology", http://academic.brooklyn.cuny.edu/chem/zhuang/QD/toppage1.htm, (Observed Feb. 25, 2003), 8 pgs.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, US, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dumoulin, Mireille, et al., "Single-domain antibody fragments with high conformational stability", Protein Science, 11, (2002), 500-515.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV3) Expressing The Hemagglutinin Protein Of Measles Virus Provides A Potential Method For Immunization Against Measles Virus and PIV3 In Early Infancy", Journal of Virology, 74(15), (Aug. 2000), 6821-6831.
Durbin, A. P., et al., "Recovery of infectious human parainfluenza virus type 3 from cDNA"; Virology, 235(2), (Sep. 1, 1997), 323-332.
Dyall, J., et al., ""Identification of inhibitors of Ebola virus with a subgenomic replication system "", Antiviral Research,70(1), 19th International Conference on Antiviral Research, San Juan, PR (May 7-11, 20006), (May 2006), p. A39.
Elhefnawi, M, et al., "Identification of novel conserved functional motifs across most Influenza A viral strains", Virology Journal, 8:44, (2011), 10 pages.
Elliott, R. M., "Emerging Viruses: The Bunyaviridae", Molecular Medicine, 3(9), (1997), 572-577.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, K., et al., "Influenza virus NS1 protein stimulates translation of the M1 protein", Journal of Virology, 68 1432-1437, (1994), 6 pgs.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation und Transkription von Marburgund Ebolavirus", [Online]. 2005, Philipps-Universitat Marburg, XP002563470, Retrieved from the Internet: <URL:http://deposit.ddb.de/cgi-bin/dokserv?>idn=977005607&dok_var=d1&dok_ext=pdf&filename=977005607 .pdf> [retrieved on Jan. 15, 2010], (2005), p. 70-p. 84.
Essere, Boris, et al., "Critical role of segment-specific packaging signals in genetic reassortment of influenza A viruses", Proc. Natl. Acad. Sci. USA, 110(40), (2013), E3840-E3848.
Fahey, J. L., et al., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Viral RNA Segment", Cell, 28, (1982), 303-313.
Fischer, W. B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.

(56) References Cited

OTHER PUBLICATIONS

Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Fujii, Y, et al., "The packaging of influenza viral genome", Virus, 52 (1), Uirusu (Japanese Journal Name), (Jun. 2002), 203-206.
Gao, Qinshan, et al., "A Nine-Segment In?uenza A Virus Carrying Subtype H1 and H3 Hemagglutinins", Journal of Virology, 84(16), (Aug. 2010), 8062-8071.
Gao, Qinshan, et al., "A Seven-Segmented Influenza A Virus Expressing the Influenza C Virus Glycoprotein HEF", Journal of Virology, 82(13), (Jul. 2008), 6419-6426.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza A Virus", Dev. Biol. Stand. Vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", Virus Research, 37(1), (1995), 37-47.
Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday.com, (Feb. 20, 2003), 3 pgs.
Genbank, "", ABD36884.1, (2007), 2 pgs.
Gerdil, C., "The Annual Production Cycle for Influenza Vaccine", Vaccine, 21 1776-1779, (2003), 4 pgs.
Ghate, Anita A, et al., "Influenza Type B Neuraminidase Can Replace the Function of Type A Neuraminidase", Virology, 264 (2), (Nov. 1999), 265-277.
Giddings, A M, et al., "The matrix protein of HIV-1 is not sufficient for assembly and release of virus-like particles", Virology, 248(1), (1998), 108-16.
Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is The Major Driving Force in Virus Budding", Journal of Virology, 74 11538-11547, (Dec. 1, 2000), 10 pgs.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265- 272.
Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.
Govorkova, E A, et al., "Replication of Influenza A Viruses in a Green Monkey Kidney Continuous Cell Line (Vero)", J. Infect. Dis. 172(1), (1995), 250-253.
Grambas, S., et al., "Influence of amantadine resistance mutations on the pH regulatory function of the M2 protein of influenza A viruses", Virology, 191(2), (Dec. 1992), 541-549.
Green, R. F., et al., "Glycosylation Does Not Determine Segregation of Viral Envelope Proteins in the Plasma Membrane of Epithelial Cells", J. Cell Biol., 89(2), (1981), 230-239.
Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.
Groseth, A., et al., "RNA Polymerase I-Driven Minigenome System for Ebola Viruses", Journal of Virology, 79(7), (2005), 4425-4433.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.
Hagen, M., et al., "Recombinant Influenza Virus Polymerase: Requirement of both 5' and 3' Viral Ends for Endonuclease Activity", Journal of Virology, 68(3), (1994), 1509-1515.
Hai, Rong, et al., "Influenza B Virus NS1-Truncated Mutants: Live-Attenuated Vaccine Approach", Journal of Virology, 82(21), (2008), 10580-10590.
Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.
Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.

(56) References Cited

OTHER PUBLICATIONS

Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.
Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.
Halstead, Scott B,, et al., "Dengue Antibody-Dependent Enhancement: Knowns and Unknowns", Microbiology Spectrum, 2(6), (2014), 1-18.
Harding, Alfred T, et al., "Rationally Designed Influenza Virus Vaccines That Are Antigenically Stable during Growth in Egg", MBIO, vol. 8, No. 3, eO0669-17, (Jul. 5, 2017), 1-16.
Harmsen, M. M., et al., "Properties, production, and applications of camelid single-domain antibody fragments", Appl Microbiol Biotechnol,77, (2007), 13-22.
Harty, R. N, et al., "A PpxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Harvey, K. F, et al., "All three WW domains of murine Nedd4 are involved in the regulation of epithelial sodium channels by intracellular Na+.", J Biol Chem., 274(18), (Apr. 30, 1999), 12525-30.
Hatada, E., et al., "Binding of Influenza A Virus NS1 Protein to dsRNA in vitro", Journal of General Virology, 73, (1992), 3325-3329.
Hatakeyama, S., et al., "Dissection and identification of regions required to form pseudoparticles by the interaction between the nucleocapsid (N) and membrane (M) proteins of SARS coronavirus", Virology, 380(1), (2008), 99-108.
Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.
Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.
Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
He, X., et al., "Generation of SARS-CoV-2 reporter replicon for high-throughput antiviral screening and testing", Proc. Natl. Acad. Sci. USA, 118(15): e2025866118, (2021), 8 pgs.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hickman, Danielle, et al., "An avian live attenuated master backbone for potential use in epidemic and pandemic influenza vaccines", Journal of General Virology, 89(Part 11), (2008), 2682-2690.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hiti, A. L., et al., "P03470—Neuraminidase", Entrez Protein Database, http://www.ncbi.nlm.nih.gov/entrez/viewer.fcgi?db=protein&val=84028231, (1982), 730-734.
Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs. ).
Ho, Y., et al., "Assembly of human severe acute respiratory syndrome coronavirus-like particles", Biochem Biophys Res Commun, 318(4), (2004), 833-838.
Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.
Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.
Hoffman, E., et al., "Ambisense Approach for the Generation of Influenza A Virus: vRNA and mRNA Synthesis from One Template", Virology 267(2) 310-317, (Feb. 15, 2006), 8 pgs.
Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Hoffmann, Erich, et al., "A DNA transfection system for generation of influenza A virus from eight plasmids", Proceedings of the National Academy of Sciences, vol. 97, No. 11, (2000), 6108- 6113.
Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.
Holsinger, L. J., et al., "Influenza A Virus M2 Ion Channel Protein: a Structure-Function Analysis", Journal of Virology, 68 (3), (1994), pp. 1551-1563.
Honda, A., et al., "RNA Polymerase of Influenza Virus: Role of NP in RNA Chain Elongation", The Journal of Biochemistry, 104(6), (1988), 1021-1026.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Horimoto, "Designing Vaccines for Pandemic Influenza", Current Topics Microbiol Immunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14) 8031-8038, (2003), 11 pgs.
Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.

(56) References Cited

OTHER PUBLICATIONS

Hossain, M. J., et al., "Establishment and Characterization of a Madin-Darby Canine Kidney Reporter Cell Line for Influenza A Virus Assays", J Clin Microbiol, 48(7), (2010), 2515-2523.

Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.

Huang, T. S, et al., "Determinaton of Influenza Virus Proteins Required for Genome Replication", Jounal of Virology, vol. 64 5669-5673, (1990), 5 pgs.

Huang, T.-S., et al., "Determination of Influenza Virus Proteins Required for Genome Replication", Journal of Virology, 64(11), (1990), 5669-5673.

Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.

Huddleston, J. A., et al., "The Sequence of the Nucleoprotein Gene of Human Influenza A Virus, Strain A/NT/60/68", Nucleic Acids Research, 10(3), (1982), 1029-1038.

Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR .(Suppl 1), XP002574255 ISSN: 0022-1899 abstract, (Feb. 1999), 240-247.

Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.

Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.

Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.

Huisman, W., et al., "Vaccine-induced enhancement of viral infections", Vaccine, 27(4), (2009), 505-512.

Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.

Hurt, A. C, et al., "Identification of a human influenza type B strain with reduced sensitivity to neuraminidase inhibitor drugs", Virus Research, Vol. (103), (2004), 205-211.

Hutchinson, Edward C., et al., "Genome packaging in influenza A virus", Journal of General Virology, 91(Pt 2), (2010), 313-328.

Hwang, Jung-Shan, et al., "Expression of Functional Influenza Virus RNA Polymerase in the Methylotrophic Yeast *Pichia pastoris*", Journal of Virology, 74(9), (2000), 4074-4084.

Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.

Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.

Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.

Iwatsuki-Horimoto, K., et al., "The cytoplasmic tail of the influenza A virus M2 protein plays a role in viral assembly.", J Virol., 80(11), (Jun. 2006), 5233-40.

Jackson, et al., "Characterization of recombinant influenza B viruses with key neuraminidase inhibitor resistance mutations,", Journal of Antimicrobial Chemotherapy, vol. (55), (2005), 162-169.

Jackson, D., et al., "A reverse genetics approach for recovery of recombinant influenza B viruses entirely from cDNA.", J Virol., 76(22), (Nov. 2002), 11744-7.

Jahrling, P. B., et al., "Ebola Hemorrhagic Fever: Evaluation of Passive Immunotherapy in Nonhuman Primates", J. Infect. Dis. 196, (2007), 4 pgs.

Jang, S.-W., et al., "Deoxygedunin, a Natural Product with Potent Neurotrophic Activity in Mice", PLoS One 5(7): e11528, (2010), 1-15.

Jasenosky, Luke D, et al., "Ebola Virus VP40-Induced Particle Formation and Association with the Lipid Bilayer", Journal of Virology, 75 (110, (Jun. 2001), 5205-5214.

Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.

Jiang, H, et al., "Influenza virus genome C4 promoter/origin attenuates its transcription and replication activity by the low polymerase recognition activity", Virology, 408(2), (2010), 190-196.

Jiang, Y., et al., "Genome wide analysis of protein protein interactions and involvement of viral proteins in Sars Cov 2 replication", Cell Biosci, 11:140, 2021, 16 pgs., (2021), 16 pgs.

Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.

Jin, H., et al., "Influenza virus hemagglutinin and neuraminidase cytoplasmic tails control particle shape", The EMBO Journal, 16(6), (1997), 1236-1247.

Jin, H., et al., "The influenza virus hemagglutinin cytoplasmic tail is not essential for virus assembly or infectivity", The EMBOL Journal, 13(22), (1994), 5504-5515.

Johnson, David A, et al., "TLR4 Agonists as Vaccine Adjuvants", Vaccine Adjuvants and Delivery Systems, (2007), 131-156.

Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135- 5144.

Ju, X., et al., "A novel cell culture system modeling the SARS-CoV-2 life cycle", PloS Pathogens, 17(3): e1009439, (2021), 23 pgs.

Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.

Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.

Kaplan, G., et al., "In vitro Synthesis of Infectious Poliovirus RNA", Proc. Natl. Acad. Sci. USA, 82, (1985), 8824-8428.

Katinger, D., et al., "Attenuated Influenza Viruses as a Vector for Mucosal Immunization Against HIV-1", Vaccines, 97, Cold Spring Harbor, (1997), 315-319.

Kato, A., et al., "Initiation of Sendai Virus Multiplication From Transfected cDNA or RNA With Negative or Positive Sense", Genes to Cells, 1, (1996), 569-579.

Kawaoka, Y, et al., "Sequence requirements for cleavage activation of influenza virus hemagglutinin expressed in mammalian cells", Proc Natl Acad Sci., 85(2), (1988), 324-328.

Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/girce/docs/2007/Kawaoka.pdf> [retrieved on Jan. 13, 2010] p. 10, under item C, -& Anonymous: "Index of GLRCE: documents from 2007" Great Lakes Regional Center of Excellence Index, [Online] 2007, XP002563469. Retrieved from the Internet: URL:http://www.rcebiodefense.org/glrce/docs/2007/> [retrieved on Jan. 14, 2010] -& Kawaoka Y.: , (2007), pp. 1-19.

Kawaoka, Y., "Mutant Cells With Altered Sialic Acid", U.S. Appl. No. 11/644,179 filed Dec. 22, 2006, 51 pgs.

Kawaoka, Y., "Prevention and Control of Ebola Virus Infection (Ongoing Research)", Great Lakes Regional Center of Excellence (GLRCE) Annual Meeting Schedule, (Abstract), [online] [retrieved

(56) References Cited

OTHER PUBLICATIONS on Jan. 14, 2010]. Retrieved from the Internet: <URL:http://www.rcebiodefense.org/glrce/annualmeeting/2007Agenda.pdf>, (Nov. 29, 2007), 4 pgs.
Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.
Kijima, H., et al., "Therapeutic Application of Ribozymes", Pharmac. Ther., 68(2), (1995), 247-267.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H., et al., "Cold adaptation generates mutations associated with the growth of influenza B vaccine viruses", Vaccine, 33(43), (2015), 5786-5793.
Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.
Kimura, N., et al., "An In Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.
Kistner, O., et al., "Development of a mammalian cell (Vero) derived candidate influenza virus vaccine", Vaccine, 16(9-10), (May-Jun. 1998), 960-8.
Kistner, O., et al., "Development of a Vero Cell-Derived Influenza Whole Virus Vaccine", Dev. Biol. Stand., 98, (1999), 101-110.
Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an Influenza A Virus Vector Expressing Biologically Active Human Interleukin-2 from the NS Gene Segment", Journal of Virology, 79(16), (Aug. 2005), 10672-10677.
Kobayashi, H., et al., "A replication-incompetent influenza virus bearing the HN glycoprotein of human parainfluenza virus as a bivalent vaccine", Vaccine, 31(52), (2013), 6239-6246.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Kon, Theone C, et al., "Influenza Vaccine Manufacturing: Effect of Inactivation, Splitting and Site of Manufacturing. Comparison of Influenza Vaccine Production Processes", PLoS One, 11(3), e0150700, (Mar. 9, 2016), 19 pgs.
Konarska, M. M., et al., "Structure of RNAs Replicated by the DNA-Dependent T7 RNA Polymerase", Cell, 63(2), (1990), 609-618.
Konduru, K., et al., "Ebola virus glycoprotein Fc fusion protein confers protection against lethal challenge in vaccinated mice", Vaccine, 29(16), (Apr. 5, 2011), 2968-77.
Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.
Kopecky, S. A, et al., "Matrix protein and another viral component contribute to induction of apoptosis in cells infected with vesicular stomatitis virus", J Virol., 75(24), (Dec. 2001), Abstract Only.
Kovacova, A., et al., "Sequence similarities and evolutionary relationships of influenza virus A hemagglutinins.", Virus Genes, 24(1), (2002), 57-63.
Kovacova, Andrea, et al., "Sequence Similarities and Evolutionary Relationships of Influenza Vrus A Hemagglutinins", Virus Genes, 24(1), (2002), 57-63.
Kovesdi, et al., "Adenoviral vectors for gene transfer", Current Opinion in Biotechnology, vol. 8, (1997), 583-589.
Kovesdi, I., et al., "Adenoviral Vectors for Gene Transfer", Current Opinion in Biotechnology, 8(5), (Oct. 1997), 583-589.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990), 9 pgs.
Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.
Kumar, P. K. R., et al., "Artificial Evolution and Natural Ribozymes", The FASEB Journal, 9, (1995), 1183-1195.
Kunik, Vered, et al., "Paratome: an online tool for systematic identification of antigen-binding regions in antibodies based on sequence or structure", Nucleic Acids Research, vol. 40, Issue W1, (2012), W521-W524.
Kunkel, T. A., "Rapid and Efficient Site-Specific Mutagenesis Without Phenotypic Selection", Proc. Natl. Acad. Sci. USA, 82, (1985), 488-492.
Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71(3), (2018), 234-238.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Latham, T, et al., "Formation of Wild-Type and Chimeric Influenza Virus-Like Particles following Simultaneous Expression of Only Four Structural Proteins", Journal of Virology 75 (13), (2001), 6154-6165.
Lawson, N. D., "Recombinant Vesicular Stomatitis Viruses From DNA", Proc. Natl. Acad. Sci. USA, 92(10), (1995), 4477-4481.
Laxman, B., "Noninvasive Real-Time Imaging of Apoptosis", PNAS, 99(26), (2002), 16551-16555.
Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.
Le, T., "CaSpeR5, a family of *Drosophila transgenesis* and shuttle vectors with improved multiple cloning sites", Biotechniques, 42(2), (Feb. 2007), 164-166.
Leahy, M. B., et al., "An Endonuclease Switching Mechanism in the Virion RNA and cRNA Promoters of Thogoto Orthomyxovirus", Journal of Virology, 72(3), (1998), 2305-2309.
Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.
Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.
Leal, et al., "New challenges in therapeutic vaccines against HIV infection", Expert Review of Vaccines, vol. 16, No. 6, (2017), 587-600.
Lee, C. W, et al., "Generation of reassortant influenza vaccines by reverse genetics that allows utilization of a DIVA (Differentiating

(56) References Cited

OTHER PUBLICATIONS

Infected from Vaccinated Animals) strategy for the control of avian influenza", Vaccine, vol. 22, (2004), 3175-3181.
Lee, D.-H., et al., "H9N2 avian influenza virus-like particle vaccine provides protective immunity and a strategy for the differentiation of infected from vaccinated animals", Vaccine, vol. 29, (2011), 4003-4007.
Lee, Dong-Hun, et al., "Progress and hurdles in development of influenza virus-like particle vaccines for veterinary use", Korean Vaccine Society, (2014), 133-139.
Lee, Jeffrey E., et al., "Complex of a Protective Antibody with Its Ebola Virus GP Peptide Epitope: Unusual Features of a V?x Light Chain", J. Mol. Biol., 375, (2007), 202-216.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6NI avian influenza viruses isolated in Taiwan between 1972 and 2005", Avian Diseases, 50(4), (Dec. 2006), 561-571.
Lefranc, Marie-Paule, et al., "IMGT unique numbering for immunoglobulin and T cell receptor variable domains and Ig superfamily V-like domains", Developmental & Comparative Immunology, 27, (2003), 55-77.
Lembo, A, et al., "Administration of a synthetic TLR4 agonist protects mice from pneumonic tularemia.", J Immunol., 180(11), 7574-81.
Levis, R., et al., "Deletion Mapping of Sindbis Virus DI RNAs Derived From cDNAs Defines the Sequences Essential for Replication and Packaging", Cell, 44, (1986), 137-145.
Li, et al., "Selection of antigenically advanced variants of seasonal influenza viruses", Nature Microbiology, 1 (6), (2016), 1-10.
Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.
Li, Junwei, et al., "Engineering Influenza Viral Vectors", Bioengineered, vol. 4, No. 1, (Jan. 1, 2013), 9-14.
Li, K. S., et al., "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Li, S., et al., "Electroporation of Influenza Virus Ribonucleoprotein Complexes for Rescue of the Nucleoprotein and Matrix Genes", Virus Research, 37(2), (1995), 153-161.
Li, S., et al., "Influenza A Virus Transfectants with Chimeric Hemagglutinins Containing Epitopes from Different Subtypes", Journal of Virology, 66(1), (1992), 399-404.
Li, S., et al., "Recombinant Influenza A Virus Vaccines for the Pathogenic Human A/Hong Kong/97 (H5N1) Viruses", J Infect Dis., 179(5), (1999), 1132-1138.
Li, Shengqiang, et al., "Influenza A Virus Transfectants with Chimeric Hemagglutinins containing Epitopes from different subtypes", Journal of Virology 399-404, (1992), 6 pgs.
Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.
Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.
Liu, C., et al., "Influenza type A virus neuraminidase does not play a role in viral entry, replication, assembly, or budding.", Journal of Virology, 69(2), (1995), 1099-1106.
Liu, C., et al., "Selection and Characterization of a Neuraminidase-Minus Mutant of Influenza Virus and its Rescue by Cloned Neuraminidase Genes", Virology, 194(1), (1993), 403-407.
Liu, Y., et al., "A live-attenuated SARS-CoV-2 vaccine candidate with accessory protein deletions", bioRxiv [online]. [retrieved Jun. 10, 2022]. Retrieved from the Internet: <URL: https://www.biorxiv.org/content/10.1101/2022.02.14.480460v1.full.pdf>, (2022), 44 pgs.
Liu, Z, et al., "Fine mapping of the antigen-antibody interaction of scFv215 A recombinant antibody inhibiting RNA polymerase II from *Drosophila melanogaster*", J. Mol. Recog. 12:103-111, (1999), 9 pgs.
Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.
Longnecker, R., et al., "WWW- and SH3-domain interactions with Epstein-Barr virus LMP2A", Exp Cell Res., 257(2), (Jun. 15, 2000), Abstract Only.
Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.
Mansky, L. M, "Retrovirus mutation rates and their role in genetic variation", J Gen Virol., 79 (Pt 6), (Jun. 1998), 1337-45.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003). 6050-6054.
Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.

(56) References Cited

OTHER PUBLICATIONS

Martin, J., et al., "Studies of the Binding Properties of Influenza Hemagglutinin Receptor-Site Mutants", Virology, 241(1), (Feb. 1, 1998), 101-111.
Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.
Martorelli Di, Genova B., et al., "Intestinal delta-6-desaturase activity determines host range for Toxoplasma sexual reproduction", PLoS Biology, vol. 17, No. 8, E3000364, (Aug. 20, 2019), XP055619380, (Aug. 20, 2019), 1-19.
Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.
Matrosovich, M, et al., "Overexpression of the [alpha]-2,6-sialyltransferase in MDCK cells increases influenza virus sensitivity to neuraminidase inhibitors", Journal of Virology, The American Society for Microbiology, US, vol. 77, No. 15, (Aug. 1, 2003), 8418-8425.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21) 12364-12373, (2014), 10 pgs.
Matta, M, et al., "Cell-surface sialoglycoconjugate structures in wild-type and mutant Crithidia fasciculata", Parasitol. Res., 85(4), (1999), 293-299.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McCullers, et al., "Multiple Genotypes of Influenza B Virus Circulated between 1979 and 2003,", Journal of Virology, vol. (78), No. (23) 12817-12828, (2004), 13 pgs.
McCullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.
McKee, Dwight L, et al., "Candidate drugs against SARS-CoV-2 and COVID-19", Pharmacological Research, Academic Press, London, GB, vol. 157, (Apr. 29, 2020), 9 pgs.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
McSharry, J. J, et al., "Phenotypic Drug Susceptibility Assay for Influenza Virus Neuraminidase Inhibitors", Clinical and Diagnostic Laboratory Immunology vol. (11), No.(2),, (2004), 10 pgs.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of biologically active influenza virus core proteins using a vaccinia virus-T7 RNA polymerase expression system", Journal of General Virology, 75 2109-2114, (1994), 6 pgs.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mishin, V. P, et al., "Protection afforded by intranasal immunization with the neuraminidase-lacking mutant of influenza A virus in a ferret model", Vaccine, 23(22), (Apr. 22, 2005), 2922-7.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Mitnaul, L. J., et al., "Balanced Hemagglutinin and Neuraminidase Activities are Critical for Efficient Replication of Influenza A Virus", Journal of Virology, 74 (13), (2000), 6015-6020.
Mittler, E., et al., "Role of the transmembrane domain of marburg virus surface protein GP in assembly of the viral envelope.", J Virol., 81(8), (Apr. 2007), 3942-8.
Miyoshi, H., et al., "Development of Self-Inactivating Lentivirus Vector", Journal of Virology, 72(10), (1998), 8150-8157.
Monto, A. S, et al., "Detection of influenza viruses resistant to neuraminidase inhibitors in global surveillance during the first 3 years of their use", Antimicrobal Agents and Chemotherapy, 50(7) 2395-2402, (2006), 8 pgs.
Monto, Arnold S, et al., "Comparative efficacy of inactivated and live attenuated influenza vaccines.", N Engl J Med., 361(13) 1260-7, (Sep. 24, 2009), 8 pgs.
Morita, S., et al., "Plat-E: an efficient and stable system for transient packaging of retroviruses", Gene Therapy, 7(12), (2000), 1063-1066.
Moss, B., et al., "New Mammalian Expression Vectors", Nature, 348, (1990), 91-92.
Moyer, S. A., et al., "Assembly and Transcription of Synthetic Vesicular Stomatitis Virus Nucleocapsids", Journal of Virology, 65(5), (1991), 2170-2178.
Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.
Muhlberger, E., et al., "Three of the four nucleocapsid proteins of Marburg virus,NP, VP35, and L, are sufficient to mediate replication and transcription of Marburg virus-specific monocistronic minigenomes", Journal of Virology, 72(11) 8756-8764, (1998), 11 pgs.
Muhlberger, Elke, "Filovirus replication and transcription", Future Virol., 2:205, (2007), 16 pgs.
Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Muramoto, Y., et al., "Hierarchy among Viral RNA (vRNA) Segments in Their Role in vRNA Incorporation into Influenza A Virions", J. Virol., 80(5), (2006), 2318-2325.
Muramoto, Yukiko, "Hierarchy among Viral RNA (vRNA) Segments in Their Role in vRNA Incorporation into Influenza A Virions", Journal of Virology, 80(5), (2006), 2318-2325.
Murphy, B. R, et al., "An influenza A live attenuated reassortant virus possessing three temperature-sensitive mutations in the PB2 polymerase gene rapidly loses temperature sensitivity following replication in hamsters", Vaccine, 15(12-13) 1372-8, (1997), 7 pgs.
Murphy, Brian R, et al., "Virulence of Avian Influenza A Viruses for Squirrel Monkeys", Infection and Immunity 37 (3), (Sep. 1982), 1119-1126.
Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.
Muyldermans, S, "Nanobodies: Natural single-domain antibodies", Ann. Rev. Biochem. 82, (2013), 1 pg.
Naim, H. Y., et al., "Basis for Selective Incorporation of Glycoproteins into the Influenza Virus Envelope", Journal of Virology, 67(8), (1993), 4831-4841.

(56) References Cited

OTHER PUBLICATIONS

Naito, S., et al., "Function and Structure of RNA Polymerase From Vesicular Stomatitis Virus", The Journal of Biological Chemistry, 251(14), (1976), 4307-4314.
Nara, et al., "How Can Vaccines Against Influenza and Other Viral Diseases Be Made More Effective?", PLoS Biology, 8 (12), (2010), e1000571.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "A Decade After the Generation of a Negative-Sense RNA Virus From Cloned cDNA-What Have We Learned?", Journal of General Virology, 83(11), (Nov. 2002), 2635-2662.
Neumann, G., et al., "An Improved Reverse Genetics System for Influenza A Virus Generation and Its Implications for Vaccine Production", Proc. Natl. Acad. Sci. USA, 102(46) 16825-16829, (2005), 5 pgs.
Neumann, G., et al., "An improved reverse genetics system for influenza A virus generation and its implications for vaccine production", Proc. Natl. Acad. Sci. USA. 102(46), (2005), 16825-16829.
Neumann, G., et al., "Emergence and pandemic potential of swine-origin HIN1 influenza virus", Nature (London), 459(7249), (Jun. 2009), 931-939.
Neumann, G., et al., "Generation of influenza A virus from cloned cDNAs—historical perspective and outlook for the new millenium.", Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.
Neumann, G., et al., "Genetic Engineering of Influenza and Other Negative-Strand RNA Viruses Containing Segmented Genomes", Advances in Virus Research, 53, (1999), 265-300.
Neumann, G., et al., "Influenza A virus NS2 protein mediates vRNP nuclear export through NES-independent interaction with hCRM1", The EMBO Journal, 19 (24), (2000), 6751-6758.
Neumann, G., et al., "Mutational analysis of influenza virus promoter elements in vivo", Journal of General Virology, 76 1709-1717, (1995), 9 pgs.
Neumann, G., et al., "Nuclear Import and Export of Influenza Virus Nucleoprotein", Journal of Virology, 71(12), (1997), 9690-9700.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "Reverse genetics of influenza virus.", Virology, 287(2), (Sep. 1, 2001), 243-50.
Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, G., et al., "Synthesis of Influenza Virus: New impetus from an old enzyme, RNA polymerase I", Virus Research 82(1-2), (Jan. 30, 2002), 153-158.
Neumann, Gabriele, "Minireview Reverse Genetics of Influenza Virus", Virology, vol. 287, (2001), 243-250.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.
Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.
Niwa, H., et al., "Efficient Selection for High-Expression Transfectants With a Novel Eukaryotic Factor", Gene, 108(2), (1991), 193-199.
Noda, Takeshi, et al., "Three-dimensional analysis of ribonucleoprotein complexes in influenza A virus", Nature Communications, 3, (2012), 1-6.
Odagiri, T., et al., "Nucleotide Sequence of the PA Gene of Influenza A/WSN/33 (H1N1)", Nucleic Acids Research, 18 (3), Department of Virology, (Jan. 9, 1990), 1 pg.
Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.
Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.
Onishi, M., et al., "Applications of retrovirus-mediated expression cloning", Experimental Hematology, 24(2), (1996), 324-329.
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Ozaki, "Generation of High-Yielding Influenza A Viruses in African Green Monkey Kidney (Vero) Cells by Reverse Genetics", J Virol 78(4), (2004), 1851-1857.
Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.
Ozawa, M., et al., "An adenovirus vector-mediated reverse genetics system for Influenza A virus generation", Journal of Virology, The American society For Microbiology, US vol. 81 (17), XP002471230, ISSN: 0022-538X, (Jun. 27, 2007), 9556-9559.
Ozawa, M., et al., "Replication-incompetent influenza A viruses that stably express a foreign gene", Journal of General Virology, 92(Part 12)., (2011), 2879-2888.
Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Scl. USA, 88(4), (1991), 1379-1383.
Pattnaik, A. K., et al., "The Termini of VSV DI Particle RNAs are Sufficient to Signal RNA Encapsidation, Replication, and Budding to Generate Infectious Particles", Virology, 206, (1995), 760-764.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Peiris, J. S. M., et al., "Re-Emergence of Fatal Human Influenza A Subtype H5N1 Disease", The Lancet, 363 617-619, (2004), 3 pgs.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

(56) References Cited

OTHER PUBLICATIONS

Pelet, T., et al., "High throughput screening assay for negative single stranded RNA virus polymerase inhibitors", Journal of Virological Methods, 128 29-36, (2005), 8 pgs.
Percy, N., et al., "Expression of a Foreign Protein by Influenza A Virus", Journal of Virology, 68(7), (1994), 4486-4492.
Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.
Perez, D. R., et al., "The Matrix 1 Protein of Influenza A Virus Inhibits the Transcriptase Activity of a Model Influenza Reporter Genome in Vivo", Virology, 249(1), (1998), 52-61.
Perez, Jasmine T., et al., "Unit 15G.4—Insertion of a GFP Reporter Gene in Influenza Virus", Curr Protoc Microbiol., (2013), 20 pgs.
Peterson, B. C., et al., "Homologous sequences other than insertion elements can serve as recombination sites in plasmid drug resistance gene amplification", Journal of Bacteriology, Oct. 1983. 156(1) 177-185, (1983), 5 pgs.
Piatti, G., "Identification of immunodominant epitopes In the filamentous Hemagglutinin of Bordetella pertusis", FEMS Immunology and Medical Microbiology, 23(3), (1999), 235-241.
Piller, S C., et al., "Vpr protein of human immunodeficiency virus type 1 forms cation-selective channels in planar lipid bilayers", PNAS, 93, (1996), 111-1115.
Ping, J., et al., "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza A virus vaccine viruses", Nature Communications, [online]. Retrieved from the Internet: <http://www.nature.com/article-assets/npg/ncomms/2015/150902/ncomms9148/extref/ncomms9148-sl.pdf>, (Sep. 2, 2015), 50 pgs.
Pinto, L. H., et al., "Influenza Virus M2 Protein Has Ion Channel Activity", Cell, 69, (May 1992), pp. 517-528.
Pittman, Kelly J., et al., "Z-DNA Binding Protein Mediates Host Control of Toxoplasma gondii Infection", Infection and Immunity, 84(10), (Oct. 2016), 3063-3070.
Plant, E P, et al., "Mutations to A/PuertoRico/8/34 PB1 gene improves seasonal reassortant influenza A virus growth kinetics", Vaccine, 31(1), (Dec. 1, 2012), 207-212.
Pleschka, S., et al., "A Plasmid-Based Reverse Genetics System for Influenza A Virus", Journal of Virology, 70(6), (1996), 4188-4192.
Pley, H. W., et al., "Three-Dimensional Structure of a Hammerhead Ribozyme", Nature, 372, (1994), 68-74.
Popova, Lyubov, et al., "Immunodominance of Antigenic Site B over Site of Hemagglutinin of Recent H3N2 Influenza Viruses", PLoS One, vol. 7 No. 7, (Jul. 25, 2012), e41895.
Portela, A., et al., "Replication of orthomyxoviruses", Advances in Virus Research, 54, (1999), 319-348.
Potter, C. W., "Chapter 1—Chronicle of Influenza Pandemics", In: Textbook of Influenza, Nicoholson, K. G., et al., Editors, (Blackwell Scientific Publication), (1998), 3-18.
Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.
Preston, Andrew, "Choosing a Cloning Vector", Methods in Molecular Biology, vol. 235, *E. coli* Plasmid Vectors 19-27, Edited by: N. Casali and A. Preston, (2003), 9 pgs.
Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.
Puzelli, S., et al., "Changes in the Hemagglutinins and Neuraminidase of Human Influenza B Viruses Isolated in Italy During the Feb. 2001, Mar. 2002, and Apr. 2003 Seasons", Journal of Medical Virology, 74(4) 629-640, (2004), 12 pgs.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981), 4 pgs.
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.
Rayner, J., et al., "Alphavirus vectors and vaccination", Reviews in Medical Virology, 12, (2002), 279-296.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Restifo, N. P., et al., "Transfectant Influenza A Viruses are Effective Recombinant Immunogens in the Treatment of Experimental Cancer", Virology, 249(1), (1998), 89-97.
Ricardo-Lax, I., et al., "Replication and single-cycle delivery of SARS-CoV-2 replicons", Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Roberts, A., et al., "Minireview—Recovery of Negative-Strand RNA Viruses From Plasmid DNAs: A Positive Approach Revitalizes a Negative Field", Virology, 247(1), (1998), 1-6.
Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.
Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 (Pt 4) 799-802, (Apr. 1984), 4 pgs.
Ruigrok, R W, et al., "Structural Characterization and Membrane Binding Properties of the Matrix Protein VP40 of Ebola Virus", Journal of Molecular Biology, 300(1), (2000), 103-112.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.
Sansom, M. S., et al., "Influenza virus M2 Protein: a molecular modelling study of the ion channel", Protein Engineering, 6 (1), (1993), pp. 65-74.
Saphire, E. O., et al., "Feverish Quest for Ebola Immunotherapy: Straight or Cocktail", Trends Microbial, 24(9), (Sep. 2016), 684-686.
Satterlee, B., "Production of H5N1 avian influenza virus vaccine by plasmid-based reverse genetics technology", Basic Biotechnology eJournal, vol. 4, pp. 93-98, (2008), 93-98 Pgs.
Saunders, Kevin O., et al., "Neutralizing antibody vaccine for pandemic and pre-emergent coronaviruses", Nature, 594, (2021), 553-559 (27 pgs.).
Schares, G., et al., "Oocysts of Neospora caninum, Hammondia heydorni, Toxoplasma gondil and Hammondia hammondi in faeces collected from dogs in Germany", International Journal of Parasitology, vol. 35, No. 14, (Dec. 1, 2005), XP027737007, (Dec. 1, 2005), 1525-1537.

(56) References Cited

OTHER PUBLICATIONS

Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Schotsaert, M, et al., "Universal M2 ectodomain-based influenza A vaccines: preclinical and clinical developments", Expert Rev V accines. Apr. 2009;8(4):, 499-508.
Schultz-Cherry, S., et al., "Influenza Virus NS1 Protein Induces Apoptosis in Cultured Cells", Journal of Virology, 75(17), (2001), 7875-7881.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Sheridan, Cormac, et al., "Innovators target vaccines for variants and shortages in global South", Nature Biotechnology, 39(4), (Apr. 2021), 393-396.
Shi, Pei-Yong, "Infectious cDNA Clone of the Epidemic West Nile Virus from New York City", Journal of Virology 5847-5856, (Jun. 2002), 10 pgs.
Shimojima, M., et al., "Tyro3 family-mediated cell entry of Ebola and Marburg viruses", J Virol., 80(20), (Oct., 2006), 10109-16.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Shortridge, K. F., et al., "Characterization of Avian H5N1 Influenza Viruses From Poultry in Hong Kong" Virology, 252 331-342, (1998), 12 pgs.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.
Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.
Skehel, J. J., et al., "On the Mechanism of Inhibition of Influenza Virus Replication by Amantadine Hydrochloride", The Journal of General Virology, 38 (1), (1977), pp. 97-110.
Smatti, Maria K., et al., "Viral-Induced Enhanced Disease Illness", Front Microbiol, vol. 9: Article 2991, (Dec. 2018), 1-19.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Smura, T, "Surface glycoprotein [Severe acute respiratory syndrome coronavirus 2]", Gen Bank Accessions QH062107, (Feb. 11, 2020), 2 pgs.
Stray, S. J., et al., "Influenza virus infection of desialylated cells", Glycobiology, 10(7), (2000), 649-658.
Strobel, I., et al., "Efficient Expression Of The Tumor-Associated Antigen MAGE-3 In Human Dendritic Cells, Using An Avian Influenza Virus Vector", Human Gene Therapy, 11(16), (2000), 2207-2218.
Stroud, Chad K., et al., "Disruption of FADS2 gene in mice impairs male reproduction and causes dermal and intestinal ulceration", Journal of Lipid Research, vol. 50, (2009), 1870-1880.
Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Characterization of an Avian Influenza A (H5N1) Virus Isolated From a Child With a Fatal Respiratory Illness", Science, 279, (1998), 393-396.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5. 2003), 192-200.
Sugawara, K., et al., "Development of Vero Cell-Derived Inactivated Japanese Encephalities Vaccine", Biologicals, 30 303-314, (2002), 12 pgs.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sun, Weina, et al., "Development of Influenza B Universal Vaccine Candidates Usingthe "Mosaic" Hemagglutinin Approach", American Society For Microbiology, Journal of Virology, Vaccines and Antiviral Agents, vol. 93, Issue 12, (Jun. 2019), 17 pgs.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Takada, A., et al., "Downregulation of beta1 integrins by Ebola virus glycoprotein: implication for virus entry", Virology, 278(1), (Dec. 2000), Abstract Only.
Takada, Ayato, et al., "A system for functional analysis of Ebola? virus?glycoprotein", Proc. Natl. Acad. Sci. USA, 94(26), (1997), 14764-14769.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Infectivity-Enhancing Antibodies to Ebola Virus Glycoprotein", Journal of Virology, 75(5), (2001), 2324-2330.
Takada, Ayato, et al., "Protective efficacy of neutralizing antibodies against Ebola virus infection", Vaccine, 25(6), (2007), 993-999.
Takada, Ayato, et al., "The pathogenesis of Ebola hemorrhagic fever", Trends in Microbiology, 9(10), (2001), 506-511.
Takada, Kosuke, et al., "A Humanized MDCK Cell Line for the Efficient Isolation and Propagation of Human Influenza Viruses",

(56) References Cited

OTHER PUBLICATIONS

Nature Microbiology, Nature Publishing Group UK, London, vol. 4, No. 8, (Apr. 29, 2019), 1268-1273.
Takeda, M., et al., "Influenza a virus M2 ion channel activity is essential for efficient replication in tissue culture.", J Virol., 76(3), (Feb. 2002), 1391-9.
Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.
Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Terry, G., et al., "The Contruction of Defective Interfering Rubella Virus Particles", Archives of Virology, 145(3), (2000), 625-633.
Tetsutani, K., et al., "Adjuvants in Influenza Vaccines", Vaccine 2012, vol. 30, (2012), 4 pgs.
Thao, Tran Thi Nhu, et al., "Rapid reconstruction of SARS-CoV-2 using a synthetic genomics platform", Nature, vol. 582 561-565, (2020), 24 pgs.
Theriault, S., "The role of reverse genetics systems in determining filovirus pathogenicity", Archives of Virology, Supplementum. 157-177. (2005), 22 pgs.
Thompson, Christine M, et al., "Critical assessment of influenza VLP production in Sf9 and HEK293 expression systems", BMC Biotechnology, 15(1), (May 16, 15), 12 pgs.
Thompson, W. W., et al., "Mortality Associated With Influenza and Respiratory Syncytial Virus in the United States", JAMA, 289(2) 179-186, (2003), 8 pgs.
Tobler, K, et al., "Effect of cytoplasmic tail truncations on the activity of the M(2) ion channel of influenza A virus", J Virol., 73(12), (Dec. 1999), 9695-9701.
Towner, J S, et al., "Generation of eGFP express ing recombinant Zaire ebolavirus for analysis of early pathogenesis events and high-throughput antiviral drug screening", Virology, Academic Press , Orlando, US, vol. 332, No. 1 20-27, XP004715289 ISSN: 0042-6822 the whole document, (Feb. 5, 2005), 8 pgs.
Treanor, J. J, et al., "The B allele of the NS gene of avian influenza viruses, but not the A allele, attenuates a human influenza a virus for squirrel monkeys", Virology, 171(1), (1989), 1-9.
Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Vaishnava, Shipra, et al., "The Antibacterial Lectin RegIlly Promotes the Spatial Segregation of Microbiota and Host in the Intestine", Science, 334 255-258, (2011), 4 pgs.
Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.nlm.nih.gov/pmc/articles/PMC7181998/pdf/main.pdf>, (Apr. 24, 2020), 17 pgs.
Varner, Chad, "Developing Synthetic Multivalent Cellular Effectors", Thesis, School of Chemical and Biomolecular Engineering, Georgia Institute of Technology, (Aug. 2017), 88 pgs.
Verma, I. M, et al., "Gene Therapy—Promises, Problems and Prospects", Nature, 389, (1997), 239-242.
Via, L. E, et al., "Isolation of restriction fragments from large plasmids recovered from bacteria with multiple plasmids", Biotechniques, 11(4), (Oct. 1991), Abstract Only.
Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisonsin—Mad, (Feb. 1, 2012), 7.
Victor, Sylvia, et al., "A Replication-Incompetent PB2-Knockout Influenza A Virus Vaccine Vector", Journal of Virology, vol. 86, No. 8, (Apr. 2012), 4123-4128.
Vincke, C, et al., "Introduction to heavy chain antibodies and derived nanobodies", Meth. Mol. Biol. 911, (2012), 13 pgs.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
Waap, Helga, et al., "In vitro isolation and seroprevalence ofin stray cats and pigeons in Lisbon, Portugal", Veterinary Parasitology, vol. 187, No. 3 XP028492469 542-547, (Jan. 17, 2012), 6 pgs.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.
Wan, Yushun, et al., "Molecular mechanism for Antibody-Dependent Enhancement of Coronavirus EntrM", Journal of Virology, 94(5): e02015-19, (2019), 1-15.
Wang, et al., "Glycoengineering of CHO Cells to Improve Product Quality", Methods in Molecular Biology book series (MIMB, vol. 1603) 25-44, (May 11, 2017), 256 pgs.
Wang, B., et al., "Construction of Non-infectious SARS-CoV-2 Replicons and Their Application in Drug Evaluation", Virologica Sinica, 36, (2021), 890-900.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Sheng-Fan, et al., "Antibody-dependent SARS coronavirus infection is mediated by antibodies against spike proteins", Biochem Biophys Res Commun, 451 208-214, (2014), 18 pgs.
Wang, Wenlig, et al., "Robust Immunity and Heterologous Protection against Influenza in Mice Elicited by a Novel Recombinant NP-M2e Fusion Protein Expressed in *E. coli*", PLoS One 7(12): e52488, (Dec. 2012), 1-13.
Wanitchang, Asawin, et al., "Characterization of influenza A virus pseudotyped with the spike protein of porcine epidemic diarrhea virus", Archives of Virology, 163(12), (2018), 3255-3264.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Warfield, et al., "", PNAS, vol. 100(26), (2003), pp. 5889-15894.

(56) References Cited

OTHER PUBLICATIONS

Watanabe, S., et al., "Ebola virus (EBOV) VP24 inhibits transcription and replication of the EBOV genome", J Infect Dis., 196(Suppl 2), (Nov. 15, 2007), S284-90.
Watanabe, S., et al., "Influenza A Virus Lacking M2 Protein as a Live Attenuated Vaccine", Journal of Virology, 83(11), (2009), 5947-5950.
Watanabe, S., et al., "Production of Novel Ebola Virus-Like Particles from cDNAs: an Alternative to Ebola Virus Generation by Reverse Genetics", Journal of Virology, 78(2). (Jan. 2004), 999-1005.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals To Generate a Novel In?uenza Virus-Based Vector Stably Expressing Two Foreign Genes", Journal of Virology, 77(19), (Oct. 2003), 10575-10583.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Weber, F., et al., "Conserved vRNA end sequences of Thogoto-orthomyxovirus suggest a new panhandle structure", Archives of Virology, 142(5), (1997), 1029-1033.
Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.
Webster, R G, et al., "Evolution and molecular epidemiology of H9N2 influenza A viruses from quail in southern China", XP002744257, retrieved from EBI accession No. UNIPROT:A3R6C9 Database accession No. A3R6C9 the whole document, (Apr. 3, 2007), 1 pg.
Wei, Hung-Ju, et al., "Fabrication of influenza virus-like particles using M2 fusion proteins for imaging single viruses and designing vaccines", Vaccine, 29, (2011), 7163-7172.
Wei, Kai, et al., "Influenza A Virus Acquires Enhanced Pathogenicity and Transmissibility after Serial Passages in Swine", Journal of Virology, 88(20), (Oct. 2014), 11981-11994.
Wentworth, D E, et al., "The NIAID Influenza Genome Sequencing Project", XP002744258, retrieved from EBI accession No. UNIPROT:U3S198 Database accession No. U3S198 the whole document, (Dec. 11, 2013), 1 pg.
Whelan, S. P. J., et al., "Efficient Recovery of Infectious Vesicular Stomatitis Virus Entirely from cDNA Clones", Proc. Natl. Acad. Scl. USA, 92, (1995), 8388-8392.
Wiedmer, T., et al., "Identification of three new members of the phospholipid scramblase gene family", Biochim Biophys Acta, 1467(1), (Jul. 31, 2000), Abstract Only.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wills, J. W., et al., "An Assembly Domain of the Rous Sarcoma Virus Gag Protein Required Late in Budding", Journal of Virology, 68(10), (1994), 6605-6618.
Wilson, et al., "Vaccine Potential of Ebola Virus VP24, VP30, VP35 and VP40 Proteins", Virology 286, (2001), 384-90.
Wilson, Julie A, et al., "Epitopes Involved in Antibody-Mediated Protection from Ebola Virus", Science, 287(5458), (Mar. 2000), 1664-1666.
Winkler, K, et al., "Changing the antigen binding specificity by single point mutations of an anti-p24 (HIV-1) antibody", J. Immunol. 165 4505-4514, (2000), 11 pgs.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wood, J. M., et al., "From Lethal Virus to Life-Saving Vaccine: Developing Inactivated Vaccines for Pandemic Influenza", Nature Reviews Microbiology, 2(10), (2004), 842-847.
Wu, Rui, et al., "A live bivalent influenza vaccine based on a H9N2 virus strain", Vaccine, 28, (2010), 673-680.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J, et al., "Modification in framework region I results in a decreased affinity of chimeric anti-Tag72 antibody", Mol. Immunol. 28(1/2), (1991), 141-148.
Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10.3390/v15010095, (2023), 23.
Xu, Ruodan, et al., "Construction of SARS-CoV-2 Virus-Like Particles by Mammalian Expression System", Frontiers in Bioengineering and Technology, 8:862, (2020), 1-6.
Xu, X., et al., "Reassortment and evolution of current human influenza A and B viruses", Virus Research, 103, (2004), 55-60.
Yagi, Y., et al., "In silico panning for a non-competitive peptide inhibitor", BMC Bioinformatics, 8(11), (2007), 11 pgs.
Yamamoto, K., et al., "Orientation Dependence in Homologous Recombination", Genetics May 1996; 143(1): 27-36, (1996), 27-36.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yang, P., et al., "Hemagglutinin Specificity and Neuraminidase Coding Capacity of Meuraminidase-Deficient Influenza Viruses", Virology, 229(1), (1997), 155-165.
Yang, Z. Y, et al., "Identification of the Ebola virus glycoprotein as the main viral determinant of vascular cell cytotoxicity and injury", Nat Med., 6(8), (Aug. 2000), Abstract Only.
Yannarell, Dean A., et al., "Factors affecting the yield of cold-adapted influenza virus vaccine", Journal of Virological Methods, vol. 64, 161-169, (1997), 1 pg.
Yasuda, J., "Growth Control of Influenza A Virus by M1 Protein: Analysis of Transfectant Viruses Carrying the Chimeric M Gene", Journal of Virology, 68(12), (1994), 8141-8146.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yip, Ming S., et al., "Antibody-dependent infection of human macrophages by severe acute respiratory syndrome coronavirus", Virology Journal, 11: 82, (2014), 11 pgs.
Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

(56) References Cited

OTHER PUBLICATIONS

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.
Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zeitlin, L., et al., "Antibody Therapeutics for Ebola Virus Disease", Curr. Opin. Viral. 17:, (2016), 11 pgs.
Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zhang, Q.-Y., et al., "SARS-CoV-2 replicon for high-throughput antiviral screening", J Gen Virol,, 102(5), (2021), 1-4.
Zhang, V. Q, et al., "Easy two-step method for randomizing and cloning gene fragments", Methods Mol Biol., 634, (2010), Abstract Only.
Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.
Zhang, Y., et al., "A bacterial artificial chromosome (BAC)-vectored noninfectious replicon of SARS-CoV-2", Antiviral Research, vol. 185, 104974, (Jan. 2021), 1-9.
Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.
Zhou, Yan, "Membrane-Anchored Incorporation of a Foreign Protein in Recombinant Influenza Virions", Virology 246(1), (1998), 83-94.
Zobel, A., et al., "RNA Polymerase I Catalysed Transcription of Insert Viral cDNA", Nucleic Acids Research, 21(16), (1993), 3607-3614.
"U.S. Appl. No. 16/170,321, Advisory Action mailed Feb. 23, 2021", 3 pgs.
"U.S. Appl. No. 16/170,321, Corrected Notice of Allowability mailed Sep. 29, 2021", 2 pgs.
"U.S. Appl. No. 16/170,321, Final Office Action mailed Dec. 14, 2020", 13 pgs.
"U.S. Appl. No. 16/170,321, Non Final Office Action malled Apr. 13, 2020", 13 pgs.
"U.S. Appl. No. 16/170,321, Notice of Allowance mailed Aug. 4, 2021", 10 pgs.
"U.S. Appl. No. 16/170,321, PTO Response to Rule 312 Communication mailed Sep. 1, 2021", 2 pgs.
"U.S. Appl. No. 16/170,321, Response filed Jan. 24, 2020 to Restriction Requirement mailed Nov. 27, 2019", 9 pgs.
"U.S. Appl. No. 16/170,321, Response filed Jan. 26, 2021 to Final Office Action malled Dec. 14, 2020", 9 pgs.
"U.S. Appl. No. 16/170,321, Response filed Mar. 9, 2021 to Advisory Action mailed Feb. 23, 2021", 9 pgs.
"U.S. Appl. No. 16/170,321, Response filed Sep. 11, 2020 to Non Final Office Action mailed Apr. 13, 2020", 9 pgs.
"U.S. Appl. No. 16/170,321, Restriction Requirement mailed Nov. 27, 2019", 10 pgs.
"European Application Serial No. 18800815.5, Response to Communication pursuant to Rules 161(1) and 162 EPC filed Dec. 15, 2020", 14 pgs.
"International Application Serial No. PCT/US2018/057576, International Preliminary Report on Patentability mailed May 7, 2020", 12 pgs.
"International Application Serial No. PCT/US2018/057576, International Search Report mailed Mar. 25, 2019", 7 pgs.
"International Application Serial No. PCT/US2018/057576, Invitation to Pay Additional Fees and Partial Search Report mailed Jan. 31, 2019", 16 pgs.
"International Application Serial No. PCT/US2018/057576, Written Opinion mailed Mar. 25, 2019", 10 pgs.
"Japanese Application Serial No. 2020-523276, Notification of Reasons for Refusal mailed Jul. 27, 2021", w/ English Translation, 12 pgs.
Kuwahara, Tomoko, et al., "Characterization of cell-derived and egg-passaged influenza A/Saitama/103/2014 (H3N2) strain", The 65th Annual Meeting of the Japanese Society of Virology, (2017), 1 pg.
Ramanunninair, Manojkumar, et al., "Molecular Signature of High Yield (Growth) Influenza A Virus Reassortants Prepared as Candidate Vaccine Seeds", PLoS One, 8(6): e65955, (2013), 1-16.
Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.
Yen, H L, et al., "Neuraminidase Inhibitor-Resistant Recombinant A/Vietnam/1203/04 (K5N1) Influenza Viruses Retain Their Replication Efficiency and Pathogenicity In Vitro and In Vivo", Journal Of Virology., vol. 81, No. 22, (Nov. 15, 2007), 12418-12426.
"Japanese Application Serial No. 2020-523276, Response filed Jan. 12, 2022 to Notification of Reasons for Refusal mailed Jul. 27, 2021", w English Claims, 27 pgs.
"Japanese Application Serial No. 2020-523276, Examiners Decision of Final Refusal mailed May 10, 2022", w English Translation, 13 pgs.
"Japanese Application Serial No. 2022-144599, Voluntary Amendment filed Nov. 9, 2022". w English Claims, 14 pgs.
U.S. Appl. No. 16/170,321, U.S. Pat. No. 11,197,926, filed Oct. 25, 2018, Recombinant Influenza Viruses With Stabilized HA for Replication in Eggs.
"U.S. Appl. No. 17/212,836, Response filed May 16, 2023 to Non Final Office Action mailed Feb. 16, 2023", 7 pgs.
"European Application Serial No. 18800815.5, Communication Pursuant to Article 94(3) EPC mailed May 9, 2023", 6 pgs.
"U.S. Appl. No. 16 785,449, Response filed May 22, 2023 to Final Office Action mailed Mar. 22, 2023", 9 pgs.
"U.S. Appl. No. 16/785,449, Advisory Action mailed Jun. 7, 2023", 17 pgs.
"U.S. Appl. No. 17/212,836, Final Office Action mailed Jun. 22, 2023", 15 pgs.
"U.S. Appl. No. 18/173,535, Preliminary Amendment filed Jun. 26, 2023", 16 pgs.
"U.S. Appl. No. 16/785,449, Response filed Jul. 13, 2023 to Advisory Action mailed Jun. 7, 2023", 12 pgs.
"U.S. Appl. No. 17/004,583, Notice of Allowability mailed Aug. 1, 2023", 2 pgs.
"U.S. Appl. No. 18/365,082, Preliminary Amendment filed Aug. 3, 2023", 4 pgs.
"U.S. Appl. No. 16/785,449, Notice of Allowance mailed Aug. 7, 2023", 14 pgs.
Abdoli, Mohsen, "Intranasal administration of cold-adapted live-attenuated SARS-CoV-2 candidate vaccine confers protection against SARS-CoV-2", Virus Research 319 198857, (2022), 10 pgs.
Faizuloev, Evgeny, "Cold-adapted SARS-CoV-2 variants with different sensitivity exhibit an attenuated phenotype and confer protective immunity", Science Direct Vaccine 41 892-902, (2023), 12 pgs.
Lu, Shan, "The SARS-CoV-2 nucleocapsid phosphoprotein forms mutually exclusive condensates with RNA and the membrane-associated M protein", nature communications 12:502, (2021), 15 pgs.
Plescia, Caroline B, "SARS-CoV-2 viral budding and entry can be modeled using BSL-2 level virus-like particles", JBC Research Article, (Nov. 19, 2020), 10 pgs.

(56) References Cited

OTHER PUBLICATIONS

Seo, Sang Heui, "Cold-Adapted Live Attenuated SARS-COV-2 Vaccine Completely Protects Human ACE2 Transgenic Mice from SARS-Cov-2 Infection", Vaccines 2020 8, 584, (Oct. 3, 2020), 17 pgs.
Swann, Heather, "Minimal system for assembly of SARS CoV 2 virus like particles", Scientific Reports 10:21877 nature portfolio, (2020), 1-5.
Zhang, Zhikuan, "Structure of SARS-CoV-2 membrane protein essential for virus assembly", nature communications 13:4399, (Aug. 5, 2022), 12 pgs.
"U.S. Appl. No. 17/212,836, Response filed Aug. 22, 2023 to Final Office Action mailed Jun. 22, 2023", 7 pgs.
"U.S. Appl. No. 17/212,836, Advisory Action mailed Aug. 29, 2023", 3 pgs.
"International Application Serial No. PCT US2023 063136, International Search Report mailed Sep. 8, 2023", 6 pgs.
"International Application Serial No. PCT US2023 063136, Written Opinion mailed Sep. 8, 2023", 7 pgs.
"U.S. Appl. No. 16/785,449, Corrected Notice of Allowability mailed Sep. 11, 2023", 10 pgs.
"Japanese Application Serial No. 2022-144599, Notification of Reasons for Refusal mailed Aug. 22, 2023", w English translation, 19 pgs.
"International Application Serial No. PCT US2023 027622, International Search Report mailed Nov. 7, 2023", 5 pgs.
"International Application Serial No. PCT US2023 027622, Written Opinion mailed Nov. 7, 2023", 6 pgs.
"U.S. Appl. No. 16/785,449, Corrected Notice of Allowability mailed Nov. 8, 2023", 10 pgs.
"U.S. Appl. No. 16/785,449, Corrected Notice of Allowability mailed Nov. 17, 2023", 10 pgs.
Liu, Shufeng, "Stable Cell Clones Harboring Self-Replicating SARS-CoV-2 RNAs for Drug Screen", Journal of Virology, vol. 96, No. 6, [Online] Retrieved from the internet:https: www.ncbi.nlm.nih.gov pmc articles PMC8941906pdf jvi.02216-21.pdf, (Mar. 23, 2022), 13 pgs.
Netland, Jason, "Immunization with an attenuated severe acute respiratory syndrome coronavirus deleted in E protein protects against lethal respiratory disease", Virolog, vol. 399, No. 1, (Jan. 27, 2010), 9 pgs.
Zhang, Xianwen, "A trans-complementation system for SARS-CoV-2 recapitulates authentic viral replication without virulence", Cell, Elsevier, Amsterdam NL, vol. 184, No. 8, (Feb. 23, 2021), 24 pgs.
"U.S. Appl. No. 17/212,836, Non Final Office Action mailed Jun. 13, 2024", 14 pgs.
"U.S. Appl. No. 18/525,460, Preliminary Amendment filed Jun. 7, 2024", 6 pgs.
"Japanese Application Serial No. 2022-144599, Notification of Reasons for Rejection mailed May 14, 2024", W/English Translation, 8 pgs.
"Japanese Application Serial No. 2022-144599, Response filed Feb. 22, 2024 to Notification of Reasons for Refusal mailed Aug. 22, 2023", w/ English claims, 8 pgs.
"International Application Serial No. PCT US2024 020952, International Search Report mailed Jul. 30, 2024", 3 pgs.
"International Application Serial No. PCT US2024 020952, Written Opinion mailed Jul. 30, 2024", 5 pgs.
"Japanese Application Serial No. 2022-144599, Response filed Aug. 14, 2024 to Notification of Reasons for Rejection mailed May 14, 2024", w English claims, 9 pgs.
"International Application Serial No. PCT US2023 063136, International Preliminary Report on Patentability mailed Sep. 6, 2024", 9 pgs.
Aria, Yasuha, "PB2 mutations arising during H9N2 influenza evolution in the Middle East confer enhanced replication and growth in mammals", PLOS Pathogens 15(7): e1007919. https: doi.org 10.1371 journal.ppat. 1007919, (Jul. 2, 2019), 25 pages.
Fan, Haitian, "Structures of influenza A virus RNA polymerase offer insight into viral genome replication", Nature 573, 287-290 (2019). https: doi.org 10.1038 s41586-019-1530-7, (Sep. 4, 2019), 35 pages.
Kamiki, Haruhiko, "Novel Biological System with Terminal Sialic Acid Knockout Cells", J Virol 96:e00416-22.https: doi.org 10.1128 jvi.00416-22, (Jul. 18, 2022), 15 pages.
Klimov, A.I., "Correlation of amino acid residues in the M1 and M2 proteins of influenza virus with high yielding properties", Virus Research, vol. 19, Issue 1,1991,pp. 105-114,ISSN 0168-1702,https: doi.org 10.10160168-1702(91)90098-G.(https: www.sciencedirect.com science article pii 016817029190098G), (Mar. 1991), 10 pages.
Ma, Wenjun, "The NS Segment of an H5N1 Highly Pathogenic Avian Influenza Virus (HPAIV) Is Sufficient To Alter Replication Efficiency, Cell Tropism, and Host Range of an H7N1 HPAIV", J Virol. Feb. 2010;84(4):2122-33. doi: 10.1128 JVI.01668-09. Epub Dec. 9, 2009. PMID: 20007264; PMCID: PMC2812369., (Feb. 2010), 12 pages.
Mahesutihan, Madina, "CypA Regulates AIP4-Mediated M1 Ubiquitination of Influenza A Virus", Virologica Sinica 33 (2018): 440-448., (Oct. 16, 2018), 9 pages.
https://pubmed.ncbi.nlm.nih.gov/30707297/ "Comparison of four adjuvants revealed the strongest protection against lethal pneumococcal challenge following immunization with PsaA-PspA fusion protein and AS02 as adjuvant", https: pubmed.ncbi.nlm.nih.gov 30707297 , 1 Med Microbiol Immunol, Apr. 2019;208(2):215-226.

Figure 1

A/Yokohama/2017/03 PB2

AGCAAAAGCAGGTCAATTATATTCAGTATGGAAAGAATAAAAGAACTACGGAACCTGATGTCGCAGTCTCGCACT
CGCGA

GATACTGACAAAAACCACAGTGGACCATATGGCCATAATTAAGAAGTACACATCGGGGAGACAGGAAAAGAACC
CGTCAC

TTAGGATGAAATGGATGATGGCAATGAAATACCCAATCACTGCTGACAAAAGGATAACAGAAATGGTTCCGGAGA
GAAAT

GAACAAGGACAAACTCTATGGAGTAAAATGAGTGATGCTGGATCAGATCGAGTGATGGTATCACCTTTGGCTGTG
ACATG

GTGGAATAGAAATGGACCCGTGACAAGTACGGTCCATTACCCAAAAGTATACAAGACTTATTTTGACAAAGTCGA
AAGGT

TAAAACATGGAACCTTTGGCCCTGTTCATTTTAGAAATCAAGTCAAGATACGCCGAAGAGTAGACACAAACCCTGG
TCAT

GCGGACCTCAGTGCCAAGGAGGCACAAGATGTAATTATGGAAGTTGTTTTTCCCAATGAAGTGGGAGCCAGGATA
CTAAC

ATCAGAATCGCAATTAACAATAACTAAAGAGAAAAAAGAAGAACTCCGAGATTGCAAAATTTCTCCCTTGATGGTT
GCAT

ACATGTTAGAGAGAGAACTTGTCCGAAAAACAAGATTTCTCCCAGTTGCTGGCGGAACAAGCAGTATATACATTG
AAGTT

TTACATTTGACTCAAGGGACGTGTTGGGAACAAATGTACACTCCAGGTGGAGAAGTGAGGAATGACGATGTTGAC
CAAAG

CCTAATTATTGCAGCCAGGAACATAGTAAGAAGAGCCGCAGTATCAGCAGATCCACTAGCATCTTTATTGGAGATG
TGCC

ACAGCACACAAATTGGCGGGACAAGGATGGTGGACATTCTTAGACAGAACCCGACTGAAGAACAAGCTGTGGAT
ATATGC

AAGGCTGCAATGGGATTGAGAATCAGCTCATCCTTCAGCTTTGGTGGGTTTACATTTAAAAGAACAAGCGGGTCAT
CAGT

CAAAAAAGAGGAAGAAGTGCTTACAGGCAATCTCCAAACATTGAAGATAAGAGTACATGAGGGGTATGAGGAGT
TCACAA

TGGTGGGGAAAAGAGCAACAGCTATACTCAGAAAAGCAACCAGAAGATTGGTTCAGCTCATAGTGAGTGGAAGA
GACGAA

Figure 1 cont.

CAGTCAATAGCCGAAGCAATAATTGTGGCCATGGTGTTTTCACAAGAGGATTGCATGATAAAAGCAGTTAGAGGT
GACCT

GAATTTCGTCAACAGAGCAAATCAGCGGTTGAACCCCATGCATCAGCTTTTAAGGCATTTTCAGAAAGATGCGAAA
GTGC

TTTTTCAGAATTGGGGAATTGAACACATCGACAGTGTAATGGGAATGGTTGGAGTATTACCAGATATGACTCCAA
GCACA

GAGATGTCAATGAGAGGAATAAGAGTCAGCAAAATGGGTGTGGATGAATACTCCAGTACAGAGAGGGTGGTGGT
TAGCAT

TGATCGGTTTTTGAGAGTTCGAGACCAACGCGGGAATGTATTATTATCTCCTGAAGAGGTTAGTGAAACACAGGG
AACTG

AGAGACTGACAATAACTTATTCATCGTCGATGATGTGGGAGATTAACGGTCCTGAGTCGGTTTTGGTCAATACTTA
TCAA

TGGATCATCAGAAATTGGGAAGCTGTCAAAATTCAATGGTCTCAGAATCCTGCAATGTTGTACAACAAAATGGAAT
TTGA

ACCATTTCAATCTTTAGTCCCCAAGGCCATTAGAAGCCAATACAGTGGGTTTGTCAGAACTCTATTCCAACAAATGA
GAG

ACGTACTTGGGACATTTGACACCACCCAGATAATAAAGCTTCTCCCTTTTGCAGCCGCTCCACCAAAGCAAAGCAG
AATG

CAGTTCTCTTCACTGACTGTAAATGTGAGGGGATCAGGGATGAGAATACTTGTAAGGGGCAATTCTCCTGTATTCA
ACTA

CAACAAGACCACTAAAAGACTAACAATTCTCGGAAAAGATGCCGGCACTTTAATTGAAGACCCAGATGAAAGCAC
ATCCG

GAGTGGAGTCCGCTGTATTGAGAGGGTTTCTCATTATAGGTAAGGAAGACAGAAGATACGGGCCAGCATTAAGC
ATCAAT

GAACTGAGTAACCTTGCAAAAGGGGAAAAGGCTAATGTGCTAATCGGGCAAGGAGACGTGGTGTTGGTAATGAA
ACGAAA

ACGGGACTCTAGCATACTTACTGACAGCCAGACAGCGACCAAAAGAATTCGGATGGCCATCAATTAATGTTGAAT
AGTTT

AAAAACGACCTTGTTTCTACT (SEQ ID NO:4)

<u>A/Yokohama/2017/03 PB1</u>

AGCAAAAGCAGGCAAACCATTTGAATGGATGTCAATCCGACTCTACTGTTCCTAAAGGTTCCAGCGCAAAATGCCA
TAAG

Figure 1 cont.

CACCACATTCCCTTATACTGGAGATCCTCCATACAGCCATGGAACAGGAACAGGGTACACCATGGACACAGTCAAC
AGAA

CACACCAATATTCAGATAAGGGGAAGTGGACGACAAATACAGAAACTGGGGCACCCCAACTCAACCCAATTGATG
GACCA

CTACCTGAGGATAATGAGCCAAGTGGATATGCACAAACAGACTGTGTCCTGGAGGCTATGGCCTTCCTTGAAGAA
TCCCA

CCCAGGTATCTTTGAGAACTCATGCCTTGAAACAATGGAAGTCGTTCAACAAACAAGGGTGGACAAACTAACCCA
AGGTC

GCCAGACTTATGATTGGACATTAAACAGAAATCAACCGGCAGCAACTGCATTAGCCAACACCATAGAAGTTTTTAG
ATCG

AATGGACTAACAGCTAATGAATCAGGAAGGCTAATAGATTTCCTCAAGGATGTGATGGAATCAATGGATAAAGAG
GAAAT

GGAGATAACAACACACTTTCAAAGAAAAAGGAGAGTAAGAGACAACATGACCAAGAAAATGGTCACACAAAGAA
CAATAG

GGAAGAAAAAACAAAGAGTGAATAAGAGAGGCTATCTAATAAGAGCTTTGACATTGAACACGATGACCAAAGAT
GCAGAG

AGAGGTAAATTAAAAAGAAGGGCTATTGCAACACCCGGGATGCAAATTAGAGGGTTCGTGTACTTCGTTGAAACT
TTAGC

TAGAAGCATTTGCGAAAAGCTTGAACAGTCTGGACTTCCGGTTGGGGGTAATGAAAAGAAGGCCAAACTGGCAA
ATGTTG

TGAGAAAAATGATGACTAATTCACAAGACACAGAGCTTTCTTTCACAATCACTGGGGACAACACTAAGTGGAATG
AAAAT

CAAAACCCTCGAATGTTTTTGGCGATGATTACATATATCACAAAAAATCAACCTGAGTGGTTCAGAAACATCCTGA
GCAT

CGCACCAATAATGTTCTCAAACAAAATGGCAAGACTGGGAAAAGGATACATGTTCGAGAGTAAGAGAATGAAACT
CCGAA

CACAAATACCCGCAGAAATGCTAGCAAACATTGACCTGAAGTATTTCAATGAATCAACAAGGAAGAAAATTGAGA
AAATA

AGGCCTCTTCTAATAGATGGCACAGCATCATTGAGCCCTGGGATGATGATGGGCATGTTCAACATGCTAAGTACG
GTTTT

AGGAGTCTCGATACTGAATCTTGGGCAAAAGAAATACACCAAGACAACATACTGGTGGGATGGGCTCCAATCCTC
CGACG

ATTTTGCCCTCATAGTGAATGCACCAAATCATGAGGGAATACAAGCAGGAGTGGATAGATTTTACAGGACCTGCA
AGTTA

Figure 1 cont.

GTGGGAATCAACATGAGCAAAAAGAAGTCCTATATAAATAAAACAGGGACATTTGAATTCACAAGCTTTTTTTATC
GATA

TGGATTTGTGGCTAATTTTAGCATGGAGCTGCCCAGTTTTGGAGTGTCTGGAATAAACGAGTCAGCTGATATGAGC
ATTG

GAGTAACAGTGATAAAGAACAACATGATAAACAATGACCTTGGACCAGCAACAGCCCAGATGGCTCTCCAATTGT
TCATC

AAAGACTACAGATATACATATAGGTGCCATAGAGGAGACACACAAATTCAGACGAGAAGATCATTCGAGCTAAAG
AAGCT

GTGGGATCAAACCCAATCAAGGGCAGGACTATTGGTATCAGATGGGGGACCAAACTTATACAATATCCGGAATCT
TCACA

TCCCTGAAGTCTGCTTAAAGTGGGAGCTAATGGATGAGAATTATCGGGGAAGACTTTGTAATCCCCTGAATCCCTT
TGTC

AGCCATAAAGAAATTGAGTCTGTAAACAATGCTGTAGTGATGCCAGCCCATGGTCCGGCCAAAAGTATGGAATAT
GATGC

CGTTGCAACTACACACTCCTGGATTCCCAAGAGGAACCGCTCTATTCTCAACACAAGCCAAAGGGGAATTCTTGAG
GATG

AACAGATGTACCAGAAGTGCTGCAACTTGTTCGAGAAATTTTTCCCTAGTAGTTCATATAGGAGACCGATTGGAAT
TTCT

AGCATGGTGGAGGCCATGGTGTCTAGGGCCCGGATTGATGCCAGAATTGACTTCGAGTCTGGACGGATTAAGAA
GGAAGA

GTTCTCTGAGATCATGAAGATCTGTTCCACCATTGAAGAACTCAGACGGCAAAAATAATGAATTTAGCTTGTCCTTC
ATG

AAAAAATGCCTTGTTTCTACT (SEQ ID NO:5)

A/Yokohama/2017/03 PA

AGCAAAAGCAGGTACTGATTCGAAATGGAAGATTTTGTGCGACAATGCTTCAACCCGATGATTGTCGAACTTGCA
GAAAA

AGCAATGAAAGAGTATGGGGAGGATCTGAAAATTGAAACAAACAAATTTGCAGCAATATGCACTCACTTGGAGGT
ATGTT

TCATGTATTCAGATTTTCATTTCATCAATGAACAAGGCGAATCAATAGTGGTAGAACTTGATGATCCAAATGCACTG
TTA

AAGCACAGATTTGAAATAATCGAGGGGAGAGACAGAACAATGGCCTGGACAGTAGTAAACAGTATCTGCAACAC
TACTGG

Figure 1 cont.

AGCTGAAAAACCGAAGTTTCTACCAGATTTGTATGATTACAAGGAGAACAGATTCATCGAAATTGGAGTGACAAG
GAGAG

AAGTCCACATATATTACCTTGAAAAGGCCAATAAGATTAAATCTGAGAACACACACATTCACATTTTCTCATTCACT
GGG

GAGGAAATGGCCACAAAGGCAGACTACACTCTCGACGAGGAAAGCAGGGCTAGGATTAAGACCAGGCTATTTAC
CATAAG

ACAAGAAATGGCCAACAGAGGCCTCTGGGATTCCTTTCGTCAGTCCGAAAGAGGCGAAGAAACAATTGAAGAAA
AATTTG

AAATCTCAGGAACTATGCGTAGGCTTGCCGACCAAAGTCTCCCACCGAACTTCTCCTGCCTTGAGAATTTTAGAGC
CTAT

GTGGATGGATTCGAACCGAACGGCTGCATTGAGGGCAAGCTTTCTCAAATGTCCAAAGAAGTGAATGCCCAAATT
GAACC

TTTTCTGAAGACAACACCAAGACCAATCAAACTTCCGAATGGACCTCCTTGTTATCAGCGGTCCAAGTTCCTCCTGA
TGG

ATGCTTTAAAATTGAGCATTGAAGACCCAAGTCACGAAGGAGAAGGGATCCCATTATATGATGCGATCAAGTGCA
TAAAA

ACATTCTTTGGATGGAAAGAACCTTATATAGTCAAACCACACGAAAAGGGAATAAATTCAAATTACCTGCTGTCAT
GGAA

GCAAGTATTGTCAGAATTGCAGGACATTGAAAATGAGGAGAAGATTCCAAGGACTAAAAACATGAAGAAAACGA
GTCAAC

TAAAGTGGGCTCTTGGTGAGAACATGGCACCAGAGAAAGTAGACTTTGAAAACTGCAGAGACATAAGCGATTTGA
AGCAA

TATGATAGTGACGAACCTGAATTAAGGTCACTTTCAAGCTGGATACAGAATGAGTTCAACAAGGCCTGCGAGCTA
ACTGA

TTCAATCTGGATAGAGCTCGATGAAATTGGAGAGGACGTAGCCCCAATTGAATACATTGCAAGCATGAGGAGGAA
TTATT

TCACAGCAGAGGTGTCCCATTGTAGAGCCACTGAGTACATAATGAAGGGGGTATACATTAATACTGCCCTGCTCAA
TGCA

TCCTGTGCAGCAATGGACGATTTTCAACTAATTCCCATGATAAGCAAGTGCAGAACTAAAGAGGGAAGGCGAAAA
ACCAA

TTTATATGGATTCATCATAAAGGGAAGATCTCATTTAAGGAATGACACAGATGTGGTAAACTTTGTGAGCATGGAG
TTTT

CTCTCACTGACCCGAGACTTGAGCCACATAAATGGGAGAAATACTGTGTCCTTGAGATAGGAGATATGTTACTAAG
AAGT

Figure 1 cont.

GCCATAGGCCAAATTTCAAGGCCTATGTTCTTGTATGTGAGGACAAACGGAACATCAAAGGTCAAAATGAAATGG
GGAAT

GGAGATGAGACGTTGCCTCCTTCAGTCACTCCAGCAGATCGAGAGCATGATTGAAGCCGAGTCCTCGGTTAAAGA
GAAAG

ACATGACCAAAGAGTTTTTTGAGAATAAATCAGAAGCATGGCCCATTGGGGAGTCCCCCAAGGGAGTGGAAGAA
GGTTCC

ATTGGGAAAGTCTGTAGGACTCTATTGGCTAAGTCAGTGTTCAATAGCCTGTATGCATCACCACAATTGGAAGGAT
TTTC

AGCGGAGTCAAGAAAACTGCTCCTTGTTGTTCAGGCTCTTAGGGACAACCTCGAACCTGGGACCTTTGATCTTGGG
GGGC

TATATGAAGCAATTGAGGAGTGCCTGATTAATGATCCCTGGGTTTTGCTCAATGCGTCTTGGTTCAACTCCTTCCTG
ACA

CATGCATTAAAATAGTTATGGCAGTGCTACTATTTGTTATCCGTACTGTCCAAAAAAGTACCTTGTTTCTACT (SEQ
ID NO:6)

<u>A/Yokohama/2017/03 HA</u>

AGCAAAAGCAGGGGATAATTCTATTAACCATGAAGACTATCATTGCTTTGAGCTACATTCTATGTCTGGTTTTCGCT
CAA

AAGCTTCCCGGAAATGACAACAGCACGGCAACGCTGTGCCTTGGGCACCATGCAGTACCAAACGGAACGATAGTG
AAAAC

AATCACGAATGACCAAATTGAAGTTACTAATGCTACTGAGCTGGTTCAGAGTTCCTCAACAGGTGGAATATGCGAC
AGTC

CTCATCAGATCCTTGATGGAGAAAACTGCACACTAATAGATGCTCTATTGGGAGACCCTCAGTGTGATGGCTTCCA
AAAT

AAGAAATGGGACCTTTTTGTTGAACGCAGCAAAGCCTACAGCAACTGTTACCCTTATGATGTGCCGGATTATGCCT
CCCT

TAGGTCACTAGTTGCCTCATCCGGCACACTGGAGTTTAACAATGAAAGCTTCAATTGGACTGGAGTCACTCAGAAT
GGAA

CAAGCTCTGCTTGCAAAAGGAGATCTAATAAAAGTTTCTTTAGTAGATTGAATTGGTTGACCCACTTAAAATACAA
ATAC

CCAGCATTGAACGTGACTATGCCAAACAATGAAAAATTTGACAAATTGTACATTTGGGGGGTTCACCACCCGGGTA
CGGA

Figure 1 cont.

CAGTGATCAAATCAGCCTATATGCTCAAGCATCAGGAAGAATCACAGTCTCTACCAAAAGAAGCCAACAAACTGTA
ATCC

CGAATATCGGATCTAGACCCAGGGTAAGGGATGTCTCCAGCAGAATAAGCATCTATTGGACAATAGTAAAACCGG
GAGAC

ATACTTTTGATTAACAGCACAGGGAATCTAATTGCTCCTCGGGGTTACTTCAAAATACGAAGTGGGAAAAGCTCAA
TAAT

GAGATCAGATGCACCCATTGGCAAATGCAATTCTGAATGCATCACTCCAAATGGAAGCATTCCCAATGACAAACCA
TTTC

AAAATGTAAACAGGATCACATATGGGGCCTGTCCCAGATATGTTAAGCAAAACACTCTGAAATTGGCAACAGGGA
TGCGA

AATGTACCAGAGAAACAAACTAGAGGCATATTTGGCGCAATCGCGGGTTTCATAGAAAATGGTTGGGAGGGAAT
GGTGGA

CGGTTGGTACGGTTTCAGGCATCAAAATTCTGAGGGCACAGGACAAGCAGCAGATCTCAAAAGCACTCAAGCAGC
AATCA

ACCAAATCAATGGGAAACTGAATAGGTTAATCGGGAAAACAAACGAGAAATTCCATCAGATTGAAAAAGAATTCT
CAGAA

GTAGAAGGGAGAATTCAGGACCTCGAGAAATATGTTGAGGACACTAAAATAGATCTCTGGTCATACAACGCGGA
GCTTCT

TGTTGCCCTGGAGAACCAACATACAATTGATCTAACTGACTCAGAAATGAACAAACTGTTTGAAAGAACAAAGAA
GCAAC

TGAGGGAAAATGCTGAGGATATGGGCAATGGTTGTTTCAAAATATACCACAAATGTGACAATGCCTGCATAGAGT
CAATC

AGAAATGGAACTTATGACCATGATGTATACAGAGATGAAGCATTAAACAACCGGTTCCAGATCAAAGGTGTTGAG
CTGAA

GTCAGGATACAAAGATTGGATCCTATGGATTTCCTTTGCCATATCATGTTTTTTGCTCTGTGTTGCTTTGTTGGGGTT
CA

TCATGTGGGCCTGCCAAAAAGGCAACATTAGGTGCAACATTTGCATTTGAGTGCATTAATTAAAAACACCCTTGTT
TCTACT (SEQ ID NO:7)

A/Yokohama/2017/03 NP

AGCAAAAGCAGGGTTAATAATCACTCACTGAGTGACATCAAAATCATGGCGTCCCAAGGCACCAAACGGTCTTAT
GAACA

Figure 1 cont.

GATGGAAACTGATGGGGATCGCCAGAATGCAACTGAGATTAGGGCATCCGTCGGGAAGATGATTGATGGAATTG
GGAGAT

TCTACATCCAAATGTGCACTGAACTTAAACTCAGTGATTATGAAGGGCGGTTGATCCAGAACAGCTTGACAATAGA
GAAA

ATGGTGCTCTCTGCTTTTGATGAAAGAAGGAATAAATATCTGGAAGAACACCCCAGCGCGGGGAAAGATCCTAAG
AAAAC

TGGGGGGCCCATATACAGGAGAGTAGATGGAAAATGGATGAGGGAACTCGTCCTTTATGACAAAGAAGAAATAA
GGCGAA

TCTGGCGCCAAGCCAACAATGGTGAGGATGCGACAGCTGGTCTAACTCACATAATGATCTGGCATTCCAATTTGAA
TGAT

GCAACATACCAGAGGACAAGAGCTCTTGTTCGAACCGGAATGGATCCCAGAATGTGCTCTCTGATGCAGGGCTCG
ACTCT

CCCTAGAAGGTCCGGAGCTGCAGGTGCTGCAGTCAAAGGAATCGGGACAATGGTGATGGAGCTGATCAGAATGG
TCAAAC

GGGGGATCAACGATCGAAATTTCTGGAGAGGTGAGAATGGGCGGAAAACAAGAAGTGCTTATGAGAGAATGTG
CAACATT

CTTAAAGGAAAATTTCAAACAGCTGCACAAAGAGCAATGGTGGATCAAGTGAGAGAAAGTCGGAACCCAGGAAA
TGCTGA

GATCGAAGATCTCATATTTTTGGCAAGATCTGCATTGATATTGAGAGGATCAGTTGCTCACAAATCTTGCCTACCTG
CCT

GTGTGTATGGACCTGCAGTATCCAGTGGGTACGACTTCGAAAAAGAGGGATATTCCTTGGTGGGAATAGACCCTT
TCAAA

CTACTTCAAAATAGCCAAGTATACAGCCTAATCAGACCTAACGAGAATCCAGCACACAAGAGTCAGCTGGTATGG
ATGGC

ATGCCATTCTGCTGCATTTGAAGATTTAAGATTGTTAAGCTTCATCAGAGGGACAAAAGTATCTCCACGAGGGAAA
CTTT

CAACTAGAGGAGTACAAATTGCTTCAAATGAGAACATGGATAATATGGGATCGAGCACTCTTGAACTGAGAAGCG
GGTAC

TGGGCCATAAGGACCAGGAGTGGAGGAAACACTAATCAACAGAGGGCCTCCGCAGGCCAAACCAGTGTGCAACC
TACGTT

TTCTGTACAAAGAAACCTCCCATTTGAAAAGTCAACCATCATGGCAGCATTCACTGGAAATACGGAGGGAAGAACT
TCAG

ACATGAGGGCAGAAATCATAAGAATGATGGAAGGTGCAAAACCAGAAGAAGTGTCGTTCCGGGGGAGGGGAGT
TTTCGAG

Figure 1 cont.

CTCTCAGACGAGAAGGCAACGAACCCGATCGTGCCCTCTTTTGATATGAGTAATGAAGGATCTTATTTCTTCGGAG
ACAA

TGCAGAAGAGTACGACAATTAAGGAAAAATACCCTTGTTTCTACT (SEQ ID NO:8)

A/Yokohama/2017/03 NA

AGCAAAAGCAGGAGTAAAGATGAATCCAAATCAAAAGATAATAACGATTGGCTCTGTTTCCCTCACCATTTCCACA
ATAT

GCTTCTTCATGCAAATTGCCATCCTGATAACTACTGTAACATTGCATTTCAAGCAATATGAATTCAACTCCCCCCCAA
AC

AACCAAGTGATGCTGTGTGAACCAACAATAATAGAAAGAAACATAACAGAGATAGTGTATCTGACCAACACCACC
ATAGA

GAAGGAAATATGCCCCAAACTAGCAGAATACAGAAATTGGTCAAAGCCGCAATGTAACATTACAGGATTTGCACC
TTTTT

CTAAGGACAATTCGATTCGGCTTTCCGCTGGTGGGGACATCTGGGTGACAAGAGAACCTTATGTGTCATGCGATCC
TGAC

AAGTGTTATCAATTTGCCCTTGGACAGGGAACAACACTAAACAACGTGCATTCAAATGACATAGTACATGATAGGA
CCCC

TTATCGGACCCTATTGATGAATGAGTTGGGTGTTCCATTTCATCTGGGGACCAAGCAAGTGTGCATAGCATGGTCC
AGCT

CAAGTTGTCACGATGGAAAAGCATGGCTGCATGTTTGTGTAACGGGGGATGATGAAAATGCAACTGCTAGCTTCA
TTTAC

AATGGGAGGCTTGCAGATAGTATTGTTTCATGGTCCAAAAAAATCCTCAGGACCCAGGAGTCAGAATGCGTTTGT
ATCAA

TGGAACTTGTACAGTAGTAATGACTGATGGGAGTGCTTCAGGAAAAGCTGATACTAAAATACTATTCATTGAGGA
GGGGA

AAATTGTTCATACTAGCACATTATCAGGAAGTGCTCAGCATGTCGAGGAGTGCTCCTGTTATCCTCGATATCCTGGT
GTC

AGATGTGTCTGCAGAGACAACTGGAAAGGCTCCAATAGGCCCATCGTAGATATAAACATAAAGGATTATAGCATT
GTTTC

CAGTTATGTGTGCTCAGGACTTGTTGGAGACACACCCAGAAAAAACGACAGCTCCAGCAGTAGCCATTGCTTGGA
TCCAA

ACAATGAGGAAGGTGGTCATGGAGTGAAAGGCTGGGCCTTTGATGATGGAAATGACGTGTGGATGGGAAGAAC
GATCAGC

Figure 1 cont.

GAGAAGTTACGCTCAGGATATGAAACCTTCAAAGTCATTGAAGGCTGGTCCAACCCTAACTCCAAATTGCAGATAA
ATAG

GCAAGTCATAGTTGACAGAGGTAACAGGTCCGGTTATTCTGGTATTTTCTCTGTTGAAGGCAAAAGCTGCATCAAT
CGGT

GCTTTTATGTGGAGTTGATAAGGGGAAGAAAACAGGAAACTGAAGTCTTGTGGACCTCAAACAGTATTGTTGTGT
TTTGT

GGCACCTCAGGTACATATGGAACAGGCTCATGGCCTGATGGGGCGGACATCAATCTCATGCCTATATAAGCTTTCG
CAAT

TTTAGAAAAAAACTCCTTGTTTCTACT (SEQ ID NO:9)

Which encodes M N P N Q K I I T I G S V S L T I S T I C F F M Q I A I L I T T V T L H F K Q Y E
F N S P P N N Q V M L C E P T I I E R N I T E I V Y L T N T T I E K E I C P K L A E Y R N W S
K P Q C N I T G F A P F S K D N S I R L S A G G D I W V T R E P Y V S C D P D K C Y Q F A L
G Q G T T L N N V H S N D I V H D R T P Y R T L L M N E L G V P F H L G T K Q V C I A W
S S S S C H D G K A W L H V C V T G D D E N A T A S F I Y N G R L A D S I V S W S K K I L
R T Q E S E C V C I N G T C T V V M T D G S A S G K A D T K I L F I E E G K I V H T S T L S
G S A Q H V E E C S C Y P R Y P G V R C V C R D N W K G S N R P I V D I N I K D Y S I V S S
Y V C S G L V G D T P R K N D S S S S S H C L D P N N E E G G H G V K G W A F D D G N D
V W M G R T I S E K L R S G Y E T F K V I E G W S N P N S K L Q I N R Q V I V D R G N R S
G Y S G I F S V E G K S C I N R C F Y V E L I R G R K Q E T E V L W T S N S I V V F C G T S G
T Y G T G S W P D G A D I N L M P I (SEQ ID NO:3)

A/Yokohama/2017/03 M

AGCAAAAGCAGGTAGATATTGAAAGATGAGCCTTCTAACCGAGGTCGAAACGTATGTTCTCTCTATCGTTCCATCA
GGCC

CCCTCAAAGCCGAGATCGCGCAGAGACTTGAAGATGTCTTTGCTGGGAAAAACACAGATCTTGAGGCTCTCATGG
AATGG

CTAAAGACAAGACCAATTCTGTCACCTCTGACTAAGGGGATTCTGGGGTTTGTGTTCACGCTCACCGTGCCCAGTG
AGCG

AGGACTGCAGCGTAGACGCTTTGTCCAAAATGCCCTCAATGGGAATGGAGATCCAAATAACATGGACAAAGCAGT
TAAAC

TGTATAGGAAACTTAAGAGGGAGATAACGTTCCATGGGGCCAAAGAAATAGCTCTCAGTTATTCTGCTGGTGCAC
TTGCC

Figure 1 cont.

AGTTGCATGGGCCTCATATACAATAGGATGGGGGCTGTAACCACTGAAGTGGCATTTGGCCTGGTATGTGCAACA
TGTGA

GCAGATTGCTGACTCCCAGCACAGGTCTCATAGGCAAATGGTGGCAACAACCAATCCATTAATAAGGCATGAGAA
CAGAA

TGGTTTTGGCCAGCACTACAGCTAAGGCTATGGAGCAAATGGCTGGATCAAGTGAGCAGGCAGCGGAGGCCATG
GAGATT

GCTAGTCAGGCCAGGCAAATGGTGCAGGCAATGAGAGCCATTGGGACTCATCCTAGCTCCAGTACTGGTCTAAGA
GATGA

TCTTCTTGAAAATTTGCAGACCTATCAGAAACGAATGGGGGTGCAGATGCAACGATTCAAGTGACCCACTTGTTGT
TGCC

GCGAGTATCATTGGGATCTTGCACTTGATATTGTGGATTCTTGATCGTCTTTTTTTCAAATGCGTCTATCGACTCTTC
AA

ACACGGCCTTAAAAGAGGCCCTTCTACGGAAGGAGTACCTGAGTCTATGAGGGAAGAGTATCGAAAGGAACAGC
AGAATG (SEQ ID NO:10)

CTGTGGATGCTGACGACAGTCATTTTGTCAGCATAGAGTTGGAGTAAAAAACTACCTTGTTTCTACT

A/Yokohama/2017/03 NS

AGCAAAAGCAGGGTGACAAAGACATAATGGATTCCAACACTGTGTCAAGTTTCCAGGTAGATTGCTTTCTTTGGCA
TATC

CGGAAACAAGTTGTAGACCAAGAACTGAGTGATGCCCCATTCCTTGATCGGCTTCGCCGAGATCAGAGGTCCCTA
AGGGG

AAGAGGCAATACTCTCGGTCTAGACATCAAAGCAGCCACCCATGTTGGAAAGCAAATTGTAGAAAAGATTCTGAA
AGAAG

AATCTGATGAGGCACTTAAAATGACCATGGTCTCCACACCTGCTTCGCGATACATAACTGACATGACTATTGAGGA
ATTG

TCAAGAAACTGGTTCATGCTAATGCCCAAGCAGAAAGTGGAAGGACCTCTTTGCATCAGAATGGACCAGGCAATC
ATGGA

GAAAAACATCATGTTGAAAGCGAATTTCAGTGTGATTTTTGACCGACTAGAGACCATAGTATTACTAAGGGCTTTC
ACCG

AAGAGGGAGCAATTGTTGGCGAAATCTCACCATTGCCTTCTTTTCCAGGACATACTATTGAGGATGTCAAAAATGC
AATT

Figure 1 cont.

GGGGTCCTCATCGGAGGACTTGAATGGAATGATAACACAGTTCGAGTCTCTAAAAATCTACAGAGATTCGCTTGG
AGAAG

CAGTAATGAGAATGGGGGACCTCCACTTACTCCAAAACAGAAACGGAAAATGGCGAGAACAGCTAGGTCAAAAG
TTTGAA

GAGATAAGATGGCTGATTGAAGAAGTGAGACACAGACTAAAAACAACTGAAAATAGCTTTGAACAAATAACATTC
ATGCA

AGCATTACAACTGCTGTTTGAAGTGGAACAGGAGATAAGAACTTTCTCATTTCAGCTTATTTAATGATAAAAAACA
CCCT

TGTTTCTACT (SEQ ID NO:11)

Figure 2

MNPNQKIITIGSVSLTISTICFFMQIAILITTVTLHFKQYEFNSPPNNQVMLCEPTIIERNVTEIVYLTNTTIEKEI
CPKPAEYRNWSKPQCGITGFAPFSKDNSIRLSAGGDIWVTREPYVSCDPDKCYQFALGQGTTLNNVHSNNTVRDRTP
YRTLLMNELGVPFHLGTKQVCIAWSSSSCHDGKAWLHVCITGDDKNATASFIYNGRLVDSVVSWSKDILRTQESECV
CINGTCTVVMTDGSASGKADTKILFIEEGKIVHTSKLSGSAQHVEECSCYPRYPGVRCVCRDNWKGSNRPIVDINIK
DHSIVSSYVCSGLVGDTPRKNDSSSSSHCLDPNNEEGGHGVKGWAFDDGNDVWMGRTINETSRLGYETFKVVEGWSN
PKSKLQINRQVIVDRGDRSGYSGIFSVEGKSCINRCFYVELIRGRKEETEVLWTSNSIVVFCGTSGTYGTGSWPDGA
DLNLMPI (SEQ ID NO:2)

Figure 3

>Y2017M3L4-NA(32A, 147N, 329D, 347Q, del46-50aa)
ATGAATCCAAATCAAAAGATAATAACGATTGGCTCTGTTTCCCTCACCATTTCCACAATA
TGCTTCTTCATGCAAATTGCCATCCTGATAACTGCTGTAACATTGCATTTCAAGCAATAT
GAATTCAACTCCCCCATGCTGTGTGAACCAACAATAATAGAAAGAAACATAACAGAGATA
GTGTATCTGACCAACACCACCATAGAGAAGGAAATATGCCCCAAACTAGCAGAATACAGA
AATTGGTCAAAGCCGCAATGTAACATTACAGGATTTGCACCTTTTTCTAAGGACAATTCG
ATTCGGCTTTCCGCTGGTGGGGACATCTGGGTGACAAGAGAACCTTATGTGTCATGCGAT
CCTGACAAGTGTTATCAATTTGCCCTTGGACAGGGAACAACACTAAACAACGTGCATTCA
AATAACATAGTACATGATAGGACCCCTTATCGGACCCTATTGATGAATGAGTTGGGTGTT
CCATTTCATCTGGGGACCAAGCAAGTGTGCATAGCATGGTCCAGCTCAAGTTGTCACGAT
GGAAAAGCATGGCTGCATGTTTGTGTAACGGGGGATGATGAAAATGCAACTGCTAGCTTC
ATTTACAATGGGAGGCTTGCAGATAGTATTGTTTCATGGTCCAAAAAAATCCTCAGGACC
CAGGAGTCAGAATGCGTTTGTATCAATGGAACTTGTACAGTAGTAATGACTGATGGGAGT
GCTTCAGGAAAAGCTGATACTAAAATACTATTCATTGAGGAGGGGAAAATTGTTCATACT
AGCACATTATCAGGAAGTGCTCAGCATGTCGAGGAGTGCTCCTGTTATCCTCGATATCCT
GGTGTCAGATGTGTCTGCAGAGACAACTGGAAAGGCTCCAATAGGCCCATCGTAGATATA
AACATAAAGGATTATAGCATTGTTTCCAGTTATGTGTGCTCAGGACTTGTTGGAGACACA
CCCAGAAAAGACGACAGCTCCAGCAGTAGCCATTGCTTGGATCCAAACAATGAGGAAGGT
GGTCAAGGAGTGAAAGGCTGGGCCTTTGATGATGGAAATGACGTGTGGATGGGAAGAACG
ATCAGCGAGAAGTTACGCTCAGGATATGAAACCTTCAAAGTCATTGAAGGCTGGTCCAAC
CCTAACTCCAAATTGCAGATAAATAGGCAAGTCATAGTTGACAGAGGTAACAGGTCCGGT
TATTCTGGTATTTTCTCTGTTGAAGGCAAAAGCTGCATCAATCGGTGCTTTTATGTGGAG
TTGATAAGGGGAAGAAAACAGGAAACTGAAGTCTTGTGGACCTCAAACAGTATTGTTGTG
TTTTGTGGCACCTCAGGTACATATGGAACAGGCTCATGGCCTGATGGGGCGGACATCAAT
CTCATGCCTATATAAGCTTTCGCAATTTTAGAAAAAAACTCCTTGTTTCTACT (SEQ ID NO:12)

M N P N Q K I I T I G S V S L T I S T I C F F M Q I A I L I T A V T L H F K Q
Y E F N S P M L C E P T I I E R N I T E I V Y L T N T T I E K E I C P K L A E
Y R N W S K P Q C N I T G F A P F S K D N S I R L S A G G D I W V T R E P
Y V S C D P D K C Y Q F A L G Q G T T L N N V H S N N I V H D R T P Y R
T L L M N E L G V P F H L G T K Q V C I A W S S S S C H D G K A W L H V
C V T G D D E N A T A S F I Y N G R L A D S I V S W S K K I L R T Q E S E
C V C I N G T C T V V M T D G S A S G K A D T K I L F I E E G K I V H T S
T L S G S A Q H V E E C S C Y P R Y P G V R C V C R D N W K G S N R P I
V D I N I K D Y S I V S S Y V C S G L V G D T P R K D D S S S S S H C L D
P N N E E G G Q G V K G W A F D D G N D V W M G R T I S E K L R S G Y
E T F K V I E G W S N P N S K L Q I N R Q V I V D R G N R S G Y S G I F S
V E G K S C I N R C F Y V E L I R G R K Q E T E V L W T S N S I V V F C G
T S G T Y G T G S W P D G A D I N L M P I (SEQ ID NO:1)

>Y2017M3L4HA
ATGAAGACTATCATTGCTTTGAGCTACATTCTATGTCTGGTTTTCGCTCAAAAGCTTCCC
GGAAATGACAACAGCACGGCAACGCTGTGCCTTGGGCACCATGCAGTACCAAACGGAACG
ATAGTGAAAACAATCACGAATGACCAAATTGAAGTTACTAATGCTACTGAGCTGGTTCAG
AGTTCCTCAACAGGTGGAATATGCGACAGTCCTCATCAGATCCTTGATGGAGAAAACTGC
ACACTAATAGATGCTCTATTGGGAGACCCTCAGTGTGATGGCTTCCAAAATAAGAAATGG

Figure 3 cont.

GACCTTTTTGTTGAACGCAGCAAAGCCTACAGCAACTGTTACCCTTATGATGTGCCGGAT
TATGCCTCCCTTAGGTCACTAGTTGCCTCATCCGGCACACTGGAGTTTAACAATGAAAGC
TTCAATTGGACTGGAGTCACTCAGAATGGAACAAGCTCTGCTTGCAAAAGGAGATCTAAT
AAAAGTTTCTTTAGTAGATTGAATTGGTTGACCCACTTAAAATACAAATACCCAGCATTG
AACGTGACTATGCCAAACAATGAAAAATTTGACAAATTGTACATTTGGGGGGTTCACCAC
CCGGGTACGGACAGTGATCAAATCAGCCTATATGCTCAAGCATCAGGAAGAATCACAGTC
TCTACCAAAAGAAGCCAACAAACTGTAATCCCGAATATCGGATCTAGACCCAGGGTAAGG
GATGTCTCCAGCAGAATAAGCATCTATTGGACAATAGTAAAACCGGGAGACATACTTTTG
ATTAACAGCACAGGGAATCTAATTGCTCCTCGGGGTTACTTCAAAATACGAAGTGGGAAA
AGCTCAATAATGAGATCAGATGCACCCATTGGCAAATGCAATTCTGAATGCATCACTCCA
AATGGAAGCATTCCCAATGACAAACCATTTCAAAATGTAAACAGGATCACATATGGGGCC
TGTCCCAGATATGTTAAGCAAAACACTCTGAAATTGGCAACAGGGATGCGAAATGTACCA
GAGAAACAAACTAGAGGCATATTTGGCGCAATCGCGGGTTTCATAGAAAATGGTTGGGAG
GGAATGGTGGACGGTTGGTACGGTTTCAGGCATCAAAATTCTGAGGGCACAGGACAAGCA
GCAGATCTCAAAAGCACTCAAGCAGCAATCAACCAAATCAATGGGAAACTGAATAGGTTA
ATCGGGAAAACAAACGAGAAATTCCATCAGATTGAAAAAGAATTCTCAGAAGTAGAAGGG
AGAATTCAGGACCTCGAGAAATATGTTGAGGACACTAAAATAGATCTCTGGTCATACAAC
GCGGAGCTTCTTGTTGCCCTGGAGAACCAACATACAATTGATCTAACTGACTCAGAAATG
AACAAACTGTTTGAAAGAACAAAGAAGCAACTGAGGGAAAATGCTGAGGATATGGGCAAT
GGTTGTTTCAAAATATACCACAAATGTGACAATGCCTGCATAGAGTCAATCAGAAATGGA
ACTTATGACCATGATGTATACAGAGATGAAGCATTAAACAACCGGTTCCAGATCAAAGGT
GTTGAGCTGAAGTCAGGATACAAAGATTGGATCCTATGGATTTCCTTTGCCATATCATGT
TTTTTGCTCTGTGTTGCTTTGTTGGGGTTCATCATGTGGGCCTGCCAAAAAGGCAACATT
AGGTGCAACATTTGCATTTGAGTGCATTAATTAAAAACACCCTTGTTTCTACT (SEQ ID NO:13)

>Y2017M3L4-M(M1-23Q)
ATGAGCCTTCTAACCGAGGTCGAAACGTATGTTCTCTCTATCGTTCCATCAGGCCCCCTC
AAAGCCCAGATCGCGCAGAGACTTGAAGATGTCTTTGCTGGGAAAAACACAGATCTTGAG
GCTCTCATGGAATGGCTAAAGACAAGACCAATTCTGTCACCTCTGACTAAGGGGATTCTG
GGGTTTGTGTTCACGCTCACCGTGCCCAGTGAGCGAGGACTGCAGCGTAGACGCTTTGTC
CAAAATGCCCTCAATGGGAATGGAGATCCAAATAACATGGACAAAGCAGTTAAACTGTAT
AGGAAACTTAAGAGGGAGATAACGTTCCATGGGGCCAAAGAAATAGCTCTCAGTTATTCT
GCTGGTGCACTTGCCAGTTGCATGGGCCTCATATACAATAGGATGGGGGCTGTAACCACT
GAAGTGGCATTTGGCCTGGTATGTGCAACATGTGAGCAGATTGCTGACTCCCAGCACAGG
TCTCATAGGCAAATGGTGGCAACAACCAATCCATTAATAAGGCATGAGAACAGAATGGTT
TTGGCCAGCACTACAGCTAAGGCTATGGAGCAAATGGCTGGATCAAGTGAGCAGGCAGCG
GAGGCCATGGAGATTGCTAGTCAGGCCAGGCAAATGGTGCAGGCAATGAGAGCCATTGGG
ACTCATCCTAGCTCCAGTACTGGTCTAAGAGATGATCTTCTTGAAAATTTGCAGACCTAT
CAGAAACGAATGGGGGTGCAGATGCAACGATTCAAGTGACCCACTTGTTGTTGCCGCGAG
TATCATTGGGATCTTGCACTTGATATTGTGGATTCTTGATCGTCTTTTTTTCAAATGCGT
CTATCGACTCTTCAAACACGGCCTTAAAAGAGGCCCTTCTACGGAAGGAGTACCTGAGTC
TATGAGGGAAGAGTATCGAAAGGAACAGCAGAATGCTGTGGATGCTGACGACAGTCATTT
TGTCAGCATAGAGTTGGAGTAAAAAACTACCTTGTTTCTACT (SEQ ID NO:14)

>Y2017M3L4-NP(101N)
ATGGCGTCCCAAGGCACCAAACGGTCTTATGAACAGATGGAAACTGATGGGGATCGCCAG
AATGCAACTGAGATTAGGGCATCCGTCGGGAAGATGATTGATGGAATTGGGAGATTCTAC
ATCCAAATGTGCACTGAACTTAAACTCAGTGATTATGAAGGGCGGTTGATCCAGAACAGC
TTGACAATAGAGAAAATGGTGCTCTCTGCTTTTGATGAAAGAAGGAATAAATATCTGGAA
GAACACCCCAGCGCGGGGAAAGATCCTAAGAAAACTGGGGGGCCCATATACAGGAGAGTA
AATGGAAAATGGATGAGGGAACTCGTCCTTTATGACAAAGAAGAAATAAGGCGAATCTGG
CGCCAAGCCAACAATGGTGAGGATGCGACAGCTGGTCTAACTCACATAATGATCTGGCAT

Figure 3 cont.

TCCAATTTGAATGATGCAACATACCAGAGGACAAGAGCTCTTGTTCGAACCGGAATGGAT
CCCAGAATGTGCTCTCTGATGCAGGGCTCGACTCTCCCTAGAAGGTCCGGAGCTGCAGGT
GCTGCAGTCAAAGGAATCGGGACAATGGTGATGGAGCTGATCAGAATGGTCAAACGGGGG
ATCAACGATCGAAATTTCTGGAGAGGTGAGAATGGGCGGAAAACAAGAAGTGCTTATGAG
AGAATGTGCAACATTCTTAAAGGAAAATTTCAAACAGCTGCACAAAGAGCAATGGTGGAT
CAAGTGAGAGAAAGTCGGAACCCAGGAAATGCTGAGATCGAAGATCTCATATTTTTGGCA
AGATCTGCATTGATATTGAGAGGATCAGTTGCTCACAAATCTTGCCTACCTGCCTGTGTG
TATGGACCTGCAGTATCCAGTGGGTACGACTTCGAAAAAGAGGGATATTCCTTGGTGGGA
ATAGACCCTTTCAAACTACTTCAAAATAGCCAAGTATACAGCCTAATCAGACCTAACGAG
AATCCAGCACACAAGAGTCAGCTGGTATGGATGGCATGCCATTCTGCTGCATTTGAAGAT
TTAAGATTGTTAAGCTTCATCAGAGGGACAAAAGTATCTCCACGAGGGAAACTTTCAACT
AGAGGAGTACAAATTGCTTCAAATGAGAACATGGATAATATGGGATCGAGCACTCTTGAA
CTGAGAAGCGGGTACTGGGCCATAAGGACCAGGAGTGGAGGAAACACTAATCAACAGAGG
GCCTCCGCAGGCCAAACCAGTGTGCAACCTACGTTTTCTGTACAAAGAAACCTCCCATTT
GAAAGTCAACCATCATGGCAGCATTCACTGGAAATACGGAGGGAAGAACTTCAGACATG
AGGGCAGAAATCATAAGAATGATGGAAGGTGCAAAACCAGAAGAAGTGTCGTTCCGGGGG
AGGGGAGTTTTCGAGCTCTCAGACGAGAAGGCAACGAACCCGATCGTGCCCTCTTTTGAT
ATGAGTAATGAAGGATCTTATTTCTTCGGAGACAATGCAGAAGAGTACGACAATTAAGGA
AAAATACCCTTGTTTCTACT (SEQ ID NO:15)

>Y2017M3L4-NS
ATGGATTCCAACACTGTGTCAAGTTTCCAGGTAGATTGCTTTCTTTGGCATATCCGGAAA
CAAGTTGTAGACCAAGAACTGAGTGATGCCCCATTCCTTGATCGGCTTCGCCGAGATCAG
AGGTCCCTAAGGGGAAGAGGCAATACTCTCGGTCTAGACATCAAAGCAGCCACCCATGTT
GGAAAGCAAATTGTAGAAAAGATTCTGAAAGAAGAATCTGATGAGGCACTTAAAATGACC
ATGGTCTCCACACCTGCTTCGCGATACATAACTGACATGACTATTGAGGAATTGTCAAGA
AACTGGTTCATGCTAATGCCCAAGCAGAAAGTGGAAGGACCTCTTTGCATCAGAATGGAC
CAGGCAATCATGGAGAAAAACATCATGTTGAAAGCGAATTTCAGTGTGATTTTTGACCGA
CTAGAGACCATAGTATTACTAAGGGCTTTCACCGAAGAGGGAGCAATTGTTGGCGAAATC
TCACCATTGCCTTCTTTTCCAGGACATACTATTGAGGATGTCAAAAATGCAATTGGGGTC
CTCATCGGAGGACTTGAATGGAATGATAACACAGTTCGAGTCTCTAAAAATCTACAGAGA
TTCGCTTGGAGAAGCAGTAATGAGAATGGGGGACCTCCACTTACTCCAAAACAGAAACGG
AAAATGGCGAGAACAGCTAGGTCAAAAGTTTGAAGAGATAAGATGGCTGATTGAAGAAGT
GAGACACAGACTAAAAACAACTGAAAATAGCTTTGAACAAATAACATTCATGCAAGCATT
ACAACTGCTGTTTGAAGTGGAACAGGAGATAAGAACTTTCTCATTTCAGCTTATTTAATG
ATAAAAAACACCCTTGTTTCTACT (SEQ ID NO:16)

>Y2017M3L4-PB1
ATGGATGTCAATCCGACTCTACTGTTCCTAAAGGTTCCAGCGCAAAATGCCATAAGCACC
ACATTCCCTTATACTGGAGATCCTCCATACAGCCATGGAACAGGAACAGGGTACACCATG
GACACAGTCAACAGAACACACCAATATTCAGATAAGGGGAAGTGGACGACAAATACAGAA
ACTGGGGCACCCCAACTCAACCCAATTGATGGACCACTACCTGAGGATAATGAGCCAAGT
GGATATGCACAAACAGACTGTGTCCTGGAGGCTATGGCCTTCCTTGAAGAATCCCACCCA
GGTATCTTTGAGAACTCATGCCTTGAAACAATGGAAGTCGTTCAACAAACAAGGGTGGAC
AAACTAACCCAAGGTCGCCAGACTTATGATTGGACATTAAACAGAAATCAACCGGCAGCA
ACTGCATTAGCCAACACCATAGAAGTTTTTAGATCGAATGGACTAACAGCTAATGAATCA
GGAAGGCTAATAGATTTCCTCAAGGATGTGATGGAATCAATGGATAAAGAGGAAATGGAG
ATAACAACACACTTTCAAAGAAAAAGGAGAGTAAGAGACAACATGACCAAGAAAATGGTC
ACACAAAGAACAATAGGGAAGAAAAAACAAAGAGTAAATAAGAGAGGCTATCTAATAAGA
GCTTTGACATTGAACACGATGACCAAAGATGCAGAGAGAGGTAAATTAAAAAGAAGGGCT
ATTGCAACACCCGGGATGCAAATTAGAGGGTTCGTGTACTTCGTTGAAACTTTAGCTAGA
AGCATTTGCGAAAAGCTTGAACAGTCTGGACTTCCGGTTGGGGGTAATGAAAAGAAGGCC

Figure 3 cont.

AAACTGGCAAATGTTGTGAGAAAAATGATGACTAATTCACAAGACACAGAGCTTTCTTTC
ACAATCACTGGGGACAACACTAAGTGGAATGAAAATCAAAACCCTCGAATGTTTTTGGCG
ATGATTACATATATCACAAAAAATCAACCTGAGTGGTTCAGAAACATCCTGAGCATCGCA
CCAATAATGTTCTCAAACAAAATGGCAAGACTGGGAAAAGGATACATGTTCGAGAGTAAG
AGAATGAAACTCCGAACACAAATACCCGCAGAAATGCTAGCAAACATTGACCTGAAGTAT
TTCAATGAATCAACAAGGAAGAAAATTGAGAAAATAAGGCCTCTTCTAATAGATGGCACA
GCATCATTGAGCCCTGGGATGATGATGGGCATGTTCAACATGCTAAGTACGGTTTTAGGA
GTCTCGATACTGAATCTTGGGCAAAAGAAATACACCAAGACAACATACTGGTGGGATGGG
CTCCAATCCTCCGACGATTTTGCCCTCATAGTGAATGCACCAAATCATGAGGGAATACAA
GCAGGAGTGGATAGATTTTACAGGACCTGCAAGTTAGTGGGAATCAACATGAGCAAAAAG
AAGTCCTATATAAATAAAACAGGGACATTTGAATTCACAAGCTTTTTTTATCGATATGGA
TTTGTGGCTAATTTTAGCATGGAGCTGCCCAGTTTTGGAGTGTCTGGAATAAACGAGTCA
GCTGATATGAGCATTGGAGTAACAGTGATAAAGAACAACATGATAAACAATGACCTTGGA
CCAGCAACAGCCCAGATGGCTCTCCAATTGTTCATCAAAGACTACAGATATACATATAGG
TGCCATAGAGGAGACACACAAATTCAGACGAGAAGATCATTCGAGCTAAAGAAGCTGTGG
GATCAAACCCAATCAAGGGCAGGACTATTGGTATCAGATGGGGGACCAAACTTATACAAT
ATCCGGAATCTTCACATCCCTGAAGTCTGCTTAAAGTGGGAGCTAATGGATGAGAATTAT
CGGGGAAGACTTTGTAATCCCCTGAATCCCTTTGTCAGCCATAAAGAAATTGAGTCTGTA
AACAATGCTGTAGTGATGCCAGCCCATGGTCCGGCCAAAAGTATGGAATATGATGCCGTT
GCAACTACACACTCCTGGATTCCCAAGAGGAACCGCTCTATTCTCAACACAAGCCAAAGG
GGAATTCTTGAGGATGAACAGATGTACCAGAAGTGCTGCAACTTGTTCGAGAAATTTTTC
CCTAGTAGTTCATATAGGAGACCGATTGGAATTTCTAGCATGGTGGAGGCCATGGTGTCT
AGGGCCCGGATTGATGCCAGAATTGACTTCGAGTCTGGACGGATTAAGAAGGAAGAGTTC
TCTGAGATCATGAAGATCTGTTCCACCATTGAAGAACTCAGACGGCAAAAATAATGAATT
TAGCTTGTCCTTCATGAAAAAATGCCTTGTTTCTACT (SEQ ID NO:17)

>Y2017M3L4-PA
ATGGAAGATTTTGTGCGACAATGCTTCAACCCGATGATTGTCGAACTTGCAGAAAAAGCA
ATGAAAGAGTATGGGGAGGATCTGAAAATTGAAACAAACAAATTTGCAGCAATATGCACT
CACTTGGAGGTATGTTTCATGTATTCAGATTTTCATTTCATCAATGAACAAGGCGAATCA
ATAGTGGTAGAACTTGATGATCCAAATGCACTGTTAAAGCACAGATTTGAAATAATCGAG
GGGAGAGACAGAACAATGGCCTGGACAGTAGTAAACAGTATCTGCAACACTACTGGAGCT
GAAAAACCGAAGTTTCTACCAGATTTGTATGATTACAAGGAGAACAGATTCATCGAAATT
GGAGTGACAAGGAGAGAAGTCCACATATATTACCTTGAAAAGGCCAATAAGATTAAATCT
GAGAACACACACATTCACATTTTCTCATTCACTGGGGAGGAAATGGCCACAAAGGCAGAC
TACACTCTCGACGAGGAAAGCAGGGCTAGGATTAAGACCAGGCTATTTACCATAAGACAA
GAAATGGCCAACAGAGGCCTCTGGGATTCCTTTCGTCAGTCCGAAAGAGGCGAAGAAACA
ATTGAAGAAAAATTTGAAATCTCAGGAACTATGCGTAGGCTTGCCGACCAAAGTCTCCCA
CCGAACTTCTCCTGCCTTGAGAATTTTAGAGCCTATGTGGATGGATTCGAACCGAACGGC
TGCATTGAGGGCAAGCTTTCTCAAATGTCCAAAGAAGTGAATGCCCAAATTGAACCTTTT
CTGAAGACAACACCAAGACCAATCAAACTTCCGAATGGACCTCCTTGTTATCAGCGGTCC
AAGTTCCTCCTGATGGATGCTTTAAAATTGAGCATTGAAGACCCAAGTCACGAAGGAGAA
GGGATCCCATTATATGATGCGATCAAGTGCATAAAAACATTCTTTGGATGGAAAGAACCT
TATATAGTCAAACCACACGAAAAGGGAATAAATTCAAATTACCTGCTGTCATGGAAGCAA
GTATTGTCAGAATTGCAGGACATTGAAAATGAGGAGAAGATTCCAAGGACTAAAAACATG
AAGAAAACGAGTCAACTAAAGTGGGCTCTTGGTGAGAACATGGCACCAGAGAAAGTAGAC
TTTGAAAACTGCAGAGACATAAGCGATTTGAAGCAATATGATAGTGACGAACCTGAATTA
AGGTCACTTTCAAGCTGGATACAGAATGAGTTCAACAAGGCCTGCGAGCTAACTGATTCA
ATCTGGATAGAGCTCGATGAAATTGGAGAGGACGTAGCCCCAATTGAATACATTGCAAGC
ATGAGGAGGAATTATTTCACAGCAGAGGTGTCCCATTGTAGAGCCACTGAGTACATAATG
AAGGGGGTATACATTAATACTGCCCTGCTCAATGCATCCTGTGCAGCAATGGACGATTTT
CAACTAATTCCCATGATAAGCAAGTGCAGAACTAAAGAGGGAAGGCGAAAAACCAATTTA
TATGGATTCATCATAAAGGGAAGATCTCATTTAAGGAATGACACAGATGTGGTAAACTTT

Figure 3 cont.

GTGAGCATGGAGTTTTCTCTCACTGACCCGAGACTTGAGCCACATAAATGGGAGAAATAC
TGTGTCCTTGAGATAGGAGATATGTTACTAAGAAGTGCCATAGGCCAAATTTCAAGGCCT
ATGTTCTTGTATGTGAGGACAAACGGAACATCAAAGGTCAAAATGAAATGGGGAATGGAG
ATGAGACGTTGCCTCCTTCAGTCACTCCAGCAGATCGAGAGCATGATTGAAGCCGAGTCC
TCGGTTAAAGAGAAAGACATGACCAAAGAGTTTTTTGAGAATAAATCAGAAGCATGGCCC
ATTGGGGAGTCCCCCAAGGGAGTGGAAGAAGGTTCCATTGGGAAAGTCTGTAGGACTCTA
TTGGCTAAGTCAGTGTTCAATAGCCTGTATGCATCACCACAATTGGAAGGATTTTCAGCG
GAGTCAAGAAAACTGCTCCTTGTTGTTCAGGCTCTTAGGGACAACCTCGAACCTGGGACC
TTTGATCTTGGGGGGCTATATGAAGCAATTGAGGAGTGCCTGATTAATGATCCCTGGGTT
TTGCTCAATGCGTCTTGGTTCAACTCCTTCCTGACACATGCATTAAAATAGTTATGGCAG
TGCTACTATTTGTTATCCGTACTGTCCAAAAAAGTACCTTGTTTCTACT (SEQ ID NO:18)

>M3L4-PB2(147I)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTTCCCAATGAAGTGGGAGCCAGGATACTAACATCAGAA
TCGCAATTAACAATAACTAAAGAGAAAAAAGAAGAACTCCGAGATTGCAAAATTTCTCCC
TTGATGGTTGCATACATGTTAGAGAGAGAACTTGTCCGAAAAACAAGATTTCTCCCAGTT
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATCTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAAGTGCTTACAGGCAATCTCCAAACATTGAAGATAAGAGTACATGAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:19)

Figure 3 cont.

>M3L4-PB2(147I,344L)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTTCCCAATGAAGTGGGAGCCAGGATACTAACATCAGAA
TCGCAATTAACAATAACTAAAGAGAAAAAAGAAGAACTCCGAGATTGCAAAATTTCTCCC
TTGATGGTTGCATACATGTTAGAGAGAGAACTTGTCCGAAAAACAAGATTCCTCCCAGTT
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATTTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAACTGCTTACAGGCAATCTCCAAACATTGAAGATAAGAGTACATGAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:20)

>M3L4-PB2(147I,344L,358K)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTTCCCAATGAAGTGGGAGCCAGGATACTAACATCAGAA
TCGCAATTAACAATAACTAAAGAGAAAAAAGAAGAACTCCGAGATTGCAAAATTTCTCCC
TTGATGGTTGCATACATGTTAGAGAGAGAACTTGTCCGAAAAACAAGATTCCTCCCAGTT

Figure 3 cont.

GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATCTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAACTGCTTACAGGCAATCTCCAAACATTGAAGATAAGAGTACATAAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:21)

| | | | | | | | | | | | |
|---|---|---|---|---|---|---|---|---|---|---|---|
| PB2 | wt | wt | mutant | wt | wt | mutant | mutant | mutant | mutant | mutant | mutant |
| NA | wt | mutant | wt | wt | wt | wt | wt | wt | mutant | mutant | mutant |
| NP | wt | wt | wt | wt | mutant | mutant | wt | mutant | wt | mutant | mutant |
| M | wt | wt | wt | mutant | wt | wt | mutant | mutant | mutant | wt | mutant |

| | | | | | | | | |
|---|---|---|---|---|---|---|---|---|
| T32A | wt | wt | mutation | mutation | mutation | mutation | wt | mutation |
| D147N | wt | mutation | wt | mutation | mutation | mutation | wt | mutation |
| N329D | wt | mutation | mutation | wt | mutation | mutation | wt | mutation |
| H347Q | wt | mutation | mutation | mutation | wt | mutant | wt | mutation |
| Δ46-50aa | wt | wt | wt | wt | wt | wt | mutation | mutation |

N.A: not analyzed

| | | | | |
|---|---|---|---|---|
| HA | HK4801 | HK4801 | HK4801 | HK4801 |
| NA | HK4801 | Y2017-M3L4 | HK4801 | Y2017-M3L4 |
| Backbone | Y2017 | Y2017 | HY-PR8 | HY-PR8 |

Figure 9

N3 (Accession No. AAO62039.1)

1 mnpnqkiiti gvvnttlsti alligvgnli fntvihekig dhqtvihptt ttpaipncsd
61 tiitynntvi nnittiitea erlfkpplpl cpfrgffpfh kdnairlgen kdvivtrepy
121 vscdndncws falaqgallg tkhsngtihd rtpyrsliqf pigtapvlgn ykeiciawss
181 sscfdgkewm hvcmtgndnd asaqiiyagr mtdsikswkr dilrtqesec qcidgtcvva
241 vtdgpaansa dhrvywireg rivkyenvpk tkiqhleecs cyvdidvyci crdnwkgsnr
301 pwmrinneti letgyvcskf hsdtprpadp stvscdspsn vnggpgvkgf gfkvgndvwl
361 grtmstsgrs gfeiikvaeg winspnhaks vtqtlvsnnd wsgysgsfiv ktkacfqpcf
421 yvelirgrpn knddvswtsn sivtfcgldn epgsgnwpdg snigfmpk (SEQ ID NO:30)

N4 (Accession No. AAO62043.1)

1 mnpnqkiiti gsvsiilttì glllqitslc siwfshynqv tqtheqpcsn nttnyynetf
61 vnvtnvqnny ttviepsapd vvhyssgrdl cpirgwapls kdngirigsr gevfvirepf
121 iscsisecrt ffltqgalln dkhsngtvkd rspfrtlmsc pigvapspsn srfesvawsa
181 tacsdgpgwl tlgitgpdat avavlkyngi itdtlkswkg nimrtqesec vcqdefcytl
241 itdgpsdaqa fykilkirkg kivsmkdvda tgfhfeecsc ypsgtdiecv crdnwrgsnr
301 pwirfnsdld yqigyvcsgi fgdnprpvdg tgscnspvnn gkgrygvkgf sfrygdgvwi
361 grtkslesrs gfemvwdang wvstdkdsng vqdiidndnw sgysgsfsir gettgrnctv
421 pcfwvemirg qpkektiwts gssiafcgvn sdttgwswpd gallpfdidk (SEQ ID NO:31)

N6 (Accession No. AAO62070.1)

1 mnpnqkiici satgmtlsvv slligianlg lniglhykmg dtpdvnipnm netnstttii
61 nnhtqnnftn itniivnkne egtflnltkp lcevnswhil skdnairige dahilvtrep
121 ylscdpqgcr mfalsqgttl rgrhangtih drspfralis wemgqapspy nvrvecigws
181 stschdgisr msicmsgann nasavvwygg rpvteipswa gnilrtqese cvchkgicpv
241 vmtdgpannr aatkiiyfke gkiqkieela gntqhieecs cygavgvikc icrdnwkgan
301 rpvitidpem mthtskylcs kiltdtsrpn dptngncdap itggspdpgv kgfafldren
361 swlgrtiskd srsgyemlkv pnaetdtqsg pishqvivnn qnwsgysgaf idywankecf
421 npcfyvelir grpkessvlw tsnsivalcg skerlgswsw hdgaeiiyfk (SEQ ID NO:32)

N7 (Accession No. AIK26357.1)

1 mnpnqklfal sgvaialsil nlligisnvg lnvslhlkgs sdqdknwtct svtqnnttli
61 entyvnnttv idketgtakp nylmlnkslc kvegwvvvak dnairfgese qiivtrepyv
121 scdplgckmy alhqgttirn khsngtihdr tafrglistp lgsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkg fgfldssntw
361 lgrtisprsr sgfemlkipn aetdpnskit erqeivdnnn wsgysgsfid ywdessecyn

Figure 9 cont.

421 pcfyvelirg rpeeakyvgw tsnslialcg spisvgsgsf pdgaqiqyfs (SEQ ID NO:33)

N8 (Accession No. AIK26315.1)

1 mnpnqkiitv gsvslglvvl nillhivsit vtvlvlpgng nnkncnetvi reynetvrie
61 kvtqwhntnv ieyiekpesg hfmnntealc dakgfapfsk dngirigsrg hvfvirepfv
121 scsptecrtf fltqgsllnd khsngtvkdr spyrtlmsve igqspnvyqa rfeavawsat
181 achdgkkwmt igvtgpdaka vavvhyggip tdvinswagd ilrtqessct ciqgecywvm
241 tdgpanrqaq yrafkakqgk ivgqteisfn gshieecscy pnegkvecvc rdnwtgtnrp
301 vlvispdlsy ragylcaglp sdtprgedsq ftgsctspvg nqgygvkgfg frqgndvwmg
361 rtisrtsrsg feilkvrngw vqnskeqikr qvvvdnlkws gysgsftlpv eltkrnclvp
421 cfwvemirgk peektiwtss ssivmcgvdh eiadwswhdg ailpfdidkm (SEQ ID NO:34)

N9 (Accession No. ALH21371)

1 mnpnqkilct satalligai avliglanlg lnlglhlkpg cncshsqpet tntsqtiinn
61 yynetnitni qmeertsrnf nnltkglcti nswhiygkdn avrigessdv lvtrepyvsc
121 dpdecrfyal sqgttirgkh sngtihdrsq yraliswpls spptvynsrv eciqwsstsc
181 hdgksrmsic isgpnnnasa vvwynrrpvt eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
421 velirgrpke dkvwwtsnsi vsmcssteflgqwnwpdgak ieyfl (SEQ ID NO:35)

Figure 10 agcgaaagca ggtcaattat attcaatatg gaaagaataa aagaactaag aaatctaatg
tcgcagtctc gcacccgcga gatactcaca aaaaccaccg tggaccatat ggccataatc
aagaagtaca catcaggaag acaggagaag aacccagcac ttaggatgaa atggatgatg
gcaatgaaat atccaattac agcagacaag aggataacgg aaatgattcc tgagagaaat
gagcaaggac aaactttatg gagtaaaatg aatgatgccg gatcagaccg agtgatggta
tcacctctgg ctgtgacatg gtggaatagg aatggaccaa tgacaaatac agttcattat
ccaaaaatct acaaaactta ttttgaaaga gtcgaaaggc taaagcatgg aacctttggc
cctgtccatt ttagaaacca agtcaaaata cgtcggagag ttgacataaa tcctggtcat
gcagatctca gtgccaagga ggcacaggat gtaatcatgg aagttgtttt ccctaacgaa
gtgggagcca ggatactaac atcggaatcg caactaacga taaccaaaga gaagaaagaa
gaactccagg attgcaaaat ttctcctttg atggttgcat acatgttgga gagagaactg
gtccgcaaaa cgagattcct cccagtggct ggtggaacaa gcagtgtgta cattgaagtg
ttgcatttga ctcaaggaac atgctgggaa cagatgtata ctccaggagg ggaagtgaag
aatgatgatg ttgatcaaag cttgattatt gctgctagga acatagtgag aagagctgca
gtatcagcag acccactagc atctttattg gagatgtgcc acagcacaca gattggtgga
attaggatgg tagacatcct taagcagaac ccaacagaag agcaagccgt ggatatatgc
aaggctgcaa tgggactgag aattagctca tccttcagtt ttggtggatt cacatttaag
agaacaagcg gatcatcagt caagagagag gaagaggtgc ttacgggcaa tcttcaaaca
ttgaagataa gagtgcatga gggatctgaa gagttcacaa tggttgggag aagagcaaca
gccatactca gaaaagcaac caggagattg attcagctga tagtgagtgg gagagacgaa
cagtcgattg ccgaagcaat aattgtggcc atggtatttt cacaagagga ttgtatgata
aaagcagtta gaggtgatct gaatttcgtc aatagggcga atcagcgact gaatcctatg
catcaacttt taagacattt tcagaaggat gcgaaagtgc tttttcaaaa ttggggagtt
gaacctatcg acaatgtgat gggaatgatt gggatattgc ccgacatgac tccaagcatc
gagatgtcaa tgagaggagt gagaatcagc aaaatgggtg tagatgagta ctccagcacg
gagagggtag tggtgagcat tgaccggttc ttgagagtca gggaccaacg aggaaatgta
ctactgtctc ccgaggaggt cagtgaaaca cagggaacag agaaactgac aataacttac
tcatcgtcaa tgatgtggga gattaatggt cctgaatcag tgttggtcaa tacctatcaa
tggatcatca gaaactggga aactgttaaa attcagtggt cccagaaccc tacaatgcta
tacaataaaa tggaatttga accatttcag tctttagtac ctaaggccat tagaggccaa
tacagtgggt ttgtaagaac tctgttccaa caaatgaggg atgtgcttgg gacatttgat
accgcacaga taataaaact tcttcccttc gcagccgctc caccaaagca aagtagaatg
cagttctcct catttactgt gaatgtgagg ggatcaggaa tgagaatact tgtaaggggc
aattctcctg tattcaacta caacaaggcc acgaagagac tcacagttct cggaaaggat
gctggcactt taaccgaaga cccagatgaa ggcacagctg gagtggagtc cgctgttctg
aggggattcc tcattctggg caaagaagac aggagatatg ggccagcatt aagcatcaat
gaactgagca accttgcgaa aggagagaag gctaatgtgc taattgggca aggagacgtg
gtgttggtaa tgaaacgaaa acgggactct agcatactta ctgacagcca gacagcgacc
aaaagaattc ggatggccat caattagtgt cgaatagttt aaaaacgacc ttgtttctac
t (SEQ ID NO:39) which encodes M E R I K E L R N L M S Q S R T R E I L T K T T V D H M A I I K K Y T S G R Q
E K N P A L R M K W M M A M K Y P I T A D K R I T E M I P E R N E Q G Q T
L W S K M N D A G S D R V M V S P L A V T W W N R N G P M T N T V H Y P
K I Y K T Y F E R V E R L K H G T F G P V H F R N Q V K I R R R V D I N P G
H A D L S A K E A Q D V I M E V V F P N E V G A R I L T S E S Q L T I T K E K
K E E L Q D C K I S P L M V A Y M L E R E L V R K T R F L P V A G G T S S V
Y I E V L H L T Q G T C W E Q M Y T P G G E V K N D D V D Q S L I I A A R N
I V R R A A V S A D P L A S L L E M C H S T Q I G G I R M V D I L K Q N P T E

Figure 10 cont.

E Q A V D I C K A A M G L R I S S S F S F G G F T F K R T S G S S V K R E E E
V L T G N L Q T L K I R V H E G S E E F T M V G R R A T A I L R K A T R R L I
Q L I V S G R D E Q S I A E A I I V A M V F S Q E D C M I K A V R G D L N F V
N R A N Q R L N P M H Q L L R H F Q K D A K V L F Q N W G V E P I D N V M
G M I G I L P D M T P S I E M S M R G V R I S K M G V D E Y S S T E R V V V
S I D R F L R V R D Q R G N V L L S P E E V S E T Q G T E K L T I T Y S S S M
M W E I N G P E S V L V N T Y Q W I I R N W E T V K I Q W S Q N P T M L Y
N K M E F E P F Q S L V P K A I R G Q Y S G F V R T L F Q Q M R D V L G T F
D T A Q I I K L L P F A A A P P K Q S R M Q F S S F T V N V R G S G M R I L V
R G N S P V F N Y N K A T K R L T V L G K D A G T L T E D P D E G T A G V
E S A V L R G F L I L G K E D R R Y G P A L S I N E L S N L A K G E K A N V L
I G Q G D V V L V M K R K R D S S I L T D S Q T A T K R I R M A I N agcgaaagca ggcaaaccat ttgaatggat gtcaatccga ccttactttt cttaaaagtg
ccagcacaaa atgctataag cacaactttc ccttataccg gagaccctcc ttacagccat
gggacaggaa caggatacac catggatact gtcaacagga cacatcagta ctcagaaaag
ggaagatgga caacaaacac cgaaactgga gcaccgcaac tcaacccgat tgatgggcca
ctgccagaag acaatgaacc aagtggttat gcccaaacag attgtgtatt ggaagcaatg
gctttccttg aggaatccca tcctggtatt tttgaaaact cgtgtattga aacgatggag
gttgttcagc aaacacgagt agacaagctg acacaaggcc gacagaccta tgactggact
ttaaatagaa accagcctgc tgcaacagca ttggccaaca caatagaagt gttcagatca
aatggcctca cggccaatga gtcaggaagg ctcatagact tccttaagga tgtaatggag
tcaatgaaaa aagaagaaat ggggatcaca actcattttc agagaaagag acgggtgaga
gacaatatga ctaagaaaat gataacacag agaacaatag gtaaaaggaa acagagattg
aacaaaaggg gttatctaat tagagcattg accctgaaca caatgaccaa agatgctgag
agagggaagc taaaacggag agcaattgca accccaggga tgcaaataag ggggtttgta
tactttgttg agacactggc aaggagtata tgtgagaaac ttgaacaatc agggttgcca
gttggaggca atgagaagaa agcaaagttg gcaaatgttg taaggaagat gatgaccaat
tctcaggaca ccgaactttc tttcaccatc actggagata acaccaaatg gaacgaaaat
cagaatcctc ggatgttttt ggccatgatc acatatatga ccagaaatca gcccgaatgg
ttcagaaatg ttctaagtat tgctccaata atgttctcaa acaaaatggc gagactggga
aaagggtata tgtttgagag caagagtatg aaacttagaa ctcaaatacc tgcagaaatg
ctagcaagca ttgatttgaa atatttcaat gattcaacaa gaaagaagat tgaaaaaatc
cgaccgctct taatagaggg gactgcatca ttgagccctg gaatgatgat gggcatgttc
aatatgttaa gcactgtatt aggcgtctcc atcctgaatc ttggacaaaa gagatacacc
aagactactt actggtggga tggtcttcaa tcctctgacg attttgctct gattgtgaat
gcacccaatc atgaagggat tcaagccgga gtcgacaggt tttatcgaac ctgtaagcta
cttggaatca atatgagcaa gaaaaagtct tacataaaca gaacaggtac atttgaattc
acaagttttt tctatcgtta tgggtttgtt gccaatttca gcatggagct tcccagtttt
ggggtgtctg ggatcaacga gtcagcggac atgagtattg gagttactgt catcaaaaac
aatatgataa acaatgatct tggtccagca acagctcaaa tggcccttca gttgttcatc
aaagattaca ggtacacgta ccgatgccat agaggtgaca cacaaataca aacccgaaga
tcatttgaaa taaagaaact gtgggagcaa acccgttcca aagctggact gctggtctcc
gacggaggcc caaatttata caacattaga aatctccaca ttcctgaagt ctgcctaaaa
tgggaattga tggatgagga ttaccagggg cgtttatgca acccactgaa cccatttgtc
agccataaag aaattgaatc aatgaacaat gcagtgatga tgccagcaca tggtccagcc
aaaaacatgg agtatgatgc tgttgcaaca acacactcct ggatccccaa aagaaatcga
tccatcttga atacaagtca aagaggagta cttgaagatg aacaaatgta ccaaaggtgc
tgcaatttat ttgaaaaatt cttccccagc agttcataca gaagaccagt cgggatatcc
agtatggtgg aggctatggt ttccagagcc cgaattgatg cacggattga tttcgaatct

Figure 10 cont.

ggaaggataa agaaagaaga gttcactgag atcatgaaga tctgttccac cattgaagag
ctcagacggc aaaaatagtg aatttagctt gtccttcatg aaaaaatgcc ttgtttctac t (SEQ ID NO:40) which encodes M D V N P T L L F L K V P A Q N A I S T T F P Y T G D P P Y S H G T G T G Y
T M D T V N R T H Q Y S E K G R W T T N T E T G A P Q L N P I D G P L P E D
N E P S G Y A Q T D C V L E A M A F L E E S H P G I F E N S C I E T M E V V
Q Q T R V D K L T Q G R Q T Y D W T L N R N Q P A A T A L A N T I E V F R
S N G L T A N E S G R L I D F L K D V M E S M K K E E M G I T T H F Q R K R
R V R D N M T K K M I T Q R T I G K R K Q R L N K R G Y L I R A L T L N T M
T K D A E R G K L K R R A I A T P G M Q I R G F V Y F V E T L A R S I C E K
L E Q S G L P V G G N E K K A K L A N V V R K M M T N S Q D T E L S F T I T
G D N T K W N E N Q N P R M F L A M I T Y M T R N Q P E W F R N V L S I A
P I M F S N K M A R L G K G Y M F E S K S M K L R T Q I P A E M L A S I D L
K Y F N D S T R K K I E K I R P L L I E G T A S L S P G M M M G M F N M L S
T V L G V S I L N L G Q K R Y T K T T Y W W D G L Q S S D D F A L I V N A P
N H E G I Q A G V D R F Y R T C K L L G I N M S K K K S Y I N R T G T F E F
T S F F Y R Y G F V A N F S M E L P S F G V S G I N E S A D M S I G V T V I K
N N M I N N D L G P A T A Q M A L Q L F I K D Y R Y T Y R C H R G D T Q I Q
T R R S F E I K K L W E Q T R S K A G L L V S D G G P N L Y N I R N L H I P E
V C L K W E L M D E D Y Q G R L C N P L N P F V S H K E I E S M N N A V M
M P A H G P A K N M E Y D A V A T T H S W I P K R N R S I L N T S Q R G V L
E D E Q M Y Q R C C N L F E K F F P S S S Y R R P V G I S S M V E A M V S R
A R I D A R I D F E S G R I K K E E F T E I M K I C S T I E E L R R Q K agcgaaagca ggtactgatt caaaatggaa gattttgtgc gacaatgctt caatccgatg
attgtcgagc ttgcggaaaa aacaatgaaa gagtatgggg aggacctgaa aatcgaaaca
aacaaatttg cagcaatatg cactcacttg gaagtatgct tcatgtattc agatttccac
ttcatcaatg agcaaggcga gtcaataatc gtagaacttg gtgatcctaa tgcacttttg
aagcacagat ttgaaataat cgagggaaga gatcgcacaa tggcctggac agtagtaaac
agtatttgca acactacagg ggctgagaaa ccaaagtttc taccagattt gtatgattac
aaggaaaata gattcatcga aattggagta acaaggagag aagttcacat atactatctg
gaaaaggcca ataaaattaa atctgagaaa acacacatcc acattttctc gttcactggg
gaagaaatgg ccacaagggc cgactacact ctcgatgaag aaagcagggc taggatcaaa
accaggctat tcaccataag acaagaaatg gccagcagag gcctctggga ttcctttcgt
cagtccgaga gaggagaaga gacaattgaa gaaaggtttg aaatcacagg aacaatgcgc
aagcttgccg accaaagtct cccgccgaac ttctccagcc ttgaaaattt tagagcctat
gtggatggat tcgaaccgaa cggctacatt gagggcaagc tgtctcaaat gtccaaagaa
gtaaatgcta gaattgaacc tttttgaaa acaacaccac gaccacttag acttccgaat
gggcctccct gtttctcagcg gtccaaattc ctgctgatgg atgccttaaa attaagcatt
gaggacccaa gtcatgaagg agagggaata ccgctatatg atgcaatcaa atgcatgaga
acattctttg gatggaagga acccaatgtt gttaaaccac acgaaaaggg aataaatcca
aattatcttc tgtcatggaa gcaagtactg gcagaactgc aggacattga gaatgaggag
aaaattccaa agactaaaaa tatgaaaaaa acaagtcagc taaagtgggc acttggtgag
aacatggcac cagaaaaggt agactttgac gactgtaaag atgtaggtga tttgaagcaa
tatgatagtg atgaaccaga attgaggtcg cttgcaagtt ggattcagaa tgagttcaac

Figure 10 cont.

aaggcatgcg aactgacaga ttcaagctgg atagagcttg atgagattgg agaagatgtg
gctccaattg aacacattgc aagcatgaga aggaattatt tcacatcaga ggtgtctcac
tgcagagcca cagaatacat aatgaagggg gtgtacatca atactgcctt acttaatgca
tcttgtgcag caatggatga tttccaatta attccaatga taagcaagtg tagaactaag
gagggaaggc gaaagaccaa cttgtatggt ttcatcataa aaggaagatc ccacttaagg
aatgacaccg acgtggtaaa ctttgtgagc atggagtttt ctctcactga cccaagactt
gaaccacaca aatgggagaa gtactgtgtt cttgagatag gagatatgct tctaagaagt
gccataggcc aggtttcaag gcccatgttc ttgtatgtga ggacaaatgg aacctcaaaa
attaaaatga aatggggaat ggagatgagg cgttgtctcc tccagtcact tcaacaaatt
gagagtatga ttgaagctga gtcctctgtc aaagagaaag acatgaccaa agagttcttt
gagaacaaat cagaaacatg gcccattgga gagtctccca aaggagtgga ggaaagttcc
attgggaagg tctgcaggac tttattagca aagtcggtat ttaacagctt gtatgcatct
ccacaactag aaggattttc agctgaatca agaaaactgc ttcttatcgt tcaggctctt
agggacaatc tggaacctgg gacctttgat cttgggggc tatatgaagc aattgaggag
tgcctaatta atgatccctg ggttttgctt aatgcttctt ggttcaactc cttccttaca
catgcattga gttagttgtg gcagtgctac tatttgctat ccatactgtc caaaaaagta
ccttgtttct act (SEQ ID NO:41) which encodes M E D F V R Q C F N P M I V E L A E K T M K E Y G E D L K I E T N K F A A I
C T H L E V C F M Y S D F H F I N E Q G E S I I V E L G D P N A L L K H R F E
I I E G R D R T M A W T V V N S I C N T T G A E K P K F L P D L Y D Y K E N
R F I E I G V T R R E V H I Y Y L E K A N K I K S E K T H I H I F S F T G E E M
A T R A D Y T L D E E S R A R I K T R L F T I R Q E M A S R G L W D S F R Q
S E R G E E T I E E R F E I T G T M R K L A D Q S L P P N F S S L E N F R A Y
V D G F E P N G Y I E G K L S Q M S K E V N A R I E P F L K T T P R P L R L P
N G P P C S Q R S K F L L M D A L K L S I E D P S H E G E G I P L Y D A I K C
M R T F F G W K E P N V V K P H E K G I N P N Y L L S W K Q V L A E L Q D I
E N E E K I P K T K N M K K T S Q L K W A L G E N M A P E K V D F D D C K
D V G D L K Q Y D S D E P E L R S L A S W I Q N E F N K A C E L T D S S W I
E L D E I G E D V A P I E H I A S M R R N Y F T S E V S H C R A T E Y I M K G
V Y I N T A L L N A S C A A M D D F Q L I P M I S K C R T K E G R R K T N L
Y G F I I K G R S H L R N D T D V V N F V S M E F S L T D P R L E P H K W E
K Y C V L E I G D M L L R S A I G Q V S R P M F L Y V R T N G T S K I K M K
W G M E M R R C L L Q S L Q Q I E S M I E A E S S V K E K D M T K E F F E N
K S E T W P I G E S P K G V E E S S I G K V C R T L L A K S V F N S L Y A S P
Q L E G F S A E S R K L L L I V Q A L R D N L E P G T F D L G G L Y E A I E E
C L I N D P W V L L N A S W F N S F L T H A L S agcaaaagca gggtagataa tcactcactg agtgacatca aaatcatggc gtcccaaggc
accaaacggt cttacgaaca gatggagact gatggagaac gccagaatgc cactgaaatc
agagcatccg tcggaaaaat gattggtgga attggacgat tctacatcca aatgtgcaca
gaacttaaac tcagtgatta tgagggacgg ttgatccaaa acagcttaac aatagagaga
atggtgctct ctgcttttga cgaaaggaga aataaatacc tggaagaaca tcccagtgcg
gggaaagatc ctaagaaaac tggaggacct atatacagaa gagtaaacgg aaagtggatg
agagaactca tcctttatga caaagaagaa ataaggcgaa tctggcgcca agctaataat
ggtgacgatg caacggctgg tctgactcac atgatgatct ggcattccaa tttgaatgat
gcaacttatc agaggacaag ggctcttgtt cgcaccggaa tggatcccag gatgtgctct

Figure 10 cont.

ctgatgcaag gttcaactct ccctaggagg tctggagccg caggtgctgc agtcaaagga
gttggaacaa tggtgatgga attggtcagg atgatcaaac gtgggatcaa tgatcggaac
ttctggaggg gtgagaatgg acgaaaaaca agaattgctt atgaaagaat gtgcaacatt
ctcaaaggga aatttcaaac tgctgcacaa aaagcaatga tggatcaagt gagagagagc
cggaacccag ggaatgctga gttcgaagat ctcacttttc tagcacggtc tgcactcata
ttgagagggt cggttgctca caagtcctgc ctgcctgcct gtgtgtatgg acctgccgta
gccagtgggt acgactttga aagagaggga tactctctag tcggaataga ccctttcaga
ctgcttcaaa acagccaagt gtacagccta atcagaccaa atgagaatcc agcacacaag
agtcaactgg tgtggatggc atgccattct gccgcatttg aagatctaag agtattgagc
ttcatcaaag ggacgaaggt ggtcccaaga gggaagcttt ccactagagg agttcaaatt
gcttccaatg aaaatatgga gactatggaa tcaagtacac ttgaactgag aagcaggtac
tgggccataa ggaccagaag tggaggaaac accaatcaac agagggcatc tgcgggccaa
atcagcatac aacctacgtt ctcagtacag agaaatctcc cttttgacag aacaaccgtt
atggcagcat tcactgggaa tacagagggg agaacatctg acatgaggac cgaaatcata
aggatgatgg aaagtgcaag accagaagat gtgtctttcc aggggcgggg agtcttcgag
ctctcggacg aaaaggcagc gagcccgatc gtgccttcct ttgacatgag taatgaagga
tcttatttct tcggagacaa tgcagaggag tacgacaatt aaagaaaaat acccttgttt
ctact (SEQ ID NO:42) which encodes M A S Q G T K R S Y E Q M E T D G E R Q N A T E I R A S V G K M I G G I G R
F Y I Q M C T E L K L S D Y E G R L I Q N S L T I E R M V L S A F D E R R N K
Y L E E H P S A G K D P K K T G G P I Y R R V N G K W M R E L I L Y D K E E
I R R I W R Q A N N G D D A T A G L T H M M I W H S N L N D A T Y Q R T R
A L V R T G M D P R M C S L M Q G S T L P R R S G A A G A A V K G V G T M
V M E L V R M I K R G I N D R N F W R G E N G R K T R I A Y E R M C N I L K
G K F Q T A A Q K A M M D Q V R E S R N P G N A E F E D L T F L A R S A L I
L R G S V A H K S C L P A C V Y G P A V A S G Y D F E R E G Y S L V G I D P
F R L L Q N S Q V Y S L I R P N E N P A H K S Q L V W M A C H S A A F E D L
R V L S F I K G T K V V P R G K L S T R G V Q I A S N E N M E T M E S S T L
E L R S R Y W A I R T R S G G N T N Q Q R A S A G Q I S I Q P T F S V Q R N L
P F D R T T V M A A F T G N T E G R T S D M R T E I I R M M E S A R P E D V
S F Q G R G V F E L S D E K A A S P I V P S F D M S N E G S Y F F G D N A E E
Y D N agcaaaagca ggtagatatt gaaagatgag tcttctaacc gaggtcgaaa cgtacgttct
ctctatcatc ccgtcaggcc ccctcaaagc cgagatcgca cagagacttg aagatgtctt
tgcagggaag aacaccgatc ttgaggttct catggaatgg ctaaagacaa gaccaatcct
gtcacctctg actaagggga ttttaggatt tgtgttcacg ctcaccgtgc ccagtgagcg
aggactgcag cgtagacgct ttgtccaaaa tgcccttaat gggaacgggg atccaaataa
catggacaaa gcagttaaac tgtataggaa gctcaagagg gagataacat tccatggggc
caaagaaatc tcactcagtt attctgctgg tgcacttgcc agttgtatgg gcctcatata
caacaggatg gggctgtga ccactgaagt ggcatttggc ctggtatgtg caacctgtga
acagattgct gactcccagc atcggtctca taggcaaatg gtgacaacaa ccaacccact
aatcagacat gagaacagaa tggttttagc cagcactaca gctaaggcta tggagcaaat
ggctggatcg agtgagcaag cagcagaggc catggaggtt gctagtcagg ctaggcaaat
ggtgcaagcg atgagaacca ttgggactca tcctagctcc agtgctggtc tgaaaaatga
tcttcttgaa aatttgcagg cctatcagaa acgaatgggg gtgcagatgc aacggttcaa
gtgatcctct cgctattgcc gcaaatatca ttgggatctt gcacttgata ttgtggattc
ttgatcgtct ttttttcaaa tgcatttacc gtcgctttaa atacggactg aaaggagggc

Figure 10 cont.

```
cttctacgga aggagtgcca aagtctatga gggaagaata tcgaaaggaa cagcagagtg
ctgtggatgc tgacgatggt cattttgtca gcatagagct ggagtaaaaa actaccttgt
ttctact (SEQ ID NO:43) which encodes
```

MS L L T E V E T Y V L S I I P S G P L K A E I A Q R L E D V F A G K N T D L
E V L M E W L K T R P I L S P L T K G I L G F V F T L T V P S E R G L Q R R R
F V Q N A L N G N G D P N N M D K A V K L Y R K L K R E I T F H G A K E I S
L S Y S A G A L A S C M G L I Y N R M G A V T T E V A F G L V C A T C E Q I
A D S Q H R S H R Q M V T T T N P L I R H E N R M V L A S T T A K A M E Q
M A G S S E Q A A E A M E V A S Q A R Q M V Q A M R T I G T H P S S S A G
L K N D L L E N L Q A Y Q K R M G V Q M Q R F K

```
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gatcagaaat ccctaagagg aaggggcagc actcttggtc     180
tggacatcga gacagccaca cgtgctggaa agcagatagt ggagcggatt ctgaaagaag     240
aatccgatga ggcacttaaa atgaccatgg cctctgtacc tgcgtcgcgt tacctaaccg     300
acatgactct tgaggaaatg tcaagggaat ggtccatgct catacccaag cagaaagtgg     360
caggccctct ttgtatcaga atggaccagg cgatcatgga taaaaacatc atactgaaag     420
cgaacttcag tgtgattttt gaccggctgg agactctaat attgctaagg gctttcaccg     480
aagagggagc aattgttggc gaaatttcac cattgccttc tcttccagga catactgctg     540
aggatgtcaa aaatgcagtt ggagtcctca tcggaggact tgaatggaat gataacacag     600
ttcgagtctc tgaaactcta cagagattcg cttggagaag cagtaatgag aatgggagac     660
ctccactcac tccaaaacag aaacgagaaa tggcgggaac aattaggtca gaagtttgaa     720
gaaataagat ggttgattga agaagtgaga cacaaactga aggtaacaga gaatagtttt     780
gagcaaataa catttatgca agccttacat ctattgcttg aagtggagca agagataaga     840
actttctcat ttcagcttat
ttaataataa aaaacaccct
tgtttctact
(SEQ ID NO:44)
```

1 mnpnqkiiti gsvcmtigma nliilqignii siwishsiql gnqnqietcn qsvityennt
61 wvnqtyvnis ntnfaaggsv vsvklagnss lcpvsgwaiy skdnsvrigs kgdvfvirep
121 fiscsplecr tffltqgall ndkhsngtik drspyrtlms cpigevpspy nsrfesvaws
181 asachdginw ltigisgpdn gavavlkyng iitdtikswr nnilrtqese cacvngscft
241 vmtdgpsngq asykifriek gkivksvemn apnyhyeecs cypdsseitc vcrdnwhgsn
301 rpwvsfnqnl eyqigyicsg ifgdnprpnd ktgscgpvss ngangvkgfs fkygngvwig
361 rtksissrng femiwdpngw tgtdnnfsik qdivginews gysgsfvqhp eltgldcirp
421 cfwvelirgr pkentiwtsg ssisfcgvns dtvgwswpdg aelpftidk

N7

1 mnpnqkifal sgvaialsil nlligisnvg lnvslhlkgs sdqdknwtct svtqnnttli
61 entyvnnttv idketgtakp nylmlnkslc kvegwvvvak dnairfgese qiivtrepyv
121 scdplgckmy alhqgttirn khsngtihdr tafrglistp lgsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkg fgfldssntw
361 lgrtisprsr sgfemlkipn aetdpnskit erqeivdnnn wsgysgsfid ywdessecyn 421 pcfyvelirg rpeeakyvgw tsnslialcg spisvgsgsf pdgaqiqyfs

N9 mnpnqkilct satailigai avligianlg lniglhlkpg cncshsqpet tntsqtiinn
61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpva eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
421 velirgrpke dkvwwtsnsi vsmcsstefl gqwnwpdgak ieyfl

N2

1 mnpnqkiiti gsvsltisti cffmqiaili ttvtlhfkqy efnsppnnqv mlceptiier
61 niteivyltn ttiekeicpk laeyrnwskp qcnitgfapf skdnsirlsa ggdiwvtrep
121 yvscdpdkcy qfalgqgttl nnvhsndivh drtpyrtllm nelgvpfhlg tkqvciawss
181 sschdgkawl hvcvtgdden atasfiyngr ladsivswsk kilrtqesec vcingtctvv
241 mtdgsasgka dtkilfieeg kivhtstlsg saqhveecsc yprypgvrcv crdnwkgsnr

Figure 11 cont.

301 pivdinikdy sivssyvcsg lvgdtprknd sssshcldp nneegghgvk gwafddgndv
361 wmgrtisekl rsgyetfkvi egwsnpnskl qinrqvivdr gnrsgysgif svegkscinr
421 cfyvelirgr kqetevlwts nsivvfcgts gtygtgswpd gadinlmpi

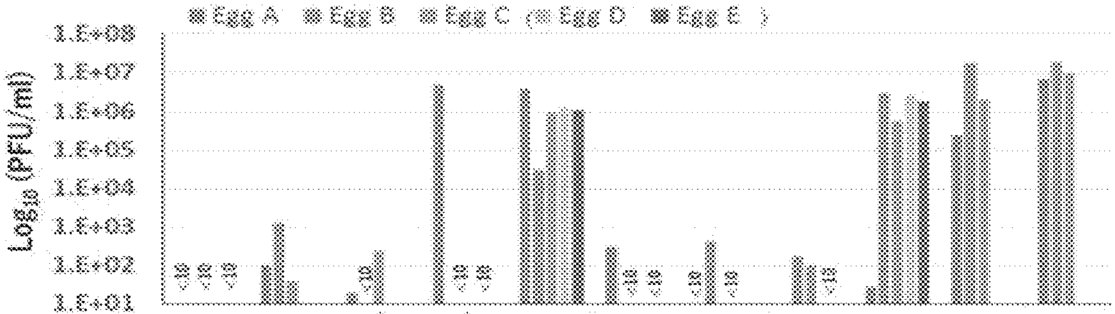

| | | | | | | | | | | | |
|---|---|---|---|---|---|---|---|---|---|---|---|
| T32A | wt | mutant | mutant | mutant | wt | mutant | mutant | mutant | wt | mutant | mutant |
| D147N | wt | mutant | mutant | wt | mutant | mutant | mutant | wt | mutant | mutant | mutant |
| N329D | wt | mutant | wt | mutant | mutant | mutant | wt | mutant | mutant | mutant | mutant |
| H347Q | wt | wt | mutant | mutant | mutant | wt | mutant | mutant | mutant | mutant | mutant |
| Δ46-50aa | wt | mutant | mutant | mutant | mutant | wt | wt | wt | wt | wt | mutant |

Figure 12

| Passage 1 | | | Passage 2 | | | Passage 3 | | |
|---|---|---|---|---|---|---|---|---|
| egg | virus titer (pfu/ml) | HA mutation | egg | virus titer (pfu/ml) | HA mutation | egg | virus titer (pfu/ml) | HA mutation |
| A | $2.6x10^6$ | none | A1 | $6.6x10^6$ | none | A1a | $5.3x10^7$ | none |
| | | | | | | A1b | $1.2x10^8$ | none |
| | | | | | | A1c | $3.7x10^7$ | none |
| | | | A2 | $3.5x10^7$ | none | A2a | $5.8x10^7$ | none |
| | | | | | | A2b | $1.0x10^8$ | none |
| | | | A3 | $2.8x10^7$ | none | A3a | $3.0x10^7$ | none |
| | | | | | | A3b | $5.5x10^7$ | none |
| B | $3.7x10^7$ | none | B1 | $1.15x10^8$ | none | B1a | $4.3x10^8$ | none |
| | | | | | | B1b | $1.6x10^8$ | none |
| | | | B2 | $4.85x10^7$ | none | B2a | $2.1x10^7$ | none |
| | | | | | | B2b | $4.3x10^7$ | none |
| C | $9.0x10^6$ | none | C1 | $2.65x10^7$ | none | C1a | $5.3x10^7$ | none |
| | | | | | | C1b | $9.3x10^6$ | none |
| | | | C2 | $6.45x10^7$ | none | C2a | $3.8x10^7$ | none |
| | | | C3 | $1.6x10^8$ | none | C3a | $3.4x10^8$ | none |
| | | | | | | C3b | $3.9x10^8$ | none |

Figure 13

| AM: amniotic cavity | AM1 | | | AM1AL1 | | | AM1AL2 | | | | AM1AL3 | | | | AM1AL4 | | | | AM1AL5 | | | |
|---|---|---|---|---|---|---|---|---|---|---|---|---|---|---|---|---|---|---|---|---|---|---|
| AL: allantoic cavity | titer | mutation | | titer | mutation | | egg | titer | mutation | | egg | titer | mutation | | egg | titer | mutation | | egg | titer | mutation | |
| | pfu/ml | HA | NA | pfu/ml | HA | NA | | pfu/ml | HA | NA | | pfu/ml | HA | NA | | pfu/ml | HA | NA | | pfu/ml | HA | NA |
| | $1.1\times10^7$ | nd | nd | $9.4\times10^6$ | none | T148K, D151E, H347G | a | $1.2\times10^7$ | none | T148K, D151E, H347G | a | $1.5\times10^7$ | none | [illegible] | a | $1.1\times10^8$ | none | [illegible] | a | $1.1\times10^7$ | none | [illegible] |
| | | | | | | | | | | | | | | | | | | | b | $2.6\times10^7$ | none | [illegible] |
| | | | | | | | | | | | | | | | | | | | c | $1.2\times10^7$ | none | [illegible] |
| Virus generated by reverse genetics | | | | | | | | | | | | | | | | | | | d | $1.1\times10^7$ | none | [illegible] |
| | | | | | | | | | | | | | | | b | $1.1\times10^8$ | none | [illegible] | a | $7.5\times10^7$ | none | [illegible] |
| HA: A/HK/4801/2014 | | | | | | | b | $1.1\times10^7$ | none | T148K, D151E, H347G | a | $2.3\times10^7$ | none | [illegible] | a | $1.2\times10^8$ | none | [illegible] | a | $1.8\times10^7$ | none | [illegible] |
| NA: A/HK/4801/2014NA(T148K, N329X, 347X | | | | | | | | | | | | | | | | | | | b | $1.6\times10^7$ | none | [illegible] |
| backbone: High Yield-PR8 | | | | | | | | | | | | | | | | | | | c | $7.3\times10^6$ | none | [illegible] |
| | | | | | | | | | | | | | | | | | | | d | $1.9\times10^7$ | none | [illegible] |
| titer: $4\times10^4$ (pfu/ml) | | | | | | | | | | | | | | | | | | | e | $2.5\times10^7$ | none | [illegible] |
| | | | | | | | | | | | | | | | b | $8.6\times10^6$ | none | [illegible] | a | $1.3\times10^7$ | none | [illegible] |
| | | | | | | | | | | | | | | | | | | | b | $1.3\times10^7$ | none | [illegible] |
| | | | | | | | | | | | | | | | | | | | c | $1.0\times10^7$ | none | [illegible] |
| | | | | | | | | | | | | | | | | | | | d | $3.2\times10^7$ | none | [illegible] |
| | | | | | | | | | | | b | $3.1\times10^7$ | none | [illegible] | a | $1.3\times10^8$ | none | [illegible] | a | $8.6\times10^6$ | none | [illegible] |
| | | | | | | | | | | | | | | | | | | | b | $1.7\times10^7$ | none | [illegible] |
| | | | | | | | | | | | | | | | | | | | c | $6.9\times10^7$ | none | [illegible] |
| | | | | | | | | | | | | | | | b | $5.8\times10^6$ | none | [illegible] | a | $2.7\times10^7$ | none | [illegible] |

Figure 14

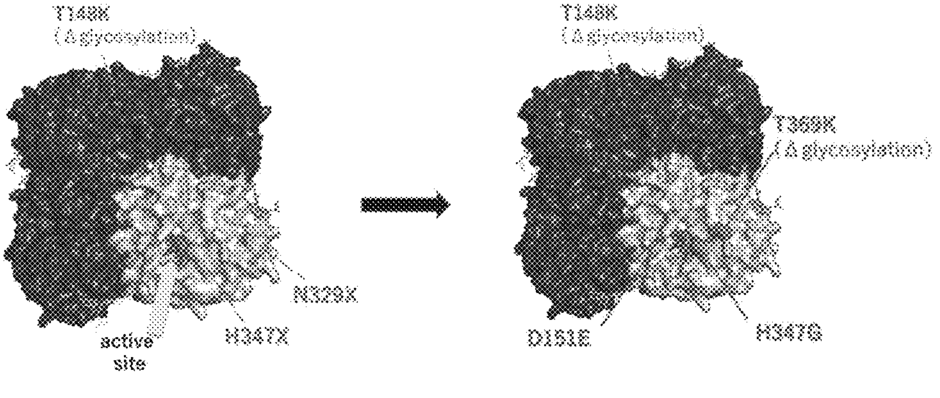

Figure 15

| | | | | | |
|---|---|---|---|---|---|
| 153 | T | N | N | N | N |
| 329 | N | T | T | D | D |
| 347 | H | H | Q | H | Q |
| 369 | T | K | K | K | K |

| Passage 1 | | | Passage 2 | | | Passage 3 | | |
|---|---|---|---|---|---|---|---|---|
| egg | virus titer (pfu/ml) | HA mutation | egg | virus titer (pfu/ml) | HA mutation | egg | virus titer (pfu/ml) | HA mutation |
| A | $2.6x10^6$ | none | A1 | $6.6x10^6$ | none | A1a | $5.3x10^7$ | none |
| | | | | | | A1b | $1.2x10^8$ | none |
| | | | | | | A1c | $3.7x10^7$ | none |
| | | | A2 | $3.5x10^7$ | none | A2a | $5.8x10^7$ | none |
| | | | | | | A2b | $1.0x10^8$ | none |
| | | | A3 | $2.8x10^7$ | none | A3a | $3.0x10^7$ | none |
| | | | | | | A3b | $5.5x10^7$ | none |
| B | $3.7x10^7$ | none | B1 | $1.15x10^8$ | none | B1a | $4.3x10^6$ | none |
| | | | | | | B1b | $1.6x10^8$ | none |
| | | | B2 | $4.85x10^7$ | none | B2a | $2.1x10^7$ | none |
| | | | | | | B2b | $4.3x10^7$ | none |
| C | $9.0x10^5$ | none | C1 | $2.65x10^7$ | none | C1a | $5.3x10^7$ | none |
| | | | | | | C1b | $9.3x10^6$ | none |
| | | | C2 | $6.45x10^7$ | none | C2a | $3.8x10^7$ | none |
| | | | C3 | $1.6x10^6$ | none | C3a | $3.4x10^8$ | none |
| | | | | | | C3b | $3.9x10^8$ | none |

Fig. 19

AM: amniotic cavity
AL: allantoic cavity

| | AM1 | | | AM1AL1 | | | AM1AL2 | | | | AM1AL3 | | | | AM1AL4 | | | | AM1AL5 | | | |
|---|---|---|---|---|---|---|---|---|---|---|---|---|---|---|---|---|---|---|---|---|---|---|
| | titer pfu/ml | mutation HA | mutation NA | titer pfu/ml | mutation HA | mutation NA | egg | titer pfu/ml | mutation HA | mutation NA | egg | titer pfu/ml | mutation HA | mutation NA | egg | titer pfu/ml | mutation HA | mutation NA | egg | titer pfu/ml | mutation HA | mutation NA |
| Virus generated by reverse genetics<br><br>HA: A/HK/4801/2014<br>NA: A/HK/4801/2014NA(T148K, N329X, 347X)<br>backbone: High Yield-PR8<br><br>titer: $4x10^4$ (pfu/ml) | $1.1x10^6$ | nd | nd | $9.4x10^6$ | none | T148K, D151E, H347G | a | $1.2x10^5$ | none | T148K, D151E, H347G | a | $1.5x10^7$ | none | 4M* | a | $1.1x10^8$ | none | 4M | a | $1.1x10^7$ | none | 4M |
| | | | | | | | | | | | | | | | | | | | b | $2.6x10^7$ | none | 4M |
| | | | | | | | | | | | | | | | | | | | c | $3.2x10^7$ | none | 4M |
| | | | | | | | | | | | | | | | | | | | d | $1.1x10^7$ | none | 4M |
| | | | | | | | | | | | | | | | b | $1.1x10^8$ | none | 4M | a | $7.5x10^6$ | none | 4M |
| | | | | | | | b | $1.1x10^7$ | none | T148K, D151E, H347G | a | $2.3x10^7$ | none | 4M | a | $1.2x10^8$ | none | 4M | a | $1.6x10^7$ | none | 4M |
| | | | | | | | | | | | | | | | | | | | b | $1.6x10^7$ | none | 4M |
| | | | | | | | | | | | | | | | | | | | c | $7.3x10^6$ | none | 4M |
| | | | | | | | | | | | | | | | | | | | d | $1.9x10^7$ | none | 4M |
| | | | | | | | | | | | | | | | | | | | e | $2.5x10^7$ | none | 4M |
| | | | | | | | | | | | | | | | b | $6.6x10^8$ | none | 4M | a | $1.3x10^7$ | none | 4M |
| | | | | | | | | | | | | | | | | | | | b | $1.3x10^7$ | none | 4M |
| | | | | | | | | | | | | | | | | | | | c | $1.0x10^7$ | none | 4M |
| | | | | | | | | | | | | | | | | | | | d | $3.2x10^7$ | none | 4M |
| | | | | | | | | | | | b | $3.1x10^7$ | none | 4M | a | $3.3x10^8$ | none | 4M | a | $8.0x10^6$ | none | 4M |
| | | | | | | | | | | | | | | | | | | | b | $1.7x10^7$ | none | 4M |
| | | | | | | | | | | | | | | | | | | | c | $6.9x10^7$ | none | 4M |
| | | | | | | | | | | | | | | | b | $5.8x10^8$ | none | 4M | a | $2.7x10^7$ | none | 4M |

| | | | Egg 1 | Egg 2 | Egg 3 | Egg 1 | Egg 2 | Egg 3 | Egg 1 | Egg 2 | Egg 3 | Egg 1 | Egg 2 | Egg 3 |
|---|---|---|---|---|---|---|---|---|---|---|---|---|---|---|
| K189E-N158K-A212T | P4 | Inoculation | 6.0 | | | 5.0 | | | 4.0 | | | 3.0 | | |
| | | Harvested | 4.3 | 2.6 | [illegible] | 1.3 | N.D. | N.D. | N.D. | N.D. | N.D. | N.D. | N.D. | N.D. |
| | P5 | Inoculation | 6.0 | | | 5.0 | | | 4.0 | | | | | |
| | | Harvested | [illegible] | 2.6 | [illegible] | 4.9 | 5.9 | [illegible] | 4.2 | 4.1 | 1.8 | | | |
| | P6 | Inoculation | 6.1 | | | 5.1 | | | 4.1 | | | | | |
| | | Harvested | [illegible] | [illegible] | [illegible] | [illegible] | [illegible] | [illegible] | [illegible] | 4.7 | [illegible] | | | |
| | P7 | Inoculation | 4.5 | | | 3.5 | | | 2.5 | | | 1.5 | | |
| | | Harvested | [illegible] | [illegible] | [illegible] | [illegible] | [illegible] | [illegible] | [illegible] | [illegible] | [illegible] | [illegible] | 2.7 | 2.1 |
| | P8 | Inoculation | 3.4 | | | 2.4 | | | 1.4 | | | 0.4 | | |
| | | Harvested | [illegible] | [illegible] | [illegible] | 2.3 | 4.6 | [illegible] | [illegible] | 4.8 | 2.7 | N.D. | N.D. | N.D. |
| | P9 | Inoculation | 2.3 | | | 1.3 | | | 0.3 | | | | | |
| | | Harvested | [illegible] | [illegible] | 3.5 | 1.8 | 1.3 | [illegible] | N.D. | N.D. | 1.8 | | | |
| | P10 | Inoculation | 3.1 | | | 2.1 | | | 1.1 | | | | | |
| | | Harvested | 3.3 | 2.9 | [illegible] | [illegible] | [illegible] | [illegible] | 4.3 | [illegible] | [illegible] | | | |
| | P11 | Inoculation | 4.0 | | | 3.0 | | | 2.0 | | | | | |
| | | Harvested | [illegible] | [illegible] | 4.8 | [illegible] | [illegible] | 6.0 | 3.0 | [illegible] | [illegible] | | | |

| Inoculation | | | <- Titer (log10 PFU/egg) |
|---|---|---|---|
| Egg 1 | Egg 2 | Egg 3 | <- Titer (log10 PFU/mL) |

Figure 22. HA/NA mutations (HA-K189E/N158K/A212T mutant virus)

| | | HA | | NA | | | |
|---|---|---|---|---|---|---|---|
| | | | | 148 | 151 | 245 | 346 |
| | Passage | | | T | D | N | G |
| K189E/N158K/A212T | E4 | No mutation | | K | E | [illegible] | |
| | E6 | No mutation | | K | E | S | V |
| | E7 | No mutation | | K | E | S | V |
| | E10 | No mutation | | K | E | S | V |

Figure 23.

Allantoic titer (35C 3days)
2x10^3 pfu/egg inoculation

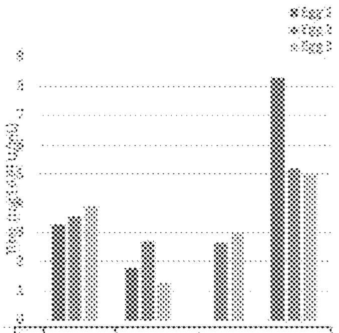

| | | WT | WT | NA mutants | | |
|---|---|---|---|---|---|---|
| Alaska NA | 148 | T | T | K | T | K |
| | 151 | D | D | E | D | E |
| | 245 | N | N | S | N | S |
| | 346 | G | G | G | V | V |
| Alaska HA | | | WT | WT | WT | WT |

Allantoic titer (35C 3days)
2x10^4 pfu/egg inoculation

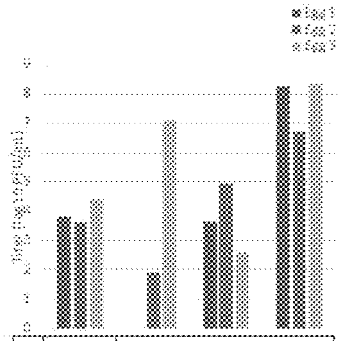

| | | WT | WT | NA mutants | | |
|---|---|---|---|---|---|---|
| Alaska NA | 148 | T | T | K | T | K |
| | 151 | D | D | E | D | E |
| | 245 | N | N | S | N | S |
| | 346 | G | G | G | V | V |
| Alaska HA | | | WT | WT | WT | WT |

RECOMBINANT INFLUENZA VIRUSES WITH STABILIZED HA FOR REPLICATION IN EGGS

CROSS-REFERENCE TO RELATED APPLICATIONS

This application is a continuation of U.S. application Ser. No. 16,170,321, filed Oct. 25, 2018, which application claims the benefit of the filing date of U.S. application Ser. No. 62/577,049, filed on Oct. 25, 2017, and U.S. application Ser. No. 62/633,400, filed on Feb. 21, 2018, the disclosures of which are incorporated by reference herein.

STATEMENT OF GOVERNMENT FUNDING

This invention was made with government support under HHSO100201500033C awarded by the Biomedical Advanced Research and Development Authority. The government has certain rights in the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, inactivated virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains.

There are four general types of influenza viruses, Type A, Type B, Type C and Type D, which are defined by the absence of serological crossreactivity between their internal proteins. Influenza Type A viruses are further classified into subtypes based on antigenic and genetic differences of their glycoproteins, the HA and NA proteins. All the known HA and NA subtypes (H1 to H18 and N1 to N11) have been isolated from aquatic birds, which are though to act as a natural reservoir for influenza.

Most influenza vaccines are produced in embryonated chicken eggs. However, the WHO-recommended influenza vaccine strains often do not replicate efficiently in embryonated chicken eggs, requiring serial passages in eggs in order to allow for adaptation of the virus. During adaptation and amplification in eggs, the hemagglutinin (HA) protein of influenza viruses often acquires egg-adapting mutations. These egg-adapting mutations in HA often alter the antigenicity of the viruses, resulting in vaccine viruses that are no longer optimally matched to the circulating virus strains.

SUMMARY

As described herein, an influenza virus was passaged 7 times in eggs (in triplicate) to study the mutations that occurred in the 6 non-immunogenic viral segments during adaptation. Surprisingly, the virus acquired no HA mutations and instead had mutations in the NA, PB2, NP, and M1 proteins. The NA mutations were identical in all three experiments, and they included a deletion and 4 amino acid mutations, The NA mutations were tested alone and it was found that they, e.g., alone or in various combinations, were responsible for the effect, which permitted efficient growth in eggs without HA mutations.

The present disclosure thus relates to influenza mutations that prevent the acquisition of antigenicity-compromising mutations in the hemagglutinin (HA) segment of influenza virus during growth in eggs. The mutations in the neuraminidase (NA) protein of human influenza viruses were found to ‘stabilize’ the HA during egg-passages, e.g., in the presence of the mutations in NA, the HA protein did not acquire egg-adapting mutations. Those NA mutations may also increase the vaccine virus yield.

The disclosure provides isolated recombinant, e.g., reassortant, influenza viruses with selected amino acid residues or deletions at specified positions in NA. In one embodiment, the NA is selected to not encode a threonine at residue 32. In one embodiment, the NA is selected to not encode an aspartic acid at position 147. In one embodiment, the NA is selected to not encode an asparagine at residue 329. In one embodiment, the NA is selected to not encode a threonine at residue 329. In one embodiment, the NA is selected to not encode a histidine at residue 347. In one embodiment, the NA is selected to not encode an arginine or an asparagine at residue 347. In one embodiment, the NA is selected to not encode a NA having a threonine at position 148. In one embodiment, the NA is selected to not encode a NA having an aspartic acid at position 151. In one embodiment, the NA is selected to not encode a NA having an asparagine at position 245. In one embodiment, the NA is selected to not encode a NA having a glycine at position 346. In one embodiment, the NA is selected to have a deletion of one or more of residues 46 to 50. The numbering for NA is based on N2. In one embodiment, the disclosure provides an isolated recombinant reassortant influenza virus having six “internal” viral segments from a vaccine influenza virus, e.g., PR8UW, a NA viral segment with one or more of the specified residues at particular positions or a deletion of specified residues, or any combination thereof, and a HA viral segment, e.g., any of H1-H18, e.g., from a circulating influenza virus. Also provided are compositions comprising the recombinant influenza virus, pharmaceutical compositions such as vaccines.

Thus, for vaccine viruses that are to be grown or passaged in cells, e.g., in eggs, replacement of the residue at position 32, 147, 329, 347, or a deletion of one or more of residues 46 to 50, or any combination thereof, in NA, e.g., by mutation, or selection of a NA viral segment for a NA to not encode a threonine at residue 32, to not encode an aspartic acid at position 147, to not encode an asparagine at residue 329, to not encode a histidine at residue 347, or to have a deletion of one or more of residues 46 to 50, or any combination thereof, wherein the numbering is based on N2, may result in stabilization of HA and/or higher viral titers. In one embodiment, for vaccine viruses that are to be grown or passaged in cells, e.g., in eggs, replacement of the residue at position 147, 329, 347, or a deletion of one or more of residues 46 to 50, or any combination thereof, in NA, e.g., by mutation, or selection of a NA viral segment for a NA to not encode an aspartic acid at position 147, to not encode an asparagine at residue 329, to not encode a histidine at residue 347, 369, or any combination thereof, or optionally not encode a threonine at residue 369. or any combination thereof, wherein the numbering is based on N2, may result in stabilization of HA and/or higher viral titers. In one embodiment, for vaccine viruses that are to be grown or passaged in cells, e.g., in eggs, replacement of the residue at position 148, 151. 245, 346, or any combination thereof, in NA, e.g., by mutation, or selection of a NA viral segment for a NA to not encode a threonine at residue 148, to not encode an aspartic acid at position 151, to not encode an asparagine at residue 245, to not encode a glycine at residue 346, or any combination thereof, wherein the numbering is based on N2, may result in stabilization of HA and/or higher viral titers. In one embodiment, for vaccine viruses that are to be grown or passaged in cells, e.g., in eggs, replacement of the residue at position 148, 151, 347, or any combination thereof, in NA, e.g., by mutation, or selection of a NA viral segment for a NA to not encode a threonine at residue 148, to not encode an aspartic acid at position 151, to not encode a histidine at residue 347, or any combination thereof, wherein the numbering is based on N2, may result in stabilization of HA and/or higher viral titers.

In one embodiment, the disclosure provides an isolated recombinant influenza virus comprising PA, PB1, PB2, NP, NS, M, and HA viral segments and a NA viral segment that encodes an NA selected to not encode a threonine at residue 32, to not encode an aspartic acid at position 147, to not encode an asparagine at residue 329, to not encode a histidine at residue 347, or to have a deletion of one or more of residues 46 to 50, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 32, does not have a deletion of residues 46 or 50, encodes an aspartic acid at position 147, encodes an asparagine at residue 329, encodes a histidine at residue 347, or any combination thereof. In one embodiment, the disclosure provides an isolated recombinant influenza virus comprising PA, PB1, PB2, NP, NS, M, and HA viral segments and a NA viral segment that encodes an NA selected to not encode a threonine at residue 148, to not encode an aspartic acid at position 151, to not encode an asparagine at residue 245, to not encode a glycine at residue 346, to not encode a histidine at residue 347, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 148, encodes an aspartic acid at position 151, encodes an asparagine at residue 245, encodes a glycine at residue 346, encodes a histidine at residue 347, or any combination thereof. In one embodiment, the isolated recombinant influenza virus is a reassortant. In one embodiment, the NA viral segment encodes a NA that has at least 80%, 85%, 90%, 95%, or 99% amino acid sequence identity to any one of SEQ ID Nos. 1-3, 30-38, 48-50, or 54. In one embodiment, the NA viral segment encodes a NA that has less than 100% amino acid sequence identity to SEQ ID NO:2 or SEQ 1D NO:3. In one embodiment, the NA viral segment encodes a N2, N3, N7, or N9 and the positions in N3, N7, or N9 with the specified residue(s) correspond to the specified positions in N2. In one embodiment, the NA viral segment encodes a N1, N4, N5, N6, N8, N10 or N11 and the positions in N1, N4, N5, N6, N8, N10 or N11 with the specified residue(s) correspond to the specified positions in N2. In one embodiment, the residue at position 32 is A, I, G, or L. In one embodiment, the deletion is a deletion of residues 46 to 50. In one embodiment, the residue at position 147 is N or Q. In one embodiment, the residue at position 329 is D or E. In one embodiment, the residue at position 347 is Q, N, 5, T, Y, C or W. In one embodiment, the HA is H1, H3, H5, H7, or H9. In one embodiment, the virus is an influenza A virus. In one embodiment, the PA, PB1, PB2, NP, M, and NS viral segments have at least 85% nucleic acid sequence identity to SEQ ID Nos. 24 to 29 or encode a polypeptide having at least 80%, 85%, 90%, 95%, or 99 amino acid sequence identity to a polypeptide encoded by SEQ ID Nos. 24 to 29 or 39-44. In one embodiment, the PB2 has I, A, L, or U at residue 147. In one embodiment, the virus is an influenza B virus.

Further provided is an isolated recombinant nucleic acid, e.g., a vector such as a viral vector, comprising a nucleic acid sequence that encodes an influenza virus NA selected to not encode a threonine at residue 32, to have a deletion of one or more of residues 46-50, to not encode an aspartic acid at position 147, to not encode an asparagine at residue 329, or to not encode a histidine at residue 347, or any combination thereof, wherein the numbering is based on N2. In one embodiment, the isolated recombinant nucleic acid does not encode a threonine at residue 148, to not encode an aspartic acid at position 151, to not encode an asparagine at residue 245, to not encode a glycine at residue 346, or any combination thereof. in one embodiment, the NA has at least 95% amino acid sequence identity to SEQ ID NO:1, SEQ ID NO:3, SEQ ID NO:48, or SEQ ID NO:49. In one embodiment, the NA has less than 100% amino acid sequence identity to SEQ ID NO:2 or SEQ ID NO:3, In one embodiment, the NA is a N2 N3, N7, or N9. In one embodiment, the NA is a N1, N4, N5, N6, N8, N10 or N11. In one embodiment, the residue at position 32 is A, I, or L. In one embodiment, the deletion is a deletion of residues 46 to 50. In one embodiment, the residue at position 147 is N or Q. In one embodiment, the residue at position 329 is D or E. In one embodiment, the residue at position 347 is Q, N, S, T, Y, C or W. In one embodiment, the residue at position 148 is K, R or H. In one embodiment, the residue at position 151 is E, N or Q. In one embodiment, the residue at position 245 is 8, T, I, IL, A, N, or V.

Also provided is a method to prepare influenza virus. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2. DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes an NA selected to not encode a threonine at residue 32, to not encode an aspartic acid at position 147, to not encode an asparagine at residue 329, to not encode a histidine at residue 347, to not encode a threonine at residue 148, to not encode an aspartic acid at position 151, to not encode an asparagine at residue 245, to not encode a glycine at residue 346, or to have a deletion of one or more of residues 46 to 50, or any combination thereof, wherein the numbering for NA residues is that for N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally comprising one or more of: a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a. promoter operably linked to a DNA segment encoding influenza virus NS1, or a vector for mRNA production comprising a promoter operably linked to a DNA segment encoding influenza virus NS2; in an amount effective to yield infectious influenza virus. In one embodiment, the NA has at least 80%, 85%, 90%, 95%, or 99% amino acid sequence identity to SEQ ID NO:1 SEQ ID NO:2, SEQ ID NO:3, SEQ ID NO:48 or SEQ ID NO:49. In one embodiment, the NA has less than 100% amino acid sequence identity to SEQ NO:2 or SEQ ID NO:3. In one embodiment, the NA is N2, N3, N7, or N9. In one embodiment, the NA is N1, N4, N5, N6, N8, N10 or N11. In one embodiment, the residue at position 32 is A, I, G, or L. In one embodiment, the deletion is a deletion of residues 46 to 50. In one embodiment, the residue at position 147 is N or Q. In one embodiment, the residue at position 329 is D or E. In one embodiment, the residue at position 346 is S, T, P, Y, W, A, N, I, L, or V. In one embodiment, the residue at position 347 is Q, N, S. T, Y, C or W. In one embodiment, the residue at position 148 is K, R or H. In one embodiment, the residue at position 151 is E, N or Q. In one embodiment, the residue at position 245 is S, T, I, L, A, N, or V.

In one embodiment, the HA is H1, H3, H5, H7, or H9. In one embodiment, the virus is an influenza A virus. In one embodiment, PA, PB1, PB2, NP, M, and NS viral segments have at least 85%, 85%, 90%, 95%, or 99% nucleic acid sequence identity to SEQ ID Nos. 24 to 29 or 39 to 44 or encode a polypeptide having at least 80% , 85%, 90%, 95%, or 99% amino acid sequence identity to a polypeptide encoded by SEQ ID Nos. 24 to 29 or 39 to 44. In one embodiment, 1132 has I, A, L, or G at residue 147. In one embodiment, HA is H2, H4, H5, H6, H8, or any of H10-H18. In one embodiment, the virus is an influenza B virus.

Further provided is a method of immunizing an avian or a mammal with a composition having an effective amount of the virus described herein. In one embodiment, the composition comprises at least one other different influenza virus, In one embodiment, the mammal is a human. In one embodiment, the composition is administered intranasally or via injection.

Thus, the invention provides a method to select for influenza viruses with enhanced replication in cell culture, e.g., in embryonated avian eggs. The method includes providing cells suitable for influenza vaccine production; serially culturing one or more influenza virus isolates in eggs; and isolating serially cultured virus with enhanced growth relative to the one or more isolates prior to serial culture. Also provided is a method to identify a NA that stabilizes HA and/or that confers altered growth of a recombinant influenza virus, e.g., in eggs. The method includes introducing one or more substitutions or deletions as described herein into a NA viral segment to yield a mutant NA viral segment; and optionally identifying whether the mutant NA viral segment, when present in a replication competent recombinant influenza virus, results in enhanced replication of the recombinant influenza virus in eggs and optionally inhibits HA mutations, relative to a corresponding replication competent influenza virus without the one or more substitutions and/or deletions in NA.

In one embodiment, the disclosure provides isolated influenza type A virus with a characteristic residue(s) and/or deletion, or a combination thereof, in NA described herein. In one embodiment, the isolated influenza type A virus with a characteristic residue(s) and/or deletion, or a combination thereof has an NA amino acid sequence with at least 80%, e.g., 90%, 92%, 95%, 97% or 99%, including any integer between 80 and 99, contiguous amino acid sequence identity to a polypeptide encoded by one of SEQ ID NOs:1, 2, 3, or 30-38. In one embodiment, the isolated influenza type A virus of the invention with a characteristic residue(s) and/or deletion, or a combination thereof, has an HA from any one of subtypes 1-18 of HA. In one embodiment the characteristic residue is a conservative substitution, e.g., relative to SEQ ID NO:2 or SEQ ID NO:3. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, a mutation is introduced into a NA viral segment of an influenza virus isolate, e.g., via recombinant DNA techniques including site-specific mutagenesis, or replacing a portion of the NA coding sequence with a portion that includes the characteristic residue(s) or deletion. In one embodiment, a NA viral segment with a characteristic residue and/or deletion described herein is combined with a HA segment, and internal viral segments of an influenza vaccine virus.

The disclosure provides a plurality of influenza virus vectors of the invention, e.g., those useful to prepare reassortant viruses including 6:1:1 reassortants, 6:2 reassortants and 7:1 reassortants. A 6:1:1 reassortant is an influenza virus with 6 internal viral segments from a vaccine virus, a HA viral segment that is from a different (second) viral isolate than the vaccine virus, and a NA viral segment with a characteristic residue(s) and/or deletion, or a combination thereof, as described herein, which is from a different viral source than the HA segment and the vaccine virus; a 6:2 reassortant is an influenza virus with 6 internal viral segments from a vaccine virus, and a NA viral segment having a characteristic residue(s) and/or deletion, or a combination thereof, which segment is from the same source as the HA segment, and a HA viral segment from a different viral isolate than the vaccine virus; and a 7:1 reassortant, in one embodiment, is an influenza virus with 6 internal viral segments and a HA segment from a vaccine virus, and a NA segment that is modified to include the characteristic residue(s) and/or deletion, or a combination thereof, which NA segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PI32, PA, NP, M, and NS, have sequences from an influenza virus that replicates to high titers in cultured mammalian cells such as Vero cells, MDCK cells, or PER.C6® cells, or embryonated eggs, and/or from a vaccine virus, e.g., one that does not cause significant disease in humans. The DNA for nRNA production of NA may be from any NA, e.g., any of N1-N9, and the DNA for vRNA production of HA may be from any HA, e.g., H1-H18. In one embodiment, the DNAs for vRNA production may be for an influenza B or C virus, For example, the DNAs for vRNA production include influenza B virus PA, PB1, PB2, NP, NS, and M or influenza B virus PA, PB1, PB2, NP, NS, M, and NA, wherein the vRNA for NA has a NA with a characteristic residue and/or deletion as described herein. The DNAs for nRNA production of NA and HA may be from different strains or isolates (6:1:1 reassortants) or from the same strain or isolate (6:2 reassortants), or the NA or HA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers, e.g., titers of at least about $10^5$ PFU/mL, e.g., at least $10^6$ PFU/mL, $10^7$ PFU/mL, or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in MDCK cells, e.g., titers of at least about $10^7$ PFU/mL, e.g., at least $10^8$ PFU/mL, or high titers in two of more of those host cells.

Other reassortants with internal genes from other PR8 isolates or vaccine viruses may be employed in recombinant reassortant viruses.

In one embodiment, the DNAs for the internal genes for PB1, PB2, PA, NP, M, and NS encode proteins with substantially the same activity as a corresponding polypeptide encoded by one of SEQ ID NOs:24-29 or 39 to 44. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ NOs:24-29 or 39 to 44. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:24-29 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs:24-29 or 39 to 44. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:24-29 or 39 to 44. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ NOs:24-29.

In one embodiment, the nucleic acid a sequence encoding a NA polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:1, 3, 30-35, 48-49, or one of Accession Nos. ACP41107.1 (N1) (SEQ ID NO:36) AIK26357.1 (N7) (SEQ ID NO:37), ALH21372.1 (N9) (SEQ ID NO:45), or BAK86313.1 (N2) (SEQ ID NO:50), the sequences of which are incorporated by reference herein. In one embodiment, the isolated and/or purified nucleic acid molecule encodes a polypeptide having at least 80%, e.g., 90%, 92%, 95%, 97% or 99%, including any integer between 80 and 99, contiguous amino acid sequence identity to a polypeptide encoded by SEQ ID NOs:1, 3, 30-35, 48-49, or one of Accession Nos. ACP41107.1 (N1) AIK26357.1 (N7), ALH21372.1 (N9), or BAK86313.1 (N2), the sequences of which are incorporated by reference herein. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:1, 3, 30-35, 48-49, or one of Accession Nos. ACP41107.1 (N1) AIK26357.1 (N7), ALH21372.1 (N9), or BAK86313.1 (N2), the sequences of which are incorporated by reference herein. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:1, 3, 30-35, 48-49, or one of Accession Nos. ACP41107.1 (N1) AIK26357.1 (N7), ALH21372.1 (N9), or BAK86313.1 (N2), the sequences of which are incorporated by reference herein.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 18 HA or 11 NA subtypes), B or C DNA (see Fields *Virology* (Fields et al. eds.), Lippincott, Williams and Wickens (2013), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:24-29 or 39 to 44, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:24-29, Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle.

In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

Thus, the modified neuraminidase comprises at least one, or at least two, or at least three modifications, wherein the modification comprise one or more amino acids within positions 29-35, one or more amino acids within positions 44-52, one or more amino acids within positions 144-154, one or more amino acid positions within 240-250, one or more amino acids within positions 326-333, one or more amino acid positions within 344-350, one or more amino acid positions within 365-375, or combinations thereof, wherein the numbering is that for N2. In one embodiment, the NA comprises a deletion of at least one proline, asparagine, glutamine, valine, or a combination of a proline, one or more asparagine(s), a glutamine, and a valine within positions 44-52; a substitution (replacement) of a threonine within positions 29-35; a substitution (replacement) of an threonine or an aspartic acid within positions 145-155; a substitution (replacement) of an asparagine within positions 240 to 250 or 326-333; a substitution (replacement) of a histidine within positions 345-350; or a combination thereof.

BRIEF DESCRIPTION OF FIGURES

FIG. 1. Nucleotide sequences for the viral segments of A/Yokohama/2017/2003 (SEQ ID Nos. 4-11), and amino acid sequence of the NA of A/Yokohama/2017/2003 (SEQ ID NO:3).

FIG. 2. Amino acid sequence for the NA of A/Saitama/103/2014 (SEQ ID NO:2)

FIG. 3. Nucleotide sequence of NA viral segment (SEQ ID NO:12) and amino acid sequences for NA of mutant of A/Yokohama/2017/2003 (SEQ ID NO:1), and nucleotide sequence of other viral segments of the mutant (SEQ ID Nos.12-21)

FIG. 9. Exemplary NA sequences for N3, N4, N6, N7, N8, and N9 (SEQ ID Nos. 30-35).

FIG. 10. Exemplary sequences for the internal viral segments for a master vaccine strain (SEQ ID Nos. 39-44 and 58-62).

FIG. 11. Exemplary NA sequences (SEQ ID Nos:51-54).

FIG. 12. Titers in eggs for various NA mutants.

FIG. 13. Titers of HK4801HA, Y2017-M3L4NA and HY-PR8 (PB2 C4U, I504V; PB1 C4, M40L/G180W; PA C4U, R401K; NP I116L; NS A30P/R118K) and analyses for HA mutations in infected eggs over time.

FIG. 14 shows data for viruses passaged in eggs that had certain NA mutants but did not result in substitutions in HA.

FIG. 15 is a schematic of the positions of certain NA residues.

FIG. 19 summarizes virus titers and HA status over time (HK4801HA, Y2017-M3L4NA and HY-PR8 (PB2 C4U, I504 PB1 C4U, M40L/G180W, PA C4U, R401K; NP I116L; NS A30P/R118K)).

FIG. 20 summarizes virus titers and HA status for viruses with different NAs.

FIG. 21 provides inoculation and harvested virus titers in allantoic passages (HA-K189E/N158K/A212T mutant virus).

FIG. 22 shows detection of HA status after multiple passages.

FIG. 23 shows egg titers for viruses with different NAs.

DETAILED DESCRIPTION

Definitions

Figure 4:
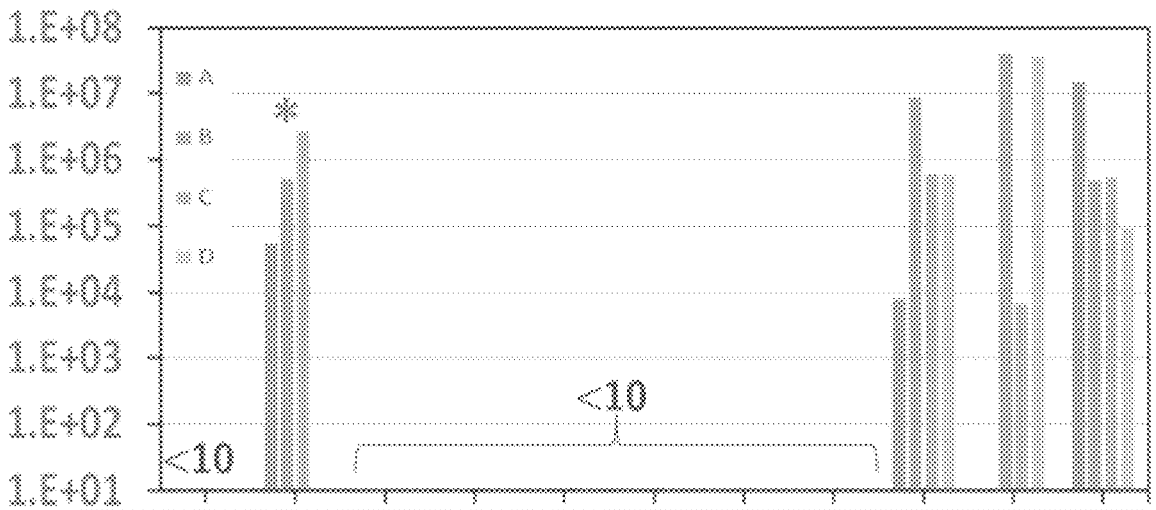
FIG. 4. Graph showing titers in eggs of various reassortants with the PB2, NA and NP segments of mutant and wild-type A/Yokohama/2017/2003. Virus inoculation: $2\times10^3$ pfu/egg into allantoic fluid, 72 h incubation at 37° C.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the disclosure, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (\'V) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence( )relative to the reference sequence, based on the designated program parameters.

Influenza Virus Structure and Propagation

Influenza. A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a viral segment with both NA and NB sequences. Influenza C virus has only seven viral segments.

Cells That Can Be Used to Produce Virus

Any cell, e.g., any avian or mammalian cell, such as avian eggs, a human, e.g., 293T or PER.C6® cells, or canine, bovine, equine, feline, swine, ovine, rodent, for instance mink, e.g., MvLul cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (h) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1987).

Virus produced by the host cell may be highly purified prior to vaccine or gene therapy formulation, Generally, the purification procedures result in extensive removal of cellular DNA and other cellular components, and adventitious agents. Procedures that extensively degrade or denature DNA may also be used.

Influenza Vaccines

A vaccine includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles.

The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone: treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (h) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes.

Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reasserted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, 0.1 to 2 μg, 0.5 to 5 μg, 1 to 10 μg, 10 μg to 20 μg, 15 μg to 30 μg, or 10 to 30 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water.

Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein, Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest, The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{20}$, e.g., $10^3$-$10^{12}$, $10^2$-$10^{10}$, $10^5$-$10^{11}$, $10^6$-$10^{15}$, $10^2$-$10^{10}$, or $10^{15}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 μg, 1 to 20 μg, 30 to 100 μg, 10 to 50 μg, 50 to 200 μg, or 150 to 300 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 0.1 μg to 1 μg, 0.5 μg to 5 μg, 1 μg to 10 μg, 10 μg to 20 μg, 15 μg to 30 μg, or 30 μg to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount. e.g., 1-50 μg or any range or value therein, or the amount recommended by the U.S. Public Health Service (PHS), which is usually 15 μg, per component for older children >3 years of age, and 7.5 μg per component for children <3 years of age. The quantity of NA can also be standardized, however, this glycoprotein can be labile during the processor purification and storage (Kendal et al., 1980; Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

Exemplary Viruses

Useful modifications of influenza neuraminidase (NA) proteins are described herein that stabilize hemagglutinin (HA) protein during egg-passages of influenza viruses that express those modified neuraminidase proteins. Modified nucleic acids are also described that encode such modified neuraminidase proteins. The modifications can include deletions, substitutions and combinations thereof within the neuraminidase protein and nucleic acid sequences. Viruses that express such modified neuraminidase proteins exhibit significantly reduced acquisition of antigenicity-compromising mutations in hemagglutinin (HA) during growth of influenza in eggs. For example, in sonic cases the modified neuraminidase can have at least one, or at least two, or at least three modifications. Amino acid positions within influenza neuraminidase proteins that can be modified include, for example, one or more amino acids within positions 29-35, one or more amino acids within positions 44-52, one or more amino acids within positions 144-154, one or more amino acid positions within 240-250, one or more amino acids within positions 326-333, one or more amino acid positions within 344-350, one or more amino acid positions within 365-375, and combinations thereof, based on N2 numbering. For example, the amino acid(s) can be any amino acid within these positions such as any of the amino acids listed in the table below.

| Original Residue | Exemplary Substitutions | Alternative Substitutions |
|---|---|---|
| Ala (A) | val; leu; ile | Val |
| Arg (R) | lys; gln; asn | Lys |
| Asn (N) | gln; his; lys; arg | Gln |
| Asp (D) | Glu, Asn | Glu; Asn |
| Cys (C) | Ser | Ser |
| Gln (Q) | Asn | Asn |
| Glu (E) | Asp | Asp |
| Gly (G) | Pro | Pro |
| His (H) | asn; gln; lys; arg; gln; | Arg; Gln |
| Ile (I) | leu; val; met; ala; phe norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala | Leu |
| Pro (P) | Gly | Gly |
| Ser (S) | Thr | Thr |
| Thr (T) | Ser, Ala | Ser, Als |
| Trp (W) | Tyr | Tyr |
| Tyr (Y) | trp; phe; thr; ser | Phe |
| Val (V) | ile; leu; met; phe; ala; norleucine | Leu |

In some cases, a selected amino acid within positions 29-35, positions 44-52, positions 144-154, positions 326-333, positions within 344-350, positions within 365-375, can have a conservative substitution. However, in other cases, the selected amino acid within positions 29-35, positions 44-52, positions 144-150, positions 326-333, positions within 344-350, positions within 365-375, can have a non-conservative substitution.

For example, a modified neuraminidase can have a deletion of at least one proline, asparagine, glutamine, valine, or a combination of a proline, one or more asparagine(s), a glutamine, and a valine within positions 44-52 of the modified neuraminidase. A modified neuraminidase can have a substitution (replacement) of a threonine within positions 29-35, where the replacement is any amino acid. A modified neuraminidase can have a substitution (replacement) of a threonine or an aspartic acid within positions 145-154 or 365 to 375, where the replacement is any amino acid. A modified neuraminidase can have a substitution (replacement) of an asparagine within positions 326-333, where the replacement is any amino acid. A modified neuraminidase can have a substitution (replacement) of a histidine within positions 345-350, where the replacement is any amino acid. Exemplary substitutions (replacements) for various types of amino acids are provided in the table above.

One example of an influenza A virus (A/Yokohama/2013/2003(H3N2)) neuraminidase protein sequence is provided below (SEQ ID NO: 55)

1 MNPNQKIITI GSVSLTISTI CFFMQIAILI TTVTLHFKQY

41 EFNSPPNNQV MLCEPTIIER NITEIVYLTN TTIEKEICPK

81 LAEYRNWSKP QCNITGFAPF SKDNSIRLSA GGDIWVTREP

-continued

121 YVSCDPDKCY QFALGQGTTL NNVHSNDIVH DRTPYRTLLM

161 NELGVPFHLG TKQVCIAWSS SSCHDGKAWL HVCVTGDDEN

201 ATASFIYNGR LADSIVSWSK KILRTQESEC VCINGTCTVV

241 MTDGSASGKA DTKILFIEEG KIVHTSTLSG SAQHVEECSC

281 YPRYPGVRCV CRDNWKGSNR PIVDINIKDY SIVSSYVCSG

321 LVGDTPRKND SSSSSHCLDP NNEEGGHGVK GWAFDDGNDV

361 WMGRTISEKL RSGYETFKVI EGWSNPNSKL QINRQVIVDR

401 GNRSGYSGIF SVEGKSCINR CFYVELIRGR KQETEVLWTS

441 NSIVVFCGTS GTYGTGSWPD GADINLMPI

Amino acids that can be modified to improve the stability of co-expressed HA are highlighted in bold and with underlining within the sequence shown above. A nucleic acid that encodes such an influenza A virus (A/Yokohama/2013/2003 (H3N2)) neuraminidase protein sequence is shown below (SEQ ID NO: 56)

1 AGCAAAAGCA GGAGTAAAGA TGAATCCAAA TCAAAAGATA

41 ATAACGATTG GCTCTGTTTC CCTCACCATT TCCACAATAT

81 GCTTCTTCAT GCAAATTGCC ATCCTGATAA CTACTGTAAC

121 ATTGCATTTC AAGCAATATG AATTCAACTC CCCCCCAAAC

161 AACCAAGTGA TGCTGTGTGA ACCAACAATA ATAGAAAGAA

201 ACATAACAGA GATAGTGTAT CTGACCAACA CCACCATAGA

241 GAAGGAAATA TGCCCCAAAC TAGCAGAATA CAGAAATTGG

281 TCAAAGCCGC AATGTAACAT TACAGGATTT GCACCTTTTT

321 CTAAGGACAA TTCGATTCGG CTTTCCGCTG GTGGGGACAT

361 CTGGGTGACA AGAGAACCTT ATGTGTCATG CGATCCTGAC

401 AAGTGTTATC AATTTGCCCT TGGACAGGGA ACAACACTAA

441 ACAACGTGCA TTCAAATGAC ATAGTACATG ATAGGACCCC

461 TTATCGGACC CTATTGATGA ATGAGTTGGG TGTTCCATTT

521 CATCTGGGGA CCAAGCAAGT GTGCATAGCA TGGTCCAGCT

561 CAAGTTGTCA CGATGGAAAA GCATGGCTGC ATGTTTGTGT

601 AACGGGGGAT GATGAAAATG CAACTGCTAG CTTCATTTAC

641 AATGGGAGGC TTGCAGATAG TATTGTTTCA TGGTCCAAAA

681 AAATCCTCAG GACCCAGGAG TCAGAATGCG TTTGTATCAA

721 TGaAACTTGT ACAGTAGTAA TGACTGATGG GAGTGCTTCA

761 GGAAAAGCTG ATACTAAAAT ACTATTCATT GAGGAGGGGA

801 AAATTGTTCA TACTAGCACA TTATCAGGAA GTGCTCAGCA

841 TGTCGAGGAG TGCTCCTGTT ATCCTCGATA TCCTGGTGTC

881 AGATGTGTCT GCAGAGACAA CTGGAAAGGC TCCAATAGGC

921 CCATCGTAGA TATAAACATA AAGGATTATA GGATTGTTTC

961 GAGTTATGTG TGCTCAGGAC TTGTTGGAGA GACACCCAGA

1001 AAAAACGACA GCTCCAGCAG TAGCCATTGC TTGGATCCAA

1041 ACAATGAGGA AGGTGGTCAT GGAGTGAAAG GCTGGGCCTT

-continued

1081 TGATGATGGA AATGACGTGT GGATGGGAAG AACGATCAGC

1121 GAGAAGTTAC GCTCAGGATA TGAAACCTTC AAAGTCATTG

1161 AAGGCTGGTC CAACCCTAAC TCGAAATTGC AGATAAATAG

1201 GCAAGTCATA GTTGACAGAG GTAACAGGTC CGGTTATTCT

1241 GGTATTTTCT CTGTTGAAGG GAAAAGCTGC ATCAATCGGT

1281 GCTTTTATGT GGAGTTGATA AGGGGAAGAA AACAGGAAAC

1321 TGAAGTCTTG TGGACCTCAA ACAGTATTGT TGTGTTTTGT

1361 GGCACCTCAG GTACATATGG AACAGGCTCA TGGCCTGATG

1401 GGGCGGACAT GAATCTCATG CCTATATAAG CTTTCGGAAT

1441 TTTAGAAAAA AACTCCTTGT TTCTACT

Modifications at the specified positions in neuraminidase can confer enhanced growth of the virus.

Another example of an influenza A virus (A/Yokohama/47/2002(H1N2))) neuraminidase sequence is shown below, with positions of modifications highlighted in bold and with underlining.

(SEQ ID NO: 57)

10 20 30 40
MNPNQKIITI GSVSLTIATI CFLMQIAILV TTVTLHFKQY 50 60 70 80
ECNSPPNNQV MLCEPTIIER NITEIVYLTN TTIEKEICPK 90 100 110 120
LAEYRNWSKP QCNITGFAPF SKDNSIRLSA GGDIWVTREP 130 140 150 160
YVSCDPDKCY QFALGQGTTL NNGHSNDTVH DRTPYRTLLM 170 180 190 200
NELGVPFHLG TKQVCIAWSS SSCHDGKAWL HVCVTGDDGN 210 220 230 240
ATASFIYNGR LVDSIGSWSK KILRTQESEC VCINGTCTVV 250 260 270 280
MTDGSASGKA DTKILFIEEG KIVHTSLLSG SAQHVEECSC 290 300 310 320
YPRYPGVRCV CRDNWKGSNR PIVDINVKDY SIVSSYVCSG 330 340 350 360
LVGDTPRKND SSSSSHCLDP NNEEGGHGVK GWAFDDGNDV 370 380 390 400
WMGRTISEKL RSGYETFKVI EGWSKPNSKL QINRQVIVDR 410 420 430 440
GNRSGYSGIF SVEGKSCINR CFYVELIRGR NQETEVLWTS 450 460
NSIVVFCGTS GTYGTGSWPD GADINLMPI

Amino acids that can be modified to improve the stability of co-expressed HA are highlighted in bold and with underlining within the sequence shown above.

In some cases, in one or more modifications can also be introduced into HA, PA, PB1, PB2, NP, M1, M2, NS2, PB1-F2, PA-X, and/or NS1 proteins (and nucleic acids encoding such proteins Enhanced growth of the virus when passaged through embryonated chicken eggs or cultured cells is observed when the modified NA proteins are expressed and such expression can result in significantly higher viral titers. Thus, the invention provides a method for making influenza viruses with enhanced replication in cell culture or in embryonated chicken eggs. The method includes providing cells suitable for influenza vaccine production; modifying nucleic acids encoding the neuraminidase; and isolating virus strains with enhanced growth relative to the one or more unmodified viral isolates, In some cases, a method for making influenza viruses with enhanced replication in cell culture can involve, serially culturing one or more influenza virus isolates in embryonated chicken eggs; and isolating serially cultured virus with enhanced growth relative to the one or more isolates prior to serial culture. In some cases, the viruses can be grown or passaged within cells in culture, e.g., MDCK or Vero cells.

The modified neuraminidases can be expressed in a variety of influenza strains. For example, A/Puerto Rico/8/34 (H1N1), "PR8," virus often serves as the genetic backbone for generation of inactivated influenza vaccines. Some vaccine strains based on PR8 backbone can replicate to relatively low titers in eggs and cell culture, resulting in delayed vaccine production and vaccine shortage. However, expression of the modified neuraminidases described herein can improve replication of the PRS (and other) influenza strains. In one embodiment of the invention, vectors for vRNA production can include a vector comprising a promoter operably linked to a modified NA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6® cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant). Vectors for mRNA production can include a vector encoding a modified NA, a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Other reassortants with internal genes from other PR8 isolates or vaccine viruses may be employed in recombinant reassortant viruses of the invention. In particular, 5:1:2 reassortants having UW-PR8 PB1, PB2, PA, NP, and M ("5") and PR8(Cam) NS ("1"); 6:1:1 reassortants having UW-PR8 (modified) NA, PB1, PB2, PA, NP, and M ("6") and PR8(Cam) NS ("1"); and 7:1 reassortants having UW-PR8 PB1, PB2, PA, NP, M, (modified) NA, and NS ("7") may be employed.

The neuraminidases that can be modified can have sequences that vary from those described herein. However, in some cases, the modified neuraminidases can have substantially the same activity as a corresponding polypeptide described by sequence herein. As used herein, "substantially the same activity" includes an activity that is about 0.1%, 1%, 10%, 30%, 50%, 90%, e.g., up to 100% or more activity, or a detectable protein level that is about 80%, 90% or more protein level, of the corresponding protein described herein. In one embodiment, the nucleic acid encodes a polypeptide which is substantially the same as, e.g., having at least 80%, e.g., 90%, 92%, 95%, 97%,98%, or 99%, including any integer between 80 and 99, contiguous amino acid sequence identity to a polypeptide encoded by one of sequences described herein. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of the nucleic acid sequences described herein. In one embodiment, a nucleic acid also encodes a polypeptide having at least 80%, e.g., 90%, 92%, 95%, 97%, 98%, or 99%, including any integer between 80 and 99, contiguous amino acid sequence identity to a polypeptide described herein.

In one embodiment, a modified influenza virus neuraminidase polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide with one of the sequences disclosed herein.

The invention thus includes the use of isolated and purified vectors or plasmids, which express or encode influenza virus proteins, or express or encode influenza NANA, both native and recombinant vRNA. The vectors comprise influenza cDNA, e.g., influenza A (e.g., any influenza A gene including any of the 18 HA or 11 NA subtypes), B or C DNA (see Fields *Virology* (Fields et al. (eds.), Lippincott, Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance, may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof, In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector, The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA. comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other nRNA vector. In one embodiment, the ribozyme sequences in a single vector are not the same.

In one embodiment, the invention provides a plurality of influenza virus vectors for a reassortant, comprising a vector for vRNA production comprising a promoter operably linked to a modified influenza virus NA DNA linked to a transcription termination sequence, a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for nRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the DNAs for the modified NA, PB1, PB2, PA, NP NS, and M are from one or more influenza vaccine seed viruses and contain two or more of the characteristic residues at the specified position(s); and a vector for mRNA production comprising a promoter operably linked to a DNA segment encoding influenza virus NA, a vector for mRNA production comprising a promoter operably linked to a DNA segment encoding influenza virus PA, a vector for mRNA production comprising a promoter operably linked to a DNA segment encoding influenza virus PB a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a promoter operably linked to a DNA segment encoding influenza virus NS1, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide described herein or encoded by a nucleic acid described herein. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

Exemplary Embodiments

An isolated recombinant influenza virus comprising a selected NA viral segment encoding a plurality of selected residues or a deletion of residues in NA is provided. In one embodiment, the selected NA viral segment does not encode a NA having a threonine at residue 32, does not encode a NA having an aspartic acid at position 147, does not encode a NA having a threonine at position 148, does not encode a NA having an aspartic acid at position 151, does not encode a NA having an asparagine at position 245, does not encode a NA having an asparagine at residue 329, does not encode a NA having a glycine at position 346, does not encode a NA having a histidine at residue 347, or encodes a NA having a deletion of one or more of residues 46 to 50, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 32. does not have a deletion of residues 46 to 50, encodes an aspartic acid at position 147, encodes a threonine at residue 148, encodes an aspartic acid at residue 151, encodes an asparagine at residue 245, encodes an asparagine at residue 329, encodes a histidine at residue 347, or any combination thereof. In one embodiment, the selected NA viral segment does not have an aspartic acid at position 147, does not have an asparagine at residue 329, and does not have an arginine or a histidine at residue 347. In one embodiment, the selected NA viral segment does not a threonine at position 148, does not have an aspartic acid at position 151, and does not have an asparagine at position 245. In one embodiment, the selected NA viral segment does not have an aspartic acid at position 147, does not have an asparagine at residue 329, and does not have an arginine or a histidine at residue 347. In one embodiment, the selected NA viral segment does not a threonine at position 148, does not have an aspartic acid at position 151, and does not have an asparagine at position 245. In one embodiment, the selected NA viral segment has at least two of: N or Q at position 147, D or E at residue 329, or Q or G at residue 347. In one embodiment, the selected NA viral segment has at least two of: K, R or H at position 148, E or Q at position 151, or S, I, T, V or G at position 245. In one embodiment, the selected NA viral segment has N or Q at position 147, D or E at residue 329, and Q or G at residue 347. In one embodiment, the selected NA viral segment has K, R or H at position 148, E or Q at position 151, and S, I, T, V or G at position 245. In one embodiment, the isolated recombinant influenza virus is a reassortant. In one embodiment, the NA viral segment encodes a NA that has at least 90% amino acid sequence identity to SEQ NO:1, SEQ ID NO:3, SEQ ID NO:48, SEQ ID NO:49, SEQ ID NO:50 or SEQ ID NO:54. In one embodiment, the NA viral segment encodes a NA that has at least 90% amino acid sequence identity to SEQ ID NO:2. In one embodiment, the NA viral segment encodes a N2, N3, N7, or N9. In one embodiment, the NA viral segment encodes a N1, N4, N5, N6, N8, N10 or N11. In one embodiment, the residue at position 32 is A, I, G, or L. In one embodiment, the deletion is a deletion of residues 46 to 50. In one embodiment, the residue at position 147 is N or Q. In one embodiment, the residue at position 148 is K, R or H. In one embodiment, the residue at position 151 is E, N or Q. In one embodiment, the residue at position 245 is S, T, I, L, A, N, W, Y, P, V, or G. In one embodiment, the residue at position 329 is D or E. In one embodiment, the residue at position 346 is S, T, P, Y, W, A, N, I, L, or V. In one embodiment, the residue at position 347 is G, Q, S, T, Y, C or W. In one embodiment, the residue at position 147 is N or Q, the residue at position 329 is D or E, the residue at position 347 is G, Q, S, T, Y, C or W, or any combination thereof. In one embodiment, the residue at position 147 is N or Q, the residue at position 329 is D or E, the residue at position 347 is G or Q, or any combination thereof. In one embodiment, the residue at position 148 is K, R or H, the residue at position 151 is E, N or Q, the residue at position 245 is S, T, I, L, A, W, Y, P, V, or G, or any combination thereof. In one embodiment, the residue at position 148 is K, R or H, the residue at position 151 is E, N or Q, the residue at position 245 is S, T, L, A, or V, or any combination thereof. In one embodiment, the selected NA viral segment does not encode a NA having an aspartic acid at position 147, does not encode a NA having a threonine at position 148, does not encode a NA having an aspartic acid at position 151, does not encode a NA having an asparagine at position 245, does not encode a NA having an asparagine or threonine at residue 329, does not encode a NA having a glycine at position 346, does not encode a NA having a histidine, arginine or an asparagine at residue 347, or any combination thereof. In one embodiment the selected NA viral segment does not encode a NA having an aspartic acid at position 147, does not encode a NA having an asparagine at residue 329, does not encode a NA having a histidine, arginine or asparagine at residue 347, or any combination thereof. In one embodiment, the selected NA viral segment does not encode a NA having a threonine at position 148, does not encode a NA having an aspartic acid at position 151, does not encode a NA having an asparagine at position 245, does not encode a NA having a glycine at position 346, or any combination thereof. In one embodiment, the virus has HA H1, H3, H7, or H9. In one embodiment, the virus is an influenza A virus. In one embodiment, the virus comprises PA, PB1, PB2, NP, M, and NS viral segments with at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. In one embodiment, the virus comprises PB2 having I, A, L, or G at residue 147.

In one embodiment, an isolated recombinant nucleic acid is provided comprising a nucleic acid sequence for an influenza virus NA viral segment that encodes a NA having a plurality of selected residues or a deletion of residues, wherein the NA viral segment does not encode a NA having a threonine at residue 32, does not encode a NA having an aspartic acid at position 147, does not encode a NA having a threonine at position 148, does not encode a NA having an aspartic acid at position 151, does not encode a NA having an asparagine at position 245, does not encode a NA having an asparagine or a threonine at residue 329, does not encode a NA having a histidine, arginine or asparagine at residue 347, or encodes a NA having a deletion of one or more of residues 46 to 50, or any combination thereof, wherein the numbering is based on N2, In one embodiment, the NA has at least 90% amino acid sequence identity to SEQ ID NO:1 or SEQ ID NO:3. In one embodiment, the NA has at least 90% amino acid sequence identity to SEQ ID NO:2. In one embodiment, the NA is a N2, N3, N7, or N9. In one embodiment, the NA is a N1, N4, N5, N6, N8, N10 or N11. In one embodiment, the residue at position 32 is A, I, G, or L. In one embodiment, the residue at position 147 is N or Q. In one embodiment, the residue at position 329 is D or E. In one embodiment, the residue at position 151 is E, N or Q. In one embodiment, the residue at position 148 is K, R or H. In one embodiment, the residue at position 245 is S, T, I, L, A, W, Y, P, V, or G. In one embodiment, the residue at position 347 is G, Q, S, or T.

In one embodiment, a method to prepare influenza virus is provided. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes a NA having a plurality of selected residues or a deletion of residues, wherein the NA does not encode a NA having a threonine at residue 32, does not encode a NA having an aspartic acid at position 147, does not encode a NA having a threonine at position 148, does not encode a NA having an aspartic acid at position 151, does not encode a NA having an asparagine at position 245, does not encode a NA having an asparagine at residue 329, does not encode a NA having a glycine at position 346, does not encode a NA having a histidine at residue 347, or encodes a NA having a deletion of one or more of residues 46 to 50, or any combination thereof, wherein the numbering for NA residues is that for N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the NA has at least 90% amino acid to SEQ ID NO:1, SEQ ID NO:2, SEQ ID NO:3, SEQ ID NO:48, or SEQ ID NO:49. In one embodiment, the NA is N2, N3, N7, or N9. In one embodiment, the residue at position 147 is N or Q. In one embodiment, the residue at position 329 is D or E. In one embodiment, the residue at position 347 is Q, N, S, T, Y, C or W. In one embodiment, the residue at position 151 is E, N or Q. In one embodiment, the residue at position 148 is K, R or H. In one embodiment, the residue at position 245 is S, T, I, L, A, N, W, Y, P, V, or G. In one embodiment, the virus HA is H1, H3, H7, or H9. In one embodiment, the PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. In one embodiment, HA is H2, H4, H5, H6, H8, or any of H10-H18. In one embodiment, virus prepared by the method is isolated. In one embodiment, virus is passaged through avian eggs.

In one embodiment, a method of immunizing an avian or a mammal is provided. The method includes administering to the avian or the mammal, e.g., a bovine, ovine, caprine, feline, canine, equine or human, a composition having an effective amount of the virus described above. In one embodiment, the composition comprises at least one other different influenza virus. In one embodiment, the composition is administered intranasally or via injection.

The invention will be described by the following non-limiting examples.

EXAMPLE 1

Exemplary Viral Sequences for a Master Vaccine Strain (PR8UW)

```
HA
                                        (SEQ ID NO: 22)
AGCAAAAGCAGGGGAAAATAAAAACAACCAAAATGAAGGCAAACCTACTGG

TCCTGTTATGTGCACTTGCAGCTGCAGATGCAGACACAATATGTATAGGCTAC

CATGCGAACAATTCAACCGACACTGTTGACACAGTACTCGAGAAGAATGTGA

CAGTGACACACTCTGTTAACCTGCTCGAAGACAGCCACAACGGAAAACTATG

TAGATTAAAAGGAATAGCCCCACTACAATTGGGGAAATGTAACATCGCCGGA

TGGCTCTTGGGAAACCCAGAATGCGACCCACTGCTTCCAGTGAGATCATGGT
```

-continued

CCTACATTGTAGAAACACCAAACTCTGAGAATGGAATATGTTATCCAGGAGA

TTTCATCGACTATGAGGAGCTGAGGGAGCAATTGAGCTCAGTGTCATCATTC

GAAAGATTCGAAATATTTCCCAAAGAAAGCTCATGGCCCAACCACAACACAA

ACGGAGTAACGGCAGCATGCTCCCATGAGGGGAAAAGCAGTTTTTACAGAAA

TTTGCTATGGCTGACGGAGAAGGAGGGCTCATACCCAAAGCTGAAAAATTCT

TATGTGAACAAAAAAGGGAAAGAAGTCCTTGTACTGTGGGGTATTCATCACC

CGCCTAACAGTAAGGAACAACAGAATCTCTATCAGAATGAAAATGCTTATGT

CTCTGTAGTGACTTCAAATTATAACAGGAGATTTACCCCGGAAATAGCAGAA

AGACCCAAAGTAAGAGATCAAGCTGGGAGGATGAACTATTACTGGACCTTGC

TAAAACCCGGAGACACAATAATATTTGAGGCAAATGGAAATCTAATAGCACC

AATGTATGCTTTCGCACTGAGTAGAGGCTTTGGGTCCGGCATCATCACCTCAA

ACGCATCAATGCATGAGTGTAACACGAAGTGTCAAACACCCCTGGGAGCTAT

AAACAGCAGTCTCCCTTACCAGAATATACACCCAGTCACAATAGGAGAGTGC

CCAAAATACGTCAGGAGTGCCAAATTGAGGATGGTTACAGGACTAAGGAAC

ATTCCGTCCATTCAATCCAGAGGTCTATTTGGAGCCATTGCCGGTTTTATTGA

AGGGGGATGGACTGGAATGATAGATGGATGGTATGGTTATCATCATCAGAAT

GAACAGGGATCAGGCTATGCAGCGGATCAAAAAAGCACACAAAATGCCATT

AACGGGATTACAAACAAGGTGAACACTGTTATCGAGAAAATGAACATTCAAT

TCACAGCTGTGGGTAAAGAATTCAACAAATTAGAAAAAAGGATGGAAAATTT

AAATAAAAAAGTTGATGATGGATTTCTGGACATTTGGACATATAATGCAGAA

TTGTTAGTTCTACTGGAAAATGAAAGGACTCTGGATTTCCATGACTCAAATGT

GAAGAATCTGTATGAGAAAGTAAAAAGCCAATTAAAGAATAATGCCAAAGA

AATCGGAAATGGATGTTTTGAGTTCTACCACAAGTGTGACAATGAATGCATG

GAAAGTGTAAGAAATGGGACTTATGATTATCCCAAATATTCAGAAGAGTCAA

AGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTC

TCCCTGGGGGCAATCAGTTTCTGGATGTGTTCTAATGGATGTTTGCAGTGCAG

AATATGCATCTGAGATTAGAATTTCAGAGATATGAGGAAAAACACCCTTGTT

TCTACT

NA (SEQ ID NO: 23)

AGCAAAAGCAGGGGTTTAAAATGAATCCAAATCAGAAAATAATAACCATTG

GATCAATCTGTCTGGTAGTCGGACTAATTAGCCTAATATTGCAAATAGGGAA

TATAATCTCAATATGGATTAGCCATTCAATTCAAACTGGAAGTCAAAACCAT

ACTGGAATATGCAACCAAAACATCATTACCTATAAAAATAGCACCTGGGTAA

AGGACACAACTTCAGTGATATTAACCGGCAATTCATCTCTTTGTCCCATCCGT

GGGTGGGCTATATACAGCAAAGACAATAGCATAAGAATTGGTTCCAAAGGA

GACGTTTTTGTCATAAGAGAGCCCTTTATTTCATGTTCTCACTTGGAATGCAG

GACCTTTTTTCTGACCCAAGGTGCCTTACTGAATGACAAGCATTCAAGTGGGA

CTGTTAAGGACAGAAGCCCTTATAGGGCCTTAATGAGCTGCCCTGTCGGTGA

AGCTCCGTCCCCGTACAATTCAAGATTTGAATCGGTTGCTTGGTCAGCAAGTG

-continued

CATGTCATGATGGCATGGGCTGGCTAACAATCGGAATTTCAGGTCCAGATAA

TGGAGCAGTGGCTGTATTAAAATACAACGGCATAATAACTGAAACCATAAAA

AGTTGGAGGAAGAAAATATTGAGGACACAAGAGTCTGAATGTGCCTGTGTAA

ATGGTTCATGTTTTACTATAATGACTGATGGCCCGAGTGATGGGCTGGCCTCG

TACAAAATTTTCAAGATCGAAAAGGGGAAGGTTACTAAATCAATAGAGTTGA

ATGCACCTAATTCTCACTATGAGGAATGTTCCTGTTACCCTGATACCGGCAAA

GTGATGTGTGTGTGCAGAGACAATTGGCATGGTTCGAACCGGCCATGGGTGT

CTTTCGATCAAAACCTGGATTATCAAATAGGATACATCTGCAGTGGGGTTTTC

GGTGACAACCCGCGTCCCGAAGATGGAACAGGCAGCTGTGGTCCAGTGTATG

TTGATGGAGCAAACGGAGTAAAGGGATTTTCATATAGGTATGGTAATGGTGT

TTGGATAGGAAGGACCAAAAGTCACAGTTCCAGACATGGGTTTGAGATGATT

TGGGATCCTAATGGATGGACAGAGACTGATAGTAAGTTCTCTGTGAGGCAAG

ATGTTGTGGCAATGACTGATTGGTCAGGGTATAGCGGAAGTTTCGTTCAACAT

CCTGAGCTGACAGGGCTAGACTGTATGAGGCCGTGCTTCTGGGTTGAATTAA

TCAGGGGACGACCTAAAGAAAAAACAATCTGGACTAGTGCGAGCAGCATTTC

TTTTTGTGGCGTGAATAGTGATACTGTAGATTGGTCTTGGCCAGACGGTGCTG

AGTTGCCATTCAGCATTGACAAGTAGTCTGTTCAAAAAACTCCTTGTTTCTAC

T

PA (SEQ ID NO: 24)

AGCGAAAGCA GGTACTGATC CAAAATGGAA GATTTTGTGC GACAATGCTT

CAATCCGATG ATTGTCGAGC TTGCGGAAAA AACAATGAAA GAGTATGGGG

AGGACCTGAA AATCGAAACA AACAAATTTG CAGCAATATG CACTCACTTG

GAAGTATGCT TCATGTATTC AGATTTTCAC TTCATCAATG AGCAAGGCGA

GTCAATAATC GTAGAACTTG GTGATCCAAA TGCACTTTTG AAGCACAGAT

TTGAAATAAT CGAGGGAAGA GATCGCACAA TGGCCTGGAC AGTAGTAAAC

AGTATTTGCA ACACTACAGG GGCTGAGAAA CCAAAGTTTC TACCAGATTT

GTATGATTAC AAGGAGAATA GATTCATCGA AATTGGAGTA ACAAGGAGAG

AAGTTCACAT ATACTATCTG GAAAAGGCCA ATAAAATTAA ATCTGAGAAA

ACACACATCC ACATTTTCTC GTTCACTGGG GAAGAAATGG CCACAAAGGC

AGACTACACT CTCGATGAAG AAAGCAGGGC TAGGATCAAA ACCAGACTAT

TCACCATAAG ACAAGAAATG GCCAGCAGAG GCCTCTGGGA TTCCTTTCGT

CAGTCCGAGA GAGGAGAAGA GACAATTGAA GAAAGGTTTG AAATCACAGG

AACAATGCGC AAGCTTGCCG ACCAAAGTCT CCCGCCGAAC TTCTCCAGCC

TTGAAAATTT TAGAGCCTAT GTGGATGGAT TCGAACCGAA CGGCTACATT

GAGGGCAAGC TGTCTCAAAT GTCCAAAGAA GTAAATGCTA GAATTGAACC

TTTTTTGAAA ACAACACCAC GACCACTTAG ACTTCCGAAT GGGCCTCCCT

GTTCTCAGCG GTCCAAATTC CTGCTGATGG ATGCCTTAAA ATTAAGCATT

GAGGACCCAA GTCATGAAGG AGAGGGAATA CCGCTATATG ATGCAATCAA

ATGCATGAGA ACATTCTTTG GATGGAAGGA ACCCAATGTT GTTAAACCAC

ACGAAAAGGG AATAAATCCA AATTATCTTC TGTCATGGAA GCAAGTACTG

GCAGAACTGC AGGACATTGA GAATGAGGAG AAAATTCCAA AGACTAAAAA

-continued

TATGAAGAAA ACAAGTCAGC TAAAGTGGGC ACTTGGTGAG AACATGGCAC

CAGAAAAGGT AGACTTTGAC GACTGTAAAG ATGTAGGTCA TTTGAAGCAA

TATGATAGTG ATGAACCAGA ATTGAGGTCG CTTGCAAGTT GGATTCAGAA

TGAGTTTAAC AAGGCATGCG AACTGACAGA TTCAAGCTGG ATAGAGCTCG

ATGAGATTGG AGAAGATGTG GCTCCAATTG AACACATTGC AAGCATGAGA

AGGAATTATT TCACATCAGA GGTGTCTCAC TGCAGAGCCA CAGAATACAT

AATGAAGGGA GTGTACATCA ATACTGCCTT GCTTAATGCA TCTTGTGCAG

CAATGGATGA TTTCCAATTA ATTCCAATGA TAAGCAAGTG TAGAACTAAG

GAGGGAAGGC GAAAGACCAA CTTGTATGGT TTCATCATAA AAGGAAGATC

CCACTTAAGG AATGACACCG ACGTGGTAAA CTTTGTGAGC ATGGAGTTTT

CTCTCACTGA CCCAAGACTT GAACCACATA AATGGGAGAA GTACTGTGTT

CTTGAGATAG GAGATATGCT TATAAGAAGT GCCATAGGCC AGGTTTCAAG

GCCCATGTTC TTGTATGTGA GAACAAATGG AACCTCAAAA ATTAAAATGA

AATGGGGAAT GGAGATGAGG CGTTGCCTCC TCCAGTCACT TCAACAAATT

GAGAGTATGA TTGAAGCTGA GTCCTCTGTC AAAGAGAAAG ACATGACCAA

AGAGTTCTTT GAGAACAAAT CAGAAACATG GCCCATTGGA GAGTCCCCCA

AAGGAGTGGA GGAAAGTTCC ATTGGGAAGG TCTGCAGGAC TTTATTAGCA

AAGTCGGTAT TCAACAGCTT GTATGCATCT CCACAACTAG AAGGATTTTC

AGCTGAATCA AGAAAACTGC TTCTTATCGT TCAGGCTCTT AGGGACAACC

TGGAACCTGG GACCTTTGAT CTTGGGGGGC TATATGAAGC AATTGAGGAG

TGCCTGATTA ATGATCCCTG GGTTTTGCTT AATGCTTCTT GGTTCAACTC

CTTCCTTACA CATGCATTGA GTTAGTTGTG GCAGTGCTAC TATTTGCTAT

CCATACTGTC CAAAAAAGTA CCTTGTTTCT ACT

PB1

(SEQ ID NO: 25)

AGCGAAAGCAGGCAAACCATTTGAATGGATGTCAATCCGACCTTACTTTTCTT

AAAAGTGCCAGCACAAAATGCTATAAGCACAACTTTCCCTTATACTGGAGAC

CCTCCTTACAGCCATGGGACAGGAACAGGATACACCATGGATACTGTCAACA

GGACACATCAGTACTCAGAAAAGGGAAGATGGACAACAAACACCGAAACTG

GAGCACCGCAACTCAACCCGATTGATGGGCCACTGCCAGAAGACAATGAACC

AAGTGGTTATGCCCAAACAGATTGTGTATTGGAGGCGATGGCTTTCCTTGAG

GAATCCCATCCTGGTATTTTTGAAAACTCGTGTATTGAAACGATGGAGGTTGT

TCAGCAAACACGAGTAGACAAGCTGACACAAGGCCGACAGACCTATGACTG

GACTCTAAATAGAAACCAACCTGCTGCAACAGCATTGGCCAACACAATAGAA

GTGTTCAGATCAAATGGCCTCACGGCCAATGAGTCTGGAAGGCTCATAGACT

TCCTTAAGGATGTAATGGAGTCAATGAACAAAGAAGAAATGGGGATCACAA

CTCATTTTCAGAGAAAGAGACGGGTGAGAGACAATATGACTAAGAAAATGAT

AACACAGAGAACAATGGGTAAAAAGAAGCAGAGATTGAACAAAAGGAGTTA

TCTAATTAGAGCATTGACCCTGAACACAATGACCAAAGATGCTGAGAGAGGG

AAGCTAAAACGGAGAGCAATTGCAACCCCAGGGATGCAAATAAGGGGGTTT

GTATACTTTGTTGAGACACTGGCAAGGAGTATATGTGAGAAACTTGAACAAT

-continued

CAGGGTTGCCAGTTGGAGGCAATGAGAAGAAAGCAAAGTTGGCAAATGTTGT

AAGGAAGATGATGACCAATTCTCAGGACACCGAACTTTCTTTCACCATCACT

GGAGATAACACCAAATGGAACGAAAATCAGAATCCTCGGATGTTTTTGGCCA

TGATCACATATATGACCAGAAATCAGCCCGAATGGTTCAGAAATGTTCTAAG

TATTGCTCCAATAATGTTCTCAAACAAAATGGCGAGACTGGGAAAAGGGTAT

ATGTTTGAGAGCAAGAGTATGAAACTTAGAACTCAAATACCTGCAGAAATGC

TAGCAAGCATCGATTTGAAATATTTCAATGATTCAACAAGAAAGAAGATTGA

AAAAATCCGACCGCTCTTAATAGAGGGGACTGCATCATTGAGCCCTGGAATG

ATGATGGGCATGTTCAATATGTTAAGCACTGTATTAGGCGTCTCCATCCTGAA

TCTTGGACAAAAGAGATACACCAAGACTACTTACTGGTGGGATGGTCTTCAA

TCCTCTGACGATTTTGCTCTGATTGTGAATGCACCCAATCATGAAGGGATTCA

AGCCGGAGTCGACAGGTTTTATCGAACCTGTAAGCTACTTGGAATCAATATG

AGCAAGAAAAAGTCTTACATAAACAGAACAGGTACATTTGAATTCACAAGTT

TTTTCTATCGTTATGGGTTTGTTGCCAATTTCAGCATGGAGCTTCCCAGTTTTG

GGGTGTCTGGGATCAACGAGTCAGCGGACATGAGTATTGGAGTTACTGTCAT

CAAAAACAATATGATAAACAATGATCTTGGTCCAGCAACAGCTCAAATGGCC

CTTCAGTTGTTCATCAAAGATTACAGGTACACGTACCGATGCCATATAGGTGA

CACACAAATACAAACCCGAAGATCATTTGAAATAAAGAAACTGTGGGAGCA

AACCCGTTCCAAAGCTGGACTGCTGGTCTCCGACGGAGGCCCAAATTTATAC

AACATTAGAAATCTCCACATTCCTGAAGTCTGCCTAAAATGGGAATTGATGG

ATGAGGATTACCAGGGGCGTTTATGCAACCCACTGAACCCATTTGTCAGCCA

TAAAGAAATTGAATCAATGAACAATGCAGTGATGATGCCAGCACATGGTCCA

GCCAAAAACATGGAGTATGATGCTGTTGCAACAACACACTCCTGGATCCCCA

AAAGAAATCGATCCATCTTGAATACAAGTCAAAGAGGAGTACTTGAGGATGA

ACAAATGTACCAAAGGTGCTGCAATTTATTTGAAAAATTCTTCCCCAGCAGTT

CATACAGAAGACCAGTCGGGATATCCAGTATGGTGGAGGCTATGGTTTCCAG

AGCCCGAATTGATGCACGGATTGATTTCGAATCTGGAAGGATAAAGAAAGAA

GAGTTCACTGAGATCATGAAGATCTGTTCCACCATTGAAGAGCTCAGACGGC

AAAAATAGTGAATTTAGCTTGTCCTTCATGAAAAAATGCCTTGTTTCTACT

PB2

(SEQ ID NO: 26)

AGCGAAAGCA GGTCAATTAT ATTCAATATG GAAAGAATAA AAGAACTACG

AAATCTAATG TCGCAGTCTC GCACCCGCGA GATACTCACA AAAACCACCG

TGGACCATAT GGCCATAATC AAGAAGTACA CATCAGGAAG ACAGGAGAAG

AACCCAGCAC TTAGGATGAA ATGGATGATG GCAATGAAAT ATCCAATTAC

AGCAGACAAG AGGATAACGG AAATGATTCC TGAGAGAAAT

GAGCAAGGAC AAACTTTATG GAGTAAAATG AATGATGCCG GATCAGACCG

AGTGATGGTA TCACCTCTGG CTGTGACATG GTGGAATAGG AATGGACCAA

TAACAAATAC AGTTCATTAT CCAAAAATCT ACAAAACTTA TTTTGAAAGA

GTCGAAAGGC TAAAGCATGG AACCTTTGGC CCTGTCCATT TTAGAAACCA

AGTCAAAATA CGTCGGAGAG TTGACATAAA TCCTGGTCAT GCAGATCTCA

GTGCCAAGGA GGCACAGGAT GTAATCATGG AAGTTGTTTT CCCTAACGAA

-continued

GTGGGAGCCA GGATACTAAC ATCGGAATCG CAACTAACGA TAACCAAAGA
GAAGAAAGAA GAACTCCAGG ATTGCAAAAT TTCTCCTTTG ATGGTTGCAT
ACATGTTGGA GAGAGAACTG GTCCGCAAAA CGAGATTCCT CCCAGTGGCT
GGTGGAACAA GCAGTGTGTA CATTGAAGTG TTGCATTTGA CTCAAGGAAC
ATGCTGGGAA CAGATGTATA CTCCAGGAGG GGAAGTGAGG AATGATGATG
TTGATCAAAG CTTGATTATT GCTGCTAGGA ACATAGTGAG AAGAGCTGCA
GTATCAGCAG ATCCACTAGC ATCTTTATTG GAGATGTGCC ACAGCACACA
GATTGGTGGA ATTAGGATGG TAGACATCCT TAGGCAGAAC CCAACAGAAG
AGCAAGCCGT GGATATATGC AAGGCTGCAA TGGGACTGAG AATTAGCTCA
TCCTTCAGTT TTGGTGGATT CACATTTAAG AGAACAAGCG GATCATCAGT
CAAGAGAGAG GAAGAGGTGC TTACGGGCAA TCTTCAAACA TTGAAGATAA
GAGTGCATGA GGGATATGAA GAGTTCACAA TGGTTGGGAG AAGAGCAACA
GCCATACTCA GAAAAGCAAC CAGGAGATTG ATTCAGCTGA TAGTGAGTGG
GAGAGACGAA CAGTCGATTG CCGAAGCAAT AATTGTGGCC ATGGTATTTT
CACAAGAGGA TTGTATGATA AAAGCAGTCA GAGGTGATCT GAATTTCGTC
AATAGGGCGA ATCAACGATT GAATCCTATG CATCAACTTT TAAGACATTT
TCAGAAGGAT GCGAAAGTGC TTTTTCAAAA TTGGGGAGTT GAACCTATCG
ACAATGTGAT GGGAATGATT GGGATATTGC CCGACATGAC TCCAAGCATC
GAGATGTCAA TGAGAGGAGT GAGAATCAGC AAAATGGGTG TAGATGAGTA
CTCCAGCACG GAGAGGGTAG TGGTGAGCAT TGACCGTTTT TTGAGAATCC
GGGACCAACG AGGAAATGTA CTACTGTCTC CCGAGGAGGT CAGTGAAACA
CAGGGAACAG AGAAACTGAC AATAACTTAC TCATCGTCAA TGATGTGGGA
GATTAATGGT CCTGAATCAG TGTTGGTCAA TACCTATCAA TGGATCATCA
GAAACTGGGA AACTGTTAAA ATTCAGTGGT CCCAGAACCC TACAATGCTA
TACAATAAAA TGGAATTTGA ACCATTTCAG TCTTTAGTAC CTAAGGCCAT
TAGAGGCCAA TACAGTGGGT TTGTAAGAAC TCTGTTCCAA CAAATGAGGG
ATGTGCTTGG GACATTTGAT ACCGCACAGA TAATAAAACT TCTTCCCTTC
GCAGCCGCTC CACCAAAGCA AAGTAGAATG CAGTTCTCCT CATTTACTGT
GAATGTGAGG GGATCAGGAA TGAGAATACT TGTAAGGGGC AATTCTCCTG
TATTCAACTA TAACAAGGCC ACGAAGAGAC TCACAGTTCT CGGAAAGGAT
GCTGGCACTT TAACTGAAGA CCCAGATGAA GGCACAGCTG GAGTGGAGTC
CGCTGTTCTG AGGGGATTCC TCATTCTGGG CAAAGAAGAC AAGAGATATG
GGCCAGCACT AAGCATCAAT GAACTGAGCA ACCTTGCGAA AGGAGAGAAG
GCTAATGTGC TAATTGGGCA AGGAGACGTG GTGTTGGTAA TGAAACGGAA
ACGGGACTCT AGCATACTTA CTGACAGCCA GACAGCGACC AAAAGAATTC
GGATGGCCAT CAATTAGTGT CGAATAGTTT AAAAACGACC TTGTTTCTAC T

NP (SEQ ID NO: 27)

AGCAAAAGCA GGGTAGATAA TCACTCACTG AGTGACATCA AAATCATGGC
GTCTCAAGGC ACCAAACGAT CTTACGAACA GATGGAGACT GATGGAGAAC
GCCAGAATGC CACTGAAATC AGAGCATCCG TCGGAAAAAT GATTGGTGGA

-continued

ATTGGACGAT TCTACATCCA AATGTGCACC GAACTCAAAC TCAGTGATTA
TGAGGGACGG TTGATCCAAA ACAGCTTAAC AATAGAGAGA ATGGTGCTCT
CTGCTTTTGA CGAAAGGAGA AATAAATACC TTGAAGAACA TCCCAGTGCG
GGGAAAGATC CTAAGAAAAC TGGAGGACCT ATATACAGGA GAGTAAACGG
AAAGTGGATG AGAGAACTCA TCCTTTATGA CAAAGAAGAA ATAAGGCGAA
TCTGGCGCCA AGCTAATAAT GGTGACGATG CAACGGCTGG TCTGACTCAC
ATGATGATCT GGCATTCCAA TTTGAATGAT GCAACTTATC AGAGGACAAG
AGCTCTTGTT CGCACCGGAA TGGATCCCAG GATGTGCTCT CTGATGCAAG
GTTCAACTCT CCCTAGGAGG TCTGGAGCCG CAGGTGCTGC AGTCAAAGGA
GTTGGAACAA TCGTGATGGA ATTGGTCAGA ATGATCAAAC GTGGGATCAA
TGATCGGAAC TTCTGGAGGG GTGAGAATGG ACGAAAAACA AGAATTGCTT
ATGAAAGAAT GTGCAACATT CTCAAAGGGA AATTTCAAAC TGCTGCACAA
AAAGCAATGA TGGATCAAGT GAGAGAGAGC CGGAACCCAG GGAATGCTGA
GTTCGAAGAT CTCACTTTTC TAGCACGGTC TGCACTCATA TTGAGAGGGT
CGGTTGCTCA CAAGTCCTGC CTGCCTGCCT GTGTGTATGG ACCTGCCGTA
GCCAGTGGGT ACGACTTTGA AAGGGAGGGA TACTCTCTAG TCGGAATAGA
CCCTTTCAGA CTGCTTCAAA ACAGCCAAGT GTACAGCCTA ATCAGACCAA
ATGAGAATCC AGCACACAAG AGTCAACTGG TGTGGATGGC ATGCCATTCT
GCCGCATTTG AAGATCTAAG AGTATTAAGC TTCATCAAAG GGACGAAGGT
GCTCCCAAGA GGGAAGCTTT CCACTAGAGG AGTTCAAATT GCTTCCAATG
AAAATATGGA GACTATGGAA TCAAGTACAC TTGAACTGAG AAGCAGGTAC
TGGGCCATAA GGACCAGAAG TGGAGGAAAC ACCAATCAAC AGAGGGCATC
TGCGGGCCAA ATCAGCATAC AACCTACGTT CTCAGTACAG AGAAATCTCC
CTTTTGACAG AACAACCATT ATGGCAGCAT TCAATGGGAA TACAGAGGGG
AGAACATCTG ACATGAGGAC CGAAATCATA AGGATGATGG AAAGTGCAAG
ACCAGAAGAT GTGTCTTTCC AGGGGCGGGG AGTCTTCGAG CTCTCGGACG
AAAAGGCAGC GAGCCCGATC GTGCCTTCCT TTGACATGAG TAATGAAGGA
TCTTATTTCT TCGGAGACAA TGCAGAGGAG TACGACAATT AAAGAAAAAT
ACCCTTGTTT CTACT

M (SEQ ID NO: 28)

AGCAAAAGCA GGTAGATATT GAAAGATGAG TCTTCTAACC GAGGTCGAAA
CGTACGTACT CTCTATCATC CCGTCAGGCC CCCTCAAAGC CGAGATCGCA
CAGAGACTTG AAGATGTCTT TGCAGGGAAG AACACCGATC TTGAGGTTCT
CATGGAATGG CTAAAGACAA GACCAATCCT GTCACCTCTG ACTAAGGGGA
TTTTAGGATT TGTGTTCACG CTCACCGTGC CCAGTGAGCG AGGACTGCAG
CGTAGACGCT TTGTCCAAAA TGCCCTTAAT GGGAACGGGG ATCCAAATAA
CATGGACAAA GCAGTTAAAC TGTATAGGAA GCTCAAGAGG GAGATAACAT
TCCATGGGGC CAAAGAAATC TCACTCAGTT ATTCTGCTGG TGCACTTGCC
AGTTGTATGG GCCTCATATA CAACAGGATG GGGGCTGTGA CCACTGAAGT
GGCATTTGGC CTGGTATGTG CAACCTGTGA ACAGATTGCT GACTCCCAGC
ATCGGTCTCA TAGGCAAATG GTGACAACAA GCAATCCACT AATCAGACAT

-continued

```
GAGAACAGAA TGGTTTTAGC CAGCACTACA GCTAAGGCTA TGGAGCAAAT

GGCTGGATCG AGTGAGCAAG CAGCAGAGGC CATGGAGGTT GCTAGTCAGG

CTAGACAAAT GGTGCAAGCG ATGAGAACCA TTGGGACTCA TCCTAGCTCC

AGTGCTGGTC TGAAAAATGA TCTTCTTGAA AATTTGCAGG CCTATCAGAA

ACGAATGGGG GTGCAGATGC AACGGTTCAA GTGATCCTCT CACTATTGCC

GCAAATATCA TTGGGATCTT GCACTTGACA TTGTGGATTC TTGATCGTCT

TTTTTTCAAA TGCATTTACC GTCGCTTTAA ATACGGACTG AAAGGAGGGC

CTTCTACGGA AGGAGTGCCA AAGTCTATGA GGGAAGAATA TCGAAAGGAA

CAGCAGAGTG CTGTGGATGC TGACGATGGT CATTTTGTCA GCATAGAGCT

GGAGTAAAAA ACTACCTTGT TTCTACT
```

NS (SEQ ID NO: 29)

```
AGCAAAAGCA GGGTGACAAA AACATAATGG ATCCAAACAC TGTGTCAAGC

TTTCAGGTAG ATTGCTTTCT TTGGCATGTC CGCAAACGAG TTGCAGACCA

AGAACTAGGC GATGCCCCAT TCCTTGATCG GCTTCGCCGA GATCAGAAAT

CCCTAAGAGG AAGGGGCAGT ACTCTCGGTC TGGACATCAA GACAGCCACA

CGTGCTGGAA AGCAGATAGT GGAGCGGATT CTGAAAGAAG AATCCGATGA

GGCACTTAAA ATGACCATGG CCTCTGTACC TGCGTCGCGT TACCTAACTG

ACATGACTCT TGAGGAAATG TCAAGGGACT GGTCCATGCT CATACCCAAG

CAGAAAGTGG CAGGCCCTCT TTGTATCAGA ATGGACCAGG CGATCATGGA

TAAGAACATC ATACTGAAAG CGAACTTCAG TGTGATTTTT GACCGGCTGG

AGACTCTAAT ATTGCTAAGG GCTTTCACCG AAGAGGGAGC AATTGTTGGC

GAAATTTCAC CATTGCCTTC TCTTCCAGGA CATACTGCTG AGGATGTCAA

AAATGCAGTT GGAGTCCTCA TCGGAGGACT TGAATGGAAT GATAACACAG

TTCGAGTCTC TGAAACTCTA CAGAGATTCG CTTGGAGAAG CAGTAATGAG

AATGGGAGAC CTCCACTCAC TCCAAAACAG AAACGAGAAA TGGCGGGAAC

AATTAGGTCA GAAGTTTGAA GAAATAAGAT GGTTGATTGA AGAAGTGAGA

CACAAACTGA AGATAACAGA GAATAGTTTT GAGCAAATAA CATTTATGCA

AGCCTTACAT CTATTGCTTG AAGTGGAGCA AGAGATAAGA ACTTTCTCGT

TTCAGCTTAT TTAGTACTAA AAAACACCCT TGTTTCTACT
```

EXAMPLE 2

Neuraminidase Modifications

Materials

Viruses: Y2017: A/Yokohama/2017/2003 (H3N2)
HK4801: A/Hong Kong/4801/2014(H3N2)
Y2017-M3L4: Y2017 passaged 7 times in eggs
HY-PR8: high yield PR8 (H1N1)

Results

Y2017 virus was passaged 7 times in eggs (3 times in the amniotic cavity, followed by 4 times in the allantoic cavity). A progeny virus, Y2017-M3L4, grew efficiently in the allantoic cavity ($10^7$ to about $10^8$ PFU/mL), whereas the original Y2017 virus did not grow at all (<10 PFU/mL).

Mutations observed in Y2017-M3L4 virus were as follows:

TABLE 1

| | PB2 | NA | NP | M1 |
|---|---|---|---|---|
| eggA | T147I, V344L and T174I, V344L, E358K | del 46-50aa, T32A, D147N, N329D, H347Q | none | E23Q |
| eggB | T147I | del 46-50aa, T32A, D147N, N329D, H347Q | D101N | none |
| eggC | T147I | del 46-50aa, T32A, D147N, N329D, H347Q | D101N | none |

A comparison of the growth ability of mutant Y2017 viruses, generated by reverse genetics, in allantoic fluid revealed that NA mutations were responsible for the high growth of Y2017-M3L4 virus (FIG. 4). A plasmid with PB2-T147I was used for virus generation (PB2-T147I, V344L and PB2-T147I, V344L, E358K were not analyzed). Mutations were not observed in the HA gene of the virus possessing a mutated NA segment and its other genes from wild-type Y2017 after replication in allantoic fluid (FIG. 4).

Figure 5:
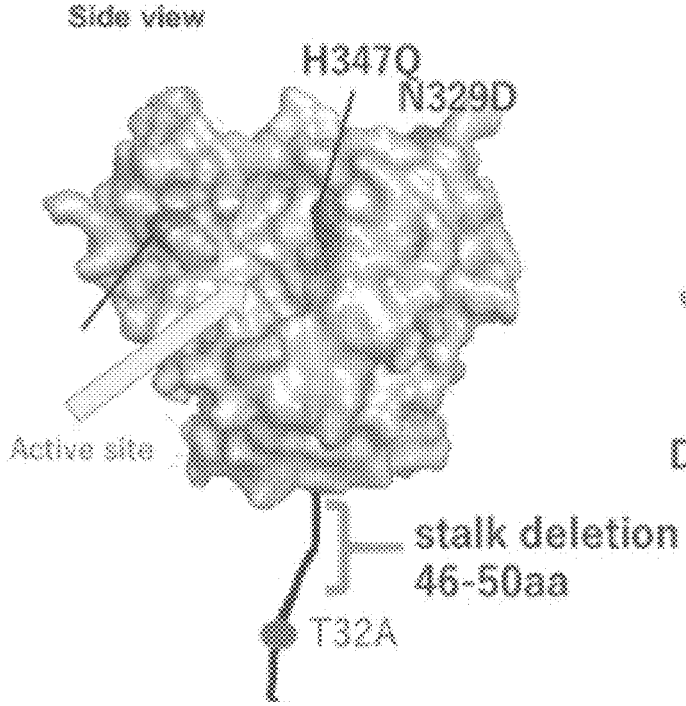
FIG. 5. Locations of the NA mutations on the 3D structure of N2 NA.

FIG. 5 shows the location of the NA mutations in Y2017-M3L4 in a 3D model.

Figure 6:
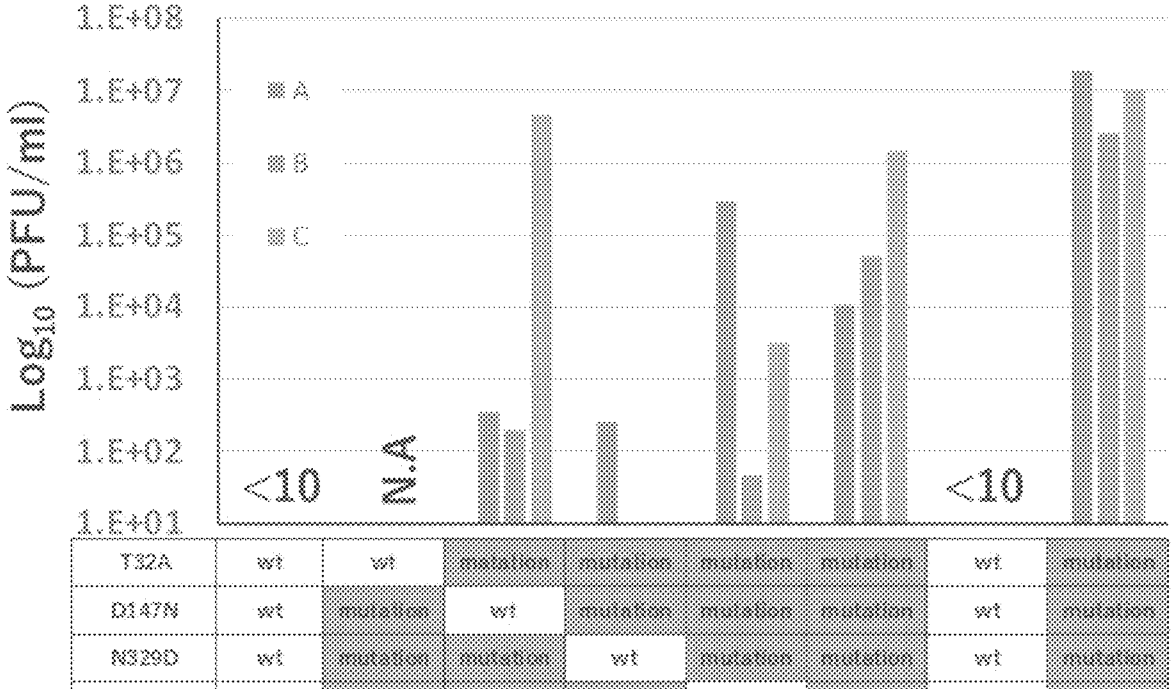
FIG. 6, Graph showing titers in eggs for recombinant viruses with specific mutations found in the mutant of A/Yokohama/2017/2003 ("Y2017-M3L4"). Virus inoculation: $2\times10^3$ pfu/egg into allantoic fluid, 72 h incubation at 37° C.

Comparison of the growth ability of Y2017 viruses with NA mutations revealed that NA-D147N, N329D, and H347Q generally contributed to the increased growth ability in allantoic fluid (FIG. 6).

Figure 7:
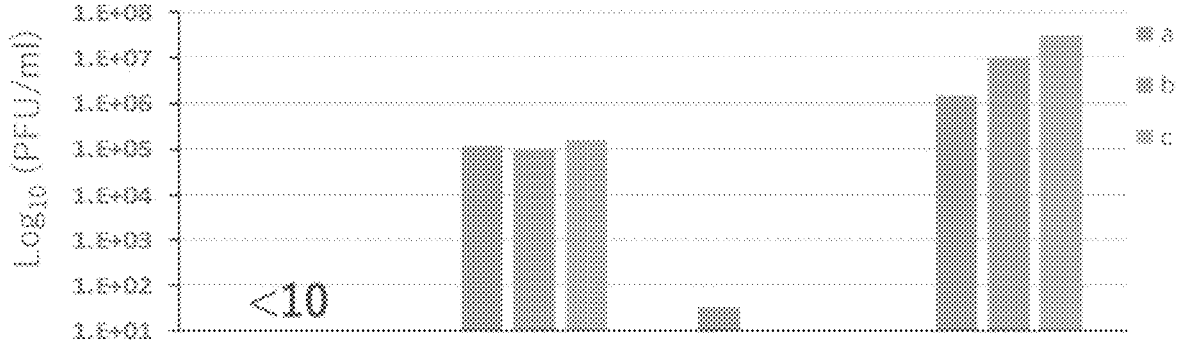
FIG. 7. Graph of virus titer in eggs for reassortants with two different backbones (PA, PB1, PB2, NP, NS and M) and two different HA and NA combinations (e.g., PB2-I504V, PB1-M40L/G180W, PA-R400K, NP-I116L, NS1-A30P/R118K; and NA of Y2017-M3L4 contains mutations; NA-T32A, D147N, N329D, H347Q and deletion of 46-50aa). Virus inoculation: $2\times10^3$ pfu/egg into allantoic fluid, 72 h incubation at 37° C.
Figure 8:
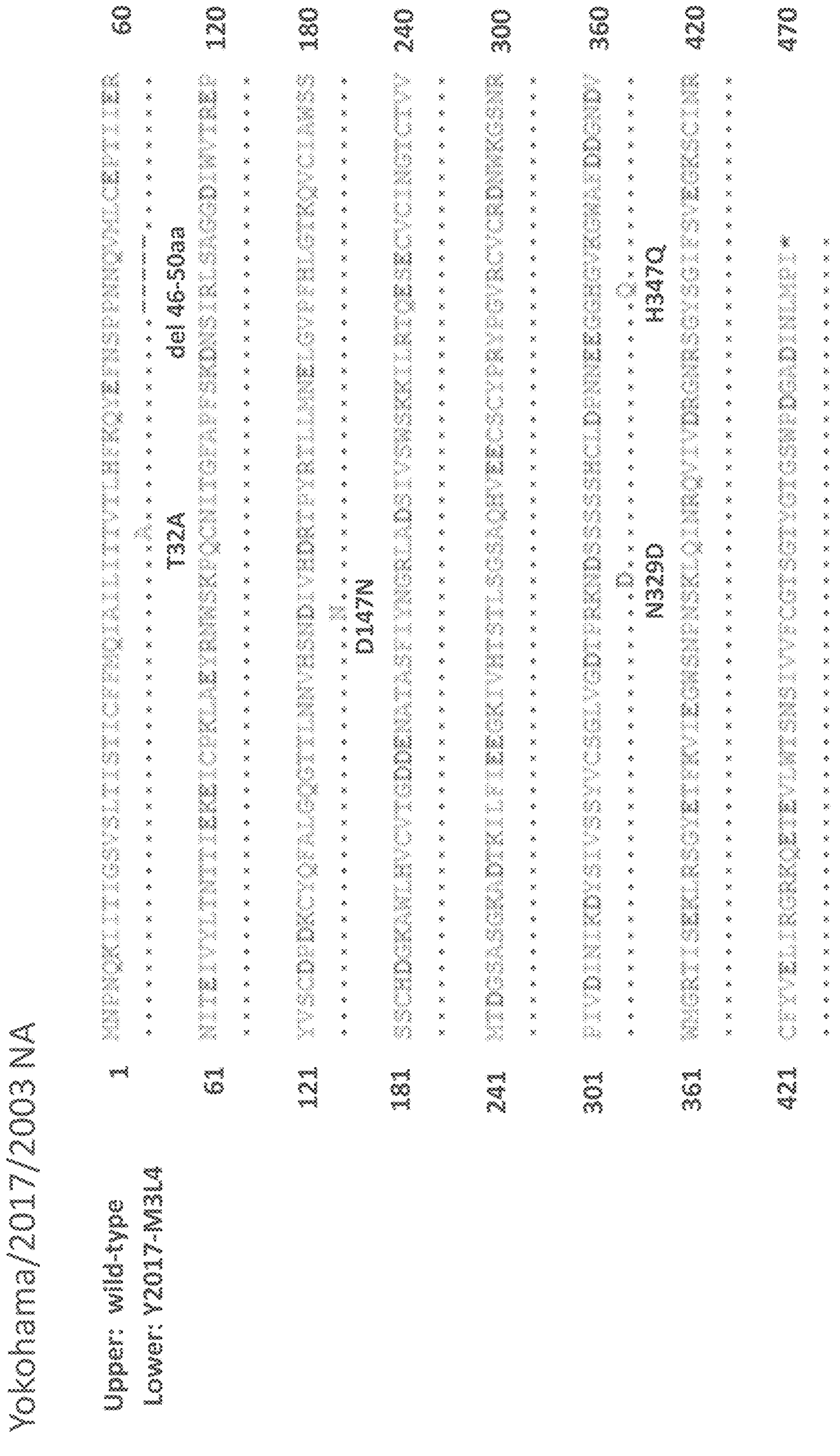
FIG. 8. Amino acid sequence comparison of Yokohama/2017/2003 NA wild-type (SEQ ID NO:3) and Y2017-M3L4 (SEQ ID NO:1).

The NA of Y2017-M3L4 allowed virus possessing HK4801HA to replicate efficiently in the allantoic cavity and the HY-PR8 backbone further enhanced the growth of this virus (FIG. 7).

In summary, described herein are influenza virus mutations that inhibit (e.g., prevent) the acquisition of antigenicity-compromising mutations in the hemagglutinin (HA) protein of influenza during growth in eggs and/or allow for enhanced replication, In one embodiment, the mutations are within the neuraminidase (NA) viral segment of human influenza viruses, and the mutant NA proteins stabilize the HA protein during egg-passages. Thus, in the presence of the mutant NA proteins, the HA protein does not acquire egg-adapting mutations. In some cases, the respective mutations in NA can also increase the yield of vaccine viruses.

EXAMPLE 3

Analysis of the growth capability of NA mutant viruses revealed that NA-D147N, N329D, and H347Q contribute to the increased growth capability of the viruses in allantoic fluid (FIG. 12). HA mutations were not observed in the virus possessing HK4801HA, Y2017-M3L4NA, and the HY-PR8 backbone (FIG. 13) after 3 passages in the allantoic cavity.

By passaging an HY-PR8 backbone virus possessing HK4801NA (T148K and the saturated mutations N329X and H347X) and HK4801HA in eggs, a virus possessing HK4801NA (T148K, D151E, H347G, and T369K) emerged that replicated efficiently in the allantoic cavity (FIG. 14; 4M=T148K, D151E, H347G, and T369K). HA mutations were not observed during passages in eggs (1× in the amniotic cavity then 5× in the allantoic cavity).

Figure 16:
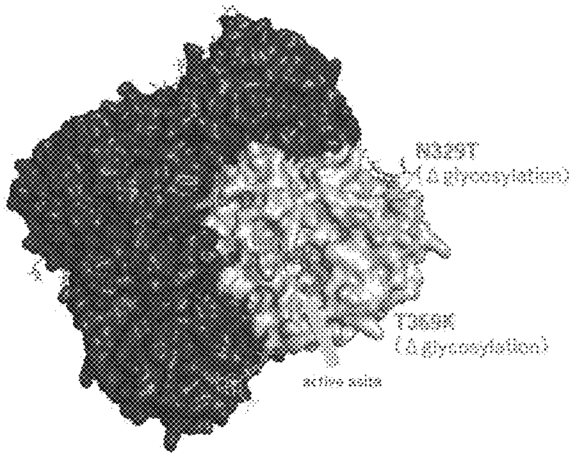
FIG. 16 is a schematic of the positions of certain NA residues.
Figure 17:
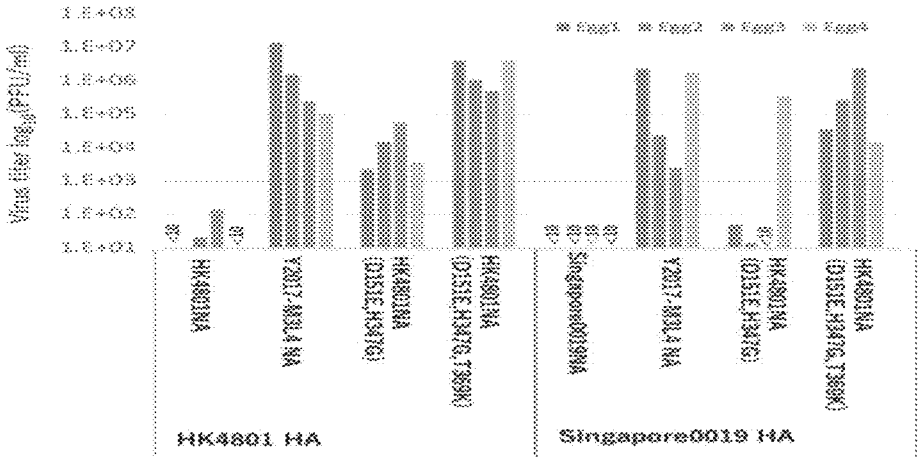
FIG. 17 shows virus titers for egg passaged isolates (HK4801NA (T148K, D151E, H347G, and T369K)) conferred efficient replication in the allantoic cavity to viruses possessing either HK4801HA or Singapore0019 HA (HY-PR8 backbone).

HK4801NA (T148K, D151E, H347G, and T369K) conferred efficient replication in the allantoic cavity to HY-PR8 backbone viruses possessing either HK4801HA or Singapore0019HA. Virus inoculation: $2\times10^3$ pfu/egg into allantoic fluid, 72 h incubation at 37° C. (FIG. 16).

The HA coding nucleic acid sequence and NA coding nucleic acid and amino acid sequences for Singapore0019 are as follows:

A/Singapore/INFINH-16-0019/2016(H3N2) HA (SEQ ID NO: 46)

```
atgaagactatcattgctttgagctacattctatgtctggttttcgctcaaaaaattcctggaaatgacaatagcacggcaacgctgt

gccttgggcaccatgcagtaccaaacggaacgatagtgaaaacaatcacaaatgaccgaattgaagttactaatgctactgagtt

ggttcagaattcctcaataggtgaaatatgcgacagtcctcatcagatccttgatggagagaactgcacactaatagatgctctatt

gggagaccctcagtgtgatggctttcaaaataagaaatgggacctttttgttgaacgaagcaaagcctacagcaactgttaccctt

atgatgtgccggattatgcctcccttaggtcactagttgcctcatccggcacactggagtttaaaaatgaaagcttcaattggactg

gagtcactcaaaacggaacaagttctgcttgcataaggggatctagtagtagtttctttagtagattaaattggttgacccacttaaa

ctacacatatccagcattgaacgtgactatgccaaacaaggaacaatttgacaaattgtacatttgggggttcaccacccgggta

cggacaaggaccaaatcttcctgtatgctcaatcatcaggaagaatcacagtatctaccaaaagaagccaacaagctgtaatccc

aaatatcggatctagacccagaataagggatatccctagcagaataagcatctattggacaatagtaaaaccgggagacatacttt

tgattaacagcacagggaatctaattgctcctaggggttacttcaaaatacgaagtgggaaaagctcaataatgagatcagatgca

cccattggcaaatgcaagtctgaatgcatcactccaaatggaagcattcccaatgacaaaccattccaaaatgtaaacaggatca

catacggggcctgtcccagatatgttaagcatagcactctgaaattggcaacaggaatgcgaaatgtaccagagaaacaaacta

gaggcatatttggcgcaatagcgggtttcatagaaaatggttgggagggaatggtggatggttggtacggtttcaggcatcaaaa

ttctgagggaagaggacaagcagcagatctcaaaagcactcaagcagcaatcgatcaaatcaatgggaagctgaataggttga

tcggaaaaaccaacgagaaattccatcagattgaaaaagaattctcagaagtagaaggaagagttcaagaccttgagaaatatgt

tgaggacactaaaatagatctctggtcatacaacgcggagcttcttgttgccctggagaaccaacatacaattgatctaactgactc

agaaatgaacaaactgtttgaaaaaacaaagaagcaactgagggaaaatgctgaggatatgggaaatggttgtttcaaaatatac

cacaaatgtgacaatgcctgcatagaatcaataagaaatgaaacttatgaccacaatgtgtacagggatgaagcattgaacaacc

ggttccagatcaagggagttgagctgaagtcaggatacaaagattggatcctatggatttcctttgccatatcatgtttttttgctttgtg

ttgctttgttggggttcatcatgtgggcctgccaaaagggcaacattagatgcaacatttgcatttga
```

A/Singapore/INFINH-16-0019/2016(H3N2) NA (SEQ ID NO: 47)

```
atgaatccaaatcaaaagataataacgattggctctgtttctctcaccatttccacaatatgcttcttcatgcaaattgccatcctgata

actactgtaacattgcatttcaagcaatatgaattcaactccccccaaacaaccaagtgatgctgtgtgaaccaacaataatagaa
```

-continued agaaacataacagagatagtgtatttgaccaacaccaccatagagaaggaaatatgccccaaaccagcagaatacagaaattg gtcaaaaccgcaatgtggcattacaggatttgcacctttctctaaggacaattcgattaggctttccgctggtggggacatctgggt gacaagagaaccttatgtgtcatgcgatcctgacaagtgttatcaatttgcccttggacagggaacaacactaaacaacgtgcatt caaataacacagtacgtgataggaccccttatcggactctattgatgaatgagttgggtgttcctttccatctggggaccaagcaag tgtgcatagcatggtccagctcaagttgtcacgatggaaaagcatggctgcatgtttgtataacgggggatgataaaaatgcaact gctagcttcatttacaatgggaggcttatagatagtgttgtttcatggtccaaagatattctcaggacccaggagtcagaatgcgttt gtatcaatggaacttgtacagtagtaatgactgatggaaatgctacaggaaaagctgatactaaaatactattcattgaggagggg aaaatcgttcatactagcaaattgtcaggaagtgctcagcatgtcgaagagtgctcttgctatcctcgatatcctggtgtcagatgtg tctgcagagacaactggaaaggatccaaccggcccatcgtagatataaacataaaggatcatagcattgtttccagttatgtgtgtt caggacttgttggagacacacccagaaaaaacgacagctccagcagtagccattgtttgaatcctaacaatgaagaaggtggtc atggagtgaaaggctgggcctttgatgatggaaatgacgtgtggatggggagaacaatcaacgagacgtcacgcttagggtat gaaaccttcaaagtcgttgaaggctggtccaaccctaagtccaaattgcagataaataggcaagtcatagttgacagaggtgata ggtccggttattctggtattttctctgttgaaggcaaaagctgcatcaatcggtgcttttatgtggagttgattaggggaagaaaaga ggaaactgaagtcttgtggacctcaaacagtattgttgtgttttgtggcacctcaggtacatatggaacaggctcatggcctgatgg ggcggacctcaatctcatgcatatataa which encodes (SEQ ID NO: 48)

M N P N Q K I I T I G S V S L T I S T I C F F M Q I A I L I T T V T L H F K

Q Y E F N S P P N N Q V M L C E P T I I E R N I T E I V Y L T N T T I E K

E I C P K P A E Y R N W S K P Q C G I T G F A P F S K D N S I R L S A G

G D I W V T R E P Y V S C D P D K C Y Q F A L G Q G T T L N N V H S N

N T V K D R T P Y R T L L M N E L G V P F H L G T K Q V C I A W S S S

S C H D G K A W L H V C I T G D D K N A T A S F I Y N G R L I D S V V

S W S K D I L R T Q E S E C V C I N G T C T V V M T D G N A T G K A D

T K I L F I E E G K I V H R T S K L S G S A Q H V E E C S C Y P R Y P G V

R C V C R D N W K G S N R P I V D I N I K D H S I V S S Y V C S G L V G

D T P R K N D S S S S S H C L N P N N E E G G H G V K G W A F D D G

N D V W M G R T I N E T S R L G Y E T F K V V E G W S N P K S K L Q I

N R Q V I V D R G D R S G Y S G I F S V E G K S C I N R C F Y V E L I R

G R K E E T E V L W T S N S I V V F C G T S G T Y G T G S W P D G A D

L N L M H I.

Figure 18:
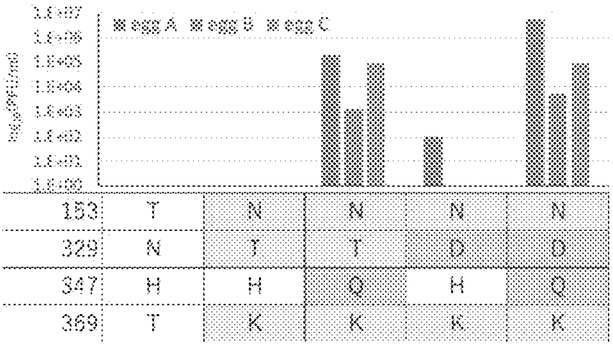
FIG. 18 shows egg titers for different combinations of selected residues at positions 153, 329, 347, and 369 in NA.
Figure 24:
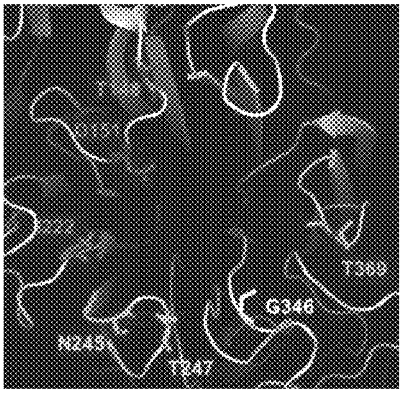
FIG. 24 is an enlarged view of the NA activity center. Most egg-adapted mutations are located in/around the NA active site.

NA mutations T153N, N329T, and T369K allowed. A/Saitama/102/2014 (H3N2) to replicate efficiently in the allantoic cavity (Kuwahara et al., 2018). Therefore, the effect of introducing NA-T153N, N329T (or D), T369K, and H347Q into HK4801NA(T148K) was examined. FIG. 18 reports on virus titers for different combinations of NA residues identified in screenings. FIGS. 19 and 20 report on virus titers for viruses with different combinations of selected NA residues.

EXAMPLE 4

A/Alaska/232/2015_HY-PR8 (H3N2) WT/mutant virus were passaged in eggs and HA and NA segments sequenced. Alaska WT (a more recent H3N2 virus where WT has 245N, prior to 2015 H3N2 WT viruses had 245S), HA-R142S, -K189E viruses did not get mutations in HA, even after 3 amniotic and 10 allantoic passages. HA-K189E/N158K/A212T mutant did not get mutations in hut had some mutations in NA which exhibited improved growth in eggs since p6 (FIG. 21). The difference of NA mutations between p4 (normal growth) (NA-N245S mutation, virus grows more than 1000 fold better than with NA-245N) and p6 (better growth) was G346V (FIG. 22). Therefore, G346V may also contribute to adaptation to eggs.

The NA for A/Alaska/232/2015 has the following sequence:

```
                                            (SEQ ID NO: 49)
mnpnqkiiti gsvsltisti cffmqiaili ttvtlhfkqy efnsppnnqv mlceptiier

niteivyltn ttiekeicpk paeyrnwskp qcgitgfapf skdnsirlsa ggdiwvtrep

yvscdpdkcy qfalgqgttl nnvhsnntvr drtpyrtllm nelgvpfhlg tkqvciawss

sschdgkawl hvcitgddkn atasfiyngr lvdsvvswsk dilrtqsec vcingtctvv

mtdgnatgka dtkilfieeg kivhtsklsg saqhveecsc yprypgvrcv crdnwkgsnr

pivdinikdh sivssyvcsg lvgdtprknd ssssshclnp nneegghgvk gwafddgndv

wmgrtinets rlgyetfkvv egwsnpkskl qinrqvivdr gdrsgysgif svegkscinr

cfyvelirgr keetevlwts nsivvfcgts gtygtgswpd gadlnlmhi.
```

NA pHH21 plasmids were constructed: Alaska NA-T148K/D151E/N245S (found in E4); Alaska NA-G346V; and Alaska NA-T148K/D151E/N245S/G346V (found in E6). Mutant NAs were combined with WT Alaska HA or HY-PR8 backbone. Eggs were inoculated with the same dosage of WT/mutant Alaska viruses and harvested viruses titrated (FIG. 23), NA-T148K/D151E/N245S/G346V mutant virus grew to a higher titer than WT virus but the single mutation G346V did not increase virus growth compared to WT. These results suggested that a combination of G346V and one (or two to three) other mutations, e.g., 3 mutations such as T148K, D151E and N245S, may be important for virus Alaska virus to grow efficiently in eggs. Harvested virus samples with high titer (>5 Log10 PFU/mL) were sequenced however none had additional mutations in HA and NA.

REFERENCES

*Avery's Drug Treatment: Principles and Practice of Clinical Pharmacology and Therapeutics,* 3rd edition, ADIS Press, Ltd., Williams and Wilkins, Baltimore, MD (1987).

Aymard-Henry et al., *Virology: A Practical Approach,* Oxford IRL Press, Oxford, 119-150 (1985).

Bachmeyer, *Intervirology,* 5: 260 (1975).

Berkow et al., eds., *The Merck Manual,* 16th edition, Merck & Co., Rahway, NJ (1992).

Hatta et al., *Science,* 293: 1840 (2001).

Horimoto et al., *J. Virol.,* 68: 3120 (1994).

Horimoto et at, *Vaccine,* 24: 3669 (2006).

Keitel et al., in Textbook of Influenza, eds. Nickolson, K. G., Webster, R. G., and Hay, A. (Blackwell, Oxford), pp. 373-390 (1998).

Kuwahara et al., *Jpn. J. Infect. Dis.,* 71: 234 (2018).

Laver & Webster, *Virology,* 69: 511 (1976).

Neumann et al., *Adv. Virus Res.,* 53: 265 (1999).

Neumann et al., *J. Gen. Virol.,* 83: 2635 (2002).

Neumann et al., *J. Virol.,* 71: 9690 (1997).

Neumann et al., *Proc. Natl. Acad. Sci. USA,* 96: 9345 (1999).

Neumann et al., *Virology.* 287: 243 (2001).

Osol (ed.), *Remington's Pharmaceutical Sciences*, Mack Publishing Co., Easton, PA 1324-4341 (1980).

Sugawara et al., *Biologicals,* 30: 303 (2002).

Webby & Webster et al., *Science,* 302: 1519 (2003).

Wood & Robertson, *Nat. Rev. Microbiol,* 2: 842 (2004).

World Health Organization TSR No. 673 (1982).

World Health Organization. Confirmed human cases of avian influenza A (H5N1). http://www.who.int/csr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. An isolated recombinant influenza virus comprising a selected NA viral segment encoding at least two selected residues in NA, wherein the residues are selected from residue S, T, I, L, A, N, W, Y, P, V, or G at position 245 and residue S, T, P, Y, W, A, N, I, L, or V at position 346, wherein the numbering is relative to SEQ ID NO:3, wherein the recombinant influenza virus has enhanced replication in avian eggs or has a reduction in HA mutations when grown in avian eggs relative to a corresponding influenza virus that has a NA that encodes an asparagine at residue 245, or encodes a glycine at residue 346, or any combination thereof.

2. The isolated virus of claim 1 wherein the NA further encodes residue G, Q, S, T, Y, C or W at position 347 or residue K, R or H at position 369.

3. The isolated recombinant influenza virus of claim 1 wherein the NA viral segment encodes a NA that has at least 90% amino acid sequence identity to SEQ ID NO:1, SEQ ID NO:2, SEQ ID NO:3, SEQ ID NO:48, SEQ ID NO:49, SEQ ID NO:50 or SEQ ID NO:54.

4. The isolated recombinant influenza virus of claim 1 wherein the NA viral segment encodes a N2, N3, N7, or N9.

5. The isolated recombinant influenza virus of claim 1 wherein the residue at position 245 is S or the residue at position 346 is V.

6. The isolated recombinant influenza virus of claim 2 wherein the residue at position 347 is G or Q.

7. The isolated recombinant influenza virus of claim 1 wherein the residue at position 245 is S, T, I, L, A, or V, or any combination thereof.

8. The isolated recombinant influenza virus of claim 1 which comprises PA, PB1, PB2, NP, M, and NS viral segments having at least 85% nucleic acid sequence identity to SEQ ID Nos. 24 to 29 or 39 to 44 or encoding a polypeptide having at least 80% amino acid sequence identity to a polypeptide encoded by SEQ ID Nos. 24 to 29 or 39 to 44.

9. A method to prepare influenza virus, comprising: contacting a cell with:

a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes a NA having a residue selected from S, T, I, L, A, N, W, Y, P, V, or G at position 245 and residue S, T, P, Y, W, A, N, I, L, or V at position 346, wherein the numbering for NA residues is relative to SEQ ID NO:3; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus.

10. The method of claim 9 wherein the NA has at least 90% amino acid sequence identity to SEQ ID NO:1, SEQ ID NO:2, SEQ ID NO:3, SEQ ID NO:48, SEQ ID NO:49, or SEQ ID NO: 54.

11. The method of claim 9 wherein the residue at position 347 is G or Q or the residue at position 245 is S.

12. The method of claim 9 wherein the virus comprises PA, PB1, PB2, NP, M, and NS viral segments having at least 85% nucleic acid sequence identity to SEQ ID Nos. 24 to 29 or 39 to 44 or encoding a polypeptide having at least 80% amino acid sequence identity to a polypeptide encoded by SEQ ID Nos. 24 to 29 or 39 to 44.

13. The method of claim 9 wherein the NA further encodes residue G, Q, S, T, Y, C or W at position 347 or residue K, R or H at position 369.

14. An isolated virus prepared by the method of claim 9.

15. A method of immunizing an avian or a mammal, comprising: administering to the avian or the mammal a composition having an effective amount of the virus of claim 1.

16. The method of claim 15 wherein the composition comprises at least one other different influenza virus.

17. The method of claim 15 wherein the mammal is a human.

18. The method of claim 15 wherein the composition is administered intranasally.

19. The method of claim 15 wherein the composition is administered via injection.

20. A method comprising passaging the virus of claim 1 in eggs.

* * * * *

SEQUENCE LISTING

<160> NUMBER OF SEQ ID NOS: 62

<210> SEQ ID NO 1
<211> LENGTH: 464
<212> TYPE: PRT
<213> ORGANISM: Influenza virus

<400> SEQUENCE: 1

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Ala
            20                  25                  30

Val Thr Leu His Phe Lys Gln Tyr Glu Phe Asn Ser Pro Met Leu Cys
        35                  40                  45

Glu Pro Thr Ile Ile Glu Arg Asn Ile Thr Glu Ile Val Tyr Leu Thr
    50                  55                  60

Asn Thr Thr Ile Glu Lys Glu Ile Cys Pro Lys Leu Ala Glu Tyr Arg
65                  70                  75                  80

Asn Trp Ser Lys Pro Gln Cys Asn Ile Thr Gly Phe Ala Pro Phe Ser
                85                  90                  95

Lys Asp Asn Ser Ile Arg Leu Ser Ala Gly Gly Asp Ile Trp Val Thr
            100                 105                 110

Arg Glu Pro Tyr Val Ser Cys Asp Pro Asp Lys Cys Tyr Gln Phe Ala
        115                 120                 125

Leu Gly Gln Gly Thr Thr Leu Asn Asn Val His Ser Asn Asn Ile Val
    130                 135                 140

His Asp Arg Thr Pro Tyr Arg Thr Leu Leu Met Asn Glu Leu Gly Val
145                 150                 155                 160

Pro Phe His Leu Gly Thr Lys Gln Val Cys Ile Ala Trp Ser Ser Ser
                165                 170                 175

Ser Cys His Asp Gly Lys Ala Trp Leu His Val Cys Val Thr Gly Asp
            180                 185                 190

Asp Glu Asn Ala Thr Ala Ser Phe Ile Tyr Asn Gly Arg Leu Ala Asp
        195                 200                 205

Ser Ile Val Ser Trp Ser Lys Lys Ile Leu Arg Thr Gln Glu Ser Glu
    210                 215                 220

Cys Val Cys Ile Asn Gly Thr Cys Thr Val Val Met Thr Asp Gly Ser
225                 230                 235                 240

Ala Ser Gly Lys Ala Asp Thr Lys Ile Leu Phe Ile Glu Glu Gly Lys
                245                 250                 255

Ile Val His Thr Ser Thr Leu Ser Gly Ser Ala Gln His Val Glu Glu
            260                 265                 270

Cys Ser Cys Tyr Pro Arg Tyr Pro Gly Val Arg Cys Val Cys Arg Asp
        275                 280                 285

Asn Trp Lys Gly Ser Asn Arg Pro Ile Val Asp Ile Asn Ile Lys Asp
    290                 295                 300

Tyr Ser Ile Val Ser Ser Tyr Val Cys Ser Gly Leu Val Gly Asp Thr
305                 310                 315                 320

Pro Arg Lys Asp Asp Ser Ser Ser Ser Ser His Cys Leu Asp Pro Asn
                325                 330                 335

Asn Glu Glu Gly Gly Gln Gly Val Lys Gly Trp Ala Phe Asp Asp Gly
            340                 345                 350

Asn Asp Val Trp Met Gly Arg Thr Ile Ser Glu Lys Leu Arg Ser Gly
        355                 360                 365
```

-continued

```
Tyr Glu Thr Phe Lys Val Ile Glu Gly Trp Ser Asn Pro Asn Ser Lys
    370                 375                 380

Leu Gln Ile Asn Arg Gln Val Ile Val Asp Arg Gly Asn Arg Ser Gly
385                 390                 395                 400

Tyr Ser Gly Ile Phe Ser Val Glu Gly Lys Ser Cys Ile Asn Arg Cys
                405                 410                 415

Phe Tyr Val Glu Leu Ile Arg Gly Arg Lys Gln Glu Thr Glu Val Leu
            420                 425                 430

Trp Thr Ser Asn Ser Ile Val Val Phe Cys Gly Thr Ser Gly Thr Tyr
        435                 440                 445

Gly Thr Gly Ser Trp Pro Asp Gly Ala Asp Ile Asn Leu Met Pro Ile
    450                 455                 460


<210> SEQ ID NO 2
<211> LENGTH: 469
<212> TYPE: PRT
<213> ORGANISM: Influenza virus

<400> SEQUENCE: 2

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Val Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285
```

```
Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met Pro Ile
465


<210> SEQ ID NO 3
<211> LENGTH: 469
<212> TYPE: PRT
<213> ORGANISM: Influenza virus

<400> SEQUENCE: 3

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
```

-continued

```
            180                 185                 190

Cys Val Thr Gly Asp Asp Glu Asn Ala Thr Ala Ser Phe Ile Tyr Asn
        195                 200                 205

Gly Arg Leu Ala Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

<210> SEQ ID NO 4
<211> LENGTH: 2341
<212> TYPE: DNA
<213> ORGANISM: Influenza virus

<400> SEQUENCE: 4

```
agcaaaagca ggtcaattat attcagtatg gaaagaataa aagaactacg gaacctgatg      60

tcgcagtctc gcactcgcga gatactgaca aaaaccacag tggaccatat ggccataatt     120

aagaagtaca catcggggag acaggaaaag aacccgtcac ttaggatgaa atggatgatg     180

gcaatgaaat acccaatcac tgctgacaaa aggataacag aaatggttcc ggagagaaat     240

gaacaaggac aaactctatg gagtaaaatg agtgatgctg gatcagatcg agtgatggta     300

tcacctttgg ctgtgacatg gtggaataga aatggacccg tgacaagtac ggtccattac     360

ccaaaagtat acaagactta ttttgacaaa gtcgaaaggt taaaacatgg aacctttggc     420

cctgttcatt ttagaaatca agtcaagata cgccgaagag tagacacaaa ccctggtcat     480
```

-continued

```
gcggacctca gtgccaagga ggcacaagat gtaattatgg aagttgtttt tcccaatgaa    540
gtgggagcca ggatactaac atcagaatcg caattaacaa taactaaaga gaaaaaagaa    600
gaactccgag attgcaaaat ttctcccttg atggttgcat acatgttaga gagagaactt    660
gtccgaaaaa caagatttct cccagttgct ggcggaacaa gcagtatata cattgaagtt    720
ttacatttga ctcaagggac gtgttgggaa caaatgtaca ctccaggtgg agaagtgagg    780
aatgacgatg ttgaccaaag cctaattatt gcagccagga acatagtaag aagagccgca    840
gtatcagcag atccactagc atctttattg gagatgtgcc acagcacaca aattggcggg    900
acaaggatgg tggacattct tagacagaac ccgactgaag aacaagctgt ggatatatgc    960
aaggctgcaa tgggattgag aatcagctca tccttcagct ttggtgggtt tacatttaaa   1020
agaacaagcg ggtcatcagt caaaaaagag gaagaagtgc ttacaggcaa tctccaaaca   1080
ttgaagataa gagtacatga ggggtatgag gagttcacaa tggtggggaa aagagcaaca   1140
gctatactca gaaaagcaac cagaagattg gttcagctca tagtgagtgg aagagacgaa   1200
cagtcaatag ccgaagcaat aattgtggcc atggtgtttt cacaagagga ttgcatgata   1260
aaagcagtta gaggtgacct gaatttcgtc aacagagcaa atcagcggtt gaaccccatg   1320
catcagcttt taaggcattt tcagaaagat gcgaaagtgc tttttcagaa ttggggaatt   1380
gaacacatcg acagtgtaat gggaatggtt ggagtattac cagatatgac tccaagcaca   1440
gagatgtcaa tgagaggaat aagagtcagc aaaatgggtg tggatgaata ctccagtaca   1500
gagagggtgg tggttagcat tgatcggttt ttgagagttc gagaccaacg cgggaatgta   1560
ttattatctc ctgaagaggt tagtgaaaca cagggaactg agagactgac aataacttat   1620
tcatcgtcga tgatgtggga gattaacggt cctgagtcgg ttttggtcaa tacttatcaa   1680
tggatcatca gaaattggga agctgtcaaa attcaatggt ctcagaatcc tgcaatgttg   1740
tacaacaaaa tggaatttga accatttcaa tctttagtcc ccaaggccat tagaagccaa   1800
tacagtgggt ttgtcagaac tctattccaa caaatgagag acgtacttgg gacatttgac   1860
accacccaga taataaagct tctccctttt gcagccgctc caccaaagca aagcagaatg   1920
cagttctctt cactgactgt aaatgtgagg ggatcaggga tgagaatact tgtaaggggc   1980
aattctcctg tattcaacta caacaagacc actaaaagac taacaattct cggaaaagat   2040
gccggcactt taattgaaga cccagatgaa agcacatccg gagtggagtc cgctgtattg   2100
agagggtttc tcattatagg taaggaagac agaagatacg ggccagcatt aagcatcaat   2160
gaactgagta accttgcaaa aggggaaaag gctaatgtgc taatcgggca aggagacgtg   2220
gtgttggtaa tgaaacgaaa acgggactct agcatactta ctgacagcca gacagcgacc   2280
aaaagaattc ggatggccat caattaatgt tgaatagttt aaaaacgacc ttgtttctac   2340
t                                                                   2341
```

<210> SEQ ID NO 5
<211> LENGTH: 2341
<212> TYPE: DNA
<213> ORGANISM: Influenza virus

<400> SEQUENCE: 5

```
agcaaaagca ggcaaaccat ttgaatggat gtcaatccga ctctactgtt cctaaaggtt     60
ccagcgcaaa atgccataag caccacattc ccttatactg gagatcctcc atacagccat    120
ggaacaggaa cagggtacac catggacaca gtcaacagaa cacaccaata ttcagataag    180
```

-continued

```
gggaagtgga cgacaaatac agaaactggg gcaccccaac tcaacccaat tgatggacca    240
ctacctgagg ataatgagcc aagtggatat gcacaaacag actgtgtcct ggaggctatg    300
gccttccttg aagaatccca cccaggtatc tttgagaact catgccttga aacaatggaa    360
gtcgttcaac aaacaagggt ggacaaacta acccaaggtc gccagactta tgattggaca    420
ttaaacagaa atcaaccggc agcaactgca ttagccaaca ccatagaagt ttttagatcg    480
aatggactaa cagctaatga atcaggaagg ctaatagatt tcctcaagga tgtgatggaa    540
tcaatggata aagaggaaat ggagataaca acacactttc aaagaaaaag gagagtaaga    600
gacaacatga ccaagaaaat ggtcacacaa agaacaatag ggaagaaaaa acaaagagtg    660
aataagagag gctatctaat aagagctttg acattgaaca cgatgaccaa agatgcagag    720
agaggtaaat taaaaagaag ggctattgca acacccggga tgcaaattag agggttcgtg    780
tacttcgttg aaactttagc tagaagcatt tgcgaaaagc ttgaacagtc tggacttccg    840
gttgggggta atgaaaagaa ggccaaactg gcaaatgttg tgagaaaaat gatgactaat    900
tcacaagaca cagagctttc tttcacaatc actggggaca acactaagtg gaatgaaaat    960
caaaaccctc gaatgttttt ggcgatgatt acatatatca caaaaaatca acctgagtgg   1020
ttcagaaaca tcctgagcat cgcaccaata atgttctcaa acaaaatggc aagactggga   1080
aaaggataca tgttcgagag taagagaatg aaactccgaa cacaaatacc cgcagaaatg   1140
ctagcaaaca ttgacctgaa gtatttcaat gaatcaacaa ggaagaaaat tgagaaaata   1200
aggcctcttc taatagatgg cacagcatca ttgagccctg ggatgatgat gggcatgttc   1260
aacatgctaa gtacggtttt aggagtctcg atactgaatc ttgggcaaaa gaaatacacc   1320
aagacaacat actggtggga tggctccaa tcctccgacg attttgccct catagtgaat    1380
gcaccaaatc atgagggaat acaagcagga gtggatagat tttacaggac ctgcaagtta   1440
gtgggaatca acatgagcaa aaagaagtcc tatataaata aaacagggac atttgaattc   1500
acaagctttt tttatcgata tggatttgtg gctaatttta gcatggagct gcccagtttt   1560
ggagtgtctg gaataaacga gtcagctgat atgagcattg gagtaacagt gataaagaac   1620
aacatgataa acaatgacct tggaccagca acagcccaga tggctctcca attgttcatc   1680
aaagactaca gatatacata taggtgccat agaggagaca cacaaattca gacgagaaga   1740
tcattcgagc taaagaagct gtgggatcaa acccaatcaa gggcaggact attggtatca   1800
gatgggggac caaacttata caatatccgg aatcttcaca tccctgaagt ctgcttaaag   1860
tgggagctaa tggatgagaa ttatcgggga agactttgta atcccctgaa tccctttgtc   1920
agccataaag aaattgagtc tgtaaacaat gctgtagtga tgccagccca tggtccggcc   1980
aaaagtatgg aatatgatgc cgttgcaact acacactcct ggattcccaa gaggaaccgc   2040
tctattctca acacaagcca aaggggaatt cttgaggatg aacagatgta ccagaagtgc   2100
tgcaacttgt tcgagaaatt tttccctagt agttcatata ggagaccgat tggaatttct   2160
agcatggtgg aggccatggt gtctagggcc cggattgatg ccagaattga cttcgagtct   2220
ggacggatta agaaggaaga gttctctgag atcatgaaga tctgttccac cattgaagaa   2280
ctcagacggc aaaaataatg aatttagctt gtccttcatg aaaaaatgcc ttgtttctac   2340
t                                                                   2341
```

<210> SEQ ID NO 6
<211> LENGTH: 2233
<212> TYPE: DNA
<213> ORGANISM: Influenza virus

<400> SEQUENCE: 6

```
agcaaaagca ggtactgatt cgaaatggaa gattttgtgc gacaatgctt caacccgatg     60
attgtcgaac ttgcagaaaa agcaatgaaa gagtatgggg aggatctgaa aattgaaaca    120
aacaaatttg cagcaatatg cactcacttg gaggtatgtt tcatgtattc agattttcat    180
ttcatcaatg aacaaggcga atcaatagtg gtagaacttg atgatccaaa tgcactgtta    240
aagcacagat ttgaaataat cgaggggaga gacagaacaa tggcctggac agtagtaaac    300
agtatctgca acactactgg agctgaaaaa ccgaagtttc taccagattt gtatgattac    360
aaggagaaca gattcatcga aattggagtg acaaggagag aagtccacat atattacctt    420
gaaaaggcca ataagattaa atctgagaac acacacattc acattttctc attcactggg    480
gaggaaatgg ccacaaaggc agactacact ctcgacgagg aaagcagggc taggattaag    540
accaggctat ttaccataag acaagaaatg gccaacagag gcctctggga ttcctttcgt    600
cagtccgaaa gaggcgaaga aacaattgaa gaaaaatttg aaatctcagg aactatgcgt    660
aggcttgccg accaaagtct cccaccgaac ttctcctgcc ttgagaattt tagagcctat    720
gtggatggat tcgaaccgaa cggctgcatt gagggcaagc tttctcaaat gtccaaagaa    780
gtgaatgccc aaattgaacc ttttctgaag acaacaccaa gaccaatcaa acttccgaat    840
ggacctcctt gttatcagcg gtccaagttc ctcctgatgg atgctttaaa attgagcatt    900
gaagacccaa gtcacgaagg agaagggatc ccattatatg atgcgatcaa gtgcataaaa    960
acattctttg gatggaaaga accttatata gtcaaaccac acgaaaaggg aataaattca   1020
aattacctgc tgtcatggaa gcaagtattg tcagaattgc aggacattga aaatgaggag   1080
aagattccaa ggactaaaaa catgaagaaa acgagtcaac taaagtgggc tcttggtgag   1140
aacatggcac cagagaaagt agactttgaa aactgcagag acataagcga tttgaagcaa   1200
tatgatagtg acgaacctga attaaggtca ctttcaagct ggatacagaa tgagttcaac   1260
aaggcctgcg agctaactga ttcaatctgg atagagctcg atgaaattgg agaggacgta   1320
gccccaattg aatacattgc aagcatgagg aggaattatt tcacagcaga ggtgtcccat   1380
tgtagagcca ctgagtacat aatgaagggg gtatacatta atactgccct gctcaatgca   1440
tcctgtgcag caatggacga ttttcaacta attcccatga taagcaagtg cagaactaaa   1500
gagggaaggc gaaaaaccaa tttatatgga ttcatcataa agggaagatc tcatttaagg   1560
aatgacacag atgtggtaaa ctttgtgagc atggagtttt ctctcactga cccgagactt   1620
gagccacata aatgggagaa atactgtgtc cttgagatag gagatatgtt actaagaagt   1680
gccataggcc aaatttcaag gcctatgttc ttgtatgtga ggacaaacgg aacatcaaag   1740
gtcaaaatga aatggggaat ggagatgaga cgttgcctcc ttcagtcact ccagcagatc   1800
gagagcatga ttgaagccga gtcctcggtt aaagagaaag acatgaccaa agagtttttt   1860
gagaataaat cagaagcatg gcccattggg gagtccccca agggagtgga agaaggttcc   1920
attgggaaag tctgtaggac tctattggct aagtcagtgt tcaatagcct gtatgcatca   1980
ccacaattgg aaggattttc agcggagtca agaaaactgc tccttgttgt tcaggctctt   2040
agggacaacc tcgaacctgg gacctttgat cttggggggc tatatgaagc aattgaggag   2100
tgcctgatta atgatccctg ggttttgctc aatgcgtctt ggttcaactc cttcctgaca   2160
catgcattaa aatagttatg gcagtgctac tatttgttat ccgtactgtc caaaaaagta   2220
ccttgtttct act                                                      2233
```

<210> SEQ ID NO 7
<211> LENGTH: 1762
<212> TYPE: DNA
<213> ORGANISM: Influenza virus

<400> SEQUENCE: 7
agcaaaagca ggggataatt ctattaacca tgaagactat cattgctttg agctacattc 60
tatgtctggt tttcgctcaa aagcttcccg gaaatgacaa cagcacggca acgctgtgcc 120
ttgggcacca tgcagtacca aacggaacga tagtgaaaac aatcacgaat gaccaaattg 180
aagttactaa tgctactgag ctggttcaga gttcctcaac aggtggaata tgcgacagtc 240
ctcatcagat ccttgatgga gaaaactgca cactaataga tgctctattg ggagaccctc 300
agtgtgatgg cttccaaaat aagaaatggg accttttgt tgaacgcagc aaagcctaca 360
gcaactgtta cccttatgat gtgccggatt atgcctccct taggtcacta gttgcctcat 420
ccggcacact ggagtttaac aatgaaagct tcaattggac tggagtcact cagaatggaa 480
caagctctgc ttgcaaaagg agatctaata aaagtttctt tagtagattg aattggttga 540
cccacttaaa atacaaatac ccagcattga acgtgactat gccaaacaat gaaaaatttg 600
acaaattgta catttggggg gttcaccacc cgggtacgga cagtgatcaa atcagcctat 660
atgctcaagc atcaggaaga atcacagtct ctaccaaaag aagccaacaa actgtaatcc 720
cgaatatcgg atctagaccc agggtaaggg atgtctccag cagaataagc atctattgga 780
caatagtaaa accgggagac atacttttga ttaacagcac agggaatcta attgctcctc 840
ggggttactt caaaatacga agtgggaaaa gctcaataat gagatcagat gcacccattg 900
gcaaatgcaa ttctgaatgc atcactccaa atggaagcat tcccaatgac aaaccatttc 960
aaaatgtaaa caggatcaca tatggggcct gtcccagata tgttaagcaa aacactctga 1020
aattggcaac agggatgcga aatgtaccag agaaacaaac tagaggcata tttggcgcaa 1080
tcgcgggttt catagaaaat ggttgggagg gaatggtgga cggttggtac ggtttcaggc 1140
atcaaaattc tgagggcaca ggacaagcag cagatctcaa aagcactcaa gcagcaatca 1200
accaaatcaa tgggaaactg aataggttaa tcgggaaaac aaacgagaaa ttccatcaga 1260
ttgaaaaaga attctcagaa gtagaaggga gaattcagga cctcgagaaa tatgttgagg 1320
acactaaaat agatctctgg tcatacaacg cggagcttct tgttgccctg gagaaccaac 1380
atacaattga tctaactgac tcagaaatga acaaactgtt tgaaagaaca aagaagcaac 1440
tgagggaaaa tgctgaggat atgggcaatg gttgtttcaa aatataccac aaatgtgaca 1500
atgcctgcat agagtcaatc agaaatggaa cttatgacca tgatgtatac agagatgaag 1560
cattaaacaa ccggttccag atcaaaggtg ttgagctgaa gtcaggatac aaagattgga 1620
tcctatggat ttcctttgcc atatcatgtt ttttgctctg tgttgctttg ttggggttca 1680
tcatgtgggc ctgccaaaaa ggcaacatta ggtgcaacat ttgcatttga gtgcattaat 1740
taaaaacacc cttgtttcta ct 1762

<210> SEQ ID NO 8
<211> LENGTH: 1565
<212> TYPE: DNA
<213> ORGANISM: Influenza virus

<400> SEQUENCE: 8
agcaaaagca gggttaataa tcactcactg agtgacatca aaatcatggc gtcccaaggc 60
accaaacggt cttatgaaca gatggaaact gatggggatc gccagaatgc aactgagatt 120

```
agggcatccg tcgggaagat gattgatgga attgggagat tctacatcca aatgtgcact    180
gaacttaaac tcagtgatta tgaagggcgg ttgatccaga acagcttgac aatagagaaa    240
atggtgctct ctgcttttga tgaaagaagg aataaatatc tggaagaaca ccccagcgcg    300
gggaaagatc ctaagaaaac tgggggggccc atatacagga gagtagatgg aaaatggatg    360
agggaactcg tcctttatga caaagaagaa ataaggcgaa tctggcgcca agccaacaat    420
ggtgaggatg cgacagctgg tctaactcac ataatgatct ggcattccaa tttgaatgat    480
gcaacatacc agaggacaag agctcttgtt cgaaccggaa tggatcccag aatgtgctct    540
ctgatgcagg gctcgactct ccctagaagg tccggagctg caggtgctgc agtcaaagga    600
atcgggacaa tggtgatgga gctgatcaga atggtcaaac gggggatcaa cgatcgaaat    660
ttctggagag gtgagaatgg gcggaaaaca agaagtgctt atgagagaat gtgcaacatt    720
cttaaaggaa aatttcaaac agctgcacaa agagcaatgg tggatcaagt gagagaaagt    780
cggaacccag gaaatgctga gatcgaagat ctcatatttt tggcaagatc tgcattgata    840
ttgagaggat cagttgctca caaatcttgc ctacctgcct gtgtgtatgg acctgcagta    900
tccagtgggt acgacttcga aaaagaggga tattccttgg tgggaataga ccctttcaaa    960
ctacttcaaa atagccaagt atacagccta atcagaccta acgagaatcc agcacacaag   1020
agtcagctgg tatggatggc atgccattct gctgcatttg aagatttaag attgttaagc   1080
ttcatcagag ggacaaaagt atctccacga gggaaacttt caactagagg agtacaaatt   1140
gcttcaaatg agaacatgga taatatggga tcgagcactc ttgaactgag aagcgggtac   1200
tgggccataa ggaccaggag tggaggaaac actaatcaac agagggcctc cgcaggccaa   1260
accagtgtgc aacctacgtt ttctgtacaa agaaacctcc catttgaaaa gtcaaccatc   1320
atggcagcat tcactggaaa tacggaggga agaacttcag acatgagggc agaaatcata   1380
agaatgatgg aaggtgcaaa accagaagaa gtgtcgttcc gggggagggg agttttcgag   1440
ctctcagacg agaaggcaac gaacccgatc gtgccctctt ttgatatgag taatgaagga   1500
tcttatttct tcggagacaa tgcagaagag tacgacaatt aaggaaaaat acccttgttt   1560
ctact                                                                1565
```

<210> SEQ ID NO 9
<211> LENGTH: 1467
<212> TYPE: DNA
<213> ORGANISM: Influenza virus

<400> SEQUENCE: 9

```
agcaaaagca ggagtaaaga tgaatccaaa tcaaaagata ataacgattg gctctgtttc     60
cctcaccatt tccacaatat gcttcttcat gcaaattgcc atcctgataa ctactgtaac    120
attgcatttc aagcaatatg aattcaactc ccccccaaac aaccaagtga tgctgtgtga    180
accaacaata atagaaagaa acataacaga gatagtgtat ctgaccaaca ccaccataga    240
gaaggaaata tgccccaaac tagcagaata cagaaattgg tcaaagccgc aatgtaacat    300
tacaggattt gcaccttttt ctaaggacaa ttcgattcgg ctttccgctg gtggggacat    360
ctgggtgaca agagaacctt atgtgtcatg cgatcctgac aagtgttatc aatttgccct    420
tggacaggga acaacactaa acaacgtgca ttcaaatgac atagtacatg ataggacccc    480
ttatcggacc ctattgatga atgagttggg tgttccattt catctgggga ccaagcaagt    540
gtgcatagca tggtccagct caagttgtca cgatggaaaa gcatggctgc atgtttgtgt    600
```

-continued

```
aacgggggat gatgaaaatg caactgctag cttcatttac aatgggaggc ttgcagatag    660
tattgtttca tggtccaaaa aaatcctcag gacccaggag tcagaatgcg tttgtatcaa    720
tggaacttgt acagtagtaa tgactgatgg gagtgcttca ggaaaagctg atactaaaat    780
actattcatt gaggaggga aaattgttca tactagcaca ttatcaggaa gtgctcagca    840
tgtcgaggag tgctcctgtt atcctcgata tcctggtgtc agatgtgtct gcagagacaa    900
ctggaaaggc tccaataggc ccatcgtaga tataaacata aaggattata gcattgtttc    960
cagttatgtg tgctcaggac ttgttggaga cacacccaga aaaaacgaca gctccagcag   1020
tagccattgc ttggatccaa acaatgagga aggtggtcat ggagtgaaag gctgggcctt   1080
tgatgatgga aatgacgtgt ggatgggaag aacgatcagc gagaagttac gctcaggata   1140
tgaaaccttc aaagtcattg aaggctggtc caaccctaac tccaaattgc agataaatag   1200
gcaagtcata gttgacagag gtaacaggtc cggttattct ggtattttct ctgttgaagg   1260
caaaagctgc atcaatcggt gcttttatgt ggagttgata aggggaagaa aacaggaaac   1320
tgaagtcttg tggacctcaa acagtattgt tgtgttttgt ggcacctcag gtacatatgg   1380
aacaggctca tggcctgatg gggcggacat caatctcatg cctatataag ctttcgcaat   1440
tttagaaaaa aactccttgt ttctact                                       1467
```

<210> SEQ ID NO 10
<211> LENGTH: 1027
<212> TYPE: DNA
<213> ORGANISM: Influenza virus

<400> SEQUENCE: 10

```
agcaaaagca ggtagatatt gaaagatgag ccttctaacc gaggtcgaaa cgtatgttct     60
ctctatcgtt ccatcaggcc ccctcaaagc cgagatcgcg cagagacttg aagatgtctt    120
tgctgggaaa aacacagatc ttgaggctct catggaatgg ctaaagacaa gaccaattct    180
gtcacctctg actaagggga ttctggggtt tgtgttcacg ctcaccgtgc ccagtgagcg    240
aggactgcag cgtagacgct ttgtccaaaa tgccctcaat gggaatggag atccaaataa    300
catggacaaa gcagttaaac tgtataggaa acttaagagg gagataacgt tccatggggc    360
caaagaaata gctctcagtt attctgctgg tgcacttgcc agttgcatgg gcctcatata    420
caataggatg gggctgtaa ccactgaagt ggcatttggc ctggtatgtg caacatgtga    480
gcagattgct gactcccagc acaggtctca taggcaaatg gtggcaacaa ccaatccatt    540
aataaggcat gagaacagaa tggttttggc cagcactaca gctaaggcta tggagcaaat    600
ggctggatca agtgagcagg cagcggaggc catggagatt gctagtcagg ccaggcaaat    660
ggtgcaggca atgagagcca ttgggactca tcctagctcc agtactggtc taagagatga    720
tcttcttgaa aatttgcaga cctatcagaa acgaatgggg gtgcagatgc aacgattcaa    780
gtgacccact tgttgttgcc gcgagtatca ttgggatctt gcacttgata ttgtggattc    840
ttgatcgtct ttttttcaaa tgcgtctatc gactcttcaa acacggcctt aaaagaggcc    900
cttctacgga aggagtacct gagtctatga gggaagagta tcgaaaggaa cagcagaatg    960
ctgtggatgc tgacgacagt cattttgtca gcatagagtt ggagtaaaaa actaccttgt   1020
ttctact                                                             1027
```

<210> SEQ ID NO 11
<211> LENGTH: 890
<212> TYPE: DNA
<213> ORGANISM: Influenza virus

<400> SEQUENCE: 11

```
agcaaaagca gggtgacaaa gacataatgg attccaacac tgtgtcaagt ttccaggtag     60
attgctttct ttggcatatc cggaaacaag ttgtagacca agaactgagt gatgccccat    120
tccttgatcg gcttcgccga gatcagaggt ccctaagggg aagaggcaat actctcggtc    180
tagacatcaa agcagccacc catgttggaa agcaaattgt agaaaagatt ctgaaagaag    240
aatctgatga ggcacttaaa atgaccatgg tctccacacc tgcttcgcga tacataactg    300
acatgactat tgaggaattg tcaagaaact ggttcatgct aatgcccaag cagaaagtgg    360
aaggacctct ttgcatcaga atggaccagg caatcatgga gaaaaacatc atgttgaaag    420
cgaatttcag tgtgattttt gaccgactag agaccatagt attactaagg gctttcaccg    480
aagagggagc aattgttggc gaaatctcac cattgccttc ttttccagga catactattg    540
aggatgtcaa aaatgcaatt ggggtcctca tcggaggact tgaatggaat gataacacag    600
ttcgagtctc taaaaatcta cagagattcg cttggagaag cagtaatgag aatgggggac    660
ctccacttac tccaaaacag aaacggaaaa tggcgagaac agctaggtca aaagtttgaa    720
gagataagat ggctgattga agaagtgaga cacagactaa aaacaactga aaatagcttt    780
gaacaaataa cattcatgca agcattacaa ctgctgtttg aagtggaaca ggagataaga    840
actttctcat ttcagcttat ttaatgataa aaaacaccct tgtttctact               890
```

<210> SEQ ID NO 12
<211> LENGTH: 1433
<212> TYPE: DNA
<213> ORGANISM: Influenza virus

<400> SEQUENCE: 12

```
atgaatccaa atcaaaagat aataacgatt ggctctgttt ccctcaccat ttccacaata     60
tgcttcttca tgcaaattgc catcctgata actgctgtaa cattgcattt caagcaatat    120
gaattcaact cccccatgct gtgtgaacca acaataatag aaagaaacat aacagagata    180
gtgtatctga ccaacaccac catagagaag gaaatatgcc ccaaactagc agaatacaga    240
aattggtcaa agccgcaatg taacattaca ggatttgcac ctttttctaa ggacaattcg    300
attcggcttt ccgctggtgg ggacatctgg gtgacaagag aaccttatgt gtcatgcgat    360
cctgacaagt gttatcaatt tgcccttgga cagggaacaa cactaaacaa cgtgcattca    420
aataacatag tacatgatag gacccettat cggaccctat tgatgaatga gttgggtgtt    480
ccatttcatc tggggaccaa gcaagtgtgc atagcatggt ccagctcaag ttgtcacgat    540
ggaaaagcat ggctgcatgt ttgtgtaacg ggggatgatg aaaatgcaac tgctagcttc    600
atttacaatg ggaggcttgc agatagtatt gtttcatggt ccaaaaaaat cctcaggacc    660
caggagtcag aatgcgtttg tatcaatgga acttgtacag tagtaatgac tgatgggagt    720
gcttcaggaa aagctgatac taaaatacta ttcattgagg aggggaaaat tgttcatact    780
agcacattat caggaagtgc tcagcatgtc gaggagtgct cctgttatcc tcgatatcct    840
ggtgtcagat gtgtctgcag agacaactgg aaaggctcca ataggcccat cgtagatata    900
aacataaagg attatagcat tgtttccagt tatgtgtgct caggacttgt tggagacaca    960
cccagaaaag acgacagctc cagcagtagc cattgcttgg atccaaacaa tgaggaaggt   1020
ggtcaaggag tgaaaggctg ggcctttgat gatggaaatg acgtgtggat gggaagaacg   1080
atcagcgaga agttacgctc aggatatgaa accttcaaag tcattgaagg ctggtccaac   1140
```

-continued

```
cctaactcca aattgcagat aaataggcaa gtcatagttg acagaggtaa caggtccggt   1200

tattctggta ttttctctgt tgaaggcaaa agctgcatca atcggtgctt ttatgtggag   1260

ttgataaggg gaagaaaaca ggaaactgaa gtcttgtgga cctcaaacag tattgttgtg   1320

ttttgtggca cctcaggtac atatggaaca ggctcatggc ctgatggggc ggacatcaat   1380

ctcatgccta tataagcttt cgcaatttta gaaaaaaact ccttgtttct act          1433
```

<210> SEQ ID NO 13
<211> LENGTH: 1733
<212> TYPE: DNA
<213> ORGANISM: Influenza virus

<400> SEQUENCE: 13

```
atgaagacta tcattgcttt gagctacatt ctatgtctgg ttttcgctca aaagcttccc     60

ggaaatgaca acagcacggc aacgctgtgc cttgggcacc atgcagtacc aaacggaacg    120

atagtgaaaa caatcacgaa tgaccaaatt gaagttacta atgctactga gctggttcag    180

agttcctcaa caggtggaat atgcgacagt cctcatcaga tccttgatgg agaaaactgc    240

acactaatag atgctctatt gggagaccct cagtgtgatg gcttccaaaa taagaaatgg    300

gacctttttg ttgaacgcag caaagcctac agcaactgtt acccttatga tgtgccggat    360

tatgcctccc ttaggtcact agttgcctca tccggcacac tggagtttaa caatgaaagc    420

ttcaattgga ctggagtcac tcagaatgga acaagctctg cttgcaaaag gagatctaat    480

aaaagtttct ttagtagatt gaattggttg acccacttaa aatacaaata cccagcattg    540

aacgtgacta tgccaaacaa tgaaaaattt gacaaattgt acatttgggg ggttcaccac    600

ccgggtacgg acagtgatca aatcagccta tatgctcaag catcaggaag aatcacagtc    660

tctaccaaaa gaagccaaca aactgtaatc ccgaatatcg gatctagacc cagggtaagg    720

gatgtctcca gcagaataag catctattgg acaatagtaa aaccgggaga catacttttg    780

attaacagca cagggaatct aattgctcct cggggttact tcaaaatacg aagtgggaaa    840

agctcaataa tgagatcaga tgcacccatt ggcaaatgca attctgaatg catcactcca    900

aatggaagca ttcccaatga caaaccattt caaaatgtaa acaggatcac atatggggcc    960

tgtcccagat atgttaagca aaacactctg aaattggcaa cagggatgcg aaatgtacca   1020

gagaaacaaa ctagaggcat atttggcgca atcgcgggtt tcatagaaaa tggttgggag   1080

ggaatggtgg acggttggta cggtttcagg catcaaaatt ctgagggcac aggacaagca   1140

gcagatctca aaagcactca agcagcaatc aaccaaatca atgggaaact gaataggtta   1200

atcgggaaaa caaacgagaa attccatcag attgaaaaag aattctcaga agtagaaggg   1260

agaattcagg acctcgagaa atatgttgag gacactaaaa tagatctctg gtcatacaac   1320

gcggagcttc ttgttgccct ggagaaccaa catacaattg atctaactga ctcagaaatg   1380

aacaaactgt ttgaaagaac aaagaagcaa ctgagggaaa atgctgagga tatgggcaat   1440

ggttgtttca aaatatacca caaatgtgac aatgcctgca tagagtcaat cagaaatgga   1500

acttatgacc atgatgtata cagagatgaa gcattaaaca accggttcca gatcaaaggt   1560

gttgagctga agtcaggata caaagattgg atcctatgga tttcctttgc catatcatgt   1620

tttttgctct gtgttgcttt gttggggttc atcatgtggg cctgccaaaa aggcaacatt   1680

aggtgcaaca tttgcatttg agtgcattaa ttaaaaacac ccttgtttct act          1733
```

<210> SEQ ID NO 14
<211> LENGTH: 1002

<212> TYPE: DNA
<213> ORGANISM: Influenza virus

<400> SEQUENCE: 14
atgagccttc taaccgaggt cgaaacgtat gttctctcta tcgttccatc aggccccctc 60
aaagcccaga tcgcgcagag acttgaagat gtctttgctg ggaaaaacac agatcttgag 120
gctctcatgg aatggctaaa gacaagacca attctgtcac ctctgactaa ggggattctg 180
gggtttgtgt tcacgctcac cgtgcccagt gagcgaggac tgcagcgtag acgctttgtc 240
caaaatgccc tcaatgggaa tggagatcca aataacatgg acaaagcagt taaactgtat 300
aggaaactta agagggagat aacgttccat ggggccaaag aaatagctct cagttattct 360
gctggtgcac ttgccagttg catgggcctc atatacaata ggatgggggc tgtaaccact 420
gaagtggcat ttggcctggt atgtgcaaca tgtgagcaga ttgctgactc ccagcacagg 480
tctcataggc aaatggtggc aacaaccaat ccattaataa ggcatgagaa cagaatggtt 540
ttggccagca ctacagctaa ggctatggag caaatggctg gatcaagtga gcaggcagcg 600
gaggccatgg agattgctag tcaggccagg caaatggtgc aggcaatgag agccattggg 660
actcatccta gctccagtac tggtctaaga gatgatcttc ttgaaaattt gcagacctat 720
cagaaacgaa tgggggtgca gatgcaacga ttcaagtgac ccacttgttg ttgccgcgag 780
tatcattggg atcttgcact tgatattgtg gattcttgat cgtctttttt tcaaatgcgt 840
ctatcgactc ttcaaacacg gccttaaaag aggcccttct acggaaggag tacctgagtc 900
tatgagggaa gagtatcgaa aggaacagca gaatgctgtg gatgctgacg acagtcattt 960
tgtcagcata gagttggagt aaaaaactac cttgtttcta ct 1002

<210> SEQ ID NO 15
<211> LENGTH: 1520
<212> TYPE: DNA
<213> ORGANISM: Influenza virus

<400> SEQUENCE: 15
atggcgtccc aaggcaccaa acggtcttat gaacagatgg aaactgatgg ggatcgccag 60
aatgcaactg agattagggc atccgtcggg aagatgattg atggaattgg gagattctac 120
atccaaatgt gcactgaact taaactcagt gattatgaag ggcggttgat ccagaacagc 180
ttgacaatag agaaaatggt gctctctgct tttgatgaaa gaaggaataa atatctggaa 240
gaacacccca gcgcggggaa agatcctaag aaaactgggg ggcccatata caggagagta 300
aatggaaaat ggatgaggga actcgtcctt tatgacaaag aagaaataag gcgaatctgg 360
cgccaagcca acaatggtga ggatgcgaca gctggtctaa ctcacataat gatctggcat 420
tccaatttga atgatgcaac ataccagagg acaagagctc ttgttcgaac cggaatggat 480
cccagaatgt gctctctgat gcagggctcg actctcccta gaaggtccgg agctgcaggt 540
gctgcagtca aaggaatcgg gacaatggtg atggagctga tcagaatggt caaacggggg 600
atcaacgatc gaaatttctg gagaggtgag aatgggcgga aaacaagaag tgcttatgag 660
agaatgtgca acattcttaa aggaaaattt caaacagctg cacaaagagc aatggtggat 720
caagtgagag aaagtcggaa cccaggaaat gctgagatcg aagatctcat atttttggca 780
agatctgcat tgatattgag aggatcagtt gctcacaaat cttgcctacc tgcctgtgtg 840
tatggacctg cagtatccag tgggtacgac ttcgaaaaag agggatattc cttggtggga 900
atagaccctt tcaaactact tcaaaatagc caagtataca gcctaatcag acctaacgag 960

-continued

```
aatccagcac acaagagtca gctggtatgg atggcatgcc attctgctgc atttgaagat   1020
ttaagattgt taagcttcat cagagggaca aaagtatctc cacgagggaa actttcaact   1080
agaggagtac aaattgcttc aaatgagaac atggataata tgggatcgag cactcttgaa   1140
ctgagaagcg ggtactgggc cataaggacc aggagtggag gaaacactaa tcaacagagg   1200
gcctccgcag gccaaaccag tgtgcaacct acgttttctg tacaaagaaa cctcccattt   1260
gaaaagtcaa ccatcatggc agcattcact ggaaatacgg agggaagaac ttcagacatg   1320
agggcagaaa tcataagaat gatggaaggt gcaaaaccag aagaagtgtc gttccggggg   1380
aggggagttt tcgagctctc agacgagaag gcaacgaacc cgatcgtgcc ctcttttgat   1440
atgagtaatg aaggatctta tttcttcgga gacaatgcag aagagtacga caattaagga   1500
aaaataccct tgtttctact                                               1520
```

<210> SEQ ID NO 16
<211> LENGTH: 864
<212> TYPE: DNA
<213> ORGANISM: Influenza virus

<400> SEQUENCE: 16

```
atggattcca acactgtgtc aagtttccag gtagattgct ttctttggca tatccggaaa     60
caagttgtag accaagaact gagtgatgcc ccattccttg atcggcttcg ccgagatcag    120
aggtccctaa ggggaagagg caatactctc ggtctagaca tcaaagcagc cacccatgtt    180
ggaaagcaaa ttgtagaaaa gattctgaaa gaagaatctg atgaggcact taaaatgacc    240
atggtctcca cacctgcttc gcgatacata actgacatga ctattgagga attgtcaaga    300
aactggttca tgctaatgcc caagcagaaa gtggaaggac ctctttgcat cagaatggac    360
caggcaatca tggagaaaaa catcatgttg aaagcgaatt tcagtgtgat ttttgaccga    420
ctagagacca tagtattact aagggctttc accgaagagg gagcaattgt tggcgaaatc    480
tcaccattgc cttcttttcc aggacatact attgaggatg tcaaaaatgc aattggggtc    540
ctcatcggag gacttgaatg gaatgataac acagttcgag tctctaaaaa tctacagaga    600
ttcgcttgga gaagcagtaa tgagaatggg ggacctccac ttactccaaa acagaaacgg    660
aaaatggcga gaacagctag gtcaaaagtt tgaagagata agatggctga ttgaagaagt    720
gagacacaga ctaaaaacaa ctgaaaatag ctttgaacaa ataacattca tgcaagcatt    780
acaactgctg tttgaagtgg aacaggagat aagaactttc tcatttcagc ttatttaatg    840
ataaaaaaca cccttgtttc tact                                           864
```

<210> SEQ ID NO 17
<211> LENGTH: 2317
<212> TYPE: DNA
<213> ORGANISM: Influenza virus

<400> SEQUENCE: 17

```
atggatgtca atccgactct actgttccta aaggttccag cgcaaaatgc cataagcacc     60
acattccctt atactggaga tcctccatac agccatggaa caggaacagg gtacaccatg    120
gacacagtca acagaacaca ccaatattca gataagggga agtggacgac aaatacagaa    180
actggggcac cccaactcaa cccaattgat ggaccactac ctgaggataa tgagccaagt    240
ggatatgcac aaacagactg tgtcctggag gctatggcct tccttgaaga atcccaccca    300
ggtatctttg agaactcatg ccttgaaaca atggaagtcg ttcaacaaac aagggtggac    360
aaactaaccc aaggtcgcca gacttatgat tggacattaa acagaaatca accggcagca    420
```

-continued actgcattag ccaacaccat agaagttttt agatcgaatg gactaacagc taatgaatca 480
ggaaggctaa tagatttcct caaggatgtg atggaatcaa tggataaaga ggaaatggag 540
ataacaacac actttcaaag aaaaaggaga gtaagagaca acatgaccaa gaaaatggtc 600
acacaaagaa caatagggaa gaaaaaacaa agagtaaata agagaggcta tctaataaga 660
gctttgacat tgaacacgat gaccaaagat gcagagagag gtaaattaaa aagaagggct 720
attgcaacac ccgggatgca aattagaggg ttcgtgtact tcgttgaaac tttagctaga 780
agcatttgcg aaaagcttga acagtctgga cttccggttg gggtaatga aaagaaggcc 840 aaactggcaa atgttgtgag aaaaatgatg actaattcac aagacacaga gctttctttc 900
acaatcactg ggacaacac taagtggaat gaaaatcaaa accctcgaat gtttttggcg 960
atgattacat atatcacaaa aaatcaacct gagtggttca gaaacatcct gagcatcgca 1020
ccaataatgt tctcaaacaa aatggcaaga ctgggaaaag gatacatgtt cgagagtaag 1080
agaatgaaac tccgaacaca aatacccgca gaaatgctag caaacattga cctgaagtat 1140
ttcaatgaat caacaaggaa gaaaattgag aaaataaggc ctcttctaat agatggcaca 1200
gcatcattga gccctgggat gatgatgggc atgttcaaca tgctaagtac ggttttagga 1260
gtctcgatac tgaatcttgg gcaaaagaaa tacaccaaga caacatactg gtgggatggg 1320
ctccaatcct ccgacgattt tgccctcata gtgaatgcac caaatcatga gggaatacaa 1380
gcaggagtgg atagatttta caggacctgc aagttagtgg gaatcaacat gagcaaaaag 1440
aagtcctata taaataaaac agggacattt gaattcacaa gctttttta tcgatatgga 1500 tttgtggcta attttagcat ggagctgccc agttttggag tgtctggaat aaacgagtca 1560
gctgatatga gcattggagt aacagtgata aagaacaaca tgataaacaa tgaccttgga 1620
ccagcaacag cccagatggc tctccaattg ttcatcaaag actacagata tacatatagg 1680
tgccatagag gagacacaca aattcagacg agaagatcat tcgagctaaa gaagctgtgg 1740
gatcaaaccc aatcaagggc aggactattg gtatcagatg gggaccaaa cttatacaat 1800 atccggaatc ttcacatccc tgaagtctgc ttaaagtggg agctaatgga tgagaattat 1860
cggggaagac tttgtaatcc cctgaatccc tttgtcagcc ataaagaaat tgagtctgta 1920
aacaatgctg tagtgatgcc agcccatggt ccggccaaaa gtatggaata tgatgccgtt 1980
gcaactacac actcctggat tcccaagagg aaccgctcta ttctcaacac aagccaaagg 2040
ggaattcttg aggatgaaca gatgtaccag aagtgctgca acttgttcga gaaatttttc 2100
cctagtagtt catataggag accgattgga atttctagca tggtggaggc catggtgtct 2160
agggcccgga ttgatgccag aattgacttc gagtctggac ggattaagaa ggaagagttc 2220
tctgagatca tgaagatctg ttccaccatt gaagaactca gacggcaaaa ataatgaatt 2280
tagcttgtcc ttcatgaaaa aatgccttgt ttctact 2317

<210> SEQ ID NO 18
<211> LENGTH: 2209
<212> TYPE: DNA
<213> ORGANISM: Influenza virus

<400> SEQUENCE: 18
atggaagatt ttgtgcgaca atgcttcaac ccgatgattg tcgaacttgc agaaaaagca 60
atgaaagagt atggggagga tctgaaaatt gaaacaaaca aatttgcagc aatatgcact 120
cacttggagg tatgtttcat gtattcagat tttcatttca tcaatgaaca aggcgaatca 180

-continued

```
atagtggtag aacttgatga tccaaatgca ctgttaaagc acagatttga aataatcgag    240

gggagagaca gaacaatggc ctggacagta gtaaacagta tctgcaacac tactggagct    300

gaaaaaccga agtttctacc agatttgtat gattacaagg agaacagatt catcgaaatt    360

ggagtgacaa ggagagaagt ccacatatat taccttgaaa aggccaataa gattaaatct    420

gagaacacac acattcacat tttctcattc actggggagg aaatggccac aaaggcagac    480

tacactctcg acgaggaaag cagggctagg attaagacca ggctatttac cataagacaa    540

gaaatggcca acagaggcct ctgggattcc tttcgtcagt ccgaaagagg cgaagaaaca    600

attgaagaaa aatttgaaat ctcaggaact atgcgtaggc ttgccgacca aagtctccca    660

ccgaacttct cctgccttga gaattttaga gcctatgtgg atggattcga accgaacggc    720

tgcattgagg gcaagctttc tcaaatgtcc aaagaagtga atgcccaaat tgaacctttt    780

ctgaagacaa caccaagacc aatcaaactt ccgaatggac ctccttgtta tcagcggtcc    840

aagttcctcc tgatggatgc tttaaaattg agcattgaag acccaagtca cgaaggagaa    900

gggatcccat tatatgatgc gatcaagtgc ataaaaacat tctttggatg gaaagaacct    960

tatatagtca aaccacacga aaagggaata aattcaaatt acctgctgtc atggaagcaa   1020

gtattgtcag aattgcagga cattgaaaat gaggagaaga ttccaaggac taaaaacatg   1080

aagaaaacga gtcaactaaa gtgggctctt ggtgagaaca tggcaccaga gaaagtagac   1140

tttgaaaact gcagagacat aagcgatttg aagcaatatg atagtgacga acctgaatta   1200

aggtcacttt caagctggat acagaatgag ttcaacaagg cctgcgagct aactgattca   1260

atctggatag agctcgatga aattggagag gacgtagccc caattgaata cattgcaagc   1320

atgaggagga attatttcac agcagaggtg tcccattgta gagccactga gtacataatg   1380

aagggggtat acattaatac tgccctgctc aatgcatcct gtgcagcaat ggacgatttt   1440

caactaattc ccatgataag caagtgcaga actaaagagg gaaggcgaaa aaccaattta   1500

tatggattca tcataaaggg aagatctcat ttaaggaatg acacagatgt ggtaaacttt   1560

gtgagcatgg agttttctct cactgacccg agacttgagc cacataaatg ggagaaatac   1620

tgtgtccttg agataggaga tatgttacta agaagtgcca taggccaaat ttcaaggcct   1680

atgttcttgt atgtgaggac aaacggaaca tcaaaggtca aaatgaaatg ggggaatggag   1740

atgagacgtt gcctccttca gtcactccag cagatcgaga gcatgattga agccgagtcc   1800

tcggttaaag agaaagacat gaccaaagag ttttttgaga ataaatcaga agcatggccc   1860

attggggagt cccccaaggg agtggaagaa ggttccattg ggaaagtctg taggactcta   1920

ttggctaagt cagtgttcaa tagcctgtat gcatcaccac aattggaagg attttcagcg   1980

gagtcaagaa aactgctcct tgttgttcag gctcttaggg acaacctcga acctgggacc   2040

tttgatcttg gggggctata tgaagcaatt gaggagtgcc tgattaatga tccctgggtt   2100

ttgctcaatg cgtcttggtt caactccttc ctgacacatg cattaaaata gttatggcag   2160

tgctactatt tgttatccgt actgtccaaa aaagtacctt gtttctact               2209
```

<210> SEQ ID NO 19
<211> LENGTH: 2314
<212> TYPE: DNA
<213> ORGANISM: Influenza virus

<400> SEQUENCE: 19

```
atggaaagaa taaaagaact acggaacctg atgtcgcagt ctcgcactcg cgagatactg     60

acaaaaacca cagtggacca tatggccata attaagaagt acacatcggg gagacaggaa    120
```

-continued

```
aagaacccgt cacttaggat gaaatggatg atggcaatga aatacccaat cactgctgac    180
aaaaggataa cagaaatggt tccggagaga aatgaacaag gacaaactct atggagtaaa    240
atgagtgatg ctggatcaga tcgagtgatg gtatcacctt tggctgtgac atggtggaat    300
agaaatggac ccgtgacaag tacggtccat tacccaaaag tatacaagac ttattttgac    360
aaagtcgaaa ggttaaaaca tggaaccttt ggccctgttc attttagaaa tcaagtcaag    420
atacgccgaa gagtagacat aaaccctggt catgcggacc tcagtgccaa ggaggcacaa    480
gatgtaatta tggaagttgt tttcccaat gaagtgggag ccaggatact aacatcagaa    540
tcgcaattaa caataactaa agagaaaaaa gaagaactcc gagattgcaa aatttctccc    600
ttgatggttg catacatgtt agagagagaa cttgtccgaa aaacaagatt tctcccagtt    660
gctggcggaa caagcagtat atacattgaa gttttacatt tgactcaagg gacgtgttgg    720
gaacaaatgt acactccagg tggagaagtg aggaatgacg atgttgacca aagcctaatt    780
attgcagcca ggaacatagt aagaagagcc gcagtatcag cagatccact agcatcttta    840
ttggagatgt gccacagcac acaaattggc gggacaagga tggtggacat tcttagacag    900
aacccgactg aagaacaagc tgtggatata tgcaaggctg caatgggatt gagaatcagc    960
tcatccttca gctttggtgg gtttacattt aaaagaacaa gcgggtcatc agtcaaaaaa   1020
gaggaagaag tgcttacagg caatctccaa acattgaaga taagagtaca tgaggggtat   1080
gaggagttca caatggtggg gaaaagagca acagctatac tcagaaaagc aaccagaaga   1140
ttggttcagc tcatagtgag tggaagagac gaacagtcaa tagccgaagc aataattgtg   1200
gccatggtgt tttcacaaga ggattgcatg ataaaagcag ttagaggtga cctgaatttc   1260
gtcaacagag caaatcagcg gttgaacccc atgcatcagc ttttaaggca ttttcagaaa   1320
gatgcgaaag tgctttttca gaattgggga attgagcaca tcgacagtgt aatgggaatg   1380
gttggagtat taccagatat gactccaagc acagagatgt caatgagagg aataagagtc   1440
agcaaaatgg gtgtggatga atactccagt acagagaggg tggtggttag cattgatcgg   1500
tttttgagag ttcgagacca acgcgggaat gtattattat ctcctgaaga ggttagtgaa   1560
acacagggaa ctgagagact gacaataact tattcatcgt cgatgatgtg ggagattaac   1620
ggtcctgagt cggttttggt caatacttat caatggatca tcagaaattg ggaagctgtc   1680
aaaattcaat ggtctcagaa tcctgcaatg ttgtacaaca aaatggaatt tgaaccattt   1740
caatctttag tccccaaggc cattagaagc caatacagtg ggtttgtcag aactctattc   1800
caacaaatga gagacgtact tgggacattt gacaccaccc agataataaa gcttctccct   1860
tttgcagccg ctccaccaaa gcaaagcaga atgcagttct cttcactgac tgtaaatgtg   1920
aggggatcag ggatgagaat acttgtaagg ggcaattctc ctgtattcaa ctacaacaag   1980
accactaaaa gactaacaat tctcggaaaa gatgccggca ctttaattga agacccagat   2040
gaaagcacat ccggagtgga gtccgctgta ttgagagggt ttctcattat aggtaaggaa   2100
gacagaagat acgggccagc attaagcatc aatgaactga gtaaccttgc aaaaggggaa   2160
aaggctaatg tgctaatcgg gcaaggagac gtggtgttgg taatgaaacg aaaacgggac   2220
tctagcatac ttactgacag ccagacagcg accaaaagaa ttcggatggc catcaattaa   2280
tgttgaatag tttaaaaacg accttgtttc tact                                 2314
```

<210> SEQ ID NO 20
<211> LENGTH: 2314
<212> TYPE: DNA

<213> ORGANISM: Influenza virus

<400> SEQUENCE: 20

```
atggaaagaa taaaagaact acggaacctg atgtcgcagt ctcgcactcg cgagatactg     60
acaaaaacca cagtggacca tatggccata attaagaagt acacatcggg gagacaggaa    120
aagaacccgt cacttaggat gaaatggatg atggcaatga aatacccaat cactgctgac    180
aaaaggataa cagaaatggt tccggagaga aatgaacaag gacaaactct atggagtaaa    240
atgagtgatg ctggatcaga tcgagtgatg gtatcacctt tggctgtgac atggtggaat    300
agaaatggac ccgtgacaag tacggtccat tacccaaaag tatacaagac ttattttgac    360
aaagtcgaaa ggttaaaaca tggaaccttt ggccctgttc attttagaaa tcaagtcaag    420
atacgccgaa gagtagacat aaaccctggt catgcggacc tcagtgccaa ggaggcacaa    480
gatgtaatta tggaagttgt ttttcccaat gaagtgggag ccaggatact aacatcagaa    540
tcgcaattaa caataactaa agagaaaaaa gaagaactcc gagattgcaa aatttctccc    600
ttgatggttg catacatgtt agagagagaa cttgtccgaa aacaagatt cctcccagtt     660
gctggcggaa caagcagtat atacattgaa gttttacatt tgactcaagg gacgtgttgg    720
gaacaaatgt acactccagg tggagaagtg aggaatgacg atgttgacca aagcctaatt    780
attgcagcca ggaacatagt aagaagagcc gcagtatcag cagatccact agcattttta    840
ttggagatgt gccacagcac acaaattggc gggacaagga tggtggacat tcttagacag    900
aacccgactg aagaacaagc tgtggatata tgcaaggctg caatgggatt gagaatcagc    960
tcatccttca gctttggtgg gtttacattt aaaagaacaa gcgggtcatc agtcaaaaaa   1020
gaggaagaac tgcttacagg caatctccaa acattgaaga taagagtaca tgaggggtat   1080
gaggagttca caatggtggg gaaaagagca acagctatac tcagaaaagc aaccagaaga   1140
ttggttcagc tcatagtgag tggaagagac gaacagtcaa tagccgaagc aataattgtg   1200
gccatggtgt tttcacaaga ggattgcatg ataaaagcag ttagaggtga cctgaatttc   1260
gtcaacagag caaatcagcg gttgaacccc atgcatcagc ttttaaggca ttttcagaaa   1320
gatgcgaaag tgctttttca gaattgggga attgagcaca tcgacagtgt aatgggaatg   1380
gttggagtat taccagatat gactccaagc acagagatgt caatgagagg aataagagtc   1440
agcaaaatgg gtgtggatga atactccagt acagagaggg tggtggttag cattgatcgg   1500
tttttgagag ttcgagacca acgcgggaat gtattattat ctcctgaaga ggttagtgaa   1560
acacaggaa ctgagagact gacaataact tattcatcgt cgatgatgtg ggagattaac    1620
ggtcctgagt cggttttggt caatacttat caatggatca tcagaaattg ggaagctgtc   1680
aaaattcaat ggtctcagaa tcctgcaatg ttgtacaaca aaatggaatt tgaaccattt   1740
caatctttag tccccaaggc cattagaagc caatacagtg ggtttgtcag aactctattc   1800
caacaaatga gagacgtact tgggacattt gacaccaccc agataataaa gcttctccct   1860
tttgcagccg ctccaccaaa gcaaagcaga atgcagttct cttcactgac tgtaaatgtg   1920
aggggatcag ggatgagaat acttgtaagg ggcaattctc ctgtattcaa ctacaacaag   1980
accactaaaa gactaacaat tctcggaaaa gatgccggca ctttaattga agacccagat   2040
gaaagcacat ccggagtgga gtccgctgta ttgagagggt ttctcattat aggtaaggaa   2100
gacagaagat acgggccagc attaagcatc aatgaactga gtaaccttgc aaaaggggaa   2160
aaggctaatg tgctaatcgg gcaaggagac gtggtgttgg taatgaaacg aaaacgggac   2220
tctagcatac ttactgacag ccagacagcg accaaaagaa ttcggatggc catcaattaa   2280
```

tgttgaatag tttaaaaacg accttgtttc tact 2314

<210> SEQ ID NO 21
<211> LENGTH: 2314
<212> TYPE: DNA
<213> ORGANISM: Influenza virus

<400> SEQUENCE: 21
atggaaagaa taaaagaact acggaacctg atgtcgcagt ctcgcactcg cgagatactg 60
acaaaaacca cagtggacca tatggccata attaagaagt acacatcggg gagacaggaa 120
aagaacccgt cacttaggat gaaatggatg atggcaatga aataccaat cactgctgac 180
aaaaggataa cagaaatggt tccggagaga aatgaacaag gacaaactct atggagtaaa 240
atgagtgatg ctggatcaga tcgagtgatg gtatcacctt tggctgtgac atggtggaat 300
agaaatggac ccgtgacaag tacggtccat tacccaaaag tatacaagac ttattttgac 360
aaagtcgaaa ggttaaaaca tggaaccttt ggccctgttc attttagaaa tcaagtcaag 420
atacgccgaa gagtagacat aaaccctggt catgcggacc tcagtgccaa ggaggcacaa 480
gatgtaatta tggaagttgt ttttcccaat gaagtgggag ccaggatact aacatcagaa 540
tcgcaattaa caataactaa agagaaaaaa gaagaactcc gagattgcaa aatttctccc 600
ttgatggttg catacatgtt agagagagaa cttgtccgaa aaacaagatt cctcccagtt 660
gctggcggaa caagcagtat atacattgaa gttttacatt tgactcaagg gacgtgttgg 720
gaacaaatgt acactccagg tggagaagtg aggaatgacg atgttgacca aagcctaatt 780
attgcagcca ggaacatagt aagaagagcc gcagtatcag cagatccact agcatcttta 840
ttggagatgt gccacagcac acaaattggc gggacaagga tggtggacat tcttagacag 900
aacccgactg aagaacaagc tgtggatata tgcaaggctg caatgggatt gagaatcagc 960
tcatccttca gctttggtgg gtttacattt aaaagaacaa gcgggtcatc agtcaaaaaa 1020
gaggaagaac tgcttacagg caatctccaa acattgaaga taagagtaca taaggggtat 1080
gaggagttca caatggtggg gaaaagagca acagctatac tcagaaaagc aaccagaaga 1140
ttggttcagc tcatagtgag tggaagagac gaacagtcaa tagccgaagc aataattgtg 1200
gccatggtgt tttcacaaga ggattgcatg ataaaagcag ttagaggtga cctgaatttc 1260
gtcaacagag caaatcagcg gttgaacccc atgcatcagc ttttaaggca ttttcagaaa 1320
gatgcgaaag tgctttttca gaattgggga attgagcaca tcgacagtgt aatgggaatg 1380
gttggagtat taccagatat gactccaagc acagagatgt caatgagagg aataagagtc 1440
agcaaaatgg gtgtggatga atactccagt acagagaggg tggtggttag cattgatcgg 1500
tttttgagag ttcgagacca acgcgggaat gtattattat ctcctgaaga ggttagtgaa 1560
acacagggaa ctgagagact gacaataact tattcatcgt cgatgatgtg ggagattaac 1620
ggtcctgagt cggttttggt caatacttat caatggatca tcagaaattg ggaagctgtc 1680
aaaattcaat ggtctcagaa tcctgcaatg ttgtacaaca aaatggaatt tgaaccattt 1740
caatctttag tccccaaggc cattagaagc caatacagtg ggtttgtcag aactctattc 1800
caacaaatga gagacgtact tgggacattt gacaccaccc agataataaa gcttctccct 1860
tttgcagccg ctccaccaaa gcaaagcaga atgcagttct cttcactgac tgtaaatgtg 1920
aggggatcag ggatgagaat acttgtaagg ggcaattctc ctgtattcaa ctacaacaag 1980
accactaaaa gactaacaat tctcggaaaa gatgccggca ctttaattga agacccagat 2040
gaaagcacat ccggagtgga gtccgctgta ttgagagggt ttctcattat aggtaaggaa 2100
gacagaagat acgggccagc attaagcatc aatgaactga gtaaccttgc aaaaggggaa 2160
aaggctaatg tgctaatcgg gcaaggagac gtggtgttgg taatgaaacg aaaacgggac 2220
tctagcatac ttactgacag ccagacagcg accaaaagaa ttcggatggc catcaattaa 2280
tgttgaatag tttaaaaacg accttgtttc tact 2314

<210> SEQ ID NO 22
<211> LENGTH: 1775
<212> TYPE: DNA
<213> ORGANISM: Influenza virus

<400> SEQUENCE: 22
agcaaaagca ggggaaaata aaaacaacca aaatgaaggc aaacctactg gtcctgttat 60
gtgcacttgc agctgcagat gcagacacaa tatgtatagg ctaccatgcg aacaattcaa 120
ccgacactgt tgacacagta ctcgagaaga atgtgacagt gacacactct gttaacctgc 180
tcgaagacag ccacaacgga aaactatgta gattaaaagg aatagcccca ctacaattgg 240
ggaaatgtaa catcgccgga tggctcttgg gaaacccaga atgcgaccca ctgcttccag 300
tgagatcatg gtcctacatt gtagaaacac caaactctga gaatggaata tgttatccag 360
gagatttcat cgactatgag gagctgaggg agcaattgag ctcagtgtca tcattcgaaa 420
gattcgaaat atttcccaaa gaaagctcat ggcccaacca caacacaaac ggagtaacgg 480
cagcatgctc ccatgagggg aaaagcagtt tttacagaaa tttgctatgg ctgacggaga 540
aggagggctc atacccaaag ctgaaaaatt cttatgtgaa caaaaaaggg aaagaagtcc 600
ttgtactgtg ggtattcat cacccgccta acagtaagga acaacagaat ctctatcaga 660
atgaaaatgc ttatgtctct gtagtgactt caaattataa caggagattt accccggaaa 720
tagcagaaag acccaaagta agagatcaag ctgggaggat gaactattac tggaccttgc 780
taaaacccgg agacacaata atatttgagg caaatggaaa tctaatagca ccaatgtatg 840
ctttcgcact gagtagaggc tttgggtccg gcatcatcac ctcaaacgca tcaatgcatg 900
agtgtaacac gaagtgtcaa acacccctgg gagctataaa cagcagtctc ccttaccaga 960
atatacaccc agtcacaata ggagagtgcc caaaatacgt caggagtgcc aaattgagga 1020
tggttacagg actaaggaac attccgtcca ttcaatccag aggtctattt ggagccattg 1080
ccggttttat tgaagggggga tggactggaa tgatagatgg atggtatggt tatcatcatc 1140
agaatgaaca gggatcaggc tatgcagcgg atcaaaaaag cacacaaaat gccattaacg 1200
ggattacaaa caaggtgaac actgttatcg agaaaatgaa cattcaattc acagctgtgg 1260
gtaaagaatt caacaaatta gaaaaaagga tggaaaattt aaataaaaaa gttgatgatg 1320
gatttctgga catttggaca tataatgcag aattgttagt tctactggaa aatgaaagga 1380
ctctggattt ccatgactca aatgtgaaga atctgtatga gaaagtaaaa agccaattaa 1440
agaataatgc caaagaaatc ggaaatggat gttttgagtt ctaccacaag tgtgacaatg 1500
aatgcatgga aagtgtaaga aatgggactt atgattatcc caaatattca gaagagtcaa 1560
agttgaacag ggaaaaggta gatggagtga aattggaatc aatggggatc tatcagattc 1620
tggcgatcta ctcaactgtc gccagttcac tggtgctttt ggtctccctg gggcaatca 1680 gtttctggat gtgttctaat ggatctttgc agtgcagaat atgcatctga gattagaatt 1740
tcagagatat gaggaaaaac acccttgttt ctact 1775

-continued

<210> SEQ ID NO 23
<211> LENGTH: 1413
<212> TYPE: DNA
<213> ORGANISM: Influenza virus

<400> SEQUENCE: 23
agcaaaagca ggggtttaaa atgaatccaa atcagaaaat aataaccatt ggatcaatct 60
gtctggtagt cggactaatt agcctaatat tgcaaatagg gaatataatc tcaatatgga 120
ttagccattc aattcaaact ggaagtcaaa accatactgg aatatgcaac caaaacatca 180
ttacctataa aaatagcacc tgggtaaagg acacaacttc agtgatatta accggcaatt 240
catctctttg tcccatccgt gggtgggcta tatacagcaa agacaatagc ataagaattg 300
gttccaaagg agacgttttt gtcataagag agccctttat ttcatgttct cacttggaat 360
gcaggacctt ttttctgacc caaggtgcct tactgaatga caagcattca agtgggactg 420
ttaaggacag aagcccttat agggccttaa tgagctgccc tgtcggtgaa gctccgtccc 480
cgtacaattc aagatttgaa tcggttgctt ggtcagcaag tgcatgtcat gatggcatgg 540
gctggctaac aatcggaatt tcaggtccag ataatggagc agtggctgta ttaaaataca 600
acggcataat aactgaaacc ataaaaagtt ggaggaagaa aatattgagg acacaagagt 660
ctgaatgtgc ctgtgtaaat ggttcatgtt ttactataat gactgatggc ccgagtgatg 720
ggctggcctc gtacaaaatt ttcaagatcg aaaaggggaa ggttactaaa tcaatagagt 780
tgaatgcacc taattctcac tatgaggaat gttcctgtta ccctgatacc ggcaaagtga 840
tgtgtgtgtg cagagacaat tggcatggtt cgaaccggcc atgggtgtct ttcgatcaaa 900
acctggatta tcaaatagga tacatctgca gtggggtttt cggtgacaac ccgcgtcccg 960
aagatggaac aggcagctgt ggtccagtgt atgttgatgg agcaaacgga gtaaagggat 1020
tttcatatag gtatggtaat ggtgtttgga taggaaggac caaaagtcac agttccagac 1080
atgggtttga gatgatttgg gatcctaatg gatggacaga gactgatagt aagttctctg 1140
tgaggcaaga tgttgtggca atgactgatt ggtcagggta tagcggaagt ttcgttcaac 1200
atcctgagct gacagggcta gactgtatga ggccgtgctt ctgggttgaa ttaatcaggg 1260
gacgacctaa agaaaaaaca atctggacta gtgcgagcag catttctttt tgtggcgtga 1320
atagtgatac tgtagattgg tcttggccag acggtgctga gttgccattc agcattgaca 1380
agtagtctgt tcaaaaaact ccttgtttct act 1413

<210> SEQ ID NO 24
<211> LENGTH: 2233
<212> TYPE: DNA
<213> ORGANISM: Influenza virus

<400> SEQUENCE: 24
agcgaaagca ggtactgatc caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agattttcac 180
ttcatcaatg agcaaggcga gtcaataatc gtagaacttg gtgatccaaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggagaata gattcatcga aattggagta acaaggagag aagttcacat atactatctg 420
gaaaaggcca ataaaattaa atctgagaaa acacacatcc acattttctc gttcactggg 480

-continued

```
gaagaaatgg ccacaaaggc agactacact ctcgatgaag aaagcagggc taggatcaaa    540
accagactat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc tttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaaggga gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacata aatgggagaa gtactgtgtt cttgagatag gagatatgct tataagaagt   1680
gccataggcc aggtttcaag gcccatgttc ttgtatgtga gaacaaatgg aacctcaaaa   1740
attaaaatga aatggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aggagtgga ggaaagttcc    1920
attgggaagg tctgcaggac tttattagca aagtcggtat tcaacagctt gtatgcatct   1980
ccacaactag aaggattttc agctgaatca agaaaactgc ttcttatcgt tcaggctctt   2040
agggacaacc tggaacctgg gacctttgat cttgggggc tatatgaagc aattgaggag    2100
tgcctgatta atgatccctg ggttttgctt aatgcttctt ggttcaactc cttccttaca   2160
catgcattga gttagttgtg gcagtgctac tatttgctat ccatactgtc caaaaaagta   2220
ccttgtttct act                                                      2233
```

<210> SEQ ID NO 25
<211> LENGTH: 2341
<212> TYPE: DNA
<213> ORGANISM: Influenza virus

<400> SEQUENCE: 25

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
```

-continued

```
gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga tgtaatggag    540

tcaatgaaca aagaagaaat ggggatcaca actcattttc agagaaagag acgggtgaga    600

gacaatatga ctaagaaaat gataacacag agaacaatgg gtaaaaagaa gcagagattg    660

aacaaaagga gttatctaat tagagcattg accctgaaca caatgaccaa agatgctgag    720

agagggaagc taaaacggag agcaattgca accccaggga tgcaaataag gggtttgta    780

tactttgttg agacactggc aaggagtata tgtgagaaac ttgaacaatc agggttgcca    840

gttggaggca atgagaagaa agcaaagttg gcaaatgttg taaggaagat gatgaccaat    900

tctcaggaca ccgaactttc tttcaccatc actggagata acaccaaatg gaacgaaaat    960

cagaatcctc ggatgttttt ggccatgatc acatatatga ccagaaatca gcccgaatgg   1020

ttcagaaatg ttctaagtat tgctccaata atgttctcaa acaaaatggc gagactggga   1080

aaagggtata tgtttgagag caagagtatg aaacttagaa ctcaaatacc tgcagaaatg   1140

ctagcaagca tcgatttgaa atatttcaat gattcaacaa gaaagaagat tgaaaaaatc   1200

cgaccgctct taatagaggg gactgcatca ttgagccctg gaatgatgat gggcatgttc   1260

aatatgttaa gcactgtatt aggcgtctcc atcctgaatc ttggacaaaa gagatacacc   1320

aagactactt actggtggga tggtcttcaa tcctctgacg attttgctct gattgtgaat   1380

gcacccaatc atgaagggat tcaagccgga gtcgacaggt tttatcgaac ctgtaagcta   1440

cttggaatca atatgagcaa gaaaaagtct tacataaaca gaacaggtac atttgaattc   1500

acaagttttt tctatcgtta tgggtttgtt gccaatttca gcatggagct tcccagtttt   1560

ggggtgtctg ggatcaacga gtcagcggac atgagtattg gagttactgt catcaaaaac   1620

aatatgataa acaatgatct tggtccagca acagctcaaa tggcccttca gttgttcatc   1680

aaagattaca ggtacacgta ccgatgccat ataggtgaca cacaaataca aacccgaaga   1740

tcatttgaaa taaagaaact gtgggagcaa acccgttcca aagctggact gctggtctcc   1800

gacggaggcc caaatttata caacattaga aatctccaca ttcctgaagt ctgcctaaaa   1860

tgggaattga tggatgagga ttaccagggg cgtttatgca acccactgaa cccatttgtc   1920

agccataaag aaattgaatc aatgaacaat gcagtgatga tgccagcaca tggtccagcc   1980

aaaaacatgg agtatgatgc tgttgcaaca acacactcct ggatccccaa aagaaatcga   2040

tccatcttga atacaagtca aagaggagta cttgaggatg aacaaatgta ccaaaggtgc   2100

tgcaatttat ttgaaaaatt cttccccagc agttcataca gaagaccagt cgggatatcc   2160

agtatggtgg aggctatggt ttccagagcc cgaattgatg cacggattga tttcgaatct   2220

ggaaggataa agaaagaaga gttcactgag atcatgaaga tctgttccac cattgaagag   2280

ctcagacggc aaaaatagtg aatttagctt gtccttcatg aaaaaatgcc ttgtttctac   2340

t                                                                   2341
```

<210> SEQ ID NO 26
<211> LENGTH: 2341
<212> TYPE: DNA
<213> ORGANISM: Influenza virus

<400> SEQUENCE: 26

```
agcgaaagca ggtcaattat attcaatatg gaaagaataa aagaactacg aaatctaatg     60
```

-continued

```
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg ggccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 27
<211> LENGTH: 1565
<212> TYPE: DNA
<213> ORGANISM: Influenza virus

<400> SEQUENCE: 27
agcaaaagca gggtagataa tcactcactg agtgacatca aaatcatggc gtctcaaggc 60
accaaacgat cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc ttgaagaaca tcccagtgcg 300
gggaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 28
<211> LENGTH: 1027
<212> TYPE: DNA
<213> ORGANISM: Influenza virus

<400> SEQUENCE: 28
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300

-continued

```
catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttgggactca tcctagctcc agtgctggtc tgaaaaatga    720

tcttcttgaa aatttgcagg cctatcagaa acgaatgggg gtgcagatgc aacggttcaa    780

gtgatcctct cactattgcc gcaaatatca ttgggatctt gcacttgaca ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                              1027
```

<210> SEQ ID NO 29
<211> LENGTH: 890
<212> TYPE: DNA
<213> ORGANISM: Influenza virus

<400> SEQUENCE: 29

```
agcaaaagca gggtgacaaa aacataatgg atccaaacac tgtgtcaagc tttcaggtag     60

attgctttct ttggcatgtc cgcaaacgag ttgcagacca agaactaggc gatgccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaga atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600

ttcgagtctc tgaaactcta cagagattcg cttggagaag cagtaatgag aatgggagac    660

ctccactcac tccaaaacag aaacgagaaa tggcgggaac aattaggtca gaagtttgaa    720

gaaataagat ggttgattga agaagtgaga cacaaactga agataacaga gaatagtttt    780

gagcaaataa catttatgca agccttacat ctattgcttg aagtggagca agagataaga    840

actttctcgt ttcagcttat ttagtactaa aaaacaccct tgtttctact               890
```

<210> SEQ ID NO 30
<211> LENGTH: 468
<212> TYPE: PRT
<213> ORGANISM: Influenza virus

<400> SEQUENCE: 30

```
Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Ile Phe Asn
            20                  25                  30

Thr Val Ile His Glu Lys Ile Gly Asp His Gln Thr Val Ile His Pro
```

```
        35                  40                  45

Thr Thr Thr Thr Pro Ala Ile Pro Asn Cys Ser Asp Thr Ile Ile Thr
    50                  55                  60

Tyr Asn Asn Thr Val Ile Asn Asn Ile Thr Thr Ile Ile Thr Glu Ala
65                  70                  75                  80

Glu Arg Leu Phe Lys Pro Pro Leu Pro Leu Cys Pro Phe Arg Gly Phe
                85                  90                  95

Phe Pro Phe His Lys Asp Asn Ala Ile Arg Leu Gly Glu Asn Lys Asp
            100                 105                 110

Val Ile Val Thr Arg Glu Pro Tyr Val Ser Cys Asp Asn Asp Asn Cys
        115                 120                 125

Trp Ser Phe Ala Leu Ala Gln Gly Ala Leu Leu Gly Thr Lys His Ser
    130                 135                 140

Asn Gly Thr Ile Lys Asp Arg Thr Pro Tyr Arg Ser Leu Ile Gln Phe
145                 150                 155                 160

Pro Ile Gly Thr Ala Pro Val Leu Gly Asn Tyr Lys Glu Ile Cys Ile
                165                 170                 175

Ala Trp Ser Ser Ser Ser Cys Phe Asp Gly Lys Glu Trp Met His Val
            180                 185                 190

Cys Met Thr Gly Asn Asp Asn Asp Ala Ser Ala Gln Ile Ile Tyr Ala
        195                 200                 205

Gly Arg Met Thr Asp Ser Ile Lys Ser Trp Lys Arg Asp Ile Leu Arg
    210                 215                 220

Thr Gln Glu Ser Glu Cys Gln Cys Ile Asp Gly Thr Cys Val Val Ala
225                 230                 235                 240

Val Thr Asp Gly Pro Ala Ala Asn Ser Ala Asp His Arg Val Tyr Trp
                245                 250                 255

Ile Arg Glu Gly Arg Ile Val Lys Tyr Glu Asn Val Pro Lys Thr Lys
            260                 265                 270

Ile Gln His Leu Glu Glu Cys Ser Cys Tyr Val Asp Ile Asp Val Tyr
        275                 280                 285

Cys Ile Cys Arg Asp Asn Trp Lys Gly Ser Asn Arg Pro Trp Met Arg
    290                 295                 300

Ile Asn Asn Glu Thr Ile Leu Glu Thr Gly Tyr Val Cys Ser Lys Phe
305                 310                 315                 320

His Ser Asp Thr Pro Arg Pro Ala Asp Pro Ser Thr Val Ser Cys Asp
                325                 330                 335

Ser Pro Ser Asn Val Asn Gly Gly Pro Gly Val Lys Gly Phe Gly Phe
            340                 345                 350

Lys Val Gly Asn Asp Val Trp Leu Gly Arg Thr Met Ser Thr Ser Gly
        355                 360                 365

Arg Ser Gly Phe Glu Ile Ile Lys Val Ala Glu Gly Trp Ile Asn Ser
    370                 375                 380

Pro Asn His Ala Lys Ser Val Thr Gln Thr Leu Val Ser Asn Asn Asp
385                 390                 395                 400

Trp Ser Gly Tyr Ser Gly Ser Phe Ile Val Lys Thr Lys Ala Cys Phe
                405                 410                 415

Gln Pro Cys Phe Tyr Val Glu Leu Ile Arg Gly Arg Pro Asn Lys Asn
            420                 425                 430

Asp Asp Val Ser Trp Thr Ser Asn Ser Ile Val Thr Phe Cys Gly Leu
        435                 440                 445

Asp Asn Glu Pro Gly Ser Gly Asn Trp Pro Asp Gly Ser Asn Ile Gly
    450                 455                 460
```

Phe Met Pro Lys
465

<210> SEQ ID NO 31
<211> LENGTH: 470
<212> TYPE: PRT
<213> ORGANISM: Influenza virus

<400> SEQUENCE: 31

Met Asn Pro Asn Gln Lys Ile Ile Thr Ile Gly Ser Val Ser Ile Ile
1 5 10 15

Leu Thr Thr Ile Gly Leu Leu Leu Gln Ile Thr Ser Leu Cys Ser Ile
20 25 30

Trp Phe Ser His Tyr Asn Gln Val Thr Gln Thr His Glu Gln Pro Cys
35 40 45

Ser Asn Asn Thr Thr Asn Tyr Tyr Asn Glu Thr Phe Val Asn Val Thr
50 55 60

Asn Val Gln Asn Asn Tyr Thr Thr Val Ile Glu Pro Ser Ala Pro Asp
65 70 75 80

Val Val His Tyr Ser Ser Gly Arg Asp Leu Cys Pro Ile Arg Gly Trp
85 90 95

Ala Pro Leu Ser Lys Asp Asn Gly Ile Arg Ile Gly Ser Arg Gly Glu
100 105 110

Val Phe Val Ile Arg Glu Pro Phe Ile Ser Cys Ser Ile Ser Glu Cys
115 120 125

Arg Thr Phe Phe Leu Thr Gln Gly Ala Leu Leu Asn Asp Lys His Ser
130 135 140

Asn Gly Thr Val Lys Asp Arg Ser Pro Phe Arg Thr Leu Met Ser Cys
145 150 155 160

Pro Ile Gly Val Ala Pro Ser Pro Ser Asn Ser Arg Phe Glu Ser Val
165 170 175

Ala Trp Ser Ala Thr Ala Cys Ser Asp Gly Pro Gly Trp Leu Thr Leu
180 185 190

Gly Ile Thr Gly Pro Asp Ala Thr Ala Val Ala Val Leu Lys Tyr Asn
195 200 205

Gly Ile Ile Thr Asp Thr Leu Lys Ser Trp Lys Gly Asn Ile Met Arg
210 215 220

Thr Gln Glu Ser Glu Cys Val Cys Gln Asp Glu Phe Cys Tyr Thr Leu
225 230 235 240

Ile Thr Asp Gly Pro Ser Asp Ala Gln Ala Phe Tyr Lys Ile Leu Lys
245 250 255

Ile Arg Lys Gly Lys Ile Val Ser Met Lys Asp Val Asp Ala Thr Gly
260 265 270

Phe His Phe Glu Glu Cys Ser Cys Tyr Pro Ser Gly Thr Asp Ile Glu
275 280 285

Cys Val Cys Arg Asp Asn Trp Arg Gly Ser Asn Arg Pro Trp Ile Arg
290 295 300

Phe Asn Ser Asp Leu Asp Tyr Gln Ile Gly Tyr Val Cys Ser Gly Ile
305 310 315 320

Phe Gly Asp Asn Pro Arg Pro Val Asp Gly Thr Gly Ser Cys Asn Ser
325 330 335

Pro Val Asn Asn Gly Lys Gly Arg Tyr Gly Val Lys Gly Phe Ser Phe
340 345 350

Arg Tyr Gly Asp Gly Val Trp Ile Gly Arg Thr Lys Ser Leu Glu Ser

```
        355                 360                 365

Arg Ser Gly Phe Glu Met Val Trp Asp Ala Asn Gly Trp Val Ser Thr
    370                 375                 380

Asp Lys Asp Ser Asn Gly Val Gln Asp Ile Ile Asp Asn Asp Asn Trp
385                 390                 395                 400

Ser Gly Tyr Ser Gly Ser Phe Ser Ile Arg Gly Glu Thr Thr Gly Arg
                405                 410                 415

Asn Cys Thr Val Pro Cys Phe Trp Val Glu Met Ile Arg Gly Gln Pro
            420                 425                 430

Lys Glu Lys Thr Ile Trp Thr Ser Gly Ser Ser Ile Ala Phe Cys Gly
        435                 440                 445

Val Asn Ser Asp Thr Thr Gly Trp Ser Trp Pro Asp Gly Ala Leu Leu
    450                 455                 460

Pro Phe Asp Ile Asp Lys
465                 470


<210> SEQ ID NO 32
<211> LENGTH: 470
<212> TYPE: PRT
<213> ORGANISM: Influenza virus

<400> SEQUENCE: 32

Met Asn Pro Asn Gln Lys Ile Ile Cys Ile Ser Ala Thr Gly Met Thr
1               5                   10                  15

Leu Ser Val Val Ser Leu Leu Ile Gly Ile Ala Asn Leu Gly Leu Asn
            20                  25                  30

Ile Gly Leu His Tyr Lys Met Gly Asp Thr Pro Asp Val Asn Ile Pro
        35                  40                  45

Asn Met Asn Glu Thr Asn Ser Thr Thr Thr Ile Ile Asn Asn His Thr
    50                  55                  60

Gln Asn Asn Phe Thr Asn Ile Thr Asn Ile Ile Val Asn Lys Asn Glu
65                  70                  75                  80

Glu Gly Thr Phe Leu Asn Leu Thr Lys Pro Leu Cys Glu Val Asn Ser
                85                  90                  95

Trp His Ile Leu Ser Lys Asp Asn Ala Ile Arg Ile Gly Glu Asp Ala
            100                 105                 110

His Ile Leu Val Thr Arg Glu Pro Tyr Leu Ser Cys Asp Pro Gln Gly
        115                 120                 125

Cys Arg Met Phe Ala Leu Ser Gln Gly Thr Thr Leu Arg Gly Arg His
    130                 135                 140

Ala Asn Gly Thr Ile His Asp Arg Ser Pro Phe Arg Ala Leu Ile Ser
145                 150                 155                 160

Trp Glu Met Gly Gln Ala Pro Ser Pro Tyr Asn Val Arg Val Glu Cys
                165                 170                 175

Ile Gly Trp Ser Ser Thr Ser Cys His Asp Gly Ile Ser Arg Met Ser
            180                 185                 190

Ile Cys Met Ser Gly Ala Asn Asn Asn Ala Ser Ala Val Val Trp Tyr
        195                 200                 205

Gly Gly Arg Pro Val Thr Glu Ile Pro Ser Trp Ala Gly Asn Ile Leu
    210                 215                 220

Arg Thr Gln Glu Ser Glu Cys Val Cys His Lys Gly Ile Cys Pro Val
225                 230                 235                 240

Val Met Thr Asp Gly Pro Ala Asn Asn Arg Ala Ala Thr Lys Ile Ile
                245                 250                 255
```

-continued

```
Tyr Phe Lys Glu Gly Lys Ile Gln Lys Ile Glu Glu Leu Ala Gly Asn
            260                 265                 270

Thr Gln His Ile Glu Glu Cys Ser Cys Tyr Gly Ala Val Gly Val Ile
        275                 280                 285

Lys Cys Ile Cys Arg Asp Asn Trp Lys Gly Ala Asn Arg Pro Val Ile
    290                 295                 300

Thr Ile Asp Pro Glu Met Met Thr His Thr Ser Lys Tyr Leu Cys Ser
305                 310                 315                 320

Lys Ile Leu Thr Asp Thr Ser Arg Pro Asn Asp Pro Thr Asn Gly Asn
                325                 330                 335

Cys Asp Ala Pro Ile Thr Gly Gly Ser Pro Asp Pro Gly Val Lys Gly
            340                 345                 350

Phe Ala Phe Leu Asp Arg Glu Asn Ser Trp Leu Gly Arg Thr Ile Ser
        355                 360                 365

Lys Asp Ser Arg Ser Gly Tyr Glu Met Leu Lys Val Pro Asn Ala Glu
    370                 375                 380

Thr Asp Thr Gln Ser Gly Pro Ile Ser His Gln Val Ile Val Asn Asn
385                 390                 395                 400

Gln Asn Trp Ser Gly Tyr Ser Gly Ala Phe Ile Asp Tyr Trp Ala Asn
                405                 410                 415

Lys Glu Cys Phe Asn Pro Cys Phe Tyr Val Glu Leu Ile Arg Gly Arg
            420                 425                 430

Pro Lys Glu Ser Ser Val Leu Trp Thr Ser Asn Ser Ile Val Ala Leu
        435                 440                 445

Cys Gly Ser Lys Glu Arg Leu Gly Ser Trp Ser Trp His Asp Gly Ala
    450                 455                 460

Glu Ile Ile Tyr Phe Lys
465                 470
```

<210> SEQ ID NO 33
<211> LENGTH: 470
<212> TYPE: PRT
<213> ORGANISM: Influenza virus

<400> SEQUENCE: 33

```
Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asp Lys Glu Thr Gly Thr Ala Lys Pro
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160
```

-continued

Leu Gly Ser Pro Pro Val Val Ser Asn Ser Asp Phe Leu Cys Val Gly
165 170 175

Trp Ser Ser Thr Ser Cys His Asp Gly Ile Gly Arg Met Thr Ile Cys
180 185 190

Val Gln Gly Asn Asn Asp Asn Ala Thr Ala Thr Val Tyr Tyr Asp Arg
195 200 205

Arg Leu Thr Thr Thr Ile Lys Thr Trp Ala Gly Asn Ile Leu Arg Thr
210 215 220

Gln Glu Ser Glu Cys Val Cys His Asn Gly Thr Cys Val Val Ile Met
225 230 235 240

Thr Asp Gly Ser Ala Ser Ser Gln Ala Tyr Thr Lys Val Leu Tyr Phe
245 250 255

His Lys Gly Leu Val Ile Lys Glu Glu Ala Leu Lys Gly Ser Ala Arg
260 265 270

His Ile Glu Glu Cys Ser Cys Tyr Gly His Asn Ser Lys Val Thr Cys
275 280 285

Val Cys Arg Asp Asn Trp Gln Gly Ala Asn Arg Pro Val Ile Glu Ile
290 295 300

Asp Met Asn Ala Met Glu His Thr Ser Gln Tyr Leu Cys Thr Gly Val
305 310 315 320

Leu Thr Asp Thr Ser Arg Pro Ser Asp Lys Ser Met Gly Asp Cys Asn
325 330 335

Asn Pro Ile Thr Gly Ser Pro Gly Ala Pro Gly Val Lys Gly Phe Gly
340 345 350

Phe Leu Asp Ser Ser Asn Thr Trp Leu Gly Arg Thr Ile Ser Pro Arg
355 360 365

Ser Arg Ser Gly Phe Glu Met Leu Lys Ile Pro Asn Ala Glu Thr Asp
370 375 380

Pro Asn Ser Lys Ile Thr Glu Arg Gln Glu Ile Val Asp Asn Asn Asn
385 390 395 400

Trp Ser Gly Tyr Ser Gly Ser Phe Ile Asp Tyr Trp Asp Glu Ser Ser
405 410 415

Glu Cys Tyr Asn Pro Cys Phe Tyr Val Glu Leu Ile Arg Gly Arg Pro
420 425 430

Glu Glu Ala Lys Tyr Val Gly Trp Thr Ser Asn Ser Leu Ile Ala Leu
435 440 445

Cys Gly Ser Pro Ile Ser Val Gly Ser Gly Ser Phe Pro Asp Gly Ala
450 455 460

Gln Ile Gln Tyr Phe Ser
465 470

<210> SEQ ID NO 34
<211> LENGTH: 470
<212> TYPE: PRT
<213> ORGANISM: Influenza virus

<400> SEQUENCE: 34

Met Asn Pro Asn Gln Lys Ile Ile Thr Val Gly Ser Val Ser Leu Gly
1 5 10 15

Leu Val Val Leu Asn Ile Leu Leu His Ile Val Ser Ile Thr Val Thr
20 25 30

Val Leu Val Leu Pro Gly Asn Gly Asn Asn Lys Asn Cys Asn Glu Thr
35 40 45

Val Ile Arg Glu Tyr Asn Glu Thr Val Arg Ile Glu Lys Val Thr Gln

-continued

```
    50                  55                  60

Trp His Asn Thr Asn Val Ile Glu Tyr Ile Glu Lys Pro Glu Ser Gly
65                  70                  75                  80

His Phe Met Asn Asn Thr Glu Ala Leu Cys Asp Ala Lys Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Thr Glu Cys Arg
        115                 120                 125

Thr Phe Phe Leu Thr Gln Gly Ser Leu Leu Asn Asp Lys His Ser Asn
    130                 135                 140

Gly Thr Val Lys Asp Arg Ser Pro Tyr Arg Thr Leu Met Ser Val Glu
145                 150                 155                 160

Ile Gly Gln Ser Pro Asn Val Tyr Gln Ala Arg Phe Glu Ala Val Ala
                165                 170                 175

Trp Ser Ala Thr Ala Cys His Asp Gly Lys Lys Trp Met Thr Ile Gly
            180                 185                 190

Val Thr Gly Pro Asp Ala Lys Ala Val Ala Val Val His Tyr Gly Gly
        195                 200                 205

Ile Pro Thr Asp Val Ile Asn Ser Trp Ala Gly Asp Ile Leu Arg Thr
    210                 215                 220

Gln Glu Ser Ser Cys Thr Cys Ile Gln Gly Glu Cys Tyr Trp Val Met
225                 230                 235                 240

Thr Asp Gly Pro Ala Asn Arg Gln Ala Gln Tyr Arg Ala Phe Lys Ala
                245                 250                 255

Lys Gln Gly Lys Ile Val Gly Gln Thr Glu Ile Ser Phe Asn Gly Ser
            260                 265                 270

His Ile Glu Glu Cys Ser Cys Tyr Pro Asn Glu Gly Lys Val Glu Cys
        275                 280                 285

Val Cys Arg Asp Asn Trp Thr Gly Thr Asn Arg Pro Val Leu Val Ile
    290                 295                 300

Ser Pro Asp Leu Ser Tyr Arg Ala Gly Tyr Leu Cys Ala Gly Leu Pro
305                 310                 315                 320

Ser Asp Thr Pro Arg Gly Glu Asp Ser Gln Phe Thr Gly Ser Cys Thr
                325                 330                 335

Ser Pro Val Gly Asn Gln Gly Tyr Gly Val Lys Gly Phe Gly Phe Arg
            340                 345                 350

Gln Gly Asn Asp Val Trp Met Gly Arg Thr Ile Ser Arg Thr Ser Arg
        355                 360                 365

Ser Gly Phe Glu Ile Leu Lys Val Arg Asn Gly Trp Val Gln Asn Ser
    370                 375                 380

Lys Glu Gln Ile Lys Arg Gln Val Val Val Asp Asn Leu Lys Trp Ser
385                 390                 395                 400

Gly Tyr Ser Gly Ser Phe Thr Leu Pro Val Glu Leu Thr Lys Arg Asn
                405                 410                 415

Cys Leu Val Pro Cys Phe Trp Val Glu Met Ile Arg Gly Lys Pro Glu
            420                 425                 430

Glu Lys Thr Ile Trp Thr Ser Ser Ser Ser Ile Val Met Cys Gly Val
        435                 440                 445

Asp His Glu Ile Ala Asp Trp Ser Trp His Asp Gly Ala Ile Leu Pro
    450                 455                 460

Phe Asp Ile Asp Lys Met
465                 470
```

<210> SEQ ID NO 35
<211> LENGTH: 465
<212> TYPE: PRT
<213> ORGANISM: Influenza virus

<400> SEQUENCE: 35

Met Asn Pro Asn Gln Lys Ile Leu Cys Thr Ser Ala Thr Ala Ile Ile
1 5 10 15

Ile Gly Ala Ile Ala Val Leu Ile Gly Ile Ala Asn Leu Gly Leu Asn
20 25 30

Ile Gly Leu His Leu Lys Pro Gly Cys Asn Cys Ser His Ser Gln Pro
35 40 45

Glu Thr Thr Asn Thr Ser Gln Thr Ile Ile Asn Asn Tyr Tyr Asn Glu
50 55 60

Thr Asn Ile Thr Asn Ile Gln Met Glu Glu Arg Thr Ser Arg Asn Phe
65 70 75 80

Asn Asn Leu Thr Lys Gly Leu Cys Thr Ile Asn Ser Trp His Ile Tyr
85 90 95

Gly Lys Asp Asn Ala Val Arg Ile Gly Glu Ser Ser Asp Val Leu Val
100 105 110

Thr Arg Glu Pro Tyr Val Ser Cys Asp Pro Asp Glu Cys Arg Phe Tyr
115 120 125

Ala Leu Ser Gln Gly Thr Thr Ile Arg Gly Lys His Ser Asn Gly Thr
130 135 140

Ile His Asp Arg Ser Gln Tyr Arg Ala Leu Ile Ser Trp Pro Leu Ser
145 150 155 160

Ser Pro Pro Thr Val Tyr Asn Ser Arg Val Glu Cys Ile Gly Trp Ser
165 170 175

Ser Thr Ser Cys His Asp Gly Lys Ser Arg Met Ser Ile Cys Ile Ser
180 185 190

Gly Pro Asn Asn Asn Ala Ser Ala Val Val Trp Tyr Asn Arg Arg Pro
195 200 205

Val Thr Glu Ile Asn Thr Trp Ala Arg Asn Ile Leu Arg Thr Gln Glu
210 215 220

Ser Glu Cys Val Cys His Asn Gly Val Cys Pro Val Val Phe Thr Asp
225 230 235 240

Gly Ser Ala Thr Gly Pro Ala Asp Thr Arg Ile Tyr Tyr Phe Lys Glu
245 250 255

Gly Lys Ile Leu Lys Trp Glu Ser Leu Thr Gly Thr Ala Lys His Ile
260 265 270

Glu Glu Cys Ser Cys Tyr Gly Glu Arg Thr Gly Ile Thr Cys Thr Cys
275 280 285

Arg Asp Asn Trp Gln Gly Ser Asn Arg Pro Val Ile Gln Ile Asp Pro
290 295 300

Val Ala Met Thr His Thr Ser Gln Tyr Ile Cys Ser Pro Val Leu Thr
305 310 315 320

Asp Asn Pro Arg Pro Asn Asp Pro Asn Ile Gly Lys Cys Asn Asp Pro
325 330 335

Tyr Pro Gly Asn Asn Asn Asn Gly Val Lys Gly Phe Ser Tyr Leu Asp
340 345 350

Gly Ala Asn Thr Trp Leu Gly Arg Thr Ile Ser Thr Ala Ser Arg Ser
355 360 365

Gly Tyr Glu Met Leu Lys Val Pro Asn Ala Leu Thr Asp Asp Arg Ser

-continued

```
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465
```

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39
<211> LENGTH: 2341
<212> TYPE: DNA
<213> ORGANISM: Influenza virus

<400> SEQUENCE: 39

```
agcgaaagca ggtcaattat attcaatatg gaaagaataa aagaactaag aaatctaatg     60

tcgcagtctc gcacccgcga gatactcaca aaaaccaccg tggaccatat ggccataatc    120

aagaagtaca catcaggaag acaggagaag aacccagcac ttaggatgaa atggatgatg    180

gcaatgaaat atccaattac agcagacaag aggataacgg aaatgattcc tgagagaaat    240

gagcaaggac aaactttatg gagtaaaatg aatgatgccg gatcagaccg agtgatggta    300

tcacctctgg ctgtgacatg gtggaatagg aatggaccaa tgacaaatac agttcattat    360

ccaaaaatct acaaaactta ttttgaaaga gtcgaaaggc taaagcatgg aacctttggc    420

cctgtccatt ttagaaacca agtcaaaata cgtcggagag ttgacataaa tcctggtcat    480

gcagatctca gtgccaagga ggcacaggat gtaatcatgg aagttgtttt ccctaacgaa    540

gtgggagcca ggatactaac atcggaatcg caactaacga taaccaaaga gaagaaagaa    600

gaactccagg attgcaaaat ttctcctttg atggttgcat acatgttgga gagagaactg    660

gtccgcaaaa cgagattcct cccagtggct ggtggaacaa gcagtgtgta cattgaagtg    720

ttgcatttga ctcaaggaac atgctgggaa cagatgtata ctccaggagg ggaagtgaag    780

aatgatgatg ttgatcaaag cttgattatt gctgctagga acatagtgag aagagctgca    840

gtatcagcag acccactagc atctttattg gagatgtgcc acagcacaca gattggtgga    900
```

```
attaggatgg tagacatcct taagcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatctgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtta gaggtgatct gaatttcgtc aatagggcga atcagcgact gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccggttc ttgagagtca gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta caacaaggcc acgaagagac tcacagttct cggaaaggat   2040
gctggcactt taaccgaaga cccagatgaa ggcacagctg gagtggagtc cgctgttctg   2100
aggggattcc tcattctggg caaagaagac aggagatatg ggccagcatt aagcatcaat   2160
gaactgagca accttgcgaa aggagagaag gctaatgtgc taattgggca aggagacgtg   2220
gtgttggtaa tgaaacgaaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 40
<211> LENGTH: 2341
<212> TYPE: DNA
<213> ORGANISM: Influenza virus

<400> SEQUENCE: 40

```
agcgaaagca ggcaaaccat ttgaatggat gtcaatccga ccttactttt cttaaaagtg     60
ccagcacaaa atgctataag cacaactttc ccttataccg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaagcaatg    300
gctttccttg aggaatccca tcctggtatt tttgaaaact cgtgtattga aacgatggag    360
gttgttcagc aaacacgagt agacaagctg acacaaggcc gacagaccta tgactggact    420
ttaaatagaa accagcctgc tgcaacagca ttggccaaca caatagaagt gttcagatca    480
aatggcctca cggccaatga gtcaggaagg ctcatagact tccttaagga tgtaatggag    540
tcaatgaaaa aagaagaaat ggggatcaca actcattttc agagaaagag acgggtgaga    600
gacaatatga ctaagaaaat gataacacag agaacaatag gtaaaaggaa acagagattg    660
```

aacaaaaggg gttatctaat tagagcattg accctgaaca caatgaccaa agatgctgag 720
agagggaagc taaaacggag agcaattgca accccaggga tgcaaataag ggggtttgta 780
tactttgttg agacactggc aaggagtata tgtgagaaac ttgaacaatc agggttgcca 840
gttggaggca atgagaagaa agcaaagttg gcaaatgttg taaggaagat gatgaccaat 900
tctcaggaca ccgaactttc tttcaccatc actggagata acaccaaatg gaacgaaaat 960
cagaatcctc ggatgttttt ggccatgatc acatatatga ccagaaatca gcccgaatgg 1020
ttcagaaatg ttctaagtat tgctccaata atgttctcaa acaaaatggc gagactggga 1080
aaagggtata tgtttgagag caagagtatg aaacttagaa ctcaaatacc tgcagaaatg 1140
ctagcaagca ttgatttgaa atatttcaat gattcaacaa gaaagaagat tgaaaaaatc 1200
cgaccgctct taatagaggg gactgcatca ttgagccctg gaatgatgat gggcatgttc 1260
aatatgttaa gcactgtatt aggcgtctcc atcctgaatc ttggacaaaa gagatacacc 1320
aagactactt actggtggga tggtcttcaa tcctctgacg attttgctct gattgtgaat 1380
gcacccaatc atgaagggat tcaagccgga gtcgacaggt tttatcgaac ctgtaagcta 1440
cttggaatca atatgagcaa gaaaaagtct tacataaaca gaacaggtac atttgaattc 1500
acaagttttt tctatcgtta tgggtttgtt gccaatttca gcatggagct tcccagtttt 1560
ggggtgtctg ggatcaacga gtcagcggac atgagtattg gagttactgt catcaaaaac 1620
aatatgataa acaatgatct tggtccagca acagctcaaa tggcccttca gttgttcatc 1680
aaagattaca ggtacacgta ccgatgccat agaggtgaca cacaaataca aacccgaaga 1740
tcatttgaaa taaagaaact gtgggagcaa acccgttcca aagctggact gctggtctcc 1800
gacggaggcc caaatttata caacattaga aatctccaca ttcctgaagt ctgcctaaaa 1860
tgggaattga tggatgagga ttaccagggg cgtttatgca acccactgaa cccatttgtc 1920
agccataaag aaattgaatc aatgaacaat gcagtgatga tgccagcaca tggtccagcc 1980
aaaaacatgg agtatgatgc tgttgcaaca acacactcct ggatccccaa aagaaatcga 2040
tccatcttga atacaagtca aagaggagta cttgaagatg aacaaatgta ccaaaggtgc 2100
tgcaatttat ttgaaaaatt cttccccagc agttcataca gaagaccagt cgggatatcc 2160
agtatggtgg aggctatggt ttccagagcc cgaattgatg cacggattga tttcgaatct 2220
ggaaggataa agaaagaaga gttcactgag atcatgaaga tctgttccac cattgaagag 2280
ctcagacggc aaaaatagtg aatttagctt gtccttcatg aaaaaatgcc ttgtttctac 2340
t 2341

<210> SEQ ID NO 41
<211> LENGTH: 2233
<212> TYPE: DNA
<213> ORGANISM: Influenza virus

<400> SEQUENCE: 41
agcgaaagca ggtactgatt caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agatttccac 180
ttcatcaatg agcaaggcga gtcaataatc gtagaacttg gtgatcctaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360

-continued

```
aaggaaaata gattcatcga aattggagta acaaggagag aagttcacat atactatctg    420

gaaaaggcca ataaaattaa atctgagaaa acacacatcc acattttctc gttcactggg    480

gaagaaatgg ccacaagggc cgactacact ctcgatgaag aaagcagggc taggatcaaa    540

accaggctat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc tttttgaaa acaacaccac gaccacttag acttccgaat    840

gggcctccct gttctcagcg gtccaaattc ctgctgatgg atgccttaaa attaagcatt    900

gaggacccaa gtcatgaagg agagggaata ccgctatatg atgcaatcaa atgcatgaga    960

acattctttg gatggaagga acccaatgtt gttaaaccac acgaaaaggg aataaatcca   1020

aattatcttc tgtcatggaa gcaagtactg gcagaactgc aggacattga gaatgaggag   1080

aaaattccaa agactaaaaa tatgaaaaaa acaagtcagc taaagtgggc acttggtgag   1140

aacatggcac cagaaaaggt agactttgac gactgtaaag atgtaggtga tttgaagcaa   1200

tatgatagtg atgaaccaga attgaggtcg cttgcaagtt ggattcagaa tgagttcaac   1260

aaggcatgcg aactgacaga ttcaagctgg atagagcttg atgagattgg agaagatgtg   1320

gctccaattg aacacattgc aagcatgaga aggaattatt tcacatcaga ggtgtctcac   1380

tgcagagcca cagaatacat aatgaagggg gtgtacatca atactgcctt acttaatgca   1440

tcttgtgcag caatggatga tttccaatta attccaatga taagcaagtg tagaactaag   1500

gagggaaggc gaaagaccaa cttgtatggt ttcatcataa aaggaagatc ccacttaagg   1560

aatgacaccg acgtggtaaa ctttgtgagc atggagtttt ctctcactga cccaagactt   1620

gaaccacaca aatgggagaa gtactgtgtt cttgagatag gagatatgct tctaagaagt   1680

gccataggcc aggtttcaag gcccatgttc ttgtatgtga ggacaaatgg aacctcaaaa   1740

attaaaatga aatggggaat ggagatgagg cgttgtctcc tccagtcact tcaacaaatt   1800

gagagtatga ttgaagctga gtcctctgtc aaagagaaag acatgaccaa agagttcttt   1860

gagaacaaat cagaaacatg gcccattgga gagtctccca aaggagtgga ggaaagttcc   1920

attgggaagg tctgcaggac tttattagca aagtcggtat ttaacagctt gtatgcatct   1980

ccacaactag aaggattttc agctgaatca agaaaactgc ttcttatcgt tcaggctctt   2040

agggacaatc tggaacctgg gacctttgat cttgggggc tatatgaagc aattgaggag    2100

tgcctaatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

```
<210> SEQ ID NO 42
<211> LENGTH: 1565
<212> TYPE: DNA
<213> ORGANISM: Influenza virus

<400> SEQUENCE: 42

agcaaaagca gggtagataa tcactcactg agtgacatca aaatcatggc gtcccaaggc     60

accaaacggt cttacgaaca gatggagact gatggagaac gccagaatgc cactgaaatc    120

agagcatccg tcggaaaaat gattggtgga attggacgat tctacatcca aatgtgcaca    180

gaacttaaac tcagtgatta tgagggacgg ttgatccaaa acagcttaac aatagagaga    240
```

```
atggtgctct ctgcttttga cgaaaggaga aataaatacc tggaagaaca tcccagtgcg    300
gggaaagatc ctaagaaaac tggaggacct atatacagaa gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
gcaacttatc agaggacaag ggctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcagg atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cggaacccag ggaatgctga gttcgaagat ctcacttttc tagcacggtc tgcactcata    840
ttgagagggt cggttgctca caagtcctgc ctgcctgcct gtgtgtatgg acctgccgta    900
gccagtgggt acgactttga aagagaggga tactctctag tcggaataga ccctttcaga    960
ctgcttcaaa acagccaagt gtacagccta atcagaccaa atgagaatcc agcacacaag   1020
agtcaactgg tgtggatggc atgccattct gccgcatttg aagatctaag agtattgagc   1080
ttcatcaaag ggacgaaggt ggtcccaaga gggaagcttt ccactagagg agttcaaatt   1140
gcttccaatg aaaatatgga gactatggaa tcaagtacac ttgaactgag aagcaggtac   1200
tgggccataa ggaccagaag tggaggaaac accaatcaac agagggcatc tgcgggccaa   1260
atcagcatac aacctacgtt ctcagtacag agaaatctcc cttttgacag aacaaccgtt   1320
atggcagcat tcactgggaa tacagagggg agaacatctg acatgaggac cgaaatcata   1380
aggatgatgg aaagtgcaag accagaagat gtgtctttcc aggggcgggg agtcttcgag   1440
ctctcggacg aaaaggcagc gagcccgatc gtgccttcct ttgacatgag taatgaagga   1500
tcttatttct tcggagacaa tgcagaggag tacgacaatt aaagaaaaat acccttgttt   1560
ctact                                                               1565
```

```
<210> SEQ ID NO 43
<211> LENGTH: 1027
<212> TYPE: DNA
<213> ORGANISM: Influenza virus

<400> SEQUENCE: 43
```

```
agcaaaagca ggtagatatt gaaagatgag tcttctaacc gaggtcgaaa cgtacgttct     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg gggggctgtga ccactgaagt ggcatttggc ctggtatgtg caacctgtga    480
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
```

-continued

```
tcttcttgaa aatttgcagg cctatcagaa acgaatgggg gtgcagatgc aacggttcaa    780

gtgatcctct cgctattgcc gcaaatatca ttgggatctt gcacttgata ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027
```

<210> SEQ ID NO 44
<211> LENGTH: 890
<212> TYPE: DNA
<213> ORGANISM: Influenza virus

<400> SEQUENCE: 44

```
agcaaaagca gggtgacaaa gacataatgg atccaaacac tgtgtcaagc tttcaggtag     60

attgctttct ttggcatgtc cgcaaacgag ttgcagacca agaactaggt gatgccccat    120

tccttgatcg gcttcgccga gatcagaaat ccctaagagg aaggggcagc actcttggtc    180

tggacatcga gacagccaca cgtgctggaa agcagatagt ggagcggatt ctgaaagaag    240

aatccgatga ggcacttaaa atgaccatgg cctctgtacc tgcgtcgcgt tacctaaccg    300

acatgactct tgaggaaatg tcaagggaat ggtccatgct catacccaag cagaaagtgg    360

caggccctct ttgtatcaga atggaccagg cgatcatgga taaaaacatc atactgaaag    420

cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600

ttcgagtctc tgaaactcta cagagattcg cttggagaag cagtaatgag aatgggagac    660

ctccactcac tccaaaacag aaacgagaaa tggcgggaac aattaggtca gaagtttgaa    720

gaaataagat ggttgattga agaagtgaga cacaaactga aggtaacaga gaatagtttt    780

gagcaaataa catttatgca agccttacat ctattgcttg aagtggagca agagataaga    840

actttctcat ttcagcttat ttaataataa aaaacaccct tgtttctact               890
```

<210> SEQ ID NO 45

<400> SEQUENCE: 45

000

<210> SEQ ID NO 46
<211> LENGTH: 1701
<212> TYPE: DNA
<213> ORGANISM: Influenza virus

<400> SEQUENCE: 46

```
atgaagacta tcattgcttt gagctacatt ctatgtctgg ttttcgctca aaaaattcct     60

ggaaatgaca atagcacggc aacgctgtgc cttgggcacc atgcagtacc aaacggaacg    120

atagtgaaaa caatcacaaa tgaccgaatt gaagttacta atgctactga gttggttcag    180

aattcctcaa taggtgaaat atgcgacagt cctcatcaga tccttgatgg agagaactgc    240

acactaatag atgctctatt gggagaccct cagtgtgatg gctttcaaaa taagaaatgg    300

gaccttttg ttgaacgaag caaagcctac agcaactgtt acccttatga tgtgccggat    360

tatgcctccc ttaggtcact agttgcctca tccggcacac tggagtttaa aaatgaaagc    420
```

-continued ttcaattgga ctggagtcac tcaaaacgga acaagttctg cttgcataag gggatctagt 480
agtagtttct ttagtagatt aaattggttg acccacttaa actacacata tccagcattg 540
aacgtgacta tgccaaacaa ggaacaattt gacaaattgt acatttgggg ggttcaccac 600
ccgggtacgg acaaggacca aatcttcctg tatgctcaat catcaggaag aatcacagta 660
tctaccaaaa gaagccaaca agctgtaatc ccaaatatcg gatctagacc cagaataagg 720
gatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca agtctgaatg catcactcca 900
aatggaagca ttcccaatga caaaccattc caaaatgtaa acaggatcac atacggggcc 960
tgtcccagat atgttaagca tagcactctg aaattggcaa caggaatgcg aaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaataggttg 1200
atcggaaaaa ccaacgagaa attccatcag attgaaaaag aattctcaga agtagaagga 1260
agagttcaag accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctgagggaaa atgctgagga tatgggaaat 1440
ggttgtttca aaatatacca caaatgtgac aatgcctgca tagaatcaat aagaaatgaa 1500
acttatgacc acaatgtgta cagggatgaa gcattgaaca accggttcca gatcaaggga 1560
gttgagctga agtcaggata caaagattgg atcctatgga tttcctttgc catatcatgt 1620
tttttgcttt gtgttgcttt gttggggttc atcatgtggg cctgccaaaa gggcaacatt 1680
agatgcaaca tttgcatttg a 1701

<210> SEQ ID NO 47
<211> LENGTH: 1410
<212> TYPE: DNA
<213> ORGANISM: Influenza virus

<400> SEQUENCE: 47
atgaatccaa atcaaaagat aataacgatt ggctctgttt ctctcaccat ttccacaata 60
tgcttcttca tgcaaattgc catcctgata actactgtaa cattgcattt caagcaatat 120
gaattcaact cccccccaaa caaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300
tctaaggaca attcgattag gctttccgct ggtggggaca tctgggtgac aagagaacct 360
tatgtgtcat gcgatcctga caagtgttat caatttgccc ttggacaggg aacaacacta 420
aacaacgtgc attcaaataa cacagtacgt gataggaccc cttatcggac tctattgatg 480
aatgagttgg gtgttccttt ccatctgggg accaagcaag tgtgcatagc atggtccagc 540
tcaagttgtc acgatggaaa agcatggctg catgtttgta taacggggga tgataaaaat 600
gcaactgcta gcttcattta caatgggagg cttatagata gtgttgtttc atggtccaaa 660
gatattctca ggacccagga gtcagaatgc gtttgtatca atggaacttg tacagtagta 720
atgactgatg gaaatgctac aggaaaagct gatactaaaa tactattcat tgaggagggg 780
aaaatcgttc atactagcaa attgtcagga agtgctcagc atgtcgaaga gtgctcttgc 840

-continued

```
tatcctcgat atcctggtgt cagatgtgtc tgcagagaca actggaaagg atccaaccgg    900

cccatcgtag atataaacat aaaggatcat agcattgttt ccagttatgt gtgttcagga    960

cttgttggag acacacccag aaaaaacgac agctccagca gtagccattg tttgaatcct   1020

aacaatgaag aaggtggtca tggagtgaaa ggctgggcct ttgatgatgg aaatgacgtg   1080

tggatgggga gaacaatcaa cgagacgtca cgcttagggt atgaaacctt caaagtcgtt   1140

gaaggctggt ccaaccctaa gtccaaattg cagataaata ggcaagtcat agttgacaga   1200

ggtgataggt ccggttattc tggtattttc tctgttgaag gcaaaagctg catcaatcgg   1260

tgcttttatg tggagttgat taggggaaga aaagaggaaa ctgaagtctt gtggacctca   1320

aacagtattg ttgtgttttg tggcacctca ggtacatatg gaacaggctc atggcctgat   1380

ggggcggacc tcaatctcat gcatatataa                                    1410
```

<210> SEQ ID NO 48
<211> LENGTH: 469
<212> TYPE: PRT
<213> ORGANISM: Influenza virus

<400> SEQUENCE: 48

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Ile Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270
```

Gln His Val Glu Glu Cys Ser Cys Tyr Pro Arg Tyr Pro Gly Val Arg
275 280 285

Cys Val Cys Arg Asp Asn Trp Lys Gly Ser Asn Arg Pro Ile Val Asp
290 295 300

Ile Asn Ile Lys Asp His Ser Ile Val Ser Ser Tyr Val Cys Ser Gly
305 310 315 320

Leu Val Gly Asp Thr Pro Arg Lys Asn Asp Ser Ser Ser Ser Ser His
325 330 335

Cys Leu Asn Pro Asn Asn Glu Glu Gly Gly His Gly Val Lys Gly Trp
340 345 350

Ala Phe Asp Asp Gly Asn Asp Val Trp Met Gly Arg Thr Ile Asn Glu
355 360 365

Thr Ser Arg Leu Gly Tyr Glu Thr Phe Lys Val Val Glu Gly Trp Ser
370 375 380

Asn Pro Lys Ser Lys Leu Gln Ile Asn Arg Gln Val Ile Val Asp Arg
385 390 395 400

Gly Asp Arg Ser Gly Tyr Ser Gly Ile Phe Ser Val Glu Gly Lys Ser
405 410 415

Cys Ile Asn Arg Cys Phe Tyr Val Glu Leu Ile Arg Gly Arg Lys Glu
420 425 430

Glu Thr Glu Val Leu Trp Thr Ser Asn Ser Ile Val Val Phe Cys Gly
435 440 445

Thr Ser Gly Thr Tyr Gly Thr Gly Ser Trp Pro Asp Gly Ala Asp Leu
450 455 460

Asn Leu Met His Ile
465

<210> SEQ ID NO 49
<211> LENGTH: 469
<212> TYPE: PRT
<213> ORGANISM: Influenza virus

<400> SEQUENCE: 49

Met Asn Pro Asn Gln Lys Ile Ile Thr Ile Gly Ser Val Ser Leu Thr
1 5 10 15

Ile Ser Thr Ile Cys Phe Phe Met Gln Ile Ala Ile Leu Ile Thr Thr
20 25 30

Val Thr Leu His Phe Lys Gln Tyr Glu Phe Asn Ser Pro Pro Asn Asn
35 40 45

Gln Val Met Leu Cys Glu Pro Thr Ile Ile Glu Arg Asn Ile Thr Glu
50 55 60

Ile Val Tyr Leu Thr Asn Thr Thr Ile Glu Lys Glu Ile Cys Pro Lys
65 70 75 80

Pro Ala Glu Tyr Arg Asn Trp Ser Lys Pro Gln Cys Gly Ile Thr Gly
85 90 95

Phe Ala Pro Phe Ser Lys Asp Asn Ser Ile Arg Leu Ser Ala Gly Gly
100 105 110

Asp Ile Trp Val Thr Arg Glu Pro Tyr Val Ser Cys Asp Pro Asp Lys
115 120 125

Cys Tyr Gln Phe Ala Leu Gly Gln Gly Thr Thr Leu Asn Asn Val His
130 135 140

Ser Asn Asn Thr Val Arg Asp Arg Thr Pro Tyr Arg Thr Leu Leu Met
145 150 155 160

Asn Glu Leu Gly Val Pro Phe His Leu Gly Thr Lys Gln Val Cys Ile

```
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met His Ile
465


<210> SEQ ID NO 50

<400> SEQUENCE: 50

000


<210> SEQ ID NO 51
<211> LENGTH: 469
<212> TYPE: PRT
<213> ORGANISM: Influenza virus

<400> SEQUENCE: 51

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30
```

-continued

```
Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445
```

-continued

```
Asn Ser Asp Thr Val Gly Trp Ser Trp Pro Asp Gly Ala Glu Leu Pro
    450                 455                 460

Phe Thr Ile Asp Lys
465


<210> SEQ ID NO 52
<211> LENGTH: 470
<212> TYPE: PRT
<213> ORGANISM: Influenza virus

<400> SEQUENCE: 52

Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asp Lys Glu Thr Gly Thr Ala Lys Pro
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
            340                 345                 350
```

```
Phe Leu Asp Ser Ser Asn Thr Trp Leu Gly Arg Thr Ile Ser Pro Arg
        355                 360                 365

Ser Arg Ser Gly Phe Glu Met Leu Lys Ile Pro Asn Ala Glu Thr Asp
    370                 375                 380

Pro Asn Ser Lys Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Glu Cys Tyr Asn Pro Cys Phe Tyr Val Glu Leu Ile Arg Gly Arg Pro
            420                 425                 430

Glu Glu Ala Lys Tyr Val Gly Trp Thr Ser Asn Ser Leu Ile Ala Leu
        435                 440                 445

Cys Gly Ser Pro Ile Ser Val Gly Ser Gly Ser Phe Pro Asp Gly Ala
    450                 455                 460

Gln Ile Gln Tyr Phe Ser
465                 470


<210> SEQ ID NO 53
<211> LENGTH: 465
<212> TYPE: PRT
<213> ORGANISM: Influenza virus

<400> SEQUENCE: 53

Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Tyr Phe Lys Glu
```

```
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
        275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
        355                 360                 365

Gly Tyr Glu Met Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465


<210> SEQ ID NO 54
<211> LENGTH: 469
<212> TYPE: PRT
<213> ORGANISM: Influenza virus

<400> SEQUENCE: 54

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140
```

Ser Asn Asp Ile Val His Asp Arg Thr Pro Tyr Arg Thr Leu Leu Met
145 150 155 160

Asn Glu Leu Gly Val Pro Phe His Leu Gly Thr Lys Gln Val Cys Ile
165 170 175

Ala Trp Ser Ser Ser Ser Cys His Asp Gly Lys Ala Trp Leu His Val
180 185 190

Cys Val Thr Gly Asp Asp Glu Asn Ala Thr Ala Ser Phe Ile Tyr Asn
195 200 205

Gly Arg Leu Ala Asp Ser Ile Val Ser Trp Ser Lys Lys Ile Leu Arg
210 215 220

Thr Gln Glu Ser Glu Cys Val Cys Ile Asn Gly Thr Cys Thr Val Val
225 230 235 240

Met Thr Asp Gly Ser Ala Ser Gly Lys Ala Asp Thr Lys Ile Leu Phe
245 250 255

Ile Glu Glu Gly Lys Ile Val His Thr Ser Thr Leu Ser Gly Ser Ala
260 265 270

Gln His Val Glu Glu Cys Ser Cys Tyr Pro Arg Tyr Pro Gly Val Arg
275 280 285

Cys Val Cys Arg Asp Asn Trp Lys Gly Ser Asn Arg Pro Ile Val Asp
290 295 300

Ile Asn Ile Lys Asp Tyr Ser Ile Val Ser Ser Tyr Val Cys Ser Gly
305 310 315 320

Leu Val Gly Asp Thr Pro Arg Lys Asn Asp Ser Ser Ser Ser Ser His
325 330 335

Cys Leu Asp Pro Asn Asn Glu Glu Gly Gly His Gly Val Lys Gly Trp
340 345 350

Ala Phe Asp Asp Gly Asn Asp Val Trp Met Gly Arg Thr Ile Ser Glu
355 360 365

Lys Leu Arg Ser Gly Tyr Glu Thr Phe Lys Val Ile Glu Gly Trp Ser
370 375 380

Asn Pro Asn Ser Lys Leu Gln Ile Asn Arg Gln Val Ile Val Asp Arg
385 390 395 400

Gly Asn Arg Ser Gly Tyr Ser Gly Ile Phe Ser Val Glu Gly Lys Ser
405 410 415

Cys Ile Asn Arg Cys Phe Tyr Val Glu Leu Ile Arg Gly Arg Lys Gln
420 425 430

Glu Thr Glu Val Leu Trp Thr Ser Asn Ser Ile Val Val Phe Cys Gly
435 440 445

Thr Ser Gly Thr Tyr Gly Thr Gly Ser Trp Pro Asp Gly Ala Asp Ile
450 455 460

Asn Leu Met Pro Ile
465

<210> SEQ ID NO 55
<211> LENGTH: 469
<212> TYPE: PRT
<213> ORGANISM: Influenza virus

<400> SEQUENCE: 55

Met Asn Pro Asn Gln Lys Ile Ile Thr Ile Gly Ser Val Ser Leu Thr
1 5 10 15

Ile Ser Thr Ile Cys Phe Phe Met Gln Ile Ala Ile Leu Ile Thr Thr
20 25 30

Val Thr Leu His Phe Lys Gln Tyr Glu Phe Asn Ser Pro Pro Asn Asn
35 40 45

-continued

```
Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Ala Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460
```

Asn Leu Met Pro Ile
465

<210> SEQ ID NO 56
<211> LENGTH: 1467
<212> TYPE: DNA
<213> ORGANISM: Influenza virus

<400> SEQUENCE: 56

```
agcaaaagca ggagtaaaga tgaatccaaa tcaaaagata ataacgattg gctctgtttc     60
cctcaccatt tccacaatat gcttcttcat gcaaattgcc atcctgataa ctactgtaac    120
attgcatttc aagcaatatg aattcaactc ccccccaaac aaccaagtga tgctgtgtga    180
accaacaata atagaaagaa acataacaga gatagtgtat ctgaccaaca ccaccataga    240
gaaggaaata tgccccaaac tagcagaata cagaaattgg tcaaagccgc aatgtaacat    300
tacaggattt gcaccttttt ctaaggacaa ttcgattcgg ctttccgctg gtggggacat    360
ctgggtgaca agagaacctt atgtgtcatg cgatcctgac aagtgttatc aatttgccct    420
tggacaggga acaacactaa acaacgtgca ttcaaatgac atagtacatg ataggacccc    480
ttatcggacc ctattgatga atgagttggg tgttccattt catctgggga ccaagcaagt    540
gtgcatagca tggtccagct caagttgtca cgatggaaaa gcatggctgc atgtttgtgt    600
aacgggggat gatgaaaatg caactgctag cttcatttac aatgggaggc ttgcagatag    660
tattgtttca tggtccaaaa aaatcctcag gacccaggag tcagaatgcg tttgtatcaa    720
tggaacttgt acagtagtaa tgactgatgg gagtgcttca ggaaaagctg atactaaaat    780
actattcatt gaggagggga aaattgttca tactagcaca ttatcaggaa gtgctcagca    840
tgtcgaggag tgctcctgtt atcctcgata tcctggtgtc agatgtgtct gcagagacaa    900
ctggaaaggc tccaataggc ccatcgtaga tataaacata aaggattata gcattgtttc    960
cagttatgtg tgctcaggac ttgttggaga cacacccaga aaaaacgaca gctccagcag   1020
tagccattgc ttggatccaa acaatgagga aggtggtcat ggagtgaaag gctgggcctt   1080
tgatgatgga aatgacgtgt ggatgggaag aacgatcagc gagaagttac gctcaggata   1140
tgaaaccttc aaagtcattg aaggctggtc caaccctaac tccaaattgc agataaatag   1200
gcaagtcata gttgacagag gtaacaggtc cggttattct ggtattttct ctgttgaagg   1260
caaaagctgc atcaatcggt gcttttatgt ggagttgata aggggaagaa aacaggaaac   1320
tgaagtcttg tggacctcaa acagtattgt tgtgttttgt ggcacctcag gtacatatgg   1380
aacaggctca tggcctgatg gggcggacat caatctcatg cctatataag ctttcgcaat   1440
tttagaaaaa aactccttgt ttctact                                       1467
```

<210> SEQ ID NO 57
<211> LENGTH: 469
<212> TYPE: PRT
<213> ORGANISM: Influenza virus

<400> SEQUENCE: 57

```
Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Asn Ser Pro Pro Asn Asn
        35                  40                  45

Gln Val Met Leu Cys Glu Pro Thr Ile Ile Glu Arg Asn Ile Thr Glu
```

-continued

```
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Gly Asn Ala Thr Ala Ser Phe Ile Tyr Asn
        195                 200                 205

Gly Arg Leu Val Asp Ser Ile Gly Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Leu Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Asn Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

<210> SEQ ID NO 58
<211> LENGTH: 759
<212> TYPE: PRT
<213> ORGANISM: Influenza virus

<400> SEQUENCE: 58

Met Glu Arg Ile Lys Glu Leu Arg Asn Leu Met Ser Gln Ser Arg Thr
1 5 10 15

Arg Glu Ile Leu Thr Lys Thr Thr Val Asp His Met Ala Ile Ile Lys
20 25 30

Lys Tyr Thr Ser Gly Arg Gln Glu Lys Asn Pro Ala Leu Arg Met Lys
35 40 45

Trp Met Met Ala Met Lys Tyr Pro Ile Thr Ala Asp Lys Arg Ile Thr
50 55 60

Glu Met Ile Pro Glu Arg Asn Glu Gln Gly Gln Thr Leu Trp Ser Lys
65 70 75 80

Met Asn Asp Ala Gly Ser Asp Arg Val Met Val Ser Pro Leu Ala Val
85 90 95

Thr Trp Trp Asn Arg Asn Gly Pro Met Thr Asn Thr Val His Tyr Pro
100 105 110

Lys Ile Tyr Lys Thr Tyr Phe Glu Arg Val Glu Arg Leu Lys His Gly
115 120 125

Thr Phe Gly Pro Val His Phe Arg Asn Gln Val Lys Ile Arg Arg Arg
130 135 140

Val Asp Ile Asn Pro Gly His Ala Asp Leu Ser Ala Lys Glu Ala Gln
145 150 155 160

Asp Val Ile Met Glu Val Val Phe Pro Asn Glu Val Gly Ala Arg Ile
165 170 175

Leu Thr Ser Glu Ser Gln Leu Thr Ile Thr Lys Glu Lys Lys Glu Glu
180 185 190

Leu Gln Asp Cys Lys Ile Ser Pro Leu Met Val Ala Tyr Met Leu Glu
195 200 205

Arg Glu Leu Val Arg Lys Thr Arg Phe Leu Pro Val Ala Gly Gly Thr
210 215 220

Ser Ser Val Tyr Ile Glu Val Leu His Leu Thr Gln Gly Thr Cys Trp
225 230 235 240

Glu Gln Met Tyr Thr Pro Gly Gly Glu Val Lys Asn Asp Asp Val Asp
245 250 255

Gln Ser Leu Ile Ile Ala Ala Arg Asn Ile Val Arg Arg Ala Ala Val
260 265 270

Ser Ala Asp Pro Leu Ala Ser Leu Leu Glu Met Cys His Ser Thr Gln
275 280 285

Ile Gly Gly Ile Arg Met Val Asp Ile Leu Lys Gln Asn Pro Thr Glu
290 295 300

Glu Gln Ala Val Asp Ile Cys Lys Ala Ala Met Gly Leu Arg Ile Ser
305 310 315 320

Ser Ser Phe Ser Phe Gly Gly Phe Thr Phe Lys Arg Thr Ser Gly Ser
325 330 335

Ser Val Lys Arg Glu Glu Glu Val Leu Thr Gly Asn Leu Gln Thr Leu
340 345 350

Lys Ile Arg Val His Glu Gly Ser Glu Glu Phe Thr Met Val Gly Arg
355 360 365

Arg Ala Thr Ala Ile Leu Arg Lys Ala Thr Arg Arg Leu Ile Gln Leu

-continued

```
            370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 59
<211> LENGTH: 757
<212> TYPE: PRT
<213> ORGANISM: Influenza virus

<400> SEQUENCE: 59

Met Asp Val Asn Pro Thr Leu Leu Phe Leu Lys Val Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Gly Arg Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu
85 90 95

Glu Ser His Pro Gly Ile Phe Glu Asn Ser Cys Ile Glu Thr Met Glu
100 105 110

Val Val Gln Gln Thr Arg Val Asp Lys Leu Thr Gln Gly Arg Gln Thr
115 120 125

Tyr Asp Trp Thr Leu Asn Arg Asn Gln Pro Ala Ala Thr Ala Leu Ala
130 135 140

Asn Thr Ile Glu Val Phe Arg Ser Asn Gly Leu Thr Ala Asn Glu Ser
145 150 155 160

Gly Arg Leu Ile Asp Phe Leu Lys Asp Val Met Glu Ser Met Lys Lys
165 170 175

Glu Glu Met Gly Ile Thr Thr His Phe Gln Arg Lys Arg Arg Val Arg
180 185 190

Asp Asn Met Thr Lys Lys Met Ile Thr Gln Arg Thr Ile Gly Lys Arg
195 200 205

Lys Gln Arg Leu Asn Lys Arg Gly Tyr Leu Ile Arg Ala Leu Thr Leu
210 215 220

Asn Thr Met Thr Lys Asp Ala Glu Arg Gly Lys Leu Lys Arg Arg Ala
225 230 235 240

Ile Ala Thr Pro Gly Met Gln Ile Arg Gly Phe Val Tyr Phe Val Glu
245 250 255

Thr Leu Ala Arg Ser Ile Cys Glu Lys Leu Glu Gln Ser Gly Leu Pro
260 265 270

Val Gly Gly Asn Glu Lys Lys Ala Lys Leu Ala Asn Val Val Arg Lys
275 280 285

Met Met Thr Asn Ser Gln Asp Thr Glu Leu Ser Phe Thr Ile Thr Gly
290 295 300

Asp Asn Thr Lys Trp Asn Glu Asn Gln Asn Pro Arg Met Phe Leu Ala
305 310 315 320

Met Ile Thr Tyr Met Thr Arg Asn Gln Pro Glu Trp Phe Arg Asn Val
325 330 335

Leu Ser Ile Ala Pro Ile Met Phe Ser Asn Lys Met Ala Arg Leu Gly
340 345 350

Lys Gly Tyr Met Phe Glu Ser Lys Ser Met Lys Leu Arg Thr Gln Ile
355 360 365

Pro Ala Glu Met Leu Ala Ser Ile Asp Leu Lys Tyr Phe Asn Asp Ser
370 375 380

Thr Arg Lys Lys Ile Glu Lys Ile Arg Pro Leu Leu Ile Glu Gly Thr
385 390 395 400

Ala Ser Leu Ser Pro Gly Met Met Met Gly Met Phe Asn Met Leu Ser

-continued

```
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755


<210> SEQ ID NO 60
<211> LENGTH: 716
<212> TYPE: PRT
<213> ORGANISM: Influenza virus

<400> SEQUENCE: 60

Met Glu Asp Phe Val Arg Gln Cys Phe Asn Pro Met Ile Val Glu Leu
1               5                   10                  15
```

-continued

```
Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Arg Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
```

```
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715


<210> SEQ ID NO 61
<211> LENGTH: 498
<212> TYPE: PRT
<213> ORGANISM: Influenza virus

<400> SEQUENCE: 61

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95
```

```
Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 62

-continued

<211> LENGTH: 252
<212> TYPE: PRT
<213> ORGANISM: Influenza virus

<400> SEQUENCE: 62

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250
```